US009458443B2

(12) United States Patent
Kettling et al.

(10) Patent No.: US 9,458,443 B2
(45) Date of Patent: Oct. 4, 2016

(54) OPTIMIZED CELLULASE ENZYMES

(75) Inventors: Ulrich Kettling, München (DE); Christoph Reisinger, München (DE); Thomas Brück, Ebenhausen (DE); Andre Koltermann, Icking (DE); Jochen Gerlach, Vienna (AT); Isabel Unterstrasser, Rimsting (DE); Lutz Röcher, München (DE); Markus Rarbach, München (DE); Jörg Claren, München (DE); Andreas Kohl, München (DE); Jan Carsten Pieck, Wilnsdorf (DE); Dominik Schlosser, München (DE)

(73) Assignee: SUD-CHEMIE IP GMBH & CO. KG, Munich (DE)

( * ) Notice: Subject to any disclaimer, the term of this patent is extended or adjusted under 35 U.S.C. 154(b) by 275 days.

(21) Appl. No.: 13/578,291

(22) PCT Filed: Feb. 11, 2011

(86) PCT No.: PCT/EP2011/052023

§ 371 (c)(1),
(2), (4) Date: Jan. 28, 2013

(87) PCT Pub. No.: WO2011/098551

PCT Pub. Date: Aug. 18, 2011

(65) Prior Publication Data

US 2013/0123115 A1 May 16, 2013

(30) Foreign Application Priority Data

Feb. 11, 2010 (EP) .................................... 10153355

(51) Int. Cl.
*C12N 9/42* (2006.01)

(52) U.S. Cl.
CPC ............... *C12N 9/42* (2013.01); *C12N 9/2437* (2013.01); *C12Y 302/01091* (2013.01)

(58) Field of Classification Search
CPC ............. C12N 9/2437; C12M 9/2445; C12Y 302/01004; C12Y 302/010921; C12Y 302/01021; Y02E 50/16; Y02E 50/17; C12P 19/14; C11D 3/38645; D21C 5/005
See application file for complete search history.

(56) References Cited

U.S. PATENT DOCUMENTS 5,686,593 A 11/1997 Woldike et al.
7,452,707 B2 11/2008 Goedegebuur et al.
(Continued)

FOREIGN PATENT DOCUMENTS

WO 0104284 A1 1/2001
WO 03000941 A2 1/2003
(Continued)

OTHER PUBLICATIONS

Guo et al., Protein tolerance to random amino acid change, 2004, Proc. Natl. Acad. Sci. USA 101: 9205-9210.*
(Continued)

*Primary Examiner* — Alexander Kim
(74) *Attorney, Agent, or Firm* — Gianna Julian-Arnold; Saul Ewing LLP

(57) ABSTRACT

The invention discloses cellulase enzymes with optimized properties for processing of cellulose- and lignocellulose-containing substrates. In particular, cellobiohydrolase enzymes with preferred characteristics are disclosed. The present invention provides fusion, insertion, deletion and/or substitution variants of such enzymes. Enzyme variants have enhanced thermostability, proteolytic stability, specific activity and/or stability at extreme pH. Nucleic acid molecules encoding said enzymes, a composition comprising said enzymes, a method for preparation, and the use for cellulose processing and/or for the production of biofuels are disclosed.

8 Claims, 10 Drawing Sheets

(56) References Cited

U.S. PATENT DOCUMENTS

| | | | | |
|---|---|---|---|---|
| 7,459,299 | B2 | 12/2008 | Goedegebuur et al. | |
| 2003/0170861 | A1 | 9/2003 | Adney et al. | |
| 2008/0057541 | A1 * | 3/2008 | Hill et al. | 435/72 |
| 2009/0042266 | A1 | 2/2009 | Vehmaanpera et al. | |
| 2009/0162916 | A1 * | 6/2009 | Adney et al. | 435/209 |

FOREIGN PATENT DOCUMENTS

| | | | | |
|---|---|---|---|---|
| WO | 2004016760 | A2 | 2/2004 | |
| WO | 2005030926 | A2 | 4/2005 | |
| WO | 2006117432 | A1 | 11/2006 | |
| WO | 2009108941 | A2 | 9/2009 | |
| WO | 2009138877 | A2 | 11/2009 | |
| WO | 2009139839 | A1 | 11/2009 | |
| WO | 2010005553 | A1 | 1/2010 | |
| WO | WO 2010/005553 | * | 1/2010 | C12N 9/42 |
| WO | 2010122141 | A1 | 10/2010 | |

OTHER PUBLICATIONS

Lazar et al., Transforming Growth Factor α: Mutation of Aspartic Acid 47 and Leucine 48 Results in Different Biological Activity, 1988, Mol. Cell. Biol. 8:1247-1252.*

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Q8TFL9 (last viewed on Aug. 5, 2014).*

Grassick, A., et al. Three-dimensional structure of a thermostable native cellobiohydrolase, CBH IB, and molecular characterization of the cel7 gene from the filamentous fungus, *Talaromyces emersonii*. Eur. J. Biochem, Nov. 2004; 271(22): 4495-4506.

Voutilainen, S.P., et al. Expression of Talaromyces emersonii cellobiohydrolase Cel7A in *Saccharomyces cerevisiae* and rational mutagenesis to improve its thermostability and activity. Protein Eng. Des. Sel. Feb. 2010; 23(2): 69-79.

Percival Zhang, Y.H., et al. Outlook for cellulase improvement: Screening and selection strategies. Biotechnol. Adv. Sep.-Oct. 2006; 24(5): 452-481.

Penttilä, M.E., et al. Efficient secretion of two fungal cellobiohydrolases by *Saccharomyces cerevisiae*. Gene. 1988; 63(1): 103-112.

Hong, J., et al. Cloning of a gene encoding thermostable cellobiohydrolase from Thermoascus aurantiacus and its expression in yeast. Appl. Microbiol. Biotechnol. Nov. 2003; 63(1): 42-50.

Tuohy, M.G., et al. Kinetic parameters and mode of action of the cellobiohydrolases produced by Talaromyces emersonii. Biochim. Biophys. Acta. Apr. 2002; 1596(2): 366-380.

Boer, H., et al. Characterization of Trichoderma reesi Cellobiohydrolase Cel7A secreted from Pichia pastoris using two different promoters. Biotechnol. Bioeng. Sep. 2000; 69(5):486-494.

Godbole, S., et al. Cloning and expression of Trichoderma reesei cellobiohydrolase I in Pichia pastoris. Biotechnol. Prog. Sep.-Oct. 1999; 15(5):828-833.

Kanokratana, P., et al. Identification and expression of cellobiohydrolase (CBHI) gene from an endophytic fungus, *Fusicoccum* sp. (BCC4124) in Pichia pastoris. Protein Expr. Purif. Mar. 2008; 58(1): 148-153. Epub Sep. 19, 2007.

Li, Y.L., et al. Cloning of a gene encoding thermostable cellobiohydrolase from the thermophilic fungus *Chaetomium thermophilum* and its expression in Pichia pastoris. J. Appl. Microbiol. Jun. 2009; 106(6): 1867-1875.

Voutilainen, S.P., et al. Cloning, expression, and characterization of novel thermostable Family 7 Cellobiohydrolases. Biotechnol. Bioeng. Oct. 2008; 101(3): 515-528. PubMed PMID: 18512263.

Viikari, L., et al. Thermostable enzymes in lignocellulose hydrolysis. Adv. Biochem. Eng. Biotechnol. 2007; 108: 121-145.

Ilmén, M., et al. High level secretion of cellobiohydrolases by *Saccharomyces cerevisiae*. Biotechnology for Biofuels. 2011 4:30. Available online at http://www.biotechnologyforbiofuels.com/content/4/1/30.

Heinzelman, P., et al. Efficient screening of fungal cellobiohydrolase class 1 enzymes for thermostabilizing sequence blocks by SCHEMA structure-guided recombination. Protein Engineering, Design & Selection. Sep. 2010; 23(11): 871-880.

Database Uni Prot [Online] Feb. 1, 2005, "Subname: Full-Cellobiohydrolase," retrieved from EBI accession No. UNIPROT:Q5MBA7 Database accession No. Q5MBA7.

Database PDB [Online] Feb. 24, 2009, Grassick, et al.: "3-Dimensional Structure of Native Cel7A From Talaromyces Emersonii" retrieved from EBI accession No. PDB:1Q9H Database accession No. 1Q9H.

International Search Report, dated Mar. 7, 2012, with respect to International Application No. PCT/EP2011/052023.

Office Action issued by Australian Patent Office, dated Jun. 2, 2014, with respect to Australian Application No. 2011214298 (Australian equivalent to instant U.S. application).

* cited by examiner

1 Plain Vector
2 *Trichoderma viride* CBHI
3 *Humicola grisea* CBHI
4 *Talaromyces emersonii* CBHI
5 *Thermoascus aurantiacus* CBHI
6 *Talaromyces emersonii* CBHI fusion with *T. reesei* CBHI CBD
7 *Humicola grisea* CBHI fusion with *T. reesei* CBHI CBD 3,6 kb

Figure 10

```
                 1                                                     50
T._reesei_CBHI   QSACTLQSET HPPLTWQKCS SGGTCTQQTG SVVIDANWRW THATNSSTNC
   SeqID_NO.2    QQAGTATAEN HPPLTWQECT APGSCTTQNG AVVLDANWRW VHDVNGYTNC

                 51                                                   100
T._reesei_CBHI   YDGNTWSSTL CPDNETCAKN CCLDGAAYAS TYGVTTSGNS LSIGFVTQSA
   SeqID_NO.2    YTGNTWDPTY CPDDETCAQN CALDGADYEG TYGVTSSGSS LKLNFVTG..

                 101                                                  150
T._reesei_CBHI   QKNVGARLYL MASDTTYQEF TLLGNEFSFD VDVSQLPCGL NGALYFVSMD
   SeqID_NO.2    .SNVGSRLYL LQDDSTYQIF KLLNREFSFD VDVSNLPCGL NGALYFVAMD

                 151                                                  200
T._reesei_CBHI   ADGGVSKYPT NTAGAKYGTG YCDSQCPRDL KFINGQANVE GWEPSSNNAN
   SeqID_NO.2    ADGGVSKYPN NKAGAKYGTG YCDSQCPRDL KFIDGEANVE GWQPSSNNAN

                 201                                                  250
T._reesei_CBHI   TGIGGHGSCC SEMDIWEANS ISEALTPHPC TTVGQEICEG DGCGGTYSDN
   SeqID_NO.2    TGIGDHGSCC AEMDVWEANS ISNAVTPHPC DTPGQTMCSG DDCGGTYSND

                 251                                                  300
T._reesei_CBHI   RYGGTCDPDG CDWNPYRLGN TSFYGPGSSF TLDTTKKLTV VTQFETSG..
   SeqID_NO.2    RYAGTCDPDG CDFNPYRMGN TSFYGPGK.. IIDTTKPFTV VTQFLTDDGT

                 301                                                  350
T._reesei_CBHI   ......AINR YYVQNGVTFQ QPNAELGSYS GNELNDDYCT AEEAEFGGSS
   SeqID_NO.2    DTGTLSEIKR FYIQNSNVIP QPNSDISGVT GNSITTEFCT AQKQAFGDTD

                 351                                                  400
T._reesei_CBHI   .FSDKGGLTQ FKKATSGGMV LVMSLWDDYY ANMLWLDSTY PTNETSSTPG
   SeqID_NO.2    DFSQHGGLAK MGAAMQQGMV LVMSLWDDYA AQMLWLDSDY PTDADPTTPG

                 401                                                  450
T._reesei_CBHI   AVRGSCSTSS GVPAQVESQS PNAKVTFSNI KFGPIGSTGN PSGGNPPGGN
   SeqID_NO.2    IARGTCPTDS GVPSDVESQS PNSYVTYSNI KFGPIGSTGN PSGGNPPGGN

                 451                                                  500
T._reesei_CBHI   RGTTTTRRPA TTTGSSPGPT QSHYGQCGGI GYSGPTVCAS GTTCQVLNPY
   SeqID_NO.2    RGTTTTRRPA TTTGSSPGPT QSHYGQCGGI GYSGPTVCAS GTTCQVLNPY

                 501
T._reesei_CBHI   YSQCL
   SeqID_NO.2    YSQCL
```

OPTIMIZED CELLULASE ENZYMES

FIELD OF INVENTION

The invention discloses cellulase enzymes with optimized properties for processing of cellulose- and lignocellulose-containing substrates. In particular, cellobiohydrolase enzymes with preferred characteristics are disclosed. The present invention provides fusion, insertion, deletion and/or substitution variants of such enzymes. Enzyme variants have enhanced thermostability, proteolytic stability, specific activity and/or stability at extreme pH. Nucleic acid molecules encoding said enzymes, a composition comprising said enzymes, a method for preparation, and the use for cellulose processing and/or for the production of biofuels are disclosed.

BACKGROUND OF THE INVENTION

The development of production processes based on renewable resources is highly desired, for example for the generation of ethanol from cellulosic and lignocellulosic materials.

Cellulose material in pure form or in combination with hemicellulose and/or lignin is a valuable and readily available raw material for the production of chemicals and fuels. A key step in processing cellulose and lignocellulose is the hydrolysis of the beta-1,4-linked glucose polymer cellulose and the subsequent release of glucose monomers and short glucose oligomers such as cellobiose, cellotriose, etc. Enzymes that catalyze this reaction are found in various organisms, especially filamentous fungi and bacteria, that are capable of degrading and hydrolysing cellulose.

Continuous processes for converting solid lignocellulosic biomass into combustible fuel products are known. Treatment to make cellulosic substrates more susceptible to enzymatic degradation comprises milling, chemical processing and/or hydrothermal processing. Examples are wet oxidation and/or steam explosion. Such treatments increase the accessibility of cellulose fibers and separate them from hemicellulose and lignin.

A number of enzyme mixtures for hydrolysis of treated biomass are known in the literature. Typically a mixture of endoglucanase, exoglucanase and beta-glucosidase enzymes are required for the degradation of cellulose polymers. Among these cellobiohydrolase (CBH) enzymes, and more specifically cellobiohydrolase I (CBHI) enzymes, play a key role in the hydrolysis step as they provide the most processive enzymatic activity. CBHI enzymes catalyze the progressive hydrolytic release of cellobiose from the reducing end of the cellulose polymers. (Lynd L R, Weimer P J, van Zyl W H, Pretorius I S. Microbial cellulose utilization: fundamentals and biotechnology. Microbiol Mol Biol Rev. 2002 September; 66(3):506-77).

Hydrolyzed cellulosic materials contain several valuable carbohydrate molecules which can be isolated from the mixtures. Sugar containing hydrolysates of cellulosic materials can be used for microbial production of a variety of fine chemicals or biopolymers, such as organic acids, ethanol or higher alcohols (also diols or polyols) or polyhydroxyalkanoates (PHAs). One of the major uses of the sugar hydrolysates is in the production of biofuels.

Kurabi et al. (2005) describes preparations of cellulases from *Trichoderma reesei* and other fungi, such as *Penicillium* sp. The performance has been analysed on steam-exploded and ethanol organosolv-pretreated Douglas-fir. Better performance of enzyme mixtures appears to be a result of improved properties of single component enzymes as well as the effect of each compound in the mixture, especially the presence of beta-glucosidase. (Kurabi A, Berlin A, Gilkes N, Kilburn D, Bura R, Robinson J, Markov A, Skomarovsky A, Gusakov A, Okunev O, Sinitsyn A, Gregg D, Xie D, Saddler J. (2005) Enzymatic hydrolysis of steam-exploded and ethanol organosolv-pretreated Douglas-Fir by novel and commercial fungal cellulases. Appl Biochem Biotechnol. 121-124: 219-30).

Cellobiohydrolase sequences of the glucohydrolase class 7 (cel7) are known to the art from several fungal sources. The *Talaromyces emersonii* Cel7 cellobiohydrolase is known and expression was reported in *Escherichia coli* (Grassick A, Murray P G, Thompson R, Collins C M, Byrnes L, Birrane G, Higgins T M, Tuohy M G. Three-dimensional structure of a thermostable native cellobiohydrolase, CBH IB, and molecular characterization of the cel7 gene from the filamentous fungus, *Talaromyces emersonii*. Eur J Biochem, 2004 November; 271(22):4495-506) and *Saccharomyces cerevisiae* (Voutilainen S P, Murray P G, Tuohy M G, Koivula A. Expression of *Talaromyces emersonii* cellobiohydrolase Cel7A in *Saccharomyces cerevisiae* and rational mutagenesis to improve its thermostability and activity. Protein Eng Des Sel. 2010 February; 23(2):69-79), however the protein was either produced in inactive form or at rather low yields (less or equal to 5 mg/l). *Hypocrea jecorina* cellobiohydrolase I can be produced from wild type or engineered strains of the genus *Hypocrea* or *Trichoderma* at high yields. Improved sequences of *Hypocrea jecorina* Cel7A are disclosed by U.S. Pat. Nos. 7,459,299B2, 7,452,707B2. WO2005/030926. WO01/04284A1 or US2009/0162916 A1.

Positions leading to improvements were deduced from alignments with sequences from reported thermostable enzymes, suggested from structural information and shuffling of identified positions followed by limited screenings. Screening of larger libraries in transformable organisms such as *Saccharomyces cerevisiae* was reported by application of very sensitive fluorescent substrates, which resemble native substrates in a very restricted way. (Percival Zhang Y H, Himmel M E, Mielenz J R. Outlook for cellulase improvement: screening and selection strategies. Biotechnol Adv. 2006 September-October; 24(5):452-81).

The production of cellobiohydrolases from other fungal systems such as *Thermoascus aurantiacus, Chrysosporium lucknowense* or *Phanerochaete chrysosporium* was reported. Expression of Cel7 cellobiohydrolase from yeasts was reported, but enzymatic yields or enzyme properties remain unsatisfactory. (Penttilä M E, André L, Lehtovaara P, Bailey M, Teeri T T, Knowles J K. Efficient secretion of two fungal cellobiohydrolases by *Saccharomyces cerevisiae;* Gene. 1988; 63(1):103-12).

WO03/000941 discloses a number of CBHs and their corresponding gene sequences. Physiological properties and applications however were not disclosed. The fusion of cellulose binding domains to catalytic subunits of cellobiohydrolases is reported to improve the hydrolytic properties of proteins without a native domain.

US 2009042266 (A1) discloses fusions of *Thermoascus aurantiacus* Cel7A with cellulose binding domains from cellobiohydrolase I from *Chaetomium thermophilum* and *Hypocrea jecorina.*

U.S. Pat. No. 5,686,593 reports the fusion of specially designed linker regions and binding domains to cellobiohydrolases.

Hong et al. (2003) describe the production of *Thermoascus aurantiacus* CBHI in yeast and its characterization.

(Hong J, Tamaki H, Yamamoto K, Kumagai H Cloning of a gene encoding thermostable cellobiohydrolase from *Thermoascus aurantiacus* and its expression in yeast. Appl Microbiol Biotechnol. 2003 November; 63(1):42-50).

Tuohy et al. (2002) report the expression and characterization of *Talaromyces emersonii* CBH. (Tuohy M G, Walsh D J, Murray P G, Claeyssens M, Cuffe M M, Savage A V, Coughlan M P.: Kinetic parameters and mode of action of the cellobiohydrolases produced by *Talaromyces emersonii*. Biochim Biophys Acta. 2002 Apr. 29; 1596(2):366-80).

Nevoigt et al. (2008) reports on the expression of cellulolytic enzymes in yeasts. (Nevoigt E. Progress in metabolic engineering of *Saccharomyces cerevisiae*. Microbiol Mol Biol Rev. 2008 September; 72(3):379-412).

Fujita et al. (2004) reports on a *Saccharomyces cervisiae* strain expressing a combination of an endoglucanase, a beta glucosidase and a CBHII displayed on the cell surface. Cellobiohydrolase I (Cel7) was not used in this setup. (Fujita Y, Ito J, Ueda M, Fukuda H, Kondo A. Synergistic saccharification, and direct fermentation to ethanol, of amorphous cellulose by use of an engineered yeast strain codisplaying three types of cellulolytic enzyme. Appl Environ Microbiol. 2004 February; 70(2):1207-12).

Boer H et al. (2000) describes the expression of GH7 classified enzymes in different yeast hosts but expressed protein levels were low. (Boer H, Teeri T T, Koivula A. Characterization of *Trichoderma reesei* cellobiohydrolase Cel7A secreted from *Pichia pastoris* using two different promoters. Biotechnol Bioeng. 2000 Sep. 5; 69(5):486-94).

Godbole et al (1999) and Hong et al (2003) found that proteins of this enzyme class expressed fom yeast were often misfolded, hyperglycosylated and hydrolytic capabilities decreased compared to the protein expressed from the homologous host. (Godbole S, Decker S R, Nieves R A, Adney W S, Vinzant T B, Baker J O, Thomas S R, Himmel M E. Cloning and expression of *Trichoderma reesei* cellobiohydrolase I in *Pichia pastoris*. Biotechnol Prog. 1999 September-October; 15(5):828-33).

Kanokratana et al (2008), Li at al (2009) as well as CN01757710 describe the efficient expression of Cel7 CBH I enzymes, however these proteins are lacking cellulose binding domains required for efficient substrate processing. (Kanokratana P, Chantasingh D, Champreda V, Tanapongpipat S, Pootanakit K, Eurwilaichitr L Identification and expression of cellobiohydrolase (CBHI) gene from an endophytic fungus, *Fusicoccum* sp. (BCC4124) in *Pichia pastoris*. LProtein Expr Purif. 2008 March; 58(1):148-53. Epub 2007 Sep. 19; Li Y L, Li H, Li A N, Li D C. Cloning of a gene encoding thermostable cellobiohydrolase from the thermophilic fungus *Chaetomium thermophilum* and its expression in *Pichia pastoris*. J Appl Microbiol. 2009 June; 106(6):1867-75).

Voutilainen (2008) and Viikari (2007) disclose Cel7 enzymes comprising thermostable cellobiohydrolases, however with only low to moderate expression levels from *Trichoderma reesei*. (Voutilainen S P, Puranen T, Siika-Aho M, Lappalainen A, Alapuranen M, Kallio J, Hooman S, Viikari L, Vehmaanperä J, Koivula A. Cloning, expression, and characterization of novel thermostable family 7 cellobiohydrolases. Biotechnol Bioeng. 2008 Oct. 15; 101(3): 515-28. PubMed PMID: 18512263; Viikari L, Alapuranen M, Puranen T, Vehmaanperä J, Siika-Aho M. Thermostable enzymes in lignocellulose hydrolysis. Adv Biochem Eng Biotechnol. 2007; 108:121-45).

Grassick et al. (2004) disclose unfolded expression of Cellobiohydrolase I from *Talaromyces emersonii* in *Escherichia coli* but not in yeast. (Grassick A, Murray P G, Thompson R, Collins C M, Byrnes L, Birrane G, Higgins T M, Tuohy M G. Three-dimensional structure of a thermostable native cellobiohydrolase, CBH IB, and molecular characterization of the cel7 gene from the filamentous fungus, *Talaromyces emersonii*. Eur J Biochem. 2004 November; 271(22):4495-506).

Therefore, there is a need for cellulase enzymes with improved characteristics for the use in technical processes for cellulose hydrolysis. In particular there is a need for CBH enzymes with higher catalytic activity and/or higher stability under process conditions. Moreover there is a need for CBH enzymes with higher productivity in fungal and/or yeast expression and secretion systems.

SUMMARY OF THE INVENTION

The present invention provides a polypeptide having cellobiohydrolase activity. In a preferred embodiment, the invention provides a thermostable polypeptide having cellobiohydrolase activity. That is, in this embodiment, the polypeptide maintains 50% of its maximum substrate conversion capacity when the conversion is done for 60 minutes at 60° C. or higher, preferably 62° C. or higher, and in a particular embodiment 64° C. or higher, such as 66° C. or higher. This polypeptide comprises an amino acid sequence with at least 54%, preferably at least 56%, more preferably at least 58%, particularly preferably at least 60%, such as at least 62%, particularly at least 64%, such as at least 66%, and most preferably preferably at least 68% sequence identity to SEQ ID NO5. The invention also provides a polypeptide which comprises an amino acid sequence with at least 85% sequence identity to SEQ ID NO: 2.

Furthermore, the present invention discloses a nucleic acid encoding the polypeptide of the present invention, preferably having at least 95% identity to SEQ ID NO: 1. a vector comprising this nucleic acid and a host transformed with said vector.

The present invention further provides a method of producing a cellobiohydrolase protein encoded by a vector of the present invention, a method for identifying polypeptides having cellobiohydrolase activity, and a method of preparing such polypeptides having cellobiohydrolase activity. It also provides a method of identifying such polypeptides which maintain 50% or more of maimum substrate conversion capacity at elevated temperatures, such as at 60° C. or more.

The present invention also provides a polypeptide having cellobiohydrolase activity, wherein the polypeptide comprises an amino acid sequence having at least 85% sequence identity to SEQ ID NO: 2 wherein one or more specific amino acid residues of the sequence defined by SEQ ID NO: 2 are modified by substitution or deletion, as well as insertion mutants. Examples of such mutants include Q1. G4. A6. T15. Q28. W40. D64. E65. A72. S86. K92, V130. V152. Y155. K159. D181. E183. N194. D202. P224. T243. Y244. I277. K304. N310, S311. N318. D320. T335. T344. D346. Q349. A358. Y374. A375. T392. T393. D410. Y422, P442. N445. R446. T456. S460. P462. G463. H468 and/or V482 of amino acids 1 to 500 of SEQ ID NO: 2. but the invention is by no means limited to these. Further specific positions are given below.

Moreover, the present invention provides a polypeptide having cellobiohydrolase activity, which is obtainable by the method of preparing a polypeptide having cellobiohydrolase activity according to the present invention, and a polypeptide having cellobiohydrolase activity, wherein the polypeptide comprises an amino acid sequence having at least 80% sequence identity to SEQ ID NO: 5. wherein one or more of the following amino acid residues of the sequence defined by SEQ ID NO: 5 are modified by substitution or deletion, as well as insertion mutants. Examples of such mutants include Q1. G4. A6. T15. Q28. W40, D64. E65. A72. S86. K92. V130. V152. Y155. K159. D181. E183. N194. D202. P224. T243, Y244. I277. K304. N310. S311. N318. D320. T335. T344. D346. Q349. A358. Y374. A375, T392. T393. D410 and/or Y422 of amino acids 1 to 440 of SEQ ID NO: 5. but the invention is by no means limited to these. Further specific positions are given below.

The present invention furthermore provides a polypeptide having cellobiohydrolase activity comprising an amino acid sequence having at least 85% sequence identity to SEQ ID NO: 12 wherein one or more of the following amino acid residues of the sequence defined by SEQ ID NO: 12 are modified by substitution or deletion as well as insertion mutants. Examples of such mutants include Q1. T15. Q28. W40. C72. V133. V155. Y158. T162. Y247, N307. G308. E317. S341. D345. Y370. T389. Q406. N441. R442. T452. S456. P458. G459, H464 and/or V478. but the invention is by no means limited to these. Further specific positions are given below.

The present invention further provides the use of a polypeptide or the composition of the present invention for the enzymatic degradation of lignocellulosic biomass, and/or for textiles processing and/or as ingredient in detergents and/or as ingredient in food or feed compositions.

A . . . wt;

B . . . G4C,A72C;

C . . . G4C,A72C,Q349K;

D . . . G4C,A72C,D181N,Q349K;

E . . . Q1L,G4C,A72C,D181N,E183K,Q349R;

F . . . Q1L,G4C,A72C,S86T, D181N,E183K,D320V, Q349R;

G . . . G4C, A72C,E183K,D202Y,N310D,Q349R;

H . . . Q1L,G4C,A72C, A145T,H203R,Q349K,T403K;

I . . . , Q1L, G4C, Q28R, E65V, A72C, D181N, E183M, S192S, P224L, S311G, D320I, D346E, Q349K, T393V, Y422F, P442S, N445D, R446G, H468L, V482I

J . . . , Q1L, G4C, Q28K, E65K, A72C, L119L, D181N, E183M, S192S, S311G, N318Y, D320I, T335I, D346E, Q349K, T393V, Y422F, N445D, R446G, H468Q, V482T

K . . . , Q1L, G4C, Q28K, E65V, A72C, L119L, D181N, E183M, S192S, D202N, P224L, S311G, T335I, D346E, Q349K, T393V, Y422F, P442S, N445D, R446G, H468Q, V482I

L . . . Q1L, G4C, Q28R, E65V, A72C, G151GCGRSG, D181N, E183M, P224L, S311G, D320I, D346E, Q349K, T393V, Y422F, P442S, N445D, R446G, H468L, V482I

M . . . Q1L, G4C, Q28R, E65V, A72C, K159KCGRNK, D181N, E183M, P224L, S311G, D320I, D346E, Q349K, T393V, Y422F, P442S, N445D, R446G, H468L, V482I

Figure 9:
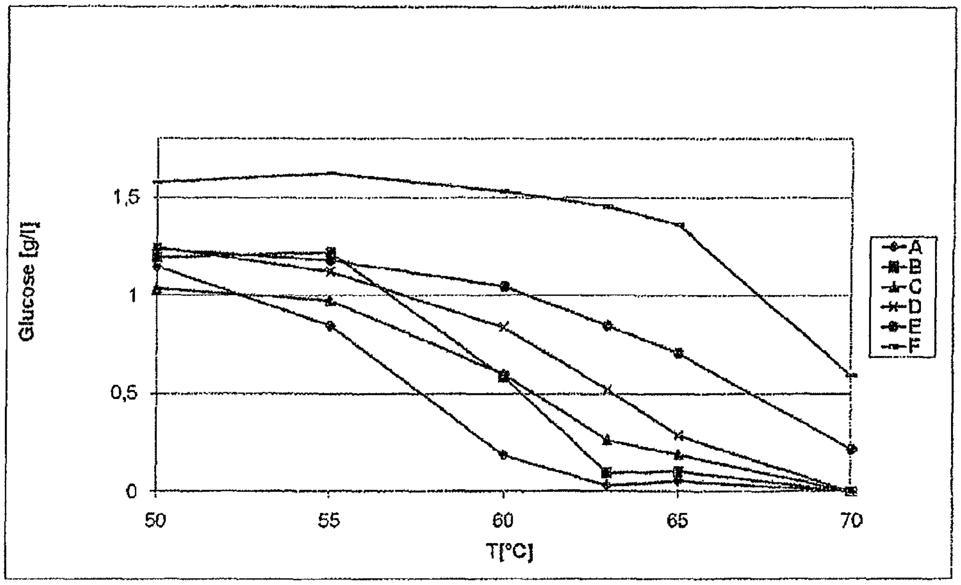

FIG. 9: Glucose yields of hydrolysis of pretreated straw with wt and mutated *Talaromyces emersonii* CBHI/

*Trichoderma reesei*-CBD (CBH-ah) fusion protein after hydrolysis for 48 hours in the presence of a β-glycosidase. The variants are characterized by the following mutations with respect to SeqID NO. 18 and were expressed from *Pichia pastoris* in shake flask cultures and isolated from the supernatant by affinity chomatography using Ni-NTA.

A: wt

B: G4C, A72C

C: G4C, A72C, Q349R

D: Q1L, G4C, A72C, D181N, E183K, Q349R

E: Q1L, G4C, Q28R, E65V, A72C, D181N, E183M, P224L, S311G, D320I, D346E, Q349K, T393V, Y422F, P442S, N445D, R446G, H468L, V482I

F: Q1L, G4C, Q28R, E65V, A72C, G151GCGRSG, D181N, E183M, P224L, S311G, D320I, D346E, Q349K, T393V, Y422F, P442S, N445D, R446G, H468L, V482I

FIG. 10: Alignment of SeqID. NO 2 with the *Trichoderma reesei* CBHI. The alignment matrix blosum62mt2 with gap opening penalty of 10 and gap extension penalty of 0.1 was used to create the alignment.

DETAILED DESCRIPTION OF THE INVENTION

The present invention provides polypeptides having cellobiohydrolase activity. In a preferred embodiment, the invention provides a thermostable polypeptide having cellobiohydrolase activity. In a preferred aspect, the invention discloses protein variants that show a high activity at high temperature over an extended period of time. Preferably, the polypeptide of the present invention maintains 50% of its maximum substrate conversion capacity when the conversion is done for 60 minutes at a temperature of 60° C. or higher. The respective temperature is also referred to as the IT50 value. In other words, the IT50 value is preferably 60° C. or higher, but more preferably 62° C. or higher. That is, in this embodiment, the polypeptide maintains 50% of its maximum substrate conversion capacity when the conversion is done for 60 minutes at 60° C. or higher, preferably 62° C. or higher, and in a particular embodiment 64° C. or higher, such as 66° C. or higher. Furthermore, the polypeptides of the present invention have preferably an IT50 value in the range of 62 to 80° C., more preferably 65 to 75° C.

"Substrate Conversion Capacity" of an enzyme is herein defined as the degree of substrate conversion catalyzed by an amount of enzyme within a certain time period under defined conditions (Substrate concentration, pH value and buffer concentration, temperature), as can be determined by end-point assaying of the enzymatic reaction under said conditions. "Maximum Substrate Conversion Capacity" of an enzyme is herein defined as the maximum in Substrate Conversion Capacity found for the enzyme within a number of measurements performed as described before, where only one parameter, e.g. the temperature, was varied within a defined range. According to the present invention, the assay described in Example 8 is used to determine these parameters.

This polypeptide comprises an amino acid sequence with at least 54%, preferably at least 56%, more preferably at least 58%, particularly preferably at least 60%, such as at least 62%, particularly at least 64%, such as at least 66%, and most preferably preferably at least 68% sequence identity to SEQ ID NO: 5. The term "Identity over a sequence length of y residues" (wherein y is any Integer, such as, as illustrative example, 200, 255, 256, 300, 400, 437, 500) means that y is a—preferably continuous—portion of the parenteral sequence (in this particular case SEQ ID NO: 5. but the same is true throughout this application, also with respect to other, specifically indicated parenteral sequences which which the sequences of this invention may be compared) which is used as a basis for the comparison of sequence identity. Thus, for the comparison of sequence identity (sequence alignment), preferably 200 or more, more preferably 300 or more, even more preferably 400 or more, and most preferably 437 positions of the parental sequence given in SEQ ID NO: 5 are taken into consideration. The details of how the percentages of sequence identities are calculated are given below. It should also be noted, that, unless explicitly otherwise specified in this specification, the entire sequence of the parental sequence (such as, in this particular case, SEQ ID NO:5) (i.e. from the first to the last amino acid residue) shall be used as a parent sequence.

In a preferred embodiment, the polypeptide capable of maintaining 50% of its maximum substrate conversion capacity when the conversion is done for 60 minutes at 60° C. or higher, preferably 62° C. or higher, is a polypeptide which differs from SEQ ID NO: 5 by at least one mutation, whereby the mutation may be an insertion, deletion or substitution of one or more amino acid residues. Also preferred are at least two such mutations, such as at least 4. at least 5. at least 6. at least 7. at least 10 such mutations with respect to the polypeptide given in SEQ ID NO: 5.

"Cellobiohydrolase" or "CBH" refers to enzymes that cleave cellulose from the end of the glucose chain and produce cellobiose as the main product. Alternative names are 1,4-beta-D-glucan cellobiohydrolases or cellulose 1,4-beta-cellobiosidases. CBHs hydrolyze the 1,4-beta-D-glucosidic linkages from the reducing or non-reducing ends of a polymer containing said linkages. "Cellobiohydrolase I" or "CBH I" act from the reducing end of the cellulose fiber. "Cellobiohydrolase II" or "CBH II" act from the non-reducing end of the cellulose fiber. Cellobiohydrolases typically have a structure consisting of a catalytic domain and one or more "cellulose-binding domains" or "CBD". Such domains can be located either at the N- or C-terminus of the catalytic domain. CBDs have carbohydrate-binding activity and they mediate the binding of the cellulase to crystalline cellulose and presence or absence of binding domains are known to have a major impact on the processivity of an enzyme especially on polymeric substrates.

In a preferred embodiment, this polypeptide is further characterized by comprising an amino acid sequence having at least 80% sequence identity to SEQ ID NO:5. more preferably at least 85% sequence identity to SEQ ID NO:5. such as at least 90% sequence identity to SEQ ID NO:5. and most preferably at least 95% sequence identity to SEQ ID NO.5.

The polypeptide having cellobiohydrolase activity as defined above is, in an even more preferred embodiment, further characterized as follows: It is the polypeptide as defined above, wherein one or more of the amino acid residues of the sequence defined by SEQ ID NO: 5 are modified by substitution or deletion at one or more positions which are preferably selected from Q1. Q2. G4. A6. T7. A8. N10. P12. T15. A21. G23. S24. T26. T27. Q28. N29. G30. A31, V32. N37. W40. V41. G46. Y47. T48. N49. C50. T52. N54. D57. T59. Y60. D64. E65. A68, Q69. A72. V84. S86. S89. S90. K92. S99. Q109. D110. D111. I116. F117. K118. L119. L120, D129. V130. G139. A145. M146. V152. K154. Y155. N157. N158. K159. K163. G167. Q172, F179. I180. D181. E183. E187. G188. Q190. S192. S193. N194. I200. D202. H203. D211, V212. A221. P224. D228. T229. G231. T233. M234. S236. T243. Y244. S245. N246. D247, G251. F260. G266. K275. I276. I277.

T280. L290. D293. G294. T295. T297. T299. S301, K304. F306. N310. S311. V313. I314. N318. D320. I321. T325. N327. T335. A340. F341, D343. T344. D345. D346. Q349. H350. A354. K355. A358. Q361. Q362. G363. M364. V367, D373. Y374. A375. A376. P386. T387. D390. T392. T393. P394. T400. P402. T403. D404, D410. N417. S418. T421. Y422 and/or one or more insertions after positions G151. K159, and in a more preferred embodiment are modified by substitution or deletion at one or more positions selected from Q1. Q2. G4. A6. T7. A8. N10. A21. S24. T26, 127. Q28. N29. G30, W40. Y47, 064. E65. A68. Q69. A72. S86. K92. K118. Y155. D181. E183. Q190. S192, N194. D202. H203. P224. T229. G231. M234. S236. T243. D247. S311. N318. D320. T335, A340. T344. D346. Q349. K355. Y374. A375. T387. D390. T392. T393. Y422 and/or one or more insertion of 1-8 amino acids after positions G151. K159 and in an even more preferred embodiment are modified by substitution or deletion at one or more positions selected from Q1. Q2. G4. A6. T7. A8. N10. Q28. E65. A72. S86. D181, E183. D202. P224. S311. N318. D320. T335. D346. Q349. T392. T393. Y422 and/or insertions at one or more after positions and/or one or more insertion of 5 amino acids after positions G151. K159 of of amino acids 1 to 437 of SEQ ID NO: 5.

Also preferred are embodiments wherein the respective mutation(s) given above is (are) introduced into the polypeptide given in SEQ ID NO: 2. as outlined below.

The skilled person will understand that several of these given mutations can be combined with each other, i.e. that a polypeptide having cellobiohydrolase activity, where, for example Q69 and T232 are substituted for other amino acid residues, is comprised in this embodiment. The term "insertion after position(s) x" is to be understood that the insertion may be at any position which is on the C-terminal side (closer to the C-terminus) of the position x; however, insertions immediately following the position x are strongly preferred (wherein x is any position).

The present invention also discloses a polypeptide having cellobiohydrolase activity, which comprises an amino acid sequence with at least 85% sequence identity to SEQ ID NO: 2. It is preferred that this polypeptide with at least 85% sequence identity to SEQ ID NO: 2 is a polypeptide which has also a degree of identity with SEQ ID NO: 5 as given above, such as having at least 60% (or more, see above) sequence identity with the polypeptide given in SEQ ID NO: 5. and/or any one or more of the more particular identity embodiments of percentage identity to SEQ ID NO: 5 as given in detail above. Thus, the polypeptide having at least 85% sequence identity to SEQ ID NO: 2 is an embodiment which is comprised in the invention relating to a polypeptide having at least 60% sequence identity with the polypeptide given in SEQ ID NO: 5. The skilled person will readily recognize the common inventive concept underlying the thermostable variants of SEQ ID NO: 2 and SEQ ID NO: 5.

Equivalent to what has been said above for SEQ ID NO: 5. for the sequence alignment of SEQ ID NO: 2 as defined herein, preferably 200 or more, more preferably 300 or more, even more preferably 400 or more, and most preferably 437 positions of SEQ ID NO: 5 are taken into consideration. The details of how the percentages of sequence identities are calculated are given below. In a more preferred embodiment, the respective polypeptide comprises an amino acid sequence having at least 85% sequence identity to SEQ ID NO: 2 over a sequence length of 500 amino acid residues. Even more preferably, the present invention comprises an amino acid sequence having at least 90%, or even more preferably of at least least 95% or 98% sequence identity to SEQ ID NO: 2 over a sequence length of 500 amino acid residues.

The parental sequence is given in SEQ ID NO: 2. The sequence derives from the C-terminal fusion of the linker domain and cellulose binding domain of *Trichoderma reesei* CBHI (SEQ ID NO: 4) to the catalytic domain of *Talaromyces emersonii* CBHI (SEQ ID NO: 5).The invention further comprises other fusion proteins comprising any cellulose binding domain and a derivative of the catalytic domain of *Talaromyces emersonii* CBHI (SEQ ID NO: 5), preferably with the temperature stability characteristics given above. The cellulose binding domain may be from any source. The polypeptides according to the invention may additionally carry a hexahistidine tag. Thus, by means of illustration, variants of any one of the polypeptides shown in SEQ ID NO: 42, 44, 46, 48 or 50 are included in this invention. The variants are preferably such that the polypeptides exhibit temperature stability, as described and defined above.

The polypeptide of the present invention preferably comprises an amino acid sequence having at least 90%, preferably at least 95%, more preferably at least 99% sequence identity to SEQ ID NO: 2. Furthermore, it is particularly preferred that the amino acid sequence of the polypeptide has the sequence as defined by SEQ ID NO: 2. or a sequence as defined by SEQ ID NO: 2 wherein 1 to 75. more preferably 1 to 35 amino acid residues are substituted, deleted, or inserted.

Particularly preferred are variants of the protein of SEQ ID NO: 2. SEQ ID NO: 5 or SEQ ID NO: 12. "Protein variants" are polypeptides whose amino acid sequence differs in one or more positions from this parental protein, whereby differences might be replacements of one amino acid by another, deletions of single or several amino acids, or insertion of additional amino acids or stretches of amino acids into the parental sequence. Per definition variants of the parental polypeptide shall be distinguished from other polypeptides by comparison of sequence identity (alignments) using the ClustalW Algorithm (Larkin M. A., Blackshields G., Brown N. P., Chenna R., McGettigan P. A., McWilliam H., Valentin F., Wallace I. M., Wilm A., Lopez R., Thompson J. D., Gibson T. J. and Higgins D. G. (2007) ClustalW and ClustalX version 2. Bloinformatics 2007 23(21): 2947-2948). Methods for the generation of such protein variants include random or site directed mutagenesis, site-saturation mutagenesis, PCR-based fragment assembly, DNA shuffling, homologous recombination in-vitro or in-vivo, and methods of gene-synthesis.

The nomenclature of amino acids, peptides, nucleotides and nucleic acids is done according to the suggestions of IUPAC. Generally amino acids are named within this document according to the one letter code.

Exchanges of single amino acids are described by naming the single letter code of the original amino acid followed by its position number and the single letter code of the replacing amino acid, i.e. the change of glutamine at position one to a leucine at this position is described as "Q1L". For deletions of single positions from the sequence the symbol of the replacing amino acid is substituted by the three letter abbreviation "del" thus the deletion of alanine at position 3 would be referred to as "A3del". Inserted additional amino acids receive the number of the preceding position extended by a small letter in alphabetical order relative to their distance to their point of insertion. Thus, the insertion of two tryptophanes after position 3 is referred to as "3aW, 3bW" or simply as A3AWW (i.e formal replacement of "A" at position 3 by the amino acid residues "AWW"). Introduction of untranslated codons TAA, TGA and TAG into the nucleic acid sequence is indicated as "*" in the amino acid sequence, thus the introduction of a terminating codon at position 4 of the amino acid sequence is referred to as "G4*".

Multiple mutations are separated by a plus sign or a slash or a comma. For example, two mutations in positions 20 and 21 substituting alanine and glutamic acid for glycine and serine, respectively, are indicated as "A20G+E21S" or "A20G/E21S" "A20G,E21S".

When an amino acid residue at a given position is substituted with two or more alternative amino acid residues these residues are separated by a comma or a slash. For example, substitution of alanine at position 30 with either glycine or glutamic acid is indicated as "A20G,E" or "A20G/E", or "A20G, A20E".

When a position suitable for modification is identified herein without any specific modification being suggested, it is to be understood that any amino acid residue may be substituted for the amino acid residue present in the position. Thus:for instance, when a modification of an alanine in position 20 is mentioned but not specified; it is to be understood that the alanine may be deleted or substituted for any other amino acid residue (i.e. any one of R, N, D, C, Q, E, G, H, I, L, K, M, F, P, S, T, W, Y and V).

The terms "similar mutation" or "similar substitution" refer to an amino acid mutation that a person skilled in the art would consider similar to a first mutation. Similar in this context means an amino acid that has similar chemical characteristics. If, for example, a mutation at a specific position leads to a substitution of a non-aliphatic amino acid residue (e.g. Ser) with an aliphatic amino acid residue (e.g. Leu), then' a substitution at the same position with a different aliphatic amino acid (e.g. Ile or Val) is referred to as a similar mutation. Further amino acid characteristics include size of the residue, hydrophobicity, polarity, charge, pK-value, and other amino acid characteristics known in the art. Accordingly, a similar mutation may include substitution such as basic for basic, acidic for acidic, polar for polar etc. The sets of amino acids thus derived are likely to be conserved for structural reasons. These sets can be described in the form of a Venn diagram (Livingstone C D. and Barton G J. (1993) "Protein sequence alignments: a strategy for the hierarchical analysis of residue conservation" Comput. Appl Biosci. 9: 745-756; Taylor W. R. (1986) "The classification of amino acid conservation" J. Theor. Biol. 119; 205-218). Similar substitutions may be made, for example, according to the following grouping of amino acids: Hydrophobic: F W Y H K M I L V A G; Aromatic: F W Y H; Aliphatic: I L V; Polar: W Y H K R E D C S T N; Charged H K R E D; Positively charged: H K R; Negatively charged: E D.

As convention for numbering of amino acids and designation of protein variants for the description of protein variants the first glutamine (Q) of the amino acid sequence QQAGTA within the parental protein sequence given in SEQ ID NO: 2 is referred to as position number 1 or Q1 or glutamine 1. The numbering of all amino acids will be according to their position in the parental sequence given in SEQ ID NO: 2 relative to this position number 1.

The present invention furthermore discloses specific variants of the polypeptides of the present invention as given above, such as variants of SEQ ID NO: 2. with changes of their sequence at one or more of the positions given hereafter. I.e., the invention provides, in a particular embodiment, the polypeptide as above, wherein one or more of the following amino acid residues of the sequence defined by SEQ ID NO: 2 are preferably modified by substitution or deletion at positions Q1. Q2. G4. A6. T7. A8. N10. P12. T15. A21. G23. S24, T26. T27. Q28. N29. G30. A31. V32. N37; W40. V41. G46. Y47. T48. N49. C50. T52. N54, D57. T59. Y60. D64. E65. A68. Q69. A72. V84. S86. S89. S90. K92. S99. Q109. D110, D111. I116. F117. K118. L119. L120. D129. V130. G139. A145. M146. V152. K154. Y155, N157. N158. K159. K163. G167. Q172. F179. I180. D181. E183. E187. G188. Q190. S192, S193. N194. I200. D202. H203. D211. V212. A221. P224. D228. T229. G231. T233. M234, S236. T243. Y244. S245. N246. D247. G251. F260. G266. K275. I276. I277. T280. L290, D293. G294. T295. T297. T299. S301. K304. F306. N310. S311. V313. I314. N318. D320, I321. T325. N327. T335. A340. F341. D343. T344. D345. D346. Q349. H350. A354. K355, A358. Q361. Q362. G363. M364. V367. D373. Y374. A375. A376. P386. T387. D390. T392, T393. P394. T400. P402. T403. D404. D410. N417. S418. T421. Y422. F427. P429. I430, G431. T433. G434. N435. P436. S437. G439. N440. P441. P442. G443. N445. R446. T448, T449. T450. T451. R453. P454. A455. T456. T457. G459. S460. S461. P462. G463. P464, T465. S467. H468. G470. C472. G474. G476. Y477. S478. P480. V482. C483. S485. G486, T488. C489. Q490. V491. L492. N493. Y495. Y496. Q498. C499. L500 and/or by one or more insertions after positions G151. K159. G434. A455 or P464; of amino acids 1 to 500 of SEQ ID NO: 2.

In a more preferred embodiment one or more of the following amino acid residues of the sequence defined by SEQ ID NO: 2 are preferably modified by substitution or deletion at positions selected from Q1. Q2. G4. A6. T7. A8. N10. A21. S24. T26. T27. Q28. N29. G30, W40. Y47. D64. E65. A68. Q69. A72. S86. K92. K118. Y155. D181. E183. Q190. S192, N194. D202. H203. P224. T229. G231. M234. S236. T243. D247. S311. N318. D320. T335, A340. T344. D346. Q349. K355. Y374. A375. T387. D390. T392. T393. Y422. P436. P442, N445. R446. T448. T451. R453. P462. G463. H468. P480. V482. S485. and/or by one or more insertion of 1-8 amino acids after positions G151. K159. G434. A455 or P464. and in an even more preferred embodiment are modified by substitution or deletion at one or more positions selected from Q1. Q2. G4. A6. T7. A8. N10. Q28. E65. A72. S86. D181. E183, D202. P224. S311. N318. D320. T335. D346. Q349. T392. T393. Y422. P442. N445. R446, H468. V482. and/or by insertions at one or more after positions and/or one or more insertion of 5 amino acids after positions G151. K159. G434. A455 or P464 of amino acids 1 to 500 of SEQ ID NO: 2.

Also comprised in the invention are the respective mutations at any one or more of the specified mutations 1 to 430 of SEQ ID NO: 5. The skilled person will recognize that residues 1 to 430 of SEQ ID NO: 5 are equivalent to positions 1 to 430 of SEQ ID NO2. and can therefore readily transfer the detailed teaching given above and below for preferred modifications of SEQ ID NO: 2 for any one or more of positions 1 to 430 to the respective one or more position (1 to 430) of SEQ ID NO5. As an illustrative and non-limiting example, it is apparent for the skilled person that, since D390 is one particular position at which a modification in SEQ ID NO: 2 is preferred, D390 is likewise a position at which a modification in SEQ ID NO: 5 is preferred.

In a preferred embodiment, the variant of the polypeptide of the present invention is a polypeptide as described above, wherein specifically one or more of the following amino acid residues of the sequence defined by SEQ ID NO: 2 are modified as shown in Table 1. Shown are preferred, more preferred and most preferred modification. Any of these mutations may be combined, with each other. However, in a particular embodiment it is preferred that the mutations are selected only among the more preferred and most preferred embodiments shown in Table 1. Even more preferably, only modifications indicated as most preferred are chosen. The skilled person will be aware that any several such mutations are combinable with each other.

TABLE 1

Preferred exchanges and similar mutations

| Position | Preferred | More Preferred | Most Preferred |
|---|---|---|---|
| Q1 | L | L | L |
| Q2 | P, S | P, S | S |
| G4 | C | C | C |
| A6 | G, L, V | G, L, V | L |
| T7 | Q | Q | Q |
| A8 | S | S | S |
| N10 | T, D | T, D | T, D |
| P12 | Q | | |
| T15 | S | | |
| A21 | S, T, C | S, T, C | |
| G23 | A, D, N | | |
| S24 | T, C, N | T, C, N | |
| T26 | I, N | I, N | |
| T27 | S, Q | S, Q | |
| Q28 | L, K, R, N | L, K, R, N | K, R |
| N29 | T, Y | T, Y | |
| G30 | A | A | |
| A31 | S | | |
| V32 | G | | |
| N37 | S | | |
| W40 | R | R | |
| V41 | T | | |
| G46 | S | | |
| Y47 | S, F | S, F | |
| T48 | A | | |
| N49 | S | | |
| C50 | S | | |
| T52 | D | | |
| N54 | S | | |
| D57 | S | | |
| T59 | M | | |
| Y60 | H | | |
| D64 | N | N | |
| E65 | V, M, K | V, M, K | V, M, K |
| A68 | T | T | |
| Q69 | K, R | K, R | |
| A72 | V, C | V, C | C |
| V84 | A | | |
| S86 | T | T | T |
| S89 | N | | |
| S90 | T, F | | |
| K92 | R | R | |
| S99 | T | | |
| Q109 | R | | |
| D110 | G, S, N | | |
| D111 | H, E | | |
| I116 | V, K, E | | |
| F117 | Y | | |
| K118 | A, T, Q | A, T, Q | |
| L119 | L, I | | |
| L120 | P, M | | |
| D129 | N | | |
| V130 | I | | |
| G139 | S | | |
| A145 | T | | |
| M146 | C | | |
| G151 | GCGRSG | GCGRSG | GCGRSG |
| V152 | A, E | | |
| K154 | R | | |
| Y155 | S, C, H | S, C, H | |
| N157 | S | | |
| N158 | D | | |
| K159 | E, KCGRNK | KCGRNK | KCGRNK |
| K163 | C | | |
| G167 | C | | |
| Q172 | Q | | |

TABLE 1-continued

Preferred exchanges and similar mutations

| Position | Preferred | More Preferred | Most Preferred |
|---|---|---|---|
| F179 | I | | |
| I180 | N | | |
| D181 | N | N | N |
| E183 | V, M, K | V, M, K | V, M, K |
| E187 | K | | |
| G188 | C | | |
| Q190 | L, K | L, K | |
| S192 | L, I, P, T, M | L, I, P, T, M | |
| S193 | L, P, T | | |
| N194 | G, L, I, V, S, C, K, R, D, Q, Y | G, L, I, V, S, C, K, R, D, Q, Y | |
| I200 | N, F | | |
| D202 | G, I, V, N, F, Y | G, I, V, N, F, Y | G, I, V, N, F, Y |
| H203 | R | R | |
| D211 | G | | |
| V212 | L | | |
| A221 | V | | |
| P224 | L | L | L |
| D228 | N | | |
| T229 | A, S, M | A, S, M | |
| G231 | D | D | |
| T233 | S | | |
| M234 | L, I, V, T, K | L, I, V, T, K | |
| S236 | F, Y | F, Y | |
| T243 | G, A, L, I, V, P, S, C, M, R, D, Q, F, Y, W | G, A, L, I, V, P, S, C, M, R, D, Q, F, Y, W | |
| Y244 | H, F | | |
| S245 | T | | |
| N246 | S, K, D | | |
| D247 | N | N | |
| G251 | R | | |
| F260 | C | | |
| G266 | S | | |
| K275 | E | | |
| I276 | V | | |
| I277 | V | | |
| T280 | A | | |
| L290 | H | | |
| D293 | R, H | | |
| G294 | A | | |
| T295 | S | | |
| T297 | N | | |
| T299 | I, S | | |
| S301 | C | | |
| K304 | R | | |
| F306 | L, Y | | |
| N310 | D, E | | |
| S311 | G, D, N | G, D, N | G, D, N |
| V313 | I | | |
| I314 | F | | |
| N318 | I, H, D, Y | I, H, D, Y | I, D, Y |
| D320 | I, V, E, N | I, V, E, N | I, V, N |
| I321 | N | | |
| T325 | A, I | | |
| N327 | Y | | |
| T335 | I | I | I |
| A340 | G, S, T | G, S, T | |
| F341 | C | | |
| D343 | A | | |
| T344 | M | M | |
| D345 | E | | |
| D346 | G, A, V, E | G, A, V, E | G, A, V, E |
| Q349 | K, R | K, R | K, R |
| H350 | Y | | |
| A354 | T | | |
| K355 | Q | Q | |
| A358 | E | | |
| Q361 | R | | |
| Q362 | G, R, H | | |
| G363 | P | | |
| M364 | L, S | | |
| V367 | A | | |
| D373 | E | | |
| Y374 | A, P, S, C, R, H, D | A, P, S, C, R, H, D | |

TABLE 1-continued

| Preferred exchanges and similar mutations | | | |
|---|---|---|---|
| Position | Preferred | More Preferred | Most Preferred |
| A375 | G, L, V, T, C, M, R, D, E, N, Q, Y | G, L, V, T, C, M, R, D, E, N, Q, Y | |
| A376 | T | | |
| P386 | L, S | | |
| T387 | A, S | A, S | |
| D390 | G, E | G, E | |
| T392 | S, M, K | S, M, K | M |
| T393 | A, I, V, S | A, I, V, S | A, I, V |
| P394 | C | | |
| T400 | S | | |
| P402 | S | | |
| T403 | K | | |
| D404 | N | | |
| D410 | G | | |
| N417 | Y | | |
| S418 | P | | |
| T421 | I | | |
| Y422 | F | F | F |
| F427 | Y | | |
| P429 | C | | |
| I430 | L | | |
| G431 | D | | |
| T433 | S, E | | |
| G434 | S, GAAATG | GAAATG | GAAATG |
| N435 | Q | | |
| P436 | S | S | |
| S437 | P | | |
| G439 | V, D | | |
| N440 | E | | |
| P441 | A, L, S | | |
| P442 | S, Q, del | S, Q | S |
| G443 | D | | |
| N445 | S, D | S, D | D |
| R446 | G, S | G, S | G, S |
| T448 | A | A | |
| T449 | A | | |
| T450 | I | | |
| T451 | A, S | A, S | |
| R453 | G, S, K | G, S, K | |
| P454 | S | | |
| A455 | V, T, AAAAPA | AAAAPA | AAAAPA |
| T456 | A, I | | |
| T457 | P | | |
| G459 | D | | |
| S460 | P | | |
| S461 | R | | |
| P462 | L, del | L | |
| G463 | V, D | V, D | |
| P464 | L, Q, PTHAAA | PTHAAA | PTHAAA |
| T465 | I, S | | |
| S467 | T | | |
| H468 | L, R, Q | L, R, Q | L, R, Q |
| G470 | D | | |
| C472 | R | | |
| G474 | S | | |
| G476 | D | | |
| Y477 | Y | | |
| S478 | Y | | |
| P480 | S | S | |
| V482 | A, I, T | A, I, T | A, I, T |
| C483 | R | | |
| S485 | T | T | |
| G486 | S, D | | |
| T488 | I | | |
| C489 | R | | |
| Q490 | L | | |
| V491 | I | | |
| L492 | Q | | |
| N493 | D | | |
| Y495 | C | | |
| Y496 | F | | |
| Q498 | K | | |
| C499 | G | | |
| L500 | I | | |

The inventors of the present inventions surprisingly found that introduction of these modifications can yield polypeptides having cellobiohydrolase activity with elevated IT50 values, which the skilled person can learn from the examples below, particularly example 8.

Even more preferably, the variant of the polypeptides of the present invention as generally defined above comprises in a particular embodiment an amino acid sequence selected from the sequences with mutations with respect to SEQ ID NO: 2. optionally fused with a C-terminal 6×-His Tag, listed in the following Table 2.

TABLE 2

| Mutations with respect to SEQ ID NO: 2: | |
|---|---|
| Consecutive Number | Mutation Pattern with respect to Seq. ID NO: 2 |
| 1 | G4C, A72C, Q349K |
| 2 | G4C, A72C, T344M, Q349K |
| 3 | G4C, A72C, T344M, D346G, Q349R |
| 4 | G4C, A72C, D320V, Q349K |
| 5 | G4C, A72C, P224L, F306Y, Q349R |
| 6 | G4C, A72C |
| 7 | A72V, D346A, T393A |
| 8 | G4C, A72C, Q349R, R446S, T456A |
| 9 | G4C, W40R, A72C, T344M, Q349K |
| 10 | A72V, D320V, D346A |
| 11 | G4C, A72C, N194Y, T243L, Q349R, Y374S, A375R |
| 12 | G4C, A72C, Q349K, T448A, T449A |
| 13 | G4C, E65V, A72C, Y244H, Q349R |
| 14 | G4C, A72C, D202G, D320N, Q349R, A358E |
| 15 | G4C, A72C, D320V, Q349R |
| 16 | G4C, A72C, Q349K, S86T |
| 17 | A72V, T335I, D346A, T393A, P436S |
| 18 | G4C, A72C, E183V, K304R, Q349K |
| 19 | G4C, A72C, T243G, Q349R, Y374P, A375M |
| 20 | G4C, A72C, Q349R, T465I |
| 21 | G4C, A72C, Q349R |
| 22 | G4C, A72C, N194V, T243M, Q349R, Y374A, A375T |
| 23 | G4C, D64N, A72C, Q349R, A358E, P464Q |
| 24 | G4C, A72C, Q349K, Q28R, S193T, Q490L |
| 25 | G4C, A72C, E183K, Q349K |
| 26 | G4C, A72C, S311N, Q349K, A455T |
| 27 | G4C, A72C, N194K, Q349R, Y374P, A375Q |
| 28 | G4C, A72C, D181N, Q349K |
| 29 | W40R, D320V, Q349K, T393A, N445D |
| 30 | W40R, T335I, D346A, T393A |
| 31 | Q1L, G4C, A72C, D181N, E183K, N327Y, Q349R |
| 32 | A72C, L119L, T335I, Q349R, G486D |
| 33 | G4C, A72C, N194K, T243P, Q349R, Y374H, A375E |
| 34 | G4C, A72V, Q349R, P462del |
| 35 | G4C, A72C, S236Y, Q349R |
| 36 | G4C, A72C, S311G, Q349K |
| 37 | A72V, D320V, T335I, D346A, T393A, N445D |
| 38 | G4C, A72C, S86T, M234V, Q349K |
| 39 | Q1L, G4C, Q28R, E65V, A72C, K159KCGRNK, D181N, E183M, P224L, S311G, D320I, D346E, Q349K, T393V, Y422F, P442S, N445D, R446G, T457TAAATT, H468L, V482I |
| 40 | G4C, A72C, G251R, Q349R |
| 41 | G4C, A72C, Q349K, D320V |
| 42 | A72V, T335I, D346A, T393A |
| 43 | G4C, A72C, E183K, Q349R |
| 44 | Q1L, G4C, A72C, H203R, Q349K, P442S |
| 45 | G4C, A72C, Q349K, G434S, G470D |
| 46 | G4C, W40R, A72C, Q349K |
| 47 | G4C, A72C, Q349R, V367A |
| 48 | Q1L, G4C, A6V, C50S, A72C, I180N, D181N, E183K, Q349R, T457P, C472R, C499G |
| 49 | G4C, A72C, S311G, D320V, Q349K |
| 50 | W40R, T335I, D346A, T393A, P436S |
| 51 | Q1L, G4C, A72C, D181N, E183K, T243S, Q349R, P386S |
| 52 | A72V, D346A, T393A, N445D |
| 53 | Q1L, G4C, A72C, K154R, Q349K, T393I |

TABLE 2-continued

Mutations with respect to SEQ ID NO: 2:

| Consecutive Number | Mutation Pattern with respect to Seq. ID NO: 2 |
|---|---|
| 54 | G4C, A72C, N194G, T243F, Q349R, Y374P, A375R |
| 55 | A72V, D320V, D346A, T393A, N445D |
| 56 | A72C, L119L, Q172Q, Q349K, T488I |
| 57 | G4C, A72C, E183V, Q349K |
| 58 | G4C, A72C, E183K, N318Y, Q349K |
| 59 | W40R, A221V, T449A, C483R |
| 60 | G4C, A72C, K92R, Q349K, N493D |
| 61 | Q1L, G4C, A72C, S90T, D181N, E183K, Q349R |
| 62 | G4C, A72C, Q349R, G459D |
| 63 | G4C, A72C, Q349R, Y422F |
| 64 | G4C, T48A, A72C, Q349R, P480S |
| 65 | E187K, D320V, P442del |
| 66 | G4C, S24N, E65K, A72C, Q349R, I430L, G439D |
| 67 | A72V, D320V, T335I, D346A, T393A, P436S |
| 68 | Q1L, G4C, A72C, S193P, Q349K, V482I |
| 69 | G4C, A72C, D320V, Q349K, G443D, L492Q |
| 70 | Q1L, G4C, A72C, DV152-K159, D181N, E183K, Q349R |
| 71 | Q1L, G4C, A72C, Q349K |
| 72 | Q1L, G4C, A72C, D181N, E183K, M234L, V313I, Q349R, H468R |
| 73 | Q1L, G4C, A72C, D181N, E183K, I200N, Q349R |
| 74 | G4C, A72C, N194K, T243Y, Q349R, A375N |
| 75 | Q1L, G4C, Q28R, A72C, Q349K, H468L |
| 76 | G4C, E65V, A72C, Q349R |
| 77 | D320V, Q349K |
| 78 | Q1L, G4C, A72C, S311G, Q349K, H468R |
| 79 | G4C, A72C, T243Q, Q349R, Y374P, A375M |
| 80 | Q1L, G4C, A72C, D320V, Q349R |
| 81 | Q1L, G4C, T15S, A72C, Y244F, Q349K |
| 82 | G4C, A72C, E183K, D346E, Q349R |
| 83 | Q1L, G4C, A72C, Q349K, T392M |
| 84 | G4C, A72C, D202N, S311N, Q349R, N493D |
| 85 | G4C, A72C, N194D, T243A, Q349R, Y374P, A375Y |
| 86 | G4C, A72C, N194Y, T243V, Q349R, Y374P |
| 87 | Q1L, G4C, A72C, Q349R |
| 88 | G4C, Q28R, E65K, A72C, S86T, D202N, H203R, S311N, D320I, A340G, D346A, Q349K, T393A, Y422F, P442S, R446S, H468L, V482A |
| 89 | G4C, A72C, D202N, Q349R |
| 90 | G4C, A72C, P224L, Q349R |
| 91 | Q1L, G4C, A72C, D181N, E183K, T229M, A340T, Q349R, V491I |
| 92 | Q1L, G4C, A72C, D181N, Q349R |
| 93 | G4C, A72C, D320V, D346V, Q349K |
| 94 | Q1L, G4C, A72C, V152A, Q349K |
| 95 | Q1L, G4C, Q28R, A72C, Q349K |
| 96 | Q1L, G4C, A72C, Q349K, Y422F |
| 97 | G4C, A72C, D202V, D320V, Q349K |
| 98 | Q1L, G4C, A72C, Y155S, D181N, E183K, Q349R |
| 99 | Q1L, G4C, A72C, D181N, D247N, Q349K |
| 100 | Q1L, G4C, A68T, A72C, Q349K, G439D, R453S |
| 101 | Q1L, G4C, A72C, Q349K, H468R |
| 102 | Q1L, G4C, D64N, A72C, Q349K |
| 103 | G4C, A72C, E183K, Q349R, P464L |
| 104 | G4C, A72C, D181N, P224L, Q349K |
| 105 | G4C, A72C, N194I, T243Y, Q349R, Y374P, A375R |
| 106 | Q1L, G4C, A72C, Q349K, P462L |
| 107 | Q1L, G4C, A72C, E183K, Q349R |
| 108 | G4C, A72C, S311G, Q349R |
| 109 | Q1L, G4C, A72C, S311N, Q349K, G463D |
| 110 | Q1L, G4C, A72C, S86T, Q349R |
| 111 | Q1L, G4C, A72C, D181N, E183K, G231D, Q349R |
| 112 | Q1L, G4C, A72C, S89N, D181N, E183K, Q349R |
| 113 | Q1L, G4C, E65K, A72C, Q349K |
| 114 | Q1L, Q2P, G4C, W40R, E65M, A72C, S86T, S192L, D202N, H203R, S311D, D320I, T335I, D346G, Q349K, T392M, Y422F, R446G |
| 115 | Q1L, G4C, S24T, T26I, Q28R, N29Y, G30A, E65V, A68T, A72C, Y155C, D181N, E183M, Q190K, P224L, S311G, D320I, D346E, Q349K, T393V, Y422F, P442S, N445D, R446G, H468L, V482I |
| 116 | G4C, A72C, E183K, D202Y, N310D, Q349R |
| 117 | G4C, A72C, N194I, T243D, Q349R, Y374P, A375Y |
| 118 | Q1L, G4C, A72C, D181N, E183K, Q349R, T456I |
| 119 | G4C, Q28R, A72C, S86T, E183K, P224L, S311N, N318Y, T335I, D346G, Q349R, T393I, P441A, P442S, R446G, H468L, V482I |
| 120 | Q1L, G4C, A72C, D181N, Q349K, T451S |
| 121 | Q1L, G4C, A72C, D181N, E183K, T243I, N246D, Q349R, T488I |
| 122 | Q1L, G4C, G23N, A72C, D110G, I116V, L119I, D181N, E183K, D211G, D293R, N310D, Q349R, Q362R, G363P, M364S |
| 123 | G439V, N440E, P441S, P442Q |
| 124 | G431D, S431V, T433E, G434S, N435Q |
| 125 | Q1L, G4C, Q28R, E65V, A68T, A72C, Y155C, D181N, E183M, P224L, S311G, D320I, D346E, Q349K, T393V, Y422F, P442S, N445D, R446G, H468L, V482I |
| 126 | Q1L, G4C, A72C, S86T, D181N, E183K, Q349R, T393S |
| 127 | Q1L, G4C, A72C, D181N, E183K, Q349R, S485T |
| 128 | Q1L, G4C, G23N, A72C, V84A, D110G, D111H, I116E, F117Y, K118A, D181N, E183K, D293R, T295S, Q349R, M364L |
| 129 | Q1L, G4C, A72C, D181N, E183K, Q349R, R453K |
| 130 | Q1L, G4C, A72C, A145T, H203R, Q349K, T403K |
| 131 | Q1L, G4C, A72C, D181N, E183K, Q349R, N445S |
| 132 | Q1L, G4C, A72C, D181N, E183K, M234I, Q349R |
| 133 | Q1L, G4C, A72C, D181N, E183K, Q349R, T465S |
| 134 | Q1L, G4C, A72C, D181N, E183K, T297N, Q349R |
| 135 | Q1L, G4C, A72C, S311G, Q349K |
| 136 | G4C, Q28R, E65M, A72C, S86T, E183K, S192I, H203R, S311N, D346E, Q349K, T392M, T393A, Y422F, N445D, R446S |
| 137 | Q1L, G4C, A72C, D202N, Q349K, G486D |
| 138 | Q1L, G4C, A72C, S99T, D181N, E183K, Q349R, T450I |
| 139 | Q1L, G4C, A72C, I200F, Q349K, L500I |
| 140 | Q1L, G4C, A72C, D181N, E183K, Q349R, G434S |
| 141 | Q1L, G4C, A31S, A72C, D181N, E183K, Q349R |
| 142 | Q1L, G4C, Q28L, A72C, D181N, E183K, Q349R |
| 143 | Q1L, G4C, A72C, D181N, E183K, Q349R, P436S |
| 144 | Q1L, G4C, A72C, D181N, E183K, T233S, Q349R |
| 145 | Q1L, G4C, A72C, D202N, Q349K |
| 146 | Q1L, G4C, A68T, A72C, Q349K |
| 147 | Q1L, G4C, A21T, A72C, D181N, E183K, Q349R, P454S |
| 148 | Q1L, G4C, A72C, D346V, Q349K |
| 149 | Q1L, G4C, Y47F, A72C, D181N, E183K, Q349R, P436S, S461R |
| 150 | Q1L, G4C, A72C, D181N, E183K, M234T, Q349R |
| 151 | Q1L, G4C, A72C, N157S, D181N, E183K, Q349R |
| 152 | Q1L, G4C, A72C, D181N, E183K, Q349R |
| 153 | G4C, A72C, N194Q, T243V, Q349R, Y374P, A375Y |
| 154 | Q1L, G4C, A72C, D181N, E183K, I314F, Q349R, N445D |
| 155 | Q1L, G4C, A72C, Q349K, T392K |
| 156 | Q1L, G4C, A72C, D181N, E183K, Q349R, T451A |
| 157 | Q1L, G4C, A72C, D181N, E183K, M234V, Q349R |
| 158 | Q1L, G4C, A21S, A72C, D181N, E183K, Q349R |
| 159 | Q1L, G4C, A72C, D181N, E183K, Q349R, N493D |
| 160 | Q1L, G4C, A72C, S311N, Q349K |
| 161 | Q1L, G4C, Q28R, E65V, A72C, D181N, E183V, D228N, S311N, N318Y, D346E, Q349R, Y422F, P442S, N445D, R446G, H468L, V482T |
| 162 | G4C, A72C, N194C, Q349R, Y374C |
| 163 | Q1L, G4C, A72C, D181N, E183K, Q349R, A455V |
| 164 | Q1L, G4C, A72C, D181N, E183K, Q349R, T400S |
| 165 | Q1L, G4C, T26I, A72C, D181N, E183K, Q349R |
| 166 | Q1L, G4C, A72C, D181N, E183K, N310D, Q349R, T392S, G463D |
| 167 | Q1L, G4C, A72C, D129N, D181N, E183K, Q190L, G266S, I276V, Q349R, P386L, F427Y |
| 168 | Q1L, G4C, A72C, D181N, E183K, D202N, Q349R |
| 169 | Q1L, G4C, A72C, Y155C, D181N, E183K, Q349R |

TABLE 2-continued

Mutations with respect to SEQ ID NO: 2:

| Consecutive Number | Mutation Pattern with respect to Seq. ID NO: 2 |
| --- | --- |
| 170 | Q1L, G4C, Q28R, E65V, A72C, D181N, E183M, P224L, S311G, D320I, D346E, Q349K, T393V, Y422F, P442S, N445D, R446G, P454PATAAA, H468L, V482I |
| 171 | Q1L, G4C, Q28R, E65V, A72C, K159KCGRNK, D181N, E183M, P224L, S311G, D320I, D346E, Q349K, T393V, Y422F, P442S, N445D, R446G, H468L, V482I |
| 172 | Q1L, G4C, A72C, D181N, E183K, N246K, Q349R |
| 173 | G4C, W40R, E65V, A72C, S86T, D181N, E183K, D202I, H203R, S311D, D320N, D346V, Q349R, T392M, T393A, Y422F, P442S, H468Q, V482A |
| 174 | Q1L, G4C, A72C, Y155C, Q349K |
| 175 | Q1L, G4C, A68T, A72C, D181N, E183K, Q349R |
| 176 | Q1L, G4C, S24T, T26I, Q28R, N29Y, G30A, Y47F, E65V, A68T, A72C, Y155C, D181N, E183M, Q190K, P224L, T229M, G231D, M234T, S311G, D320I, A340S, D346E, Q349K, D390E, T393V, Y422F, P442S, N445D, R446G, T448A, R453G, H468L, P480S, V482I |
| 177 | Q1L, G4C, W40R, E65M, A72C, S86T, S192L, D202N, H203R, S311D, D320I, T335I, D346G, Q349K, T392M, Y422F, R446G |
| 178 | Q1L, G4C, A72C, S86T, D181N, E183K, D320V, Q349R |
| 179 | G4C, Q28K, A72C, S86T, E183M, D202N, P224L, S311G, N318Y, D320N, D346A, Q349R, T392M, T393I, P442S, H468L, V482I |
| 180 | Q1L, Q2P, G4C, Q28R, W40R, E65K, A72C, D181N, S192L, D202I, H203R, P224L, S311G, D320I, D343A, D346A, Q349K, P442S, N445D, R446G, V482A |
| 181 | Q1L, G4C, Q28R, E65K, A72C, E183M, D202I, P224L, D320N, D346V, Q349K, T392M, T393V, Y422F, N445D, R446G, H468L, V482T |
| 182 | Q1L, G4C, Q28R, E65V, A72C, S86T, E183K, D202V, S311G, N318Y, D320I, D346G, Q349K, T393V, Y422F, N445D, R446S, H468Q, V482T |
| 183 | Q1L, G4C, W40R, E65M, A72C, D181N, E183K, S192P, D202N, P224L, S311D, N318Y, D320V, D346G, Q349K, T392M, N445D, R446G, H468L, V482T |
| 184 | Q1L, G4C, E65V, A72C, D181N, E183K, P224L, S311G, D320N, D346G, Q349R, T392M, T393I, R446G, H468L, V482I |
| 185 | Q1L, G4C, Q28R, E65V, A72C, G151GCGRSG, D181N, E183M, P224L, S311G, D320I, D346E, Q349K, T393V, Y422F, P442S, N445D, R446G, H468L, V482I |
| 186 | Q1L, G4C, E65M, A72C, D181N, E183M, D202Y, P224L, S311D, N318Y, D320I, T335I, D346A, Q349K, T392M, T393I, N445D, R446G, T448A, H468Q, V482A |
| 187 | Q1L, G4C, G23A, A72C, D110S, D111H, I116V, F117Y, K118A, L120M, D181N, E183K, D293H, G294A, N310E, Q349R, Q362G, M364S |
| 188 | Q1L, G4C, A72C, D181N, E183K, Q349R, T421I, G439D |
| 189 | G4C, Q28K, E65M, A72C, S86T, V152A, D181N, E183V, S192L, D202N, S311N, D320N, D346E, Q349R, T387A, T392M, T393I, Y422F, P442S, R446S, H468L, G476D, V482I |
| 190 | Q1L, G4C, W40R, E65V, A72C, S86T, E183V, G188C, S192T, D202Y, H203R, P224L, S311N, D320V, D346E, Q349K, T393V, Y422F, N445D, R446G, H468Q, V482I |
| 191 | Q1L, G4C, E65M, A72C, S86T, E183M, D202N, P224L, T335I, D346G, Q349K, T392M, T393A, P442S, N445D, R446G, H468Q, V482A |
| 192 | Q1L, G4C, Q28R, E65V, A72C, D181N, E183M, P224L, S311G, D320I, A340S, D346E, Q349K, D390E, T393V, Y422F, P442S, N445D, R446G, H468L, P480S, V482I |
| 193 | G4C, W40R, A72C |

TABLE 2-continued

Mutations with respect to SEQ ID NO: 2:

| Consecutive Number | Mutation Pattern with respect to Seq. ID NO: 2 |
| --- | --- |
| 194 | Q1L, G4C, W40R, E65K, A72C, S86T, E183K, S192L, D202Y, P224L, D320I, D346E, Q349R, P442S, R446G, H468R, V482T |
| 195 | Q1L, G4C, A21T, T26I, Q28R, E65V, A68T, A72C, Y155C, D181N, E183M, Q190K, D202N, P224L, S311G, N318Y, D320I, D346E, Q349K, T393V, Y422F, N445D, R446G, R453G, H468Q, P480S, V482I |
| 196 | Q1L, G4C, Q28R, E65V, A72C, S86T, D181N, D202N, P224L, S311G, N318Y, D320I, T335I, D346E, Q349K, T393V, Y422F, N445D, R446G, H468Q, V482I |
| 197 | Q1L, G4C, Q28R, E65V, A72C, D181N, E183M, P224L, S311G, D320I, D346E, Q349K, T393V, Y422F, P442S, N445D, R446G, P464PTHAAA, H468L, V482I |
| 198 | Q1L, G4C, Q28R, E65V, A72C, E183M, S311G, D346E, Q349K, T393V, Y422F, P442S, N445D, R446G, H468L, V482I |
| 199 | Q1L, G4C, T7Q, A8S, N10T, S24T, T27Q, Q28R, N29T, V41T, G46S, Y47S, T52D, D57S, D64N, E65V, Q69K, A72C, D181N, P224L, S311D, N318Y, D320N, D346A, Q349K, T392M, T393I, Y422F, N445D, R446G, H468Q, V482I |
| 200 | Q1L, G4C, Q28R, E65V, A72C, K159KCGRNK, E183M, P224L, S311G, D320I, D346E, Q349K, T393V, Y422F, P442S, N445D, R446G, T457TAAATT, H468L, V482I |
| 201 | Q1L, G4C, Q28K, W40R, E65V, A72C, D181N, E183V, S192P, D202V, H203R, S311G, D320N, D346E, Q349K, T392M, T393A, Y422F, V482I |
| 202 | Q1L, G4C, Q28R, E65V, A72C, G139S, D181N, E183M, P224L, S311G, D320I, D346E, Q349K, T393V, Y422F, P442S, N445D, R446G, H468L, V482I |
| 203 | Q1L, G4C, Q28R, E65V, A72C, S86T, D181N, E183M, D202N, P224L, S311G, N318Y, T335I, D346E, Q349K, T393V, Y422F, N445D, R446G, H468L, V482I |
| 204 | Q1L, G4C, Q28R, E65K, A72C, D181N, S311N, N318Y, D346E, Q349K, T393V, Y422F, N445D, R446G, H468Q, V482I |
| 205 | Q1L, G4C, W40R, A72C, S192L, D202N, H203R, P224L, S311N, D320I, T335I, D346V, Q349R, T393I, N445D, R446G, H468Q, V482T |
| 206 | Q1L, G4C, Q28K, E65K, A72C, E183M, D202N, P224L, T229S, S311G, D320I, T335I, D346V, Q349R, T393V, H468Q, V482A |
| 207 | Q1L, G4C, Q28R, G30A, E65M, A72C, D181N, D202N, P224L, S311D, N318Y, D346E, Q349K, T392M, T393V, Y422F, P442S, N445D, R446S |
| 208 | Q1L, G4C, Q28R, E65V, A72C, S68T, E183M, S311N, T335I, D346E, Q349K, T393V, Y422F, N445D, R446G, H468L, V482T |
| 209 | Q1L, G4C, Q28K, E65K, A72C, D181N, D202N, S311N, N318Y, T335I, D346E, Q349K, T393V, Y422F, P442S, N445D, R446G, H468L, V482I |
| 210 | T243C, A375C, N194C, Y374C |
| 211 | Q1L, G4C, Q28K, E65K, A72C, S86T, E183M, S311G, D346V, Q349R, R392M, T393V, Y422F, P442S, N445D, R446R, H468L, S478Y, V482I |
| 212 | Q1L, G4C, Q28R, E65V, A72C, D181N, E183M, S311G, D346E, Q349K, T393V, Y422F, P442S, N445D, R446G, H468L, V482I |
| 213 | Q1L, G4C, Q28R, E65V, A72C, S86T, D181N, D202N, S311N, N318Y, D320I, T335I, D346E, Q349K, T393I, Y422F, N445D, R446G, H468Q, V482I |
| 214 | Q1L, G4C, Q28R, E65K, A72C, S86T, E183K, D202N, P224L, S311G, T335I, D346A, Q349K, T393V, Y422F, N445D, R446G, H468L, V482T |
| 215 | Q1L, G4C, Q28R, E65V, A72C, L120P, D181N, E183M, P224L, S311G, D320I, D346E, Q349K, T393V, Y422F, P442S, N445D, R446G, H468L, V482I |

TABLE 2-continued

| Mutations with respect to SEQ ID NO: 2: | |
|---|---|
| Consecutive Number | Mutation Pattern with respect to Seq. ID NO: 2 |
| 216 | Q1L, G4C, Q28K, E65V, A72C, S86T, E183M, S311N, N318H, D320V, D346V, Q349K, T392M, T393A, R446S, H468L, V482I |
| 217 | Q1L, G4C, Q28K, E65V, A72C, D202N, H203R, S311G, T335I, D346V, Q349K, T393A, P442S, R446G, H468L, V482I |
| 218 | Q1L, G4C, Q28R, E65V, A72C, E183M, S311G, D320I, D346E, Q349K, T393V, Y422F, P442S, N445D, R446G, H468L, V482I |
| 219 | Q1L, G4C, Q28R, E65K, A72C, D181N, D202N, H203R, P224L, S311D, D346G, Q349K, P442S, R446S, H468Q, V482T |
| 220 | Q1L, G4C, Q28R, E65M, A72C, D181N, E183M, S311G, N318Y, D320I, T335I, D346E, Q349K, D390E, T393V, Y422F, P442S, N445D, R446G, H468Q, V482T |
| 221 | Q1L, G4C, T27S, Q28R, E65V, Q69R, A72C, L120P, D181N, E183M, D202N, D247N, S311G, D346E, Q349K, K355Q, T387S, T393V, Y422F, N445D, R446G, T451S, G463V, H468Q, V482T, S485T |
| 222 | Q1L, G4C, Q28R, E65K, A72C, E183V, S192T, D202N, S311G, D320V, D346A, Q349K, P442S, N445D, R446G, H468R, V482A |
| 223 | Q1L, G4C, W40R, E65V, A72C, S86T, E183M, D202N, P224L, S311G, D320V, D346E, Q349R, T393I, P442S, R446G, H468R, V482I |
| 224 | Q1L, G4C, Q28N, E65K, A72C, D181N, E183M, D202N, H203R, S311G, N318Y, D320N, Q349R, T393V, Y422F, P442S, N445D, R446G, H468L, V482I |
| 225 | Q1L, G4C, Q28R, V41T, G46S, Y47S, T52D, E65V, A72C, D181N, P224L, S311D, N318Y, D320N, D346A, Q349K, T392M, T393I, Y422F, N445D, R446G, H468Q, V482I |
| 226 | Q1L, G4C, Q28R, E65K, A72C, D181N, E183M, P224L, S311G, D320I, D346E, Q349K, T393V, Y422F, P442S, N445D, R446G, H468L, V482I |
| 227 | Q1L, G4C, Q28R, W40R, A72C, S86T, D181N, S192T, D202N, P224L, S311G, N318Y, D320V, D346E, Q349K, T392M, T393I, P442S, N445D, R446G, H468Q, V482I |
| 228 | Q1L, G4C, A21T, T26I, Q28R, G30A, E65V, A68T, A72C, Y155C, D181N, Q190K, D202N, P224L, T229M, S311G, N318Y, D320I, T335I, D346E, Q349K, T393V, Y422F, N445D, R446G, R453G, H468Q, V482I |
| 229 | Q1L, G4C, Q28K, W40R, A72C, S86T, D181N, E183M, S192I, D202Y, T299S, S311N, N318Y, D320I, D346V, Q349R, T393I, P442S, H468L |
| 230 | Q1L, G4C, Q28R, E65V, A72C, D181N, E183M, P224L, T229M, G231D, M234T, S311G, D320I, D346E, Q349K, T393V, Y422F, P442S, N445D, R446G, H468L, V482I |
| 231 | Q1L, G4C, S24T, T26I, Q28R, N29Y, G30A, E65V, A68T, A72C, Y155C, D181N, E183M, Q190K, P224L, T229M, G231D, M234T, S311G, D320I, A340S, D346E, Q349K, D390E, T393V, Y422F, P442S, N445D, R446G, T448A, R453G, H468L, P480S, V482I |
| 232 | Q1L, G4C, Q28R, E65V, A72C, D181N, E183M, P224L, S311G, D320I, D346E, Q349K, T393V, Y422F, P442S, N445D, R446G, G463V, H468L, V482I |
| 233 | Q1L, G4C, Q28R, E65K, A72C, E183M, P224L, S311G, D346E, Q349K, T393V, Y422F, P442S, N445D, R446G, H468L, V482I |
| 234 | Q1L, G4C, Q28R, E65V, A72C, S86T, D181N, E183M, D202N, P224L, S311G, N318Y, D346E, Q349K, T393V, Y422F, P442S, N445D, R446G, H468L, V482T |
| 235 | Q1L, G4C, Q28R, W40R, E65V, A72C, S86T, S192T, D202V, H203R, S311N, N318Y, D346A, Q349K, T392M, T393A, Y422F, P442S, N445D, V482A |
| 236 | Q1L, G4C, Q28R, E65V, A72C, K159KCGRNK, E183M, P224L, S311G, D320I, D346E, Q349K, T393V, Y422F, G434GAAATG, P442S, N445D, R446G, T457TAAATT, H468L, V482I |
| 237 | Q1L, G4C, Q28K, E65K, A72C, D181N, H203R, P224L, S311G, D320V, D346G, Q349K, T392M, T393I, P442S, N445D, R446G, H468L, V482A |
| 238 | Q1L, G4C, Q28R, E65K, A72C, E183M, S311G, D346E, Q349K, T393V, Y422F, P442S, N445D, R446G, H468L, V482I |
| 239 | Q1L, G4C, Q28R, E65M, A72C, D181N, E183M, S311G, N318Y, D346E, Q349K, T393V, Y422F, P442S, N445D, R446G, H468Q, V482I |
| 240 | Q1L, G4C, Q28R, E65V, A72C, E183K, D202I, P224L, S311G, D320I, Q349K, T393V, P442S, N445D, R446S, H468L, V482I |
| 241 | Q1L, G4C, Q28K, A72C, S86T, D181N, E183V, S192T, D202N, P224L, S311G, N318Y, D320V, D346G, Q349R, T392M, Y422F, P442S, N445D, R446S, H468L, V482A |
| 242 | G4C, Q28R, E65K, A72C, S86T, D181N, E183M, S192L, D202N, H203R, P224L, S311D, D346E, Q349R, T392M, T393A, Y422F, P442S, N445D, R446G, P462L, H468L, V482T |
| 243 | Q1L, G4C, W40R, E65K, A72C, Q109R, D181N, E183M, S192I, D202I, H203R, S245T, D346A, Q349R, T393A, Y422F, P442S, N445D, R446G, H468R, V482A |
| 244 | Q1L, G4C, Q28K, E65M, A72C, D181N, D202N, S311N, T335I, D346E, Q349K, T393I, Y422F, P442S, N445D, R446G, H468Q, V482I |
| 245 | Q1L, G4C, N10D, Q28R, E65V, Q69R, A72C, D181N, E183M, P224L, S311G, D320I, D346E, Q349R, T393V, N417Y, Y422F, P442S, N445D, R446G, H468L, V482I |
| 246 | Q1L, G4C, Q28R, W40R, E65V, A72C, D202Y, H203R, P224L, T299I, N318Y, D320V, D346A, Q349K, T392M, T393A, P442S, N445D, R446G, H468R, V482T |
| 247 | G4C, Q28R, E65V, A72C, E183M, D202N, P224L, S311G, N318Y, D320V, D346G, Q349K, T392M, Y422F, R446G, H468Q |
| 248 | Q1L, G4C, Q28K, A72C, S86T, E183K, S311G, D320V, D346A, Q349R, T392M, T393I, Y422F, P442S, R446S, H468Q |
| 249 | Q1L, G4C, Q28R, E65M, A72C, D181N, P224L, S311N, D320N, T335I, D346E, Q349K, T392M, Y422F, N445D, R446S, H468L, V482T |
| 250 | Q1L, G4C, Q28K, E65V, A72C, D181N, D202N, S311G, T335I, D346E, Q349K, T393V, Y422F, N445D, R446G, H468Q, V482I |
| 251 | Q1L, G4C, Q28R, E65K, A72C, D181N, E183M, S311N, N318Y, T335I, D346E, Q349K, T393V, Y422F, N445D, R446G, H468L, V482I |
| 252 | Q1L, G4C, Q28R, E65K, A72C, E183M, S311G, D320I, D346E, Q349K, T393V, Y422F, P442S, N445D, R446G, H468L, V482I |
| 253 | Q1L, G4C, Q28R, E65V, A72C, D181N, E183M, S311G, D320I, D346E, Q349K, T393V, Y422F, P442S, N445D, R446G, H468L, V482I |
| 254 | Q1L, G4C, W40R, E65V, A72C, S86T, D181N, S192T, D202N, H203R, P224L, S311G, N318Y, T335I, D346G, Q349K, T392M, T393V, Y422F, N445D, R446G, H468Q |
| 255 | Q1L, G4C, Q28R, E65K, A72C, E183M, S311N, D320I, D346E, Q349K, T393I, Y422F, P442S, N445D, R446G, H468Q, V482T |
| 256 | Q1L, G4C, T7Q, A8S, N10T, Q28R, D57S, D64N, E65V, Q69K, A72C, D181N, P224L, S311D, N318Y, D320N, D346A, Q349K, T392M, T393I, Y422F, N445D, R446G, H468Q, V482I |
| 257 | Q1L, G4C, Q28R, E65M, A72C, S86T, D181N, E183M, D202N, P224L, S311G, D346A, Q349K, T393I, Y422F, P442S, N445D, R446G, H468Q, V482T |

TABLE 2-continued

| Mutations with respect to SEQ ID NO: 2: | |
|---|---|
| Consecutive Number | Mutation Pattern with respect to Seq. ID NO: 2 |
| 258 | Q1L, G4C, N10D, Q28R, E65V, Q69R, A72C, K92R, K118Q, D181N, E183M, D202N, T280A, S311G, T335I, D346E, Q349K, K355Q, T387S, T393V, D404N, Y422F, N445D, R446G, P462L, G463V, H468Q, V482I, S485T |
| 259 | Q1L, G4C, Q28R, E65M, A72C, E183M, D202N, S311G, D320I, T335I, D346E, Q349K, T393I, Y422F, N445D, R446G, H468Q, V482I |
| 260 | Q1L, G4C, Q28K, E65K, A72C, D181N, E183M, D202N, S311D, D320V, T335I, D346G, Q349K, T393I, Y422F, P442S, N445D, H468L, V482I |
| 261 | Q1L, G4C, Q28K, E65K, A72C, S86T, P224L, S311N, D320I, T335I, D346E, Q349K, T393V, Y422F, N445D, R446G, H468Q, V482T |
| 262 | Q1L, G4C, Q28R, E65V, A72C, S86T, D181N, E183M, D202N, P224L, S311N, D320I, D346E, Q349K, T393V, Y422F, P442S, N445D, R446G, H468Q, V482T |
| 263 | G4C, E65K, A72C, S86T, E183M, D202I, P224L, S311N, N318Y, D320N, T335I, D346V, Q349R, T393V, Y422F, P442S, R446S, H468L |
| 264 | Q1L, G4C, Q28R, E65K, A72C, D202N, S311N, T335I, D346E, Q349K, T393I, Y422F, P442S, N445D, R446G, H468L, V482T |
| 265 | Q1L, G4C, E65V, A72C, D181N, E183K, D202G, Q349R |
| 266 | Q1L, G4C, Q28R, E65K, A72C, E183M, P224L, S311G, D320I, D346E, Q349K, T393V, Y422F, P442S, N445D, R446G, H468L, V482I |
| 267 | Q1L, G4C, Q28R, E65V, A72C, D181N, E183M, P224L, F306L, S311G, D320I, D346E, Q349K, T393V, Y422F, P442S, N445D, R446G, H468L, V482I |
| 268 | Q1L, G4C, Q28R, E65V, A72C, S86T, D202N, P224L, S311G, N318Y, D320I, D346A, Q349K, T393I, Y422F, N445D, R446G, H468Q, V482T |
| 269 | Q1L, G4C, Q28K, E65K, A72C, D181N, E183K, S192P, P224L, S311G, N318Y, D320V, D346E, Q349R, T392M, T393I, Y422F, P442S, H468Q |
| 270 | Q1L, G4C, Q28K, E65M, A72C, S86T, E183M, H203R, S311D, D320V, T335I, D346E, Q349R, T393A, N445D, R446G, H468Q, V482A |
| 271 | Q1L, G4C, Q28R, A72C, D181N, E183V, D202I, H203R, P224L, S311D, D320V, D346V, Q349R, T392M, T393I, N445D, H468L |
| 272 | Q1L, G4C, Q28K, W40R, E65K, A72C, S86T, D181N, E183K, S192L, D202I, H203R, S311N, D320N, D346V, Q349K, T392M, T393A, Y422F, N445D, R446S |
| 273 | G4C, E65V, A72C, S86T, Y155H, D181N, E183V, Q190K, P224L, S311N, D320V, D346V, Q349K, T392M, T393V, Y422F, P442S, N445D, R446G, H468L, V482A |
| 274 | Q1L, G4C, Q28R, E65M, A72C, S86T, E183M, D202N, S311D, N318Y, D320N, T335I, D346A, Q349R, T392M, T393I, Y422F, P442S, N445D, R446G, H468L, V482A |
| 275 | Q1L, G4C, Q28R, E65V, A72C, D181N, E183M, S311N, N318Y, D320I, T335I, D346E, Q349K, T393V, Y422F, N445D, R446G, H468L, V482T |
| 276 | Q1L, G4C, Q28R, E65K, A72C, S86T, D181N, D202N, S311G, D346E, Q349K, T393I, Y422F, N445D, R446G, H468L, V482I |
| 277 | Q1L, G4C, Q28R, E65K, A72C, D181N, D202N, S311N, N318Y, D320I, D346E, Q349K, T393I, Y422F, N445D, R446G, H468L, V482T |
| 278 | Q1L, G4C, T7Q, A8S, N10T, S24T, T27Q, Q28R, N29T, D57S, D64N, E65V, Q69K, A72C, D181N, P224L, S311D, N318Y, D320N, D346A, Q349K, T392M, T393I, Y422F, N445D, R446G, H468Q, V482I |
| 279 | Q1L, G4C, Q28R, E65K, A72C, S86T, D202N, S311G, N318Y, D320I, D346A, Q349K, T393I, Y422F, N445D, R446G, H468L, V482I |

TABLE 2-continued

| Mutations with respect to SEQ ID NO: 2: | |
|---|---|
| Consecutive Number | Mutation Pattern with respect to Seq. ID NO: 2 |
| 280 | Q1L, G4C, Q28R, A72C, D181N, S311G, N318Y, D320V, D346E, Q349K, T393I, Y422F, P442S, N445D, R446G, H468Q |
| 281 | Q1L, G4C, Q28R, E65K, A72C, D181N, E183M, S311G, D320I, D346E, Q349K, T393V, Y422F, P442S, N445D, R446G, H468L, V482I |
| 282 | Q1L, G4C, Q28R, E65K, A72C, D181N, E183M, S311G, D346E, Q349K, T393V, Y422F, P442S, N445D, R446G, H468L, V482I |
| 283 | Q1L, G4C, Q28R, E65V, A72C, E183M, D202N, S311N, D320I, D346E, Q349K, T393V, Y422F, N445D, R446G, H468Q, V482T |
| 284 | Q1L, G4C, Q28R, E65K, A72C, E183M, S311G, T335I, D346E, Q349K, T393V, Y422F, N445D, R446G, H468Q, V482I |
| 285 | Q1L, G4C, Q28R, E65V, A72C, S86T, D181N, D202N, S311N, N318Y, T335I, D346E, Q349K, T393V, Y422F, N445D, R446G, H468Q, V482I |
| 286 | Q1L, G4C, E65M, A72C, S86T, E183K, D202Y, S311G, D320N, T335I, D346A, Q349K, T393V, Y422F, R446G, H468Q, V482T |
| 287 | Q1L, G4C, Q28R, E65V, A72C, S86T, E183M, D202N, P224L, S311N, D320I, T335I, A340S, D346A, Q349K, T393V, Y422F, N445D, R446G, H468Q, V482T |
| 288 | Q1L, G4C, Q28K, E65K, A72C, S86T, D181N, E183M, H203R, P224L, S311D, D320I, D346E, Q349R, T392M, Y422F, R446G, H468L |
| 289 | Q1L, G4C, Q28K, E65V, A72C, S86T, D181N, E183M, P224L, S311G, D320I, D346E, Q349K, T393V, Y422F, P442S, N445D, R446G, H468Q, V482I |
| 290 | Q1L, G4C, Q28K, N29Y, E65K, A72C, D181N, S311G, T335I, D346E, Q349K, T393V, Y422F, N445D, R446G, H468Q, V482T |
| 291 | Q1L, G4C, Q28K, E65M, A72C, E183M, S311G, D346E, Q349K, T393V, Y422F, P442S, N445D, R446G, H468L, V482T |
| 292 | Q1L, G4C, Q28K, E65V, A72C, S86T, D181N, E183K, D202N, S311N, N318Y, D320N, T335I, D346A, Q349K, T392M, T393V, P442S, N445D, R446G, H468Q |
| 293 | Q1L, G4C, Q28K, E65K, A72C, S86T, D181N, E183M, D202N, S311G, N318Y, T335I, D346E, Q349K, T393I, Y422F, N445D, R446G, H468Q, V482I |
| 294 | Q1L, G4C, Q28R, E65K, A72C, E183V, S192T, D202N, S311G, D320V, D346A, Q349K, T393V, P442S, N445D, H468L, V482A |
| 295 | Q1L, G4C, Q28R, E65V, A72C, E183M, D202N, S311N, N318Y, D320I, T335I, D346E, Q349K, T393V, Y422F, N445D, R446G, H468L, V482T |
| 296 | Q1L, G4C, S24T, Q28R, E65K, A72C, D202N, S311G, T335I, D346E, Q349K, T393I, Y422F, N445D, R446G, H468Q, V482T |
| 297 | Q1L, G4C, A72C, S86T, D181N, S192L, D202N, P224L, S311G, N318Y, D320V, T335I, D346G, Q349K, T393I, R446G, H468Q |
| 298 | Q1L, G4C, Q28R, E65V, A72C, D181N, P224L, S311D, N318Y, D320N, D346A, Q349K, T392M, T393I, Y422F, N445D, R446G, H468Q, V482I |
| 299 | Q1L, G4C, Q28R, E65M, A72C, D181N, E183M, D202N, P224L, S311G, D346A, Q349K, T393I, Y422F, P442S, N445D, R446G, H468L, V482T |
| 300 | Q1L, G4C, Q28K, E65V, A72C, S86T, E183V, S192I, D202V, D320I, T335I, D346V, Q349K, T392M, T393I, Y422F, P442S, N445D, R446G, H468R, V482A |
| 301 | Q1L, G4C, Q28K, E65M, A72C, S86T, D181N, E183M, D202N, P224L, S311G, D320I, T335I, D346E, Q349K, T393V, Y422F, N445D, R446G, H468Q, V482T |
| 302 | Q1L, G4C, Q28K, A72C, D181N, D202I, S311D, N318Y, T335I, D346E, Q349K, T392M, Y422F, R446G, H468L |

TABLE 2-continued

| Mutations with respect to SEQ ID NO: 2: | |
|---|---|
| Consecutive Number | Mutation Pattern with respect to Seq. ID NO: 2 |
| 303 | Q1L, G4C, Q28R, E65V, A72C, D181N, E183M, P224L, S311G, D320N, D346E, Q349K, T393V, Y422F, T433S, P442S, N445D, R446G, H468L, V482I |
| 304 | Q1L, G4C, Q28K, E65V, A72C, D181N, E183M, D202N, S311G, N318Y, D346E, Q349K, T393I, Y422F, N445D, R446G, H468Q, V482I |
| 305 | Q1L, G4C, Q28K, E65K, A72C, D181N, D202N, S311G, N318Y, D346A, Q349K, T393I, Y422F, N445D, R446G, H468Q, V482T |
| 306 | Q1L, G4C, Q28R, E65K, A72C, S86T, E183M, D202N, D320I, T335I, D346A, Q349K, T392M, Y422F, N445D, R446G, H468L, V482T |
| 307 | Q1L, G4C, Q28K, E65M, A72C, S86T, E183M, S311N, N318Y, D320I, T335I, D346E, Q349K, T393I, Y422F, P442S, H468Q, V482I |
| 308 | Q1L, G4C, E65M, A72C, S86T, E183V, S192L, D202I, H203R, P224L, S311G, N318Y, D320V, D346A, Q349K, P442S, N445D, R446G, H468R, V482A |
| 309 | Q1L, G4C, T7Q, A8S, N10T, Q28R, E65V, A72C, D181N, P224L, S311D, N318Y, D320N, D346A, Q349K, T392M, T393I, Y422F, N445D, R446G, H468Q, V482I |
| 310 | Q1L, G4C, E65K, A72C, S86T, D202V, S311N, D320V, T335I, D346V, Q349R, T392M, Y422F, N445D, R446G, H468L |
| 311 | Q1L, G4C, Q28R, E65K, A72C, D181N, E183M, P224L, S311G, D346E, Q349K, T393V, Y422F, P442S, N445D, R446G, H468L, V482I |
| 312 | Q1L, G4C, Q28R, D57S, D64N, E65V, Q69K, A72C, D181N, P224L, S311D, N318Y, D320N, D346A, Q349K, T392M, T393I, Y422F, N445D, R446G, H468Q, V482I |
| 313 | Q1L, G4C, Q28R, A72C, S86T, E183M, S192T, D202N, H203R, P224L, S311N, T335I, D346V, Q349R, T392M, T393V, P442S, N445D, R446G, H468Q, V482A |
| 314 | Q1L, G4C, Q28K, E65V, A72C, D181N, D202N, S311N, D346A, Q349K, T393I, Y422F, N445D, R446G, H468Q, V482I |
| 315 | Q1L, G4C, Q28R, E65V, A72C, D181N, E183M, P224L, S311G, D320I, D346E, Q349K, T393V, Y422F, P442S, N445D, R446G, H468L, V482I, S485T |
| 316 | G4C, Q28K, E65M, A72C, S86T, E183M, D202N, P224L, S311G, T335I, D346E, Q349K, T393V, Y422F, P442S, N445D, R446G, H468L, V482I |
| 317 | G434GAAATG, T457TAAATT, Q1L, G4C, Q28R, E65V, A72C, E183M, P224L, S311G, D320I, D346E, Q349K, T393V, Y422F, P442S, N445D, R446G, H468L, V482I |
| 318 | G4C, Q28R, E65M, A72C, S86T, D181N, E183M, D202Y, P224L, S311N, D346A, Q349K, T393I, Y422F, N445D, R446S, H468Q, V482A |
| 319 | Q1L, G4C, Q28K, E65V, A72C, S86T, D181N, E183K, D202N, P224L, S311G, D320I, D346E, Q349K, T393I, Y422F, P442S, N445D, R446G, H468Q, V482T |
| 320 | Q1L, G4C, T27S, Q28R, E65V, A72C, D181N, E183M, P224L, S311G, D320I, D346E, Q349K, T393V, Y422F, P442S, N445D, R446G, H468L, V482I |
| 321 | Q1L, G4C, Q28R, E65M, A72C, S86T, D181N, E183M, P224L, S311G, T335I, D346A, Q349K, T393V, Y422F, P442S, N445D, R446G, H468Q, V482T |
| 322 | Q2S, G4C, A6L, T7Q, A8S, N10T, Q28R, E65V, A72C, D181N, P224L, S311D, N318Y, D320N, D346A, Q349K, T392M, T393I, Y422F, N445D, R446G, H468Q, V482I |
| 323 | Q1L, G4C, Q28R, E65V, A72C, S86T, D202N, P224L, S311G, D320I, D346E, Q349K, T393V, Y422F, N445D, R446G, H468Q, V482I |

TABLE 2-continued

| Mutations with respect to SEQ ID NO: 2: | |
|---|---|
| Consecutive Number | Mutation Pattern with respect to Seq. ID NO: 2 |
| 324 | Q1L, G4C, Q28K, E65V, A72C, E183M, D202N, S311G, D320I, D346E, Q349K, T393V, Y422F, P442S, N445D, R446G, H468L, V482I |
| 325 | Q1L, G4C, Q28R, E65K, A72C, D181N, P224L, S311N, N318Y, D320I, D346E, Q349K, T393V, Y422F, N445D, R446G, H468L, V482I |
| 326 | Q1L, G4C, Q28R, E65M, A72C, S90F, D181N, P224L, S311G, N318Y, D346E, Q349K, T393I, Y422F, P442S, N445D, R446G, H468Q, V482I |
| 327 | G4C, Q28R, A72C, S86T, D181N, E183V, S192L, D202V, N246S, S311D, N318Y, D320V, D346A, Q349K, T393V, P442S, N445D, H468L, V482A |
| 328 | Q1L, G4C, Q28K, E65V, A72C, D181N, E183M, D202N, P224L, S311N, N318Y, D320I, T335I, D346A, Q349K, T393I, Y422F, N445D, R446G, H468Q, V482T |
| 329 | Q1L, G4C, Q28R, A72C, S86T, E183M, S192L, H203R, S311D, D320V, T335I, D346V, Q349K, N445D, H468Q, V482A |
| 330 | Q1L, G4C, Q28R, T59M, E65K, A68T, A72C, S86T, D181N, S192L, D202N, H203R, S311D, D320V, T335I, Q349R, T393A, P442S, N445D, R446G, H468L, V482A |
| 331 | Q1L, G4C, Q28R, E65V, A72C, D181N, E183M, D202N, P224L, S311G, N318Y, T335I, D346E, Q349K, T393V, Y422F, P442S, N445D, R446G, H468Q, V482I |
| 332 | Q1L, G4C, Q28R, E65V, A72C, D181N, E183M, P224L, S311G, D320I, D346E, Q349K, K355Q, T393V, Y422F, P442S, N445D, R446G, H468L, V482I |
| 333 | Q1L, G4C, Q28R, E65V, A72C, D181N, E183M, P224L, S311G, N318Y, T335I, D346A, Q349K, T393V, Y422F, P442S, N445D, R446G, H468L, V482T |
| 334 | Q1L, G4C, Q28R, E65V, A72C, D181N, E183M, P224L, S311G, D320I, D346E, G349K, T393V, Y422F, P442S, N445D, R446G, T448A, R453G, H468L, V482I |
| 335 | Q1L, G4C, Q28R, E65M, A72C, S86T, D181N, E183M, S311N, N318Y, T335I, D346E, Q349K, T393V, Y422F, N445D, R446G, H468Q, V482I |
| 336 | Q1L, G4C, E65M, A72C, E183M, D202I, P224L, S311D, N318Y, D320V, T335I, D346A, Q349K, T393A, Y422F, P442S, N445D, R446G, R453G, H468Q, V482I |
| 337 | Q1L, G4C, Q28R, E65V, A72C, E183M, P224L, S311G, D346E, Q349K, T393V, Y422F, P442S, N445D, R446G, H468L, V482I |
| 338 | Q1L, G4C, Q28R, E65V, A72C, S86T, D181N, E183M, S311G, N318Y, D346A, Q349K, T393V, Y422F, N445D, R446G, H468L, V482T |
| 339 | Q1L, G4C, S24T, T27Q, Q28R, N29T, E65V, A72C, D181N, P224L, S311D, N318Y, D320N, D346A, Q349K, T392M, T393I, Y422F, N445D, R446G, H468Q, V482I |
| 340 | Q1L, G4C, E65V, A72C, D181N, E183M, S192T, P224L, S311G, D320V, T335I, D346G, Q349K, T393A, Y422F, P442S, N445D, R446G, H468L, V482T |
| 341 | Q1L, G4C, Q28R, E65V, A72C, D181N, E183M, P224L, S311G, D320I, D346E, Q349K, T393V, Y422F, P442S, N445D, R446G, H468L, V482I |
| 342 | Q1L, G4C, Q28R, E65V, A72C, D181N, E183M, D202F, S311G, N318Y, T335I, Q349K, T393V, Y422F, P442S, N445D, R446G, H468Q |
| 343 | Q1L, G4C, Q28K, E65K, A72C, S86T, D181N, D202N, P224L, S311D, N318Y, D320N, D346A, Q349R, T392M, T393I, Y422F, N445D, R446G, H468R |
| 344 | Q1L, G4C, Q28R, E65V, A72C, D181N, D202N, S311N, D320I, T335I, D346E, Q349K, T393V, Y422F, N445D, R446G, H468Q, V482T |

TABLE 2-continued

| Mutations with respect to SEQ ID NO: 2: | |
|---|---|
| Consecutive Number | Mutation Pattern with respect to Seq. ID NO: 2 |
| 345 | Q1L, G4C, Q28K, E65K, A72C, D181N, D202N, P224L, S311G, N318Y, T335I, D346E, Q349K, T393V, Y422F, N445D, R446G, H468Q, V482I |
| 346 | Q1L, G4C, Q28R, E65V, A72C, D181N, E183M, D202N, P224L, S311G, D320I, D346E, Q349K, T393V, Y422F, P442S, N445D, R446G, H468L, V482I |
| 347 | Q1L, G4C, Q28R, E65V, A72C, D181N, E183M, D202N, S311N, T335I, D346A, Q349K, T393V, Y422F, P442S, N445D, R446G, H468L, V482T |
| 348 | Q1L, G4C, Q28K, E65K, A72C, S86T, E183M, P224L, S311G, N318Y, D320I, T335I, D346E, Q349K, T393V, Y422F, P442S, N445D, R446G, H468Q, V482T |
| 349 | Q1L, G4C, A21T, T26I, Q28R, G30A, E65V, A68T, A72C, Y155C, D181N, D190K, D202N, T229M, S311G, D320I, T335I, D346E, Q349K, T393V, Y422F, N445D, R446G, H468Q, P480S, V482I |
| 350 | Q1L, G4C, Q28K, E65M, A72C, D181N, E183M, S311G, T335I, D346E, Q349K, T393V, Y422F, N445D, R446G, H468L, V482T |
| 351 | Q1L, G4C, Q28R, E65V, A72C, D181N, E183M, P224L, S311G, D320I, D346E, Q349K, T393V, D404N, Y422F, P442S, N445D, R446G, T451S, H468L, V482I |
| 352 | Q1L, G4C, Q28R, E65V, A72C, D181N, E183M, P224L, S311G, D320I, D346E, Q349K, T393V, Y422F, P442S, N445D, R446G, P462L, H468L, V482I |
| 353 | Q1L, G4C, Q28R, E65V, A72C, E183M, D202N, P224L, S311G, N318Y, T335I, D346E, Q349K, T393V, Y422F, N445D, R446G, H468L, V482I |
| 354 | Q1L, G4C, Q28R, E65V, A72C, D181N, E183M, P224L, T280A, S311G, D320I, D346E, Q349K, T393V, Y422F, P442S, N445D, R446G, H468L, V482I |
| 355 | Q1L, G4C, Q28R, E65V, Q69R, A72C, D181N, E183M, P224L, S311G, D320I, D346E, Q349K, T393V, Y422F, P442S, N445D, R446G, H468L, V482I |
| 356 | Q1L, G4C, Q28R, E65V, A72C, D181N, E183M, P224L, K275E, S311G, D320I, D346E, Q349K, T393V, Y422F, P442S, N445D, R446G, H468L, V482I |
| 357 | Q1L, G4C, Q28K, E65V, A72C, E183K, D202N, P224L, S311N, D320I, D346E, Q349K, T393V, Y422F, P442S, N445D, R446G, H468L, V482T |
| 358 | Q1L, G4C, Q28K, E65V, A72C, D181N, E183M, S311G, N318Y, D320I, D346A, Q349K, T393I, Y422F, N445D, R446G, H468Q, V482T |
| 359 | Q1L, G4C, Q28R, E65V, A72C, D181N, E183M, P224L, S311G, D320I, D346E, Q349K, T393V, Y422F, P442S, N445D, R446G, A455AAAAPA, H468L, V482I |
| 360 | Q1L, G4C, S24T, T26I, Q28R, N29Y, G30A, E65V, A72C, D181N, E183M, P224L, S311G, D320I, D346E, Q349K, T393V, Y422F, P442S, N445D, R446G, H468L, V482I |
| 361 | Q1L, G4C, Q28R, E65M, A72C, E183M, S311G, D320I, D346A, Q349K, T393V, Y422F, N445D, R446G, H468Q, V482I |
| 362 | Q1L, G4C, Q28R, E65V, A72C, D181N, E183M, D202N, S311G, D346E, Q349K, T393I, Y422F, N445D, R446G, H468Q, V482I |
| 363 | Q1L, G4C, Q28R, E65V, A72C, E183M, P224L, S311G, D320I, D346E, Q349K, T393V, Y422F, P442S, N445D, R446G, H468L, V482I |
| 364 | Q1L, G4C, Q28K, E65K, A72C, D181N, E183M, S311G, N318Y, D320I, T335I, D346E, Q349K, T393V, Y422F, N445D, R446G, H468Q, V482T |
| 365 | Q1L, G4C, Q28R, E65V, A72C, S311G, N318Y, D320I, T335I, D346E, Q349K, T393V, Y422F, N445D, R446G, H468L, V482T |
| 366 | Q1L, G4C, S24C, Q28R, G30A, E65V, A72C, Y155C, D181N, Q190K, D202N, P224L, S311G, T335I, D346E, Q349K, D390E, T393V, Y422F, N445D, R446G, R453G, H468Q, P480S, V482I |
| 367 | Q1L, G4C, Q28R, E65V, A72C, D181N, E183M, P224L, S311G, D320I, D346E, Q349K, T393V, P402S, Y422F, P442S, N445D, R446G, H468L, V482I |
| 368 | Q1L, G4C, Q28R, E65K, A72C, E183M, D202N, P224L, S311N, N318Y, T335I, D346E, Q349K, T393V, Y422F, P442S, N445D, R446G, H468Q, V482I |
| 369 | Q1L, G4C, A21T, T26I, Q28R, N29Y, E65V, A72C, Y155C, D181N, D202N, P224L, M234T, S311G, D320I, D346E, Q349K, Q390E, T393V, Y422F, N445D, R446G, R453G, H468Q, V482I |
| 370 | Q1L, G4C, Q28R, E65K, A72C, S86T, D202N, P224L, S311D, D320N, T335I, D346V, Q349K, T392M, T393V, Y422F, P442S, R446S, H468L |
| 371 | Q1L, G4C, Q28R, E65V, A72C, S86T, E183K, D202N, S311G, N318Y, D320I, D346A, Q349K, T393V, Y422F, P442S, N445D, R446G, H468Q, V482I |
| 372 | Q1L, G4C, W40R, E65M, A72C, S86T, E183V, S192L, D202I, H203R, P224L, S311G, N318Y, D320V, D346A, Q349K, P442S, N445D, R446G, H468R, V482A |
| 373 | Q1L, G4C, Q28R, E65V, A72C, D181N, E183M, P224L, S311G, D346E, Q349K, T393V, Y422F, P442S, N445D, R446G, H468L, V482I |
| 374 | Q1L, G4C, Q28R, E65V, A72C, D181N, E183M, P224L, S311G, D320I, D346E, Q349K, T393V, Y422F, G434GAAATG, P442S, N445D, R446G, T457TAAATT, H468L, V482I |
| 375 | Q1L, G4C, Q28R, E65V, A72C, K118Q, D181N, E183M, P224L, D247N, S311G, D320I, D346E, Q349K, T393V, Y422F, P442S, N445D, R446G, H468L, V482I |
| 376 | Q1L, G4C, Q28R, E65V, A72C, D181N, E183M, D202N, P224L, S311N, D320I, D346E, Q349K, T393V, Y422F, N445D, R446G, H468Q, V482I |
| 377 | Q1L, G4C, Q28R, E65V, A72C, S86T, D202N, P224L, S311G, N318Y, T335I, D346E, Q349K, T393V, Y422F, N445D, R446G, H468L, V482T |
| 378 | Q1L, G4C, Q28K, E65M, A72C, D181N, E183M, D202N, S311G, N318Y, D346A, Q349K, T393V, Y422F, P442S, N445D, R446G, H468L, V482T |
| 379 | Q1L, G4C, Q28R, E65V, A72C, D181N, E183M, P224L, S311G, D320I, D346E, Q349K, T393V, Y422F, P442S, N445D, R446G, P454PVRPQP, H468L, V482I |
| 380 | Q1L, G4C, Q28R, A72C, D181N, E183V, S192M, D202N, P224L, S311D, N318Y, D320N, D346E, Q349R, T393V, Y422F, P442S, R446G, H468L, P480S |
| 381 | Q1L, G4C, Q28R, A72C, S86T, D181N, S192L, D202N, P224L, S311G, N318Y, D320V, T335I, D345E, D346A, Q349K, Y422F, P442S, N445D, R446G, H468Q, H505Q |
| 382 | Q1L, G4C, Q28R, E65V, A72C, S86T, D181N, E183K, P224L, S311G, N318Y, D320I, D346A, Q349K, T393V, Y422F, P442S, N445D, R446G, H468L, V482I |
| 383 | Q1L, G4C, Q28R, G30A, E65V, A68T, A72C, D181N, E183M, D202N, P224L, D346E, Q349K, T393V, Y422F, N445D, R446G, T448A, R453G, H468Q, V482I |
| 384 | Q1L, G4C, Q28R, E65V, A72C, K92R, L120P, D181N, E183M, D202N, S236F, T280A, S311G, D346E, Q349K, K355Q, T387S, T393V, P402S, D404N, Y422F, N445D, R446G, T451S, G463V, H468Q, V482I, S485T |
| 385 | Q1L, G4C, Q28R, E65V, A72C, D181N, D202N, S236F, S311G, T335I, D346E, Q349K, T387S, T393V, Y422F, N445D, R446G, G463V, H468Q, V482I, S485T |

TABLE 2-continued

Mutations with respect to SEQ ID NO: 2:

| Consecutive Number | Mutation Pattern with respect to Seq. ID NO: 2 |
|---|---|
| 386 | Q1L, G4C, Q28R, E65M, A72C, D181N, E183K, D202N, P224L, S311G, D320I, D346E, Q349K, T393V, Y422F, P442S, N445D, R446G, H468Q, V482I |
| 387 | Q1L, G4C, A21T, T26I, Q28R, G30A, E65V, A68T, A72C, Y155C, D181N, E183M, Q190K, D202N, S311G, D320I, D346E, Q349K, T393V, Y422F, N445D, R446G, T448A, H468Q, V482I |
| 388 | Q1L, G4C, Q28R, E65V, A72C, D181N, D202N, S311G, T335I, D346A, Q349K, T393I, Y422F, P442S, N445D, R446G, H468L, V482I |
| 389 | Q1L, G4C, Q28R, E65V, A72C, D181N, E183M, P224L, D247N, S311G, D320I, D346E, Q349K, T387S, T393V, Y422F, P442S, N445D, R446G, H468L, V482I |
| 390 | Q1L, G4C, Q28R, E65V, A72C, D181N, D202N, P224L, S311G, D346A, Q349K, T393V, Y422F, N445D, R446G, H468L, V482I |
| 391 | Q1L, G4C, Q28R, E65V, A72C, K92R, K118Q, D181N, E183M, D202N, S236F, S311N, N318I, D346E, Q349K, K355Q, T387S, T393V, D404N, Y422F, N445D, R446G, H468Q, V482I |
| 392 | Q1L, G4C, T27S, Q28R, E65V, Q69R, A72C, K118Q, D181N, E183M, D202N, D247N, I277V, S311G, T335I, D346E, Q349K, K355Q, T393V, Y422F, N445D, R446G, H468Q, V482T |
| 393 | Q1L, G4C, Q28R, G30A, E65V, A72C, Y155C, D181N, E183M, D202N, M234T, S311G, D346E, Q349K, T393V, Y422F, N445D, R446G, T448A, R453G, H468Q, V482T |
| 394 | Q1L, G4C, Q28R, E65V, A72C, D181N, E183M, P224L, S311G, D320I, D346E, Q349K, T393V, Y422F, G434GAAATG, P442S, N445D, R446G, H468L, V482I |
| 395 | Q1L, G4C, Q28R, E65V, Q69R, A72C, K92R, D181N, D202N, D247N, I277V, S311G, N318D, T335I, D346E, Q349K, K355Q, T387S, T393V, Y422F, N445D, R446G, G463V, H468Q, V482I |
| 396 | Q1L, G4C, T27S, Q28R, E65V, Q69R, A72C, D181N, D202N, S236F, I277V, S311G, T335I, D346E, Q349K, K355Q, T387S, T393V, Y422F, N445D, R446G, G463V, H468Q, V482I |
| 397 | Q1L, G4C, N10D, Q28R, E65V, Q69R, A72C, K92R, K118Q, D181N, E183M, D202N, S311G, T335I, D346E, Q349K, T387S, T393V, Y422F, N445D, R446G, P462L, H468Q, V482T, S485T |
| 398 | Q1L, G4C, A21T, Q28R, G30A, E65V, A72C, Y155C, D181N, E183M, D202N, M234T, S311G, T335I, D346E, Q349K, T393V, Y422F, N445D, R446G, R453G, H468Q, V482T |
| 399 | Q1L, G4C, Q28R, E65V, A72C, D181N, E183M, P224L, S311G, D320I, D346E, Q349K, T393V, Y422F, P442S, N445D, R446G, T457TAAATT, H468L, V482I |
| 400 | Q1L, G4C, T26I, Q28R, E65V, A68T, A72C, Y155C, D181N, Q190K, D202N, P224L, M234T, S311G, D320I, D346E, Q349K, D390E, T393V, Y422F, N445D, R446G, R453G, H468Q, V482I |
| 401 | Q1L, G4C, Q28K, E65V, A72C, S86T, E183K, S192L, D202N, D320N, T335I, D346A, Q349R, T393A, Y422F, P442S, R446G, H468R, V482A |
| 402 | Q1L, G4C, Q28R, E65V, A72C, D181N, E183M, P224L, S236F, S311G, D320I, D346E, Q349K, T393V, Y422F, P442S, N445D, R446G, H468L, V482I |
| 403 | Q1L, G4C, T26I, Q28R, E65V, A68T, A72C, Y155C, D181N, D202N, M234T, S311G, T335I, D346E, Q349K, T393V, Y422F, N445D, R446G, H468Q, V482T |
| 404 | Q1L, G4C, A21T, T26I, Q28R, N29Y, E65V, A72C, Y155C, D181N, E183M, D202N, P224L, M234T, S311G, D320I, T335I, A340S, D346E, Q349K, D390E, T393V, Y422F, N445D, R446G, T448A, R453G, H468Q, P480S, V482I |

TABLE 2-continued

Mutations with respect to SEQ ID NO: 2:

| Consecutive Number | Mutation Pattern with respect to Seq. ID NO: 2 |
|---|---|
| 405 | Q1L, G4C, Q28R, E65K, A72C, D202I, P224L, S311G, N318Y, D320V, T335I, D346A, Q349R, T392M, T393A, N445D, R446G, H468L |
| 406 | Q1L, G4C, E65M, A72C, S86T, E183V, D202I, P224L, S311G, N318Y, D320V, D346A, Q349K, P442S, N445D, R446G, H468L, V482A |
| 407 | Q1L, G4C, N10D, Q28R, E65V, A72C, K92R, D181N, E183M, D202N, S311G, D346E, Q349K, T387S, T393V, Y422F, N445D, R446G, T451S, P462L, H468Q, V482T |
| 408 | Q2S, G4C, A6L, T7Q, A8S, N10T, Q28K, E65M, A72C, S86T, E183M, D202N, P224L, S311G, D320I, T335I, (DeletionS437-P441), D346E, Q349K, T393V, Y422F, N445D, R446G, H468Q, V482T |
| 409 | Q2S, G4C, A6L, T7Q, A8S, N10T, S24T, T26I, Q28R, N29Y, G30A, E65V, A72C, E183M, P224L, S311G, D320I, D346E, Q349K, T393V, Y422F, P442S, N445D, R446G, H468L, V482I |
| 410 | Q1L, G4C, Q28R, E65V, A72C, K92R, D181N, E183M, P224L, I277V, S311G, D320I, D346E, Q349K, T393V, Y422F, P442S, N445D, R446G, H468L, V482I |
| 411 | Q2S, G4C, A6L, T7Q, A8S, N10T, Q28R, E65V, A72C, E183M, P224L, S311G, D320I, D346E, Q349K, T393V, Y422F, P442S, N445D, R446G, H468L, V482I |
| 412 | Q2S, G4C, A6L, T7Q, A8S, N10T, Q28R, E65V, A72C, E183M, P224L, S311G, D320I, D346E, Q349K, T393V, Y422F, P442S, N445D, R446G, P454PVRPQP, H468L, V482I |
| 413 | Q2S, G4C, A6L, T7Q, A8S, N10T, Q28R, E65V, A72C, E183M, P224L, S311G, D320I, D346E, Q349K, T393V, Y422F, P442S, N445D, R446G, P464THAAA, H468L, V482I |
| 414 | Q2S, G4C, A6L, T7Q, A8S, N10T, Q28R, E65V, A72C, E183M, P224L, S311G, D320I, D346E, Q349K, T393V, Y422F, P442S, N445D, R446G, P464PTHAAA, H468L, V482I |
| 415 | Q2S, G4C, A6L, T7Q, A8S, N10T, Q28R, E65V, A72C, G151GCGRSG, E183M, P224L, S311G, D320I, D346E, Q349K, T393V, Y422F, P442S, N445D, R446G, H468L, V482I |
| 416 | Q2S, G4C, A6L, T7Q, A8S, N10T, Q28R, E65V, A72C, K159KCGRNK, E183M, P224L, S311G, D320I, D346E, Q349K, T393V, Y422F, P442S, N445D, R446G, H468L, V482I |
| 417 | Q2S, G4C, A6L, T7Q, A8S, N10T, Q28R, E65V, A72C, E183M, P224L, S311G, D320I, D346E, Q349K, T393V, Y422F, P442S, N445D, R446G, P454ATAAA, H468L, V482I |
| 418 | Q2S, G4C, A6L, T7Q, A8S, N10T, Q28K, E65K, A72C, E183M, S311G, N318Y, D320I, T335I, D346E, Q349K, T393V, Y422F, N445D, R446G, H468Q, V482T |
| 419 | Q2S, G4C, A6L, T7Q, A8S, N10T, Q28K, E65V, A72C, E183M, D202N, P224L, S311G, T335I, D346E, Q349K, T393V, Y422F, P442S, N445D, R446G, H468Q, V482I |
| 420 | Q2S, G4C, A6L, T7Q, A8S, N10T, Q28R, E65M, A72C, S86T, E183M, S311N, N318Y, T335I, D346E, Q349K, T393V, Y422F, N445D, R446G, H468Q, V482I |
| 421 | Q2S, G4C, A6L, T7Q, A8S, N10T, Q28R, E65M, A72C, E183M, S311G, N318Y, D346E, Q349K, T393V, Y422F, P442S, N445D, R446G, H468Q, V482I |
| 422 | Q2S, G4C, A6L, T7Q, A8S, N10T, Q28R, E65V, A72C, E183M, D202N, P224L, S311G, N318Y, T335I, D346E, Q349K, T393V, Y422F, P442S, N445D, R446G, H468Q, V482I |
| 423 | Q2S, G4C, A6L, T7Q, A8S, N10T, Q28R, E65V, A72C, E183M, P224L, S311G, N318Y, T335I, D346A, Q349K, T393V, Y422F, P442S, N445D, R446G, H468L, V482T |

TABLE 2-continued

Mutations with respect to SEQ ID NO: 2:

| Consecutive Number | Mutation Pattern with respect to Seq. ID NO: 2 |
|---|---|
| 424 | Q2S, G4C, A6L, T7Q, A8S, N10T, Q28R, E65V, A72C, P224L, S311D, N318Y, D320N, D346A, Q349K, T392M, T393I, Y422F, N445D, R446G, H468Q, V482I |
| 425 | Q2S, G4C, A6L, T7Q, A8S, N10T, Q28R, E65K, A72C, S311N, N318Y, D346E, Q349K, T393V, Y422F, (DeletionbeiG439-G444), N445D, R446G, H468Q, V482I |
| 426 | Q2S, G4C, A6L, T7Q, A8S, N10T, Q28K, N29Y, E65K, A72C, S311G, T335I, D346E, Q349K, T393V, Y422F, N445D, R446G, H468Q, V482T |
| 427 | Q2S, G4C, A6L, T7Q, A8S, N10T, S24T, T26I, Q28R, N29Y, G30A, E65V, A68T, A72C, E183M, Q190K, P224L, S311G, D320I, D346E, Q349K, T393V, Y422F, P442S, N445D, R446G, H468L, V482I |
| 428 | Q2S, G4C, A6L, T7Q, A8S, N10T, S24T, T26I, Q28R, N29Y, G30A, Y47F, E65V, A68T, A72C, E183M, Q190K, P224L, T229M, G231D, M234T, S311G, D320I, A340S, D346E, Q349K, D390E, T393V, N445D, R446G, T448A, R453G, H468L, P480S, V482I, Y422F, P442S |
| 429 | Q2S, G4C, A6L, T7Q, A8S, N10T, Q28R, E65V, A72C, K159KCGRNK, E183M, P224L, S311G, D320I, D346E, Q349K, T393V, Y422F, P442S, N445D, R446G, T457TAAATT, H468L, V482I |
| 430 | Q2S, G4C, A6L, T7Q, A8S, N10T, Q28R, E65V, A72C, E183M, P224L, S311G, D320I, D346E, Q349K, T393V, Y422F, P442S, N445D, R446G, T457TAAATT, H468L, V482I |
| 431 | Q1L, G4C, A72C, S86T, D181N, E283K, D202V, P224L, S311G, D320V, D346E, Q349R, T393A, Y422F, P442S, N445D, R446G, H468L |
| 432 | Q1L, G4C, Q28R, E65V, A72C, K159CGRNKE183M, P224L, S311G, D320I, D346E, Q349K, T393V, Y422F, P442S, N445D, R446G, H468L, V482I |
| 433 | Q2S, G4C, A6L, T7Q, A8S, N10T, S24T, Q28R, E65K, A72C, D202N, S311G, T335I, D346E, Q349K, T393I, Y422F, N445D, R446G, H468Q, V482T |
| 434 | Q2S, G4C, A6L, T7Q, A8S, N10T, Q28R, E65M, A72C, E183K, D202N, P224L, S311G, D320I, D346E, Q349K, T393V, Y422F, P442S, N445D, R446G, H468Q, V482I |
| 435 | Q1L, G4C, Q28K, E65M, A72C, S86T, E183M, D202N, P224L, S311G, D320I, T335I, D346E, Q349K, T393V, Y422F, (S437-P441), N445D, R446G, H468Q, V482T |
| 436 | Q1L, G4C, S24T, T26I, Q28R, N29Y, G30A, E65V, A72C, E183M, P224L, S311G, D320I, D346E, Q349K, T393V, Y422F, P442S, N445D, R446G, H468L, V482I |
| 437 | Q1L, G4C, Q28R, E65V, A72C, E183M, P224L, S311G, D320I, D346E, Q349K, T393V, Y422F, P442S, N445D, R446G, T457TAAATT, H468L, V482I |
| 438 | Q1L, G4C, Q28R, E65V, A72C, E183M, P224L, S311G, D320I, D346E, Q349K, T393V, Y422F, P442S, N445D, R446G, P454PVRPQP, H468L, V482I |
| 439 | Q1L, G4C, Q28R, E65V, A72C, E183M, P224L, S311G, D320I, D346E, Q349K, T393V, Y422F, P442S, N445D, R446G, P464THAAA, H468L, V482I |
| 440 | Q1L, G4C, Q28R, E65V, A72C, E183M, P224L, S311G, D320I, D346E, Q349K, T393V, Y422F, P442S, N445D, R446G, P454PATAAA, H468L, V482I |
| 441 | Q1L, G4C, Q28R, E65V, A72C, E183M, P224L, S311G, D320I, D346E, Q349K, T393V, Y422F, G434GAAATG, P442S, N445D, R446G, H468L, V482I |
| 442 | Q1L, G4C, Q28R, E65V, A72C, D181N, E183M, P224L, S311G, D320I, D346E, Q349K, T393V, Y422F, P442S, N445D, R446G, H468L, V482I, Q1L, G4C, Q28R, E65V, A72C, E183M, P224L, S311G, D320I, D346E, Q349K, T393V, Y422F, P442S, N445D, R446G, H468L, V482I |
| 443 | Q1L, G4C, Q28R, E65V, A72C, G151GCGRSG, E183M, P224L, S311G, D320I, D346E, Q349K, T393V, Y422F, P442S, N445D, R446G, H468L, V482I |
| 444 | Q1L, G4C, Q28R, E65V, A72C, E183M, P224L, S311G, D320I, D346E, Q349K, T393V, Y422F, P442S, N445D, R446G, P454ATAAA, H468L, V482I |
| 445 | Q1L, G4C, Q28R, E65K, A72C, S311N, N318Y, D346E, Q349K, T393V, Y422F, (DG439-G444) N445D, R446G, H468Q, V482I |
| 446 | Q1L, G4C, S24T, T26I, Q28R, N29Y, G30A, E65V, A68T, A72C, E183M, Q190K, P224L, S311G, D320I, D346E, Q349K, T393V, Y422F, P442S, N445D, R446G, H468L, V482I |
| 447 | Q1L, G4C, S24T, T26I, Q28R, N29Y, G30A, Y47F, E65V, A68T, A72C, E183M, Q190K, P224L, T229M, G231D, M234T, S311G, D320I, A340S, D346E, Q349K, D390E, T393V, N445D, R446G, T448A, R453G, H468L, P480S, V482I, Y422F, P442S |
| 448 | Q1L, G4C, A21T, T26I, Q28R, N29Y, G30A, E65V, A68T, A72C, D181N, Q190K, D202N, T229M, M234T, S311G, D320I, A340S, D346E, Q349K, D390E, T393V, Y422F, N445D, R446G, T448A, H468Q, V482I |
| 449 | Q1L, G4C, N10D, T27S, Q28R, E65V, A72C, K92R, K118Q, D181N, D202N, S236F, I277V, S311G, D346E, Q349K, K355Q, T387S, T393V, D404N, N417Y, Y422F, N445D, R446G, P462L, H468Q, V482I, S485T |
| 450 | Q1L, G4C, A21T, T26I, Q28R, G30A, E65V, A68T, A72C, Y155C, D181N, Q190K, D202N, P224L, T229M, S311N, D320I, D346E, Q349K, T393V, Y422F, N445D, R446G, R453G, H468Q, V482I |
| 451 | Q1L, G4C, N10D, T27S, Q28R, E65V, A72C, K92R, K118Q, D181N, E183M, D202N, D247N, S311G, D320I, T335I, D346E, Q349K, T393V, Y422F, N445D, R446G, H468Q, V482T |
| 452 | Q1L, G4C, T26I, Q28R, G30A, E65V, A72C, Y155C, D181N, D202N, T229M, G231D, S311G, T335I, D346E, Q349K, T393V, Y422F, N445D, R446G, T448A, R453G, H468Q, V482T |
| 453 | Q1L, G4C, S24R, 726I, Q28R, G30A, E65V, A72C, D181N, E183M, D202N, P224L, S311N, T335I, D346E, Q349K, D390E, T393V, Y422F, N445D, R446G, H468Q, V482T |
| 454 | Q1L, G4C, N10D, T27S, Q28R, E65V, Q69R, A72C, D181N, E183M, D202N, S236F, D247N, I277V, S311N, T335I, D346E, Q349K, T387S, T393V, N417Y, Y422F, T433S, N445D, R446G, P462L, H468Q, V482I |
| 455 | Q1L, G4C, A21T, Q28R, E65V, A72C, Y155C, D181N, D202N, P224L, S311G, N318Y, D346E, Q349K, D390E, T393V, Y422F, N445D, R446G, T448A, H468Q, V482I |
| 456 | Q1L, G4C, T26I, Q28R, N29Y, E65V, A68T, A72C, Y155C, D181N, E183M, D202N, P224L, M234T, S311N, N318Y, D346E, Q349K, T393V, Y422F, N445D, R446G, T448A, R453G, H468Q, V482I |
| 457 | Q1L, G4C, A21T, T26I, Q28R, N29Y, E65V, A68T, A72C, Y155C, D181N, D202N, P224L, T229M, M234T, S311G, N318Y, D346E, Q349K, T393V, Y422F, N445D, R446G, R453G, H468Q, V482I |
| 458 | Q1L, G4C, N10D, Q28R, E65V, A72C, K92R, K118Q, D181N, E183M, D202N, P224L, S236F, D247N, F306L, S311G, D346E, Q349K, K355Q, T393V, D404N, N417Y, Y422F, N445D, R446G, H468Q, V482I, S485T |
| 459 | Q1L, G4C, N10D, Q28R, E65V, A72C, K92R, K118Q, D181N, E183M, D202N, S236F, D247N, |

TABLE 2-continued

| Mutations with respect to SEQ ID NO: 2: | |
|---|---|
| Consecutive Number | Mutation Pattern with respect to Seq. ID NO: 2 |
| | S311G, N318I, T335I, D346E, Q349K, K355Q, T393V, Y422F, T433S, N445D, R446G, T451S, G463V, H468Q, V482I |
| 460 | G4C, Q28K, E65M, A72C, S86T, G151GCGRSG, E183M, D202N, P224L, S311G, T335I, D346E, Q349K, T393V, Y422F, P442S, N445D, R446G, H468L, V482I |
| 461 | G4C, Q28K, E65M, A72C, S86T, K159KCGRNK, E183M, D202N, P224L, S311G, T335I, D346E, Q349K, T393V, Y422F, P442S, N445D, R446G, H468L, V482I |
| 462 | G4C, Q28K, E65M, A72C, S86T, G151GCGRSG, K159KCGRNK, E183M, D202N, P224L, S311G, T335I, D346E, Q349K, T393V, Y422F, P442S, N445D, R446G, H468L, V482I |
| 463 | G4C, Q28K, E65M, A72C, S86T, G151GCGRSG, E183M, D202N, P224L, S311G, T335I, D346E, Q349K, T393V, Y422F, P442S, N445D, R446G, T457TAAATT, H468L, V482I |
| 464 | G4C, Q28K, E65M, A72C, S86T, K159KCGRNK, E183M, D202N, P224L, S311G, T335I, D346E, Q349K, T393V, Y422F, P442S, N445D, R446G, T457TAAATT, H468L, V482I |
| 465 | G4C, Q28K, E65M, A72C, S86T, G151GCGRSG, E183M, D202N, P224L, S311G, T335I, D346E, Q349K, T393V, Y422F, G434GAAATG, P442S, N445D, R446G, T457TAAATT, H468L, V482I |
| 466 | G4C, Q28K, E65M, A72C, S86T, K159KCGRNK, E183M, D202N, P224L, S311G, T335I, D346E, Q349K, T393V, Y422F, G434GAAATG, P442S, N445D, R446G, T457TAAATT, H468L, V482I |
| 467 | G4C, Q28K, E65M, A72C, S86T, G151GCGRSG, K159KCGRNK, E183M, D202N, P224L, S311G, T335I, D346E, Q349K, T393V, Y422F, G434GAAATG, P442S, N445D, R446G, H468L, V482I, T457TAAATT, |
| 468 | Q1L, G4C, Q28K, E65V, A72C, D181N, E183M, D202N, P224L, S311G, T335I, D346E, Q349K, T393V, Y422F, P442S, N445D, R446G, H468Q, V482I |
| 469 | Q1L, G4C, Q28K, E65V, A72C, S86T, D181N, E183K, S192L, D202V, S311G, D320I, D346V, Q349R, T393A, Y422F, P442S, N445D, R446G, H468Q, V482I |
| 470 | Q1L, G4C, Q28R, E65V, A72C, S86T, D181N, D202N, P224L, S311N, N318Y, D320I, D346A, Q349K, T393V, Y422F, N445D, R446G, H468L, V482T |
| 471 | Q1L, G4C, A21T, T26I, Q28R, G30A, E65V, A68T, A72C, D181N, E183M, D202N, T229M, S311G, A340S, D346E, Q349K, T393V, Y422F, N445D, R446G, H468Q, V482T |

In a further aspect, the present invention discloses a nucleic acid encoding the polypeptide of the present invention. The nucleic acid is a polynucleotide sequence (DNA or RNA) which is, when set under control of an appropriate promoter and transferred into a suitable biological host or chemical environment, processed to the encoded polypeptide, whereby the process also includes all post-translational and post-transcriptional steps necessary. The coding sequence can be easily adapted by variation of degenerated base-triplets, alteration of signal sequences, or by introduction of introns, without affecting the molecular properties of the encoded protein. The nucleic acid of the present invention has preferably at least 95%, more preferably at least 97%, and most preferably 100% identity to SEQ ID NO: 1. The present invention also provides a vector comprising this nucleic acid and a host transformed with said vector.

The present invention also discloses methods for the production of polypeptides of the present invention and variants thereof in various host cells, including yeast and fungal hosts. It also discloses the use of the resulting strains for the improvement of protein properties by variation of the sequence. Furthermore, the present invention discloses methods for the application of such polypeptides in the hydrolysis of cellulose.

A further aspect of the invention discloses vectors and methods for the production of protein variants of SEQ ID NO; 2. expressing them in yeast and testing their activity on cellulosic material by measuring the released mono- and/or oligomeric sugar molecules.

The present invention further relates to a method of producing a cellobiohydrolase protein, comprising the steps:

a. obtaining a host cell, which has been transformed with a vector comprising the nucleic acid of the present invention;
b. cultivation of the host cell under conditions under which the cellobiohydrolase protein is expressed; and
c. recovery of the cellobiohydrolase protein.

In a particular embodiment, this method of producing a cellobiohydrolase protein is restricted to a method for the production of a cellobiohydrolase protein as provided by this invention, such as having the IT50 value given above, and/or being one of the specific variants of SEQ ID NO2 or SEQ ID NO: 5 as provided with this application and described in detail elsewhere in this specification.

In a more preferred embodiment, the host cell is derived from the group consisting of *Saccharomyces, Schizosaccharomyces, Kluyveromyces, Pichia, Hansenula, Aspergillus, Trichoderma, Penicillium, Candida* and *Yarrowina*. The host cell is preferably capable of producing ethanol, wherein most preferred yeasts include *Saccharomyces cerevisiae, Pichia stipitis, Pachysolen tannophilus*. or a methylotrophic yeast, preferably derived from the group of host cells comprising *Pichia methanolica, Pichia pastoris, Pichia angusta, Hansenula polymorpha.*

It has surprisingly been found that the polypeptide according to the present invention and variants thereof can be expressed from yeast at high levels. "Yeast" shall herein refer to all lower eukaryotic organisms showing a unicellular vegetative state in their life cycle. This especially includes organisms of the class Saccharomycetes, in particular of the genus *Saccharomyces, Pachysolen, Pichia, Candida, Yarrowina, Debaromyces, Klyveromyces, Zygosaccharomyces.*

Thus, one aspect of the invention relates to the expression of the claimed polypeptide and variants thereof in yeast. The efficient expression of this fusion protein (SEQ ID NO: 2) and derivative protein variants of SEQ ID NO: 2 from yeast can be achieved by insertion of the nucleic acid molecule of SEQ ID NO: 1 starting from nucleotide position 1 into an expression vector under control of at least one appropriate promoter sequence and fusion of the nucleotide molecule to an appropriate signal peptide, for example to the signal peptide of the mating factor alpha of *Saccharomyces cerevisiae.*

In a preferred embodiment, the polypeptide of the present invention and variants thereof are expressed and secreted at a level of more than 100 mg/l, more preferably of more than 200 mg/l, particularly preferably of more than 500 mg/l, or most preferably of more than 1 g/l into the supernatant after introduction of a nucleic acid encoding a polypeptide having an amino acid sequence with at least 85% sequence identity to the SEQ ID NO: 2 into a yeast. To determine the level of expression in yeast, the cultivation and isolation of the supernatant can be carried out as described in Example 3.

A further aspect the invention discloses methods for the production of a polypeptide according to the present invention in a filamentous fungus, preferably in a fungus of the genus *Aspergillus* or *Trichoderma*. more preferably in a fungus of the genus *Trichoderma,* most preferably in *Trichoderma reesei*. "Filamentous fungi" or "fungi" shall herein refer to all lower eukaryotic organisms showing hyphal growth during at least one state in their life cycle. This especially includes organisms of the phylum Ascomycota and Basidiomycota, in particular of the genus *Trichoderma, Talaromyces, Aspergillus, Penicillium, Chrysosporium, Phanerochaete, Thermoascus, Agaricus, Pleutrus, Irpex*. The polypeptide is expressed by fusion of the coding region of a compatible signal sequence to the nucleic acid molecule starting with nucleotide position 52 of SEQ ID NO: 3. as it was done in SEQ ID NO: 3 with the signal sequence of the *Trichoderma reesei* CBHI, and the positioning of the fusion peptide under control of a sufficiently strong promoter followed by transfer of the genetic construct to the host cell. Examples for such promoters and signal sequences as well as techniques for an efficient transfer have been described in the art.

In a further aspect the present invention further relates to a method for identifying a polypeptide or polypeptides having cellobiohydrolase activity, comprising the steps of:

a. Generating a library of mutant genes encoding mutant proteins by mutagenesis of a nucleic acid according to claim 9 or a nucleic acid having the sequence defined by SEQ ID NO: 6 (encoding SEQ ID NO: 5), preferably having the sequence defined by SEQ ID NO: 1;
b. Inserting each mutant gene into an expression vector;
c. Transforming yeast cells with each expression vector to provide a library of yeast transformants;
d. Cultivation of each yeast transformant under conditions under which the mutant protein is expressed and secreted;
e. Incubating the expressed mutant protein with a substrate;
f. Determining the catalytic activity of the mutant protein;
g. Selecting a mutant protein according to the determined catalytic activity.

Specifically, step d. may be performed by utilizing a well-plate format. This format preferably allows the high-throughput performance of the method for identifying polypeptides having cellobiohydrolase activity.

In a preferred embodiment, this method for identifying polypeptides having cellobiohydrolase activity is restricted to a method, wherein the polypeptide(s) having cellobiohydrolase activity is one or more polypeptide(s) as provided by this invention, such as having the IT50 value given above, and/or being one of the specific variants of SEQ ID NO2 or SEQ ID NO: 5 as below.

Preferably, the steps e. to g. of the method for identifying polypeptides having cellobiohydrolase activity are performed as follows:

e. Incubating the expressed mutant protein with cellulosic material;
f. Determining the amount of released sugar;
g. Selecting a mutant protein according to the amount of released sugar.

In another embodiment, the method for identifying polypeptides having cellobiohydrolase activity comprises the additional steps of:

h. Sequencing the selected mutant gene or protein;
i. Identifying the amino acid modification(s) by comparing the sequence of the selected mutant protein with the amino acid sequence of SEQ ID NO: 2.

In a particular embodiment, the method is further characterized by measuring the IT50 value of the obtained polypeptide. The IT50 value may be measured as described in the examples below. Optionally, this may be followed by a step of selection of those polypeptides, which display the a desired IT 50 value, such as at least 60° C., at least 62° C. and the like. Thus, in this particular embodiment, the method is suitable for identifying polypeptides exhibiting cellobiohydrolase activity and an elevated IT50 value, i.e. thermostable polypeptides with cellobiohydrolase activity.

The present invention further provides a method of preparing a polypeptide having cellobiohydrolase activity, comprising the steps:

a. Providing a polypeptide having cellobiohydrolase activity comprising an amino sequence having at least 54% sequence identity to the catalytic domain of SEQ ID NO: 2 (SEQ ID NO: 5) (such as preferably, at least 60%, at least 62%, at least 64%, at least 66%, at least 68% or at least 70%, whereby at least 68% or at least 70% are the most preferred embodiments);
b. Identifying the amino acids of this polypeptide which correspond to the amino acids which are modified with respect to the amino acid sequence of SEQ ID NO: 2. as identified in step i. of the method for identifying polypeptides having cellobiohydrolase activity; and
c. Preparing a mutant polypeptide of the polypeptide provided in step a. by carrying out the amino acid modification(s) identified in step b. through site-directed mutagenesis.

In one embodiment, preferably, the polypeptide provided in step a. of the method of preparing a polypeptide having cellobiohydrolase activity is a wild type cellobiohydrolase derived from *Trichoderma reesei.*

The present invention further provides polypeptides having cellobiohydrolase activity, which are obtainable by the method of preparing a polypeptide having cellobiohydrolase activity according to the present invention.

Furthermore, the present invention provides a composition comprising a polypeptide and/or variants thereof of the present invention and one or more cellulases, e.g. one or more endoglucanases and/or one or more beta-glucosidases and/or one or more further cellobiohydrolases and/or one or more xylanases. "Cellulases" or "Cellulolytic enzymes" are defined as enzymes capable of hydrolysing cellulosic substrates or derivatives or mixed feedstocks comprising cellulosic polymers. Such enzymes are referred to as having "cellulolytic activity", thus being able to hydrolyze cellulose molecules from such material into smaller oligo- or monosaccharides. Cellulolytic enzymes include cellulases and hemicellulases, in particular they include cellobiohydrolases (CBHs), endoglucanases (EGs) and beta-glucosidases (BGLs).

The present invention further provides a polypeptide having cellobiohydrolase activity, wherein the polypeptide comprises an amino acid sequence having at least 80%, preferably at least 95%, more preferably at least 98%, even more. preferably at least 99%, and most preferably 99, 6% sequence identity to SEQ ID NO: 5. Particularly, it is preferred that such a polypeptide is a polypeptide wherein one or more of the following amino acid residues of the sequence defined by SEQ ID NO: 5 are modified by substitution or deletion of: Q1. Q2, G4. A6. T7. A8. N10. P12. T15. A21. G23. S24. T26. T27. Q28. N29. G30. A31. V32. N37, W40. V41. G46. Y47. T48. N49. C50. T52. N54. D57. T59. Y60. D64. E65. A68. Q69. A72, V84. S86. S89. S90. K92. S99. Q109. D110. D111. I116. F117. K118. L119. L120. D129, V130. G139. A145. M146. V152. K154. Y155. N157. N158. K159. K163. G167. Q172. F179, I180. D181. E183. E187. G188. Q190. S192. S193; N194. I200. D202.

H203. D211. V212, A221. P224. D228. T229. G231. T233. M234. S236. T243. Y244. S245. N246. D247. G251, F260. G266. K275. I276. I277. T280. L290. D293. G294. T295. T297. T299. S301. K304, F306. N310. S311. V313. I314. N318. D320. I321. T325. N327. T335. A340. F341. D343, T344. D345. D346. Q349. H350. A354. K355. A358. Q361. Q362. G363. M364. V367. D373, Y374. A375. A376. P386. T387. D390. T392. T393. P394. T400. P402. T403. D404. D410, N417. S418. T421. Y422 and/or one or more insertions after positions G151. K159

In a preferred embodiment, the polypeptide having cellobiohydrolase activity with an amino acid sequence having at least 80% sequence identity to SEQ ID NO: 5 comprises one or more modified amino acid residues of the sequence defined by SEQ ID NO: 5: Thus, the polypeptide given in SEQ ID NO: 5 may, by means of example, be modified as follows: Q1L, G4. A6G/V, T15S, Q28Q/R, W40R, D64N, E65K/V, A72V, S86T, K92K/R, V130I/V, V152A/E, Y155C, K159E, D181N, E183V/K, N194C/R/Y/D/K/I/L/G/Q/S/V, D202Y/N/G, P224L, T243I/R/Y/A/F/Q/P/D/V/W/L/M, Y244F/H, I277V, K304R, N310D, S311G/N, N318Y, D320V/E/N, T335I, T344M, D346G/A/E/V, Q349R/K, A358E, Y374C/P/R/H/S/A, A375D/N/Y/R/Q/L/V/E/G/T/M, T392C/D/K, T393A, D410G, Y422F.

More preferably, the polypeptide having cellobiohydrolase activity comprises one or more modified amino acid residues of the sequence defined by SEQ ID NO: 5 as indicated in the following Table 3. As said above, for the specific modifications of SEQ ID NO: 2. two or more of such specific modifications may be combined with each other, such as preferably two or more of the more preferred or most preferred modifications may be combined with each other, and, which is particularly preferred, two or more of the most preferred modifications according to Table 3 may be combined with each other.

TABLE 3

Mutations with respect to SEQ ID NO: 5

| Position | Preferred | More Preferred | Most Preferred |
|---|---|---|---|
| Q1 | L | L | L |
| Q2 | P, S | P, S | S |
| G4 | C | C | C |
| A6 | G, L, V | G, L, V | L |
| T7 | Q | Q | Q |
| A8 | S | S | S |
| N10 | T, D | T, D | T, D |
| P12 | Q | | |
| T15 | S | | |
| A21 | S, T, C | S, T, C | |
| G23 | A, D, N | | |
| S24 | T, C, N | T, C, N | |
| T26 | I, N | I, N | |
| T27 | S, Q | S, Q | |
| Q28 | L, K, R, N | L, K, R, N | K, R |
| N29 | T, Y | T, Y | |
| G30 | A | A | |
| A31 | S | | |
| V32 | G | | |
| N37 | S | | |
| W40 | R | R | |
| V41 | T | | |
| G46 | S | | |
| Y47 | S, F | S, F | |
| T48 | A | | |
| N49 | S | | |
| C50 | S | | |
| T52 | D | | |
| N54 | S | | |
| D57 | S | | |

TABLE 3-continued

Mutations with respect to SEQ ID NO: 5

| Position | Preferred | More Preferred | Most Preferred |
|---|---|---|---|
| T59 | M | | |
| Y60 | H | | |
| D64 | N | N | |
| E65 | V, M, K | V, M, K | V, M, K |
| A68 | T | T | |
| Q69 | K, R | K, R | |
| A72 | V, C | V, C | C |
| V84 | A | | |
| S86 | T | T | T |
| S89 | N | | |
| S90 | T, F | | |
| K92 | R | R | |
| S99 | T | | |
| Q109 | R | | |
| D110 | G, S, N | | |
| D111 | H, E | | |
| I116 | V, K, E | | |
| F117 | Y | | |
| K118 | A, T, Q | A, T, Q | |
| L119 | L, I | | |
| L120 | P, M | | |
| D129 | N | | |
| V130 | I | | |
| G139 | S | | |
| A145 | T | | |
| M146 | C | | |
| G151 | GCGRSG | GCGRSG | GCGRSG |
| V152 | A, E | | |
| K154 | R | | |
| Y155 | S, C, H | S, C, H | |
| N157 | S | | |
| N158 | D | | |
| K159 | E, KCGRNK | KCGRNK | KCGRNK |
| K163 | C | | |
| G167 | C | | |
| Q172 | Q | | |
| F179 | I | | |
| I180 | N | | |
| D181 | N | N | N |
| E183 | V, M, K | V, M, K | V, M, K |
| E187 | K | | |
| G188 | C | | |
| Q190 | L, K | L, K | |
| S192 | L, I, P, T, M | L, I, P, T, M | |
| S193 | L, P, T | | |
| N194 | G, L, I, V, S, C, K, R, D, Q, Y | G, L, I, V, S, C, K, R, D, Q, Y | |
| I200 | N, F | | |
| D202 | G, I, V, N, F, Y | G, I, V, N, F, Y | G, I, V, N, F, Y |
| H203 | R | R | |
| D211 | G | | |
| V212 | L | | |
| A221 | V | | |
| P224 | L | L | L |
| D228 | N | | |
| T229 | A, S, M | A, S, M | |
| G231 | D | D | |
| T233 | S | | |
| M234 | L, I, V, T, K | L, I, V, T, K | |
| S236 | F, Y | F, Y | |
| | G, A, L, I, V, P, S, C, M, R, D, Q, F, Y, | G, A, L, I, V, P, S, C, M, R, D, Q, F, Y, | |
| T243 | W | W | |
| Y244 | H, F | | |
| S245 | T | | |
| N246 | S, K, D | | |
| D247 | N | N | |
| G251 | R | | |
| F260 | C | | |
| G266 | S | | |
| K275 | E | | |
| I276 | V | | |
| I277 | V | | |
| T280 | A | | |

TABLE 3-continued

| Mutations with respect to SEQ ID NO: 5 | | | |
|---|---|---|---|
| Position | Preferred | More Preferred | Most Preferred |
| L290 | H | | |
| D293 | R, H | | |
| G294 | A | | |
| T295 | S | | |
| T297 | N | | |
| T299 | I, S | | |
| S301 | C | | |
| K304 | R | | |
| F306 | L, Y | | |
| N310 | D, E | | |
| S311 | G, D, N | G, D, N | G, D, N |
| V313 | I | | |
| I314 | F | | |
| N318 | I, H, D, Y | I, H, D, Y | I, D, Y |
| D320 | I, V, E, N | I, V, E, N | I, V, N |
| I321 | N | | |
| T325 | A, I | | |
| N327 | Y | | |
| T335 | I | I | I |
| A340 | G, S, T | G, S, T | |
| F341 | C | | |
| D343 | A | | |
| T344 | M | M | |
| D345 | E | | |
| D346 | G, A, V, E | G, A, V, E | G, A, V, E |
| Q349 | K, R | K, R | K, R |
| H350 | Y | | |
| A354 | T | | |
| K355 | Q | Q | |
| A358 | E | | |
| Q361 | R | | |

TABLE 3-continued

| Mutations with respect to SEQ ID NO: 5 | | | |
|---|---|---|---|
| Position | Preferred | More Preferred | Most Preferred |
| Q362 | G, R, H | | |
| G363 | P | | |
| M364 | L, S | | |
| V367 | A | | |
| D373 | E | | |
| Y374 | A, P, S, C, R, H, D | A, P, S, C, R, H, D | |
| A375 | G, L, V, T, C, M, R, D, E, N, Q, Y | G, L, V, T, C, M, R, D, E, N, Q, Y | |
| A376 | T | | |
| P386 | L, S | | |
| T387 | A, S | A, S | |
| D390 | G, E | G, E | |
| T392 | S, M, K | S, M, K | M |
| T393 | A, I, V, S | A, I, V, S | A, I, V |
| P394 | C | | |
| T400 | S | | |
| P402 | S | | |
| T403 | K | | |
| D404 | N | | |
| D410 | G | | |
| N417 | Y | | |
| S418 | P | | |
| T421 | I | | |
| Y422 | F | F | F |

Particularly preferred is a polypeptide as defined above, further characterized by comprising a modification of SEQ ID NO: 5. which is a specific modification as given in the following Table 3a. Each of these polypeptides defines a mutant version of the polypeptide given in SEQ ID NO: 5.

TABLE 3a

| specific mutants with respect to SEQ ID NO: 5: | |
|---|---|
| Mutant Number | Mutants with respect to Seq. ID NO: 5 |
| 1 | G4C, A72C, Q349K |
| 2 | G4C, A72C, T344M, Q349K |
| 3 | G4C, A72C, T344M, D346G, Q349R |
| 4 | G4C, A72C, D320V, Q349K |
| 5 | G4C, A72C, P224L, F306Y, Q349R |
| 6 | G4C, A72C |
| 7 | A72V, D346A, T393A |
| 8 | G4C, A72C, Q349R |
| 9 | G4C, W40R, A72C, T344M, Q349K |
| 10 | A72V, D320V, D346A |
| 11 | G4C, A72C, N194Y, T243L, Q349R, Y374S, A375R |
| 12 | G4C, E65V, A72C, Y244H, Q349R |
| 13 | G4C, A72C, D202G, D320N, Q349R, A358E |
| 14 | G4C, A72C, D320V, Q349R |
| 15 | G4C, A72C, Q349K, S86T |
| 16 | A72V, T335I, D346A, T393A |
| 17 | G4C, A72C, E183V, K304R, Q349K |
| 18 | G4C, A72C, T243G, Q349R, Y374P, A375M |
| 19 | G4C, A72C, N194V, T243M, Q349R, Y374A, A375T |
| 20 | G4C, D64N, A72C, Q349R, A358E |
| 21 | G4C, A72C, Q349K, Q28R, S193T |
| 22 | G4C, A72C, E183K, Q349K |
| 23 | G4C, A72C, S311N, Q349K |
| 24 | G4C, A72C, N194K, Q349R, Y374P, A375Q |
| 25 | G4C, A72C, D181N, Q349K |
| 26 | W40R, D320V, Q349K, T393A |
| 27 | W40R, T335I, D346A, T393A |
| 28 | Q1L, G4C, A72C, D181N, E183K, N327Y, Q349R |
| 29 | A72C, T335I, Q349R |
| 30 | G4C, A72C, N194K, T243P, Q349R, Y374H, A375E |
| 31 | G4C, A72V, Q349R, P462del |
| 32 | G4C, A72C, S236Y, Q349R |
| 33 | G4C, A72C, S311G, Q349K |
| 34 | A72V, D320V, T335I, D346A, T393A |

TABLE 3a-continued

| specific mutants with respect to SEQ ID NO: 5: | |
|---|---|
| Mutant Number | Mutants with respect to Seq. ID NO: 5 |
| 35 | G4C, A72C, S86T, M234V, Q349K |
| 36 | Q1L, G4C, Q28R, E65V, A72C, K159KCGRNK, D181N, E183M, P224L, S311G, D320I, D346E, Q349K, T393V, Y422F |
| 37 | G4C, A72C, G251R, Q349R |
| 38 | G4C, A72C, Q349K, D320V |
| 39 | G4C, A72C, E183K, Q349R |
| 40 | Q1L, G4C, A72C, H203R, Q349K |
| 41 | G4C, W40R, A72C, Q349K |
| 42 | G4C, A72C, Q349R, V367A |
| 43 | Q1L, G4C, A6V, C50S, A72C, I180N, D181N, E183K, Q349R |
| 44 | G4C, A72C, S311G, D320V, Q349K |
| 45 | Q1L, G4C, A72C, D181N, E183K, T243S, Q349R, P386S |
| 46 | Q1L, G4C, A72C, K154R, Q349K, T393I |
| 47 | G4C, A72C, N194G, T243F, Q349R, Y374P, A375R |
| 48 | A72V, D320V, D346A, T393A |
| 49 | A72C, Q349K |
| 50 | G4C, A72C, E183V, Q349K |
| 51 | G4C, A72C, E183K, N318Y, Q349K |
| 52 | W40R, A221V |
| 53 | G4C, A72C, K92R, Q349K |
| 54 | Q1L, G4C, A72C, S90T, D181N, E183K, Q349R |
| 55 | G4C, A72C, Q349R, Y422F |
| 56 | G4C, T48A, A72C, Q349R |
| 57 | E187K, D320V |
| 58 | G4C, S24N, E65K, A72C, Q349R |
| 59 | Q1L, G4C, A72C, S193P, Q349K |
| 60 | Q1L, G4C, A72C, delV152-K159, D181N, E183K, Q349R |
| 61 | Q1L, G4C, A72C, Q349K |
| 62 | Q1L, G4C, A72C, D181N, E183K, M234L, V313I, Q349R |
| 63 | Q1L, G4C, A72C, D181N, E183K, I200N, Q349R |
| 64 | G4C, A72C, N194K, T243Y, Q349R, A375N |
| 65 | Q1L, G4C, Q28R, A72C, Q349K |
| 66 | G4C, E65V, A72C, Q349R |
| 67 | D320V, Q349K |
| 68 | Q1L, G4C, A72C, S311G, Q349K |
| 69 | G4C, A72C, T243Q, Q349R, Y374P, A375M |
| 70 | Q1L, G4C, A72C, D320V, Q349R |
| 71 | Q1L, G4C, T15S, A72C, Y244F, Q349K |
| 72 | G4C, A72C, E183K, D346E, Q349R |
| 73 | Q1L, G4C, A72C, Q349K, T392M |
| 74 | G4C, A72C, D202N, S311N, Q349R |
| 75 | G4C, A72C, N194D, T243A, Q349R, Y374P, A375Y |
| 76 | G4C, A72C, N194Y, T243V, Q349R, Y374P |
| 77 | Q1L, G4C, A72C, Q349R |
| 78 | G4C, Q28R, E65K, A72C, S86T, D202N, H203R, S311N, D320I, A340G, D346A, Q349K, T393A, Y422F |
| 79 | G4C, A72C, D202N, Q349R |
| 80 | G4C, A72C, P224L, Q349R |
| 81 | Q1L, G4C, A72C, D181N, E183K, T229M, A340T, Q349R |
| 82 | Q1L, G4C, A72C, D181N, Q349R |
| 83 | G4C, A72C, D320V, D346V, Q349K |
| 84 | Q1L, G4C, A72C, V152A, Q349K |
| 85 | Q1L, G4C, A72C, Q349K, Y422F |
| 86 | G4C, A72C, D202V, D320V, Q349K |
| 87 | Q1L, G4C, A72C, Y155S, D181N, E183K, Q349R |
| 88 | Q1L, G4C, A72C, D181N, D247N, Q349K |
| 89 | Q1L, G4C, A68T, A72C, Q349K |
| 90 | Q1L, G4C, D64N, A72C, Q349K |
| 91 | G4C, A72C, D181N, P224L, Q349K |
| 92 | G4C, A72C, N194I, T243Y, Q349R, Y374P, A375R |
| 93 | Q1L, G4C, A72C, E183K, Q349R |
| 94 | G4C, A72C, S311G, Q349R |
| 95 | Q1L, G4C, A72C, S311N, Q349K |
| 96 | Q1L, G4C, A72C, S86T, Q349R |
| 97 | Q1L, G4C, A72C, D181N, E183K, G231D, Q349R |
| 98 | Q1L, G4C, A72C, S89N, D181N, E183K, Q349R |
| 99 | Q1L, G4C, E65K, A72C, Q349K |
| 100 | Q1L, Q2P, G4C, W40R, E65M, A72C, S86T, S192L, D202N, H203R, S311D, D320I, T335I, D346G, Q349K, T392M, Y422F |
| 101 | Q1L, G4C, S24T, T26I, Q28R, N29Y, G30A, E65V, A68T, A72C, Y155C, D181N, E183M, Q190K, P224L, S311G, D320I, D346E, Q349K, T393V, Y422F |
| 102 | G4C, A72C, E183K, D202Y, N310D, Q349R |
| 103 | G4C, A72C, N194I, T243D, Q349R, Y374P, A375Y |
| 104 | Q1L, G4C, A72C, D181N, E183K, Q349R |

TABLE 3a-continued

| specific mutants with respect to SEQ ID NO: 5: | |
|---|---|
| Mutant Number | Mutants with respect to Seq. ID NO: 5 |
| 105 | G4C, Q28R, A72C, S86T, E183K, P224L, S311N, N318Y, T335I, D346G, Q349R, T393I |
| 106 | Q1L, G4C, A72C, D181N, Q349K |
| 107 | Q1L, G4C, A72C, D181N, E183K, T243I, N246D, Q349R |
| 108 | Q1L, G4C, G23N, A72C, D110G, I116V, L119I, D181N, E183K, D211G, D293R, N310D, Q349R, Q362R, G363P, M364S |
| 109 | Q1L, G4C, Q28R, E65V, A68T, A72C, Y155C, D181N, E183M, P224L, S311G, D320I, D346E, Q349K, T393V, Y422F |
| 110 | Q1L, G4C, A72C, S86T, D181N, E183K, Q349R, T393S |
| 111 | Q1L, G4C, G23N, A72C, V84A, D110G, D111H, I116E, F117Y, K118A, D181N, E183K, D293R, T295S, Q349R, M364L |
| 112 | Q1L, G4C, A72C, A145T, H203R, Q349K, T403K |
| 113 | Q1L, G4C, A72C, D181N, E183K, M234I, Q349R |
| 114 | Q1L, G4C, A72C, D181N, E183K, T297N, Q349R |
| 115 | G4C, Q28R, E65M, A72C, S86T, E183K, S192I, H203R, S311N, D346E, Q349K, T392M, T393A, Y422F |
| 116 | Q1L, G4C, A72C, D202N, Q349K |
| 117 | Q1L, G4C, A72C, S99T, D181N, E183K, Q349R |
| 118 | Q1L, G4C, A72C, I200F, Q349K |
| 119 | Q1L, G4C, A31S, A72C, D181N, E183K, Q349R |
| 120 | Q1L, G4C, Q28L, A72C, D181N, E183K, Q349R |
| 121 | Q1L, G4C, A72C, D181N, E183K, T233S, Q349R |
| 122 | Q1L, G4C, A21T, A72C, D181N, E183K, Q349R |
| 123 | Q1L, G4C, A72C, D346V, Q349K |
| 124 | Q1L, G4C, Y47F, A72C, D181N, E183K, Q349R |
| 125 | Q1L, G4C, A72C, D181N, E183K, M234T, Q349R |
| 126 | Q1L, G4C, A72C, N157S, D181N, E183K, Q349R |
| 127 | G4C, A72C, N194Q, T243V, Q349R, Y374P, A375Y |
| 128 | Q1L, G4C, A72C, D181N, E183K, I314F, Q349R |
| 129 | Q1L, G4C, A72C, Q349K, T392K |
| 130 | Q1L, G4C, A72C, D181N, E183K, M234V, Q349R |
| 131 | Q1L, G4C, A21S, A72C, D181N, E183K, Q349R |
| 132 | Q1L, G4C, Q28R, E65V, A72C, D181N, E183V, D228N, S311N, N318Y, D346E, Q349R, Y422F |
| 133 | G4C, A72C, N194C, Q349R, Y374C |
| 134 | Q1L, G4C, A72C, D181N, E183K, Q349R, T400S |
| 135 | Q1L, G4C, T26I, A72C, D181N, E183K, Q349R |
| 136 | Q1L, G4C, A72C, D181N, E183K, N310D, Q349R, T392S |
| 137 | Q1L, G4C, A72C, D129N, D181N, E183K, Q190L, G266S, I276V, Q349R, P386L |
| 138 | Q1L, G4C, A72C, D181N, E183K, D202N, Q349R |
| 139 | Q1L, G4C, A72C, Y155C, D181N, E183K, Q349R |
| 140 | Q1L, G4C, Q28R, E65V, A72C, D181N, E183M, P224L, S311G, D320I, D346E, Q349K, T393V, Y422F |
| 141 | Q1L, G4C, A72C, D181N, E183K, N246K, Q349R |
| 142 | G4C, W40R, E65V, A72C, S86T, D181N, E183K, D202I, H203R, S311D, D320N, D346V, Q349R, T392M, T393A, Y422F |
| 143 | Q1L, G4C, A72C, Y155C, Q349K |
| 144 | Q1L, G4C, A68T, A72C, D181N, E183K, Q349R |
| 145 | Q1L, G4C, S24T, T26I, Q28R, N29Y, G30A, Y47F, E65V, A68T, A72C, Y155C, D181N, E183M, Q190K, P224L, T229M, G231D, M234T, S311G, D320I, A340S, D346E, Q349K, D390E, T393V, Y422F |
| 146 | Q1L, G4C, W40R, E65M, A72C, S86T, S192L, D202N, H203R, S311D, D320I, T335I, D346G, Q349K, T392M, Y422F |
| 147 | Q1L, G4C, A72C, S86T, D181N, E183K, D320V, Q349R |
| 148 | G4C, Q28K, A72C, S86T, E183M, D202N, P224L, S311G, N318Y, D320N, D346A, Q349R, T392M, T393I |
| 149 | Q1L, Q2P, G4C, Q28R, W40R, E65K, A72C, D181N, S192L, D202I, H203R, P224L, S311G, D320I, D343A, D346A, Q349K |
| 150 | Q1L, G4C, Q28R, E65K, A72C, E183M, D202I, P224L, D320N, D346V, Q349K, T392M, T393V, Y422F |
| 151 | Q1L, G4C, Q28R, E65V, A72C, S86T, E183K, D202V, S311G, N318Y, D320I, D346G, Q349K, T393V, Y422F |
| 152 | Q1L, G4C, W40R, E65M, A72C, D181N, E183K, S192P, D202N, P224L, S311D, N318Y, D320V, D346G, Q349K, T392M |
| 153 | Q1L, G4C, E65V, A72C, D181N, E183K, P224L, S311G, D320N, D346G, Q349R, T392M, T393I |
| 154 | Q1L, G4C, Q28R, E65V, A72C, G151GCGRSG, D181N, E183M, P224L, S311G, D320I, D346E, Q349K, T393V, Y422F |
| 155 | Q1L, G4C, E65M, A72C, D181N, E183M, D202Y, P224L, S311D, N318Y, D320I, T335I, D346A, Q349K, T392M, T393I |
| 156 | Q1L, G4C, G23A, A72C, D110S, D111H, I116V, F117Y, K118A, L120M, D181N, E183K, D293H, G294A, N310E, Q349R, Q362G, M364S |
| 157 | Q1L, G4C, A72C, D181N, E183K, Q349R, T421I |

TABLE 3a-continued

| specific mutants with respect to SEQ ID NO: 5: | |
|---|---|
| Mutant Number | Mutants with respect to Seq. ID NO: 5 |
| 158 | G4C, Q28K, E65M, A72C, S86T, V152A, D181N, E183V, S192L, D202N, S311N, D320N, D346E, Q349R, T387A, T392M, T393I, Y422F |
| 159 | Q1L, G4C, W40R, E65V, A72C, S86T, E183V, G188C, S192T, D202Y, H203R, P224L, S311N, D320V, D346E, Q349K, T393V, Y422F |
| 160 | Q1L, G4C, E65M, A72C, S86T, E183M, D202N, P224L, T335I, D346G, Q349K, T392M, T393A |
| 161 | Q1L, G4C, Q28R, E65V, A72C, D181N, E183M, P224L, S311G, D320I, A340S, D346E, Q349K, D390E, T393V, Y422F |
| 162 | G4C, W40R, A72C |
| 163 | Q1L, G4C, W40R, E65K, A72C, S86T, E183K, S192L, D202Y, P224L, D320I, D346E, Q349R |
| 164 | Q1L, G4C, A21T, T26I, Q28R, E65V, A68T, A72C, Y155C, D181N, E183M, Q190K, D202N, P224L, S311G, N318Y, D320I, D346E, Q349K, T393V, Y422F |
| 165 | Q1L, G4C, Q28R, E65V, A72C, S86T, D181N, D202N, P224L, S311G, N318Y, D320I, T335I, D346E, Q349K, T393V, Y422F |
| 166 | Q1L, G4C, Q28R, E65V, A72C, E183M, S311G, D346E, Q349K, T393V, Y422F |
| 167 | Q1L, G4C, T7Q, A8S, N10T, S24T, T27Q, Q28R, N29T, V41T, G46S, Y47S, T52D, D57S, D64N, E65V, Q69K, A72C, D181N, P224L, S311G, N318Y, D320N, D346A, Q349K, T392M, T393I, Y422F |
| 168 | Q1L, G4C, Q28R, E65V, A72C, K159KCGRNK, E183M, P224L, S311G, D320I, D346E, Q349K, T393V, Y422F |
| 169 | Q1L, G4C, Q28K, W40R, E65V, A72C, D181N, E183V, S192P, D202V, H203R, S311G, D320N, D346E, Q349K, T392M, T393A, Y422F |
| 170 | Q1L, G4C, Q28R, E65V, A72C, G139S, D181N, E183M, P224L, S311G, D320I, D346E, Q349K, T393V, Y422F |
| 171 | Q1L, G4C, Q28R, E65V, A72C, S86T, D181N, E183M, D202N, P224L, S311G, N318Y, T335I, D346E, Q349K, T393V, Y422F |
| 172 | Q1L, G4C, Q28R, E65K, A72C, D181N, S311N, N318Y, D346E, Q349K, T393V, Y422F |
| 173 | Q1L, G4C, W40R, A72C, S192L, D202N, H203R, P224L, S311N, D320I, T335I, D346V, Q349R, T393I |
| 174 | Q1L, G4C, Q28K, E65K, A72C, E183M, D202N, P224L, T229S, S311G, D320I, T335I, D346V, Q349R, T393V |
| 175 | Q1L, G4C, Q28R, G30A, E65M, A72C, D181N, D202N, P224L, S311D, N318Y, D346E, Q349K, T392M, T393V, Y422F |
| 176 | Q1L, G4C, Q28R, E65V, A72C, S68T, E183M, S311N, T335I, D346E, Q349K, T393V, Y422F |
| 177 | Q1L, G4C, Q28K, E65K, A72C, D181N, D202N, S311N, N318Y, T335I, D346E, Q349K, T393V, Y422F |
| 178 | T243C, A375C, N194C, Y374C |
| 179 | Q1L, G4C, Q28K, E65K, A72C, S86T, E183M, S311G, D346V, Q349R, T392M, T393V, Y422F |
| 180 | Q1L, G4C, Q28R, E65V, A72C, D181N, E183M, S311G, D346E, Q349K, T393V, Y422F |
| 181 | Q1L, G4C, Q28R, E65V, A72C, S86T, D181N, D202N, S311N, N318Y, D320I, T335I, D346E, Q349K, T393I, Y422F |
| 182 | Q1L, G4C, Q28R, E65K, A72C, S86T, E183K, D202N, P224L, S311G, T335I, D346A, Q349K, T393V, Y422F |
| 183 | Q1L, G4C, Q28R, E65V, A72C, L120P, D181N, E183M, P224L, S311G, D320I, D346E, Q349K, T393V, Y422F |
| 184 | Q1L, G4C, Q28K, E65V, A72C, S86T, E183M, S311N, N318H, D320V, D346V, Q349K, T392M, T393A |
| 185 | Q1L, G4C, Q28K, E65V, A72C, D202N, H203R, S311G, T335I, D346V, Q349K, T393A |
| 186 | Q1L, G4C, Q28R, E65V, A72C, E183M, S311G, D320I, D346E, Q349K, T393V, Y422F |
| 187 | Q1L, G4C, Q28R, E65K, A72C, D181N, D202N, H203R, P224L, S311D, D346G, Q349K |
| 188 | Q1L, G4C, Q28R, E65M, A72C, D181N, E183M, S311G, N318Y, D320I, T335I, D346E, Q349K, D390E, T393V, Y422F |
| 189 | Q1L, G4C, T27S, Q28R, E65V, Q69R, A72C, L120P, D181N, E183M, D202N, D247N, S311G, D346E, Q349K, K355Q, T387S, T393V, Y422F |
| 190 | Q1L, G4C, Q28R, E65K, A72C, E183V, S192T, D202N, S311G, D320V, D346A, Q349K |
| 191 | Q1L, G4C, W40R, E65V, A72C, S86T, E183M, D202N, P224L, S311G, D320V, D346E, Q349R, T393I |
| 192 | Q1L, G4C, Q28N, E65K, A72C, D181N, E183M, D202N, H203R, S311G, N318Y, D320N, Q349R, T393V, Y422F |
| 193 | Q1L, G4C, Q28R, V41T, G46S, Y47S, T52D, E65V, A72C, D181N, P224L, S311D, N318Y, D320N, D346A, Q349K, T392M, T393I, Y422F |
| 194 | Q1L, G4C, Q28R, E65K, A72C, D181N, E183M, P224L, S311G, D320I, D346E, Q349K, T393V, Y422F |

TABLE 3a-continued

| specific mutants with respect to SEQ ID NO: 5: | |
|---|---|
| Mutant Number | Mutants with respect to Seq. ID NO: 5 |
| 195 | Q1L, G4C, Q28R, W40R, A72C, S86T, D181N, S192T, D202N, P224L, S311G, N318Y, D320V, D346E, Q349K, T392M, T393I |
| 196 | Q1L, G4C, A21T, T26I, Q28R, G30A, E65V, A68T, A72C, Y155C, D181N, Q190K, D202N, P224L, T229M, S311G, N318Y, D320I, T335I, D346E, Q349K, T393V, Y422F |
| 197 | Q1L, G4C, Q28K, W40R, A72C, S86T, D181N, E183M, S192I, D202Y, T299S, S311N, N318Y, D320I, D346V, Q349R, T393I |
| 198 | Q1L, G4C, Q28R, E65V, A72C, D181N, E183M, P224L, T229M, G231D, M234T, S311G, D320I, D346E, Q349K, T393V, Y422F |
| 199 | Q1L, G4C, S24T, T26I, Q28R, N29Y, G30A, E65V, A68T, A72C, Y155C, D181N, E183M, Q190K, P224L, T229M, G231D, M234T, S311G, D320I, A340S, D346E, Q349K, D390E, T393V, Y422F |
| 200 | Q1L, G4C, Q28R, E65K, A72C, E183M, P224L, S311G, D346E, Q349K, T393V, Y422F |
| 201 | Q1L, G4C, Q28R, E65V, A72C, S86T, D181N, E183M, D202N, P224L, S311G, N318Y, D346E, Q349K, T393V, Y422F |
| 202 | Q1L, G4C, Q28R, W40R, E65V, A72C, S86T, S192T, D202V, H203R, S311N, N318Y, D346A, Q349K, T392M, T393A, Y422F |
| 203 | Q1L, G4C, Q28K, E65K, A72C, D181N, H203R, P224L, S311G, D320V, D346G, Q349K, T392M, T393I |
| 204 | Q1L, G4C, Q28R, E65K, A72C, E183M, S311G, D346E, Q349K, T393V, Y422F |
| 205 | Q1L, G4C, Q28R, E65M, A72C, D181N, E183M, S311G, N318Y, D346E, Q349K, T393V, Y422F |
| 206 | Q1L, G4C, Q28R, E65V, A72C, E183K, D202I, P224L, S311G, D320I, Q349K, T393V |
| 207 | Q1L, G4C, Q28K, A72C, S86T, D181N, E183V, S192T, D202N, P224L, S311G, N318Y, D320V, D346G, Q349R, T392M, Y422F |
| 208 | G4C, Q28R, E65K, A72C, S86T, D181N, E183M, S192L, D202N, H203R, P224L, S311D, D346E, Q349R, T392M, T393A, Y422F |
| 209 | Q1L, G4C, W40R, E65K, A72C, Q109R, D181N, E183M, S192I, D202I, H203R, S245T, D346A, Q349R, T393A, Y422F |
| 210 | Q1L, G4C, Q28K, E65M, A72C, D181N, D202N, S311N, T335I, D346E, Q349K, T393I, Y422F |
| 211 | Q1L, G4C, N10D, Q28R, E65V, Q69R, A72C, D181N, E183M, P224L, S311G, D320I, D346E, Q349R, T393V, N417Y, Y422F |
| 212 | Q1L, G4C, Q28R, W40R, E65V, A72C, D202Y, H203R, P224L, T299I, N318Y, D320V, D346A, Q349K, T392M, T393A |
| 213 | G4C, Q28R, E65V, A72C, E183M, D202N, P224L, S311G, N318Y, D320V, D346G, Q349K, T392M, Y422F |
| 214 | Q1L, G4C, Q28K, A72C, S86T, E183K, S311G, D320V, D346A, Q349R, T392M, T393I, Y422F |
| 215 | Q1L, G4C, Q28R, E65M, A72C, D181N, P224L, S311N, D320N, T335I, D346E, Q349K, T392M, Y422F |
| 216 | Q1L, G4C, Q28K, E65V, A72C, D181N, D202N, S311G, T335I, D346E, Q349K, T393V, Y422F |
| 217 | Q1L, G4C, Q28R, E65K, A72C, D181N, E183M, S311N, N318Y, T335I, D346E, Q349K, T393V, Y422F |
| 218 | Q1L, G4C, Q28R, E65K, A72C, E183M, S311G, D320I, D346E, Q349K, T393V, Y422F |
| 219 | Q1L, G4C, Q28R, E65V, A72C, D181N, E183M, S311G, D320I, D346E, Q349K, T393V, Y422F |
| 220 | Q1L, G4C, W40R, E65V, A72C, S86T, D181N, S192T, D202N, H203R, P224L, S311G, N318Y, T335I, D346G, Q349K, T392M, T393V, Y422F |
| 221 | Q1L, G4C, Q28R, E65K, A72C, E183M, S311N, D320I, D346E, Q349K, T393I, Y422F |
| 222 | Q1L, G4C, T7Q, A8S, N10T, Q28R, D57S, D64N, E65V, Q69K, A72C, D181N, P224L, S311D, N318Y, D320N, D346A, Q349K, T392M, T393I, Y422F |
| 223 | Q1L, G4C, Q28R, E65M, A72C, S86T, D181N, E183M, D202N, P224L, S311G, D346A, Q349K, T393I, Y422F |
| 224 | Q1L, G4C, N10D, Q28R, E65V, Q69R, A72C, K92R, K118Q, D181N, E183M, D202N, T280A, S311G, T335I, D346E, Q349K, K355Q, T387S, T393V, D404N, Y422F |
| 225 | Q1L, G4C, Q28R, E65M, A72C, E183M, D202N, S311G, D320I, T335I, D346E, Q349K, T393I, Y422F |
| 226 | Q1L, G4C, Q28K, E65K, A72C, D181N, E183M, D202N, S311D, D320V, T335I, D346G, Q349K, T393I, Y422F |
| 227 | Q1L, G4C, Q28K, E65K, A72C, S86T, P224L, S311N, D320I, T335I, D346E, Q349K, T393V, Y422F |
| 228 | Q1L, G4C, Q28R, E65V, A72C, S86T, D181N, E183M, D202N, P224L, S311N, D320I, D346E, Q349K, T393V, Y422F |
| 229 | G4C, E65K, A72C, S86T, E183M, D202I, P224L, S311N, N318Y, D320N, T335I, D346V, Q349R, T393V, Y422F |

TABLE 3a-continued specific mutants with respect to SEQ ID NO: 5:

| Mutant Number | Mutants with respect to Seq. ID NO: 5 |
|---|---|
| 230 | Q1L, G4C, Q28R, E65K, A72C, D202N, S311N, T335I, D346E, Q349K, T393I, Y422F |
| 231 | Q1L, G4C, E65V, A72C, D181N, E183K, D202G, Q349R |
| 232 | Q1L, G4C, Q28R, E65K, A72C, E183M, P224L, S311G, D320I, D346E, Q349K, T393V, Y422F |
| 233 | Q1L, G4C, Q28R, E65V, A72C, D181N, E183M, P224L, F306L, S311G, D320I, D346E, Q349K, T393V, Y422F |
| 234 | Q1L, G4C, Q28R, E65V, A72C, S86T, D202N, P224L, S311G, N318Y, D320I, D346A, Q349K, T393I, Y422F |
| 235 | Q1L, G4C, Q28K, E65K, A72C, D181N, E183K, S192P, P224L, S311G, N318Y, D320V, D346E, Q349R, T392M, T393I, Y422F |
| 236 | Q1L, G4C, Q28K, E65M, A72C, S86T, E183M, H203R, S311D, D320V, T335I, D346E, Q349R, T393A |
| 237 | Q1L, G4C, Q28R, A72C, D181N, E183V, D202I, H203R, P224L, S311D, D320V, D346V, Q349R, T392M, T393I |
| 238 | Q1L, G4C, Q28K, W40R, E65K, A72C, S86T, D181N, E183K, S192L, D202I, H203R, S311N, D320N, D346V, Q349K, T392M, T393A, Y422F |
| 239 | G4C, E65V, A72C, S86T, Y155H, D181N, E183V, Q190K, P224L, S311N, D320V, D346V, Q349K, T392M, T393V, Y422F |
| 240 | Q1L, G4C, Q28R, E65M, A72C, S86T, E183M, D202N, S311D, N318Y, D320N, T335I, D346A, Q349R, T392M, T393I, Y422F |
| 241 | Q1L, G4C, Q28R, E65V, A72C, D181N, E183M, S311N, N318Y, D320I, T335I, D346E, Q349K, T393V, Y422F |
| 242 | Q1L, G4C, Q28R, E65K, A72C, S86T, D181N, D202N, S311G, D346E, Q349K, T393I, Y422F |
| 243 | Q1L, G4C, Q28R, E65K, A72C, D181N, D202N, S311N, N318Y, D320I, D346E, Q349K, T393I, Y422F |
| 244 | Q1L, G4C, T7Q, A8S, N10T, S24T, T27Q, Q28R, N29T, D57S, D64N, E65V, Q69K, A72C, D181N, P224L, S311D, N318Y, D320N, D346A, Q349K, T392M, T393I, Y422F |
| 245 | Q1L, G4C, Q28R, E65K, A72C, S86T, D202N, S311G, N318Y, D320I, D346A, Q349K, T393I, Y422F |
| 246 | Q1L, G4C, Q28R, A72C, D181N, S311G, N318Y, D320V, D346E, Q349K, T393I, Y422F |
| 247 | Q1L, G4C, Q28R, E65K, A72C, D181N, E183M, S311G, D320I, D346E, Q349K, T393V, Y422F |
| 248 | Q1L, G4C, Q28R, E65K, A72C, D181N, E183M, S311G, D346E, Q349K, T393V, Y422F |
| 249 | Q1L, G4C, Q28R, E65V, A72C, E183M, D202N, S311N, D320I, D346E, Q349K, T393V, Y422F |
| 250 | Q1L, G4C, Q28R, E65K, A72C, E183M, S311G, T335I, D346E, Q349K, T393V, Y422F |
| 251 | Q1L, G4C, Q28R, E65V, A72C, S86T, D181N, D202N, S311N, N318Y, T335I, D346E, Q349K, T393V, Y422F |
| 252 | Q1L, G4C, E65M, A72C, S86T, E183K, D202Y, S311G, D320N, T335I, D346A, Q349K, T393V, Y422F |
| 253 | Q1L, G4C, Q28R, E65V, A72C, S86T, E183M, D202N, P224L, S311N, D320I, T335I, A340S, D346A, Q349K, T393V, Y422F |
| 254 | Q1L, G4C, Q28K, E65K, A72C, S86T, D181N, E183M, H203R, P224L, S311D, D320I, D346E, Q349R, T392M, Y422F |
| 255 | Q1L, G4C, Q28K, E65V, A72C, S86T, D181N, E183M, P224L, S311G, D320I, D346E, Q349K, T393V, Y422F |
| 256 | Q1L, G4C, Q28K, N29Y, E65K, A72C, D181N, S311G, T335I, D346E, Q349K, T393V, Y422F |
| 257 | Q1L, G4C, Q28K, E65M, A72C, E183M, S311G, D346E, Q349K, T393V, Y422F |
| 258 | Q1L, G4C, Q28K, E65V, A72C, S86T, D181N, E183K, D202N, S311N, N318Y, D320N, T335I, D346A, Q349K, T392M, T393V |
| 259 | Q1L, G4C, Q28K, E65K, A72C, S86T, D181N, E183M, D202N, S311G, N318Y, T335I, D346E, Q349K, T393I, Y422F |
| 260 | Q1L, G4C, Q28R, E65K, A72C, E183V, S192T, D202N, S311G, D320V, D346A, Q349K, T393V |
| 261 | Q1L, G4C, Q28R, E65V, A72C, E183M, D202N, S311N, N318Y, D320I, T335I, D346E, Q349K, T393V, Y422F |
| 262 | Q1L, G4C, S24T, Q28R, E65K, A72C, D202N, S311G, T335I, D346E, Q349K, T393I, Y422F |
| 263 | Q1L, G4C, A72C, S86T, D181N, S192L, D202N, P224L, S311G, N318Y, D320V, T335I, D346G, Q349K, T393I |
| 264 | Q1L, G4C, Q28R, E65V, A72C, D181N, P224L, S311D, N318Y, D320N, D346A, Q349K, T392M, T393I, Y422F |
| 265 | Q1L, G4C, Q28R, E65M, A72C, D181N, E183M, D202N, P224L, S311G, D346A, Q349K, T393I, Y422F |
| 266 | Q1L, G4C, Q28K, E65V, A72C, S86T, E183V, S192I, D202V, D320I, T335I, D346V, Q349K, T392M, T393I, Y422F |

TABLE 3a-continued

| specific mutants with respect to SEQ ID NO: 5: | |
|---|---|
| Mutant Number | Mutants with respect to Seq. ID NO: 5 |
| 267 | Q1L, G4C, Q28K, E65M, A72C, S86T, D181N, E183M, D202N, P224L, S311G, D320I, T335I, D346E, Q349K, T393V, Y422F |
| 268 | Q1L, G4C, Q28K, A72C, D181N, D202I, S311D, N318Y, T335I, D346E, Q349K, T392M, Y422F |
| 269 | Q1L, G4C, Q28R, E65V, A72C, D181N, E183M, P224L, S311G, D320N, D346E, Q349K, T393V, Y422F |
| 270 | Q1L, G4C, Q28K, E65V, A72C, D181N, E183M, D202N, S311G, N318Y, D346E, Q349K, T393I, Y422F |
| 271 | Q1L, G4C, Q28K, E65K, A72C, D181N, D202N, S311G, N318Y, D346A, Q349K, T393I, Y422F |
| 272 | Q1L, G4C, Q28R, E65K, A72C, S86T, E183M, D202N, D320I, T335I, D346A, Q349K, T392M, Y422F |
| 273 | Q1L, G4C, Q28K, E65M, A72C, S86T, E183M, S311N, N318Y, D320I, T335I, D346E, Q349K, T393I, Y422F |
| 274 | Q1L, G4C, E65M, A72C, S86T, E183V, S192L, D202I, H203R, P224L, S311G, N318Y, D320V, D346A, Q349K |
| 275 | Q1L, G4C, T7Q, A8S, N10T, Q28R, E65V, A72C, D181N, P224L, S311D, N318Y, D320N, D346A, Q349K, T392M, T393I, Y422F |
| 276 | Q1L, G4C, E65K, A72C, S86T, D202V, S311N, D320V, T335I, D346V, Q349R, T392M, Y422F |
| 277 | Q1L, G4C, Q28R, E65K, A72C, D181N, E183M, P224L, S311G, D346E, Q349K, T393V, Y422F |
| 278 | Q1L, G4C, Q28R, D57S, D64N, E65V, Q69K, A72C, D181N, P224L, S311D, N318Y, D320N, D346A, Q349K, T392M, T393I, Y422F |
| 279 | Q1L, G4C, Q28R, A72C, S86T, E183M, S192T, D202N, H203R, P224L, S311N, T335I, D346V, Q349R, T392M, T393V |
| 280 | Q1L, G4C, Q28K, E65V, A72C, D181N, D202N, S311N, D346A, Q349K, T393I, Y422F |
| 281 | G4C, Q28K, E65M, A72C, S86T, E183M, D202N, P224L, S311G, T335I, D346E, Q349K, T393V, Y422F |
| 282 | G434GAAATG, T457TAAATT, Q1L, G4C, Q28R, E65V, A72C, E183M, P224L, S311G, D320I, D346E, Q349K, T393V, Y422F |
| 283 | G4C, Q28R, E65M, A72C, S86T, D181N, E183M, D202Y, P224L, S311N, D346A, Q349K, T393I, Y422F |
| 284 | Q1L, G4C, Q28K, E65V, A72C, S86T, D181N, E183K, D202N, P224L, S311G, D320I, D346E, Q349K, T393I, Y422F |
| 285 | Q1L, G4C, T27S, Q28R, E65V, A72C, D181N, E183M, P224L, S311G, D320I, D346E, Q349K, T393V, Y422F |
| 286 | Q1L, G4C, Q28R, E65M, A72C, S86T, D181N, E183M, P224L, S311G, T335I, D346A, Q349K, T393V, Y422F |
| 287 | Q2S, G4C, A6L, T7Q, A8S, N10T, Q28R, E65V, A72C, D181N, P224L, S311D, N318Y, D320N, D346A, Q349K, T392M, T393I, Y422F |
| 288 | Q1L, G4C, Q28R, E65V, A72C, S86T, D202N, P224L, S311G, D320I, D346E, Q349K, T393V, Y422F |
| 289 | Q1L, G4C, Q28K, E65V, A72C, E183M, D202N, S311G, D320I, D346E, Q349K, T393V, Y422F |
| 290 | Q1L, G4C, Q28R, E65K, A72C, D181N, P224L, S311N, N318Y, D320I, D346E, Q349K, T393V, Y422F |
| 291 | Q1L, G4C, Q28R, E65M, A72C, S90F, D181N, P224L, S311G, N318Y, D346E, Q349K, T393I, Y422F |
| 292 | G4C, Q28R, A72C, S86T, D181N, E183V, S192L, D202V, N246S, S311D, N318Y, D320V, D346A, Q349K, T393V |
| 293 | Q1L, G4C, Q28K, E65V, A72C, D181N, E183M, D202N, P224L, S311N, N318Y, D320I, T335I, D346A, Q349K, T393I, Y422F |
| 294 | Q1L, G4C, Q28R, A72C, S86T, E183M, S192L, H203R, S311D, D320V, T335I, D346V, Q349K |
| 295 | Q1L, G4C, Q28R, T59M, E65K, A68T, A72C, S86T, D181N, S192L, D202N, H203R, S311D, D320V, T335I, Q349R, T393A |
| 296 | Q1L, G4C, Q28R, E65V, A72C, D181N, E183M, D202N, P224L, S311G, N318Y, T335I, D346E, Q349K, T393V, Y422F |
| 297 | Q1L, G4C, Q28R, E65V, A72C, D181N, E183M, P224L, S311G, D320I, D346E, Q349K, K355Q, T393V, Y422F |
| 298 | Q1L, G4C, Q28R, E65V, A72C, D181N, E183M, P224L, S311G, N318Y, T335I, D346A, Q349K, T393V, Y422F |
| 299 | Q1L, G4C, Q28R, E65M, A72C, S86T, D181N, E183M, S311N, N318Y, T335I, D346E, Q349K, T393V, Y422F |
| 300 | Q1L, G4C, E65M, A72C, E183M, D202I, P224L, S311D, N318Y, D320V, T335I, D346A, Q349K, T393A, Y422F |
| 301 | Q1L, G4C, Q28R, E65V, A72C, E183M, P224L, S311G, D346E, Q349K, T393V, Y422F |
| 302 | Q1L, G4C, Q28R, E65V, A72C, S86T, D181N, E183M, S311G, N318Y, D346A, Q349K, T393V, Y422F |
| 303 | Q1L, G4C, S24T, T27Q, Q28R, N29T, E65V, A72C, D181N, P224L, S311D, N318Y, D320N, D346A, Q349K, T392M, T393I, Y422F |

TABLE 3a-continued specific mutants with respect to SEQ ID NO: 5:

| Mutant Number | Mutants with respect to Seq. ID NO: 5 |
|---|---|
| 304 | Q1L, G4C, E65V, A72C, D181N, E183M, S192T, P224L, S311G, D320V, T335I, D346G, Q349K, T393A, Y422F |
| 305 | Q1L, G4C, Q28R, E65V, A72C, D181N, E183M, D202F, S311G, N318Y, T335I, Q349K, T393V, Y422F |
| 306 | Q1L, G4C, Q28K, E65K, A72C, S86T, D181N, D202N, P224L, S311D, N318Y, D320N, D346A, Q349R, T392M, T393I, Y422F |
| 307 | Q1L, G4C, Q28R, E65V, A72C, D181N, D202N, S311N, D320I, T335I, D346E, Q349K, T393V, Y422F |
| 308 | Q1L, G4C, Q28K, E65K, A72C, D181N, D202N, P224L, S311G, N318Y, T335I, D346E, Q349K, T393V, Y422F |
| 309 | Q1L, G4C, Q28R, E65V, A72C, D181N, E183M, D202N, P224L, S311G, D320I, D346E, Q349K, T393V, Y422F |
| 310 | Q1L, G4C, Q28R, E65V, A72C, D181N, E183M, D202N, S311N, T335I, D346A, Q349K, T393V, Y422F |
| 311 | Q1L, G4C, Q28K, E65K, A72C, S86T, E183M, P224L, S311G, N318Y, D320I, T335I, D346E, Q349K, T393V, Y422F |
| 312 | Q1L, G4C, A21T, T26I, Q28R, G30A, E65V, A68T, A72C, Y155C, D181N, Q190K, D202N, T229M, S311G, D320I, T335I, D346E, Q349K, T393V, Y422F |
| 313 | Q1L, G4C, Q28K, E65M, A72C, D181N, E183M, S311G, T335I, D346E, Q349K, T393V, Y422F |
| 314 | Q1L, G4C, Q28R, E65V, A72C, D181N, E183M, P224L, S311G, D320I, D346E, Q349K, T393V, D404N, Y422F |
| 315 | Q1L, G4C, Q28R, E65V, A72C, E183M, D202N, P224L, S311G, N318Y, T335I, D346E, Q349K, T393V, Y422F |
| 316 | Q1L, G4C, Q28R, E65V, A72C, D181N, E183M, P224L, T280A, S311G, D320I, D346E, Q349K, T393V, Y422F |
| 317 | Q1L, G4C, Q28R, E65V, Q69R, A72C, D181N, E183M, P224L, S311G, D320I, D346E, Q349K, T393V, Y422F |
| 318 | Q1L, G4C, Q28R, E65V, A72C, D181N, E183M, P224L, K275E, S311G, D320I, D346E, Q349K, T393V, Y422F |
| 319 | Q1L, G4C, Q28K, E65V, A72C, E183K, D202N, P224L, S311N, D320I, D346E, Q349K, T393V, Y422F |
| 320 | Q1L, G4C, Q28K, E65V, A72C, D181N, E183M, S311G, N318Y, D320I, D346A, Q349K, T393I, Y422F |
| 321 | Q1L, G4C, S24T, T26I, Q28R, N29Y, G30A, E65V, A72C, D181N, E183M, P224L, S311G, D320I, D346E, Q349K, T393V, Y422F |
| 322 | Q1L, G4C, Q28R, E65M, A72C, E183M, S311G, D320I, D346A, Q349K, T393V, Y422F |
| 323 | Q1L, G4C, Q28R, E65V, A72C, D181N, E183M, D202N, S311G, D346E, Q349K, T393I, Y422F |
| 324 | Q1L, G4C, Q28R, E65V, A72C, E183M, P224L, S311G, D320I, D346E, Q349K, T393V, Y422F |
| 325 | Q1L, G4C, Q28K, E65K, A72C, D181N, E183M, S311G, N318Y, D320I, T335I, D346E, Q349K, T393V, Y422F |
| 326 | Q1L, G4C, Q28R, E65V, A72C, S311G, N318Y, D320I, T335I, D346E, Q349K, T393V, Y422F |
| 327 | Q1L, G4C, S24C, Q28R, G30A, E65V, A72C, Y155C, D181N, Q190K, D202N, P224L, S311G, T335I, D346E, Q349K, D390E, T393V, Y422F |
| 328 | Q1L, G4C, Q28R, E65V, A72C, D181N, E183M, P224L, S311G, D320I, D346E, Q349K, T393V, P402S, Y422F |
| 329 | Q1L, G4C, Q28R, E65K, A72C, E183M, D202N, P224L, S311N, N318Y, T335I, D346E, Q349K, T393V, Y422F |
| 330 | Q1L, G4C, A21T, T26I, Q28R, N29Y, E65V, A72C, Y155C, D181N, D202N, P224L, M234T, S311G, D320I, D346E, Q349K, D390E, T393V, Y422F |
| 331 | Q1L, G4C, Q28R, E65K, A72C, S86T, D202N, P224L, S311D, D320N, T335I, D346V, Q349K, T392M, T393V, Y422F |
| 332 | Q1L, G4C, Q28R, E65V, A72C, S86T, E183K, D202N, S311G, N318Y, D320I, D346A, Q349K, T393V, Y422F |
| 333 | Q1L, G4C, W40R, E65M, A72C, S86T, E183V, S192L, D202I, H203R, P224L, S311G, N318Y, D320V, D346A, Q349K |
| 334 | Q1L, G4C, Q28R, E65V, A72C, D181N, E183M, P224L, S311G, D346E, Q349K, T393V, Y422F |
| 335 | Q1L, G4C, Q28R, E65V, A72C, K118Q, D181N, E183M, P224L, D247N, S311G, D320I, D346E, Q349K, T393V, Y422F |
| 336 | Q1L, G4C, Q28R, E65V, A72C, D181N, E183M, D202N, P224L, S311N, D320I, D346E, Q349K, T393V, Y422F |
| 337 | Q1L, G4C, Q28R, E65V, A72C, S86T, D202N, P224L, S311G, N318Y, T335I, D346E, Q349K, T393V, Y422F |
| 338 | Q1L, G4C, Q28K, E65M, A72C, D181N, E183M, D202N, S311G, N318Y, D346A, Q349K, T393V, Y422F |
| 339 | Q1L, G4C, Q28R, E65V, A72C, D181N, E183M, P224L, S311G, D320I, D346E, Q349K, T393V, Y422F, P454PVRPQP |
| 340 | Q1L, G4C, Q28R, A72C, D181N, E183V, S192M, D202N, P224L, S311D, N318Y, D320N, D346E, Q349R, T393V, Y422F |

TABLE 3a-continued

| specific mutants with respect to SEQ ID NO: 5: | |
|---|---|
| Mutant Number | Mutants with respect to Seq. ID NO: 5 |
| 341 | Q1L, G4C, Q28R, A72C, S86T, D181N, S192L, D202N, P224L, S311G, N318Y, D320V, T335I, D345E, D346A, Q349K, Y422F |
| 342 | Q1L, G4C, Q28R, E65V, A72C, S86T, D181N, E183K, P224L, S311G, N318Y, D320I, D346A, Q349K, T393V, Y422F |
| 343 | Q1L, G4C, Q28R, G30A, E65V, A68T, A72C, D181N, E183M, D202N, P224L, D346E, Q349K, T393V, Y422F |
| 344 | Q1L, G4C, Q28R, E65V, A72C, K92R, L120P, D181N, E183M, D202N, S236F, T280A, S311G, D346E, Q349K, K355Q, T387S, T393V, P402S, D404N, Y422F |
| 345 | Q1L, G4C, Q28R, E65V, A72C, D181N, D202N, S236F, S311G, T335I, D346E, Q349K, T387S, T393V, Y422F |
| 346 | Q1L, G4C, Q28R, E65M, A72C, D181N, E183K, D202N, P224L, S311G, D320I, D346E, Q349K, T393V, Y422F |
| 347 | Q1L, G4C, A21T, T26I, Q28R, G30A, E65V, A68T, A72C, Y155C, D181N, E183M, Q190K, D202N, S311G, D320I, D346E, Q349K, T393V, Y422F |
| 348 | Q1L, G4C, Q28R, E65V, A72C, D181N, D202N, S311G, T335I, D346A, Q349K, T393I, Y422F |
| 349 | Q1L, G4C, Q28R, E65V, A72C, D181N, E183M, P224L, D247N, S311G, D320I, D346E, Q349K, T387S, T393V, Y422F |
| 350 | Q1L, G4C, Q28R, E65V, A72C, D181N, D202N, P224L, S311G, D346A, Q349K, T393V, Y422F |
| 351 | Q1L, G4C, Q28R, E65V, A72C, K92R, K118Q, D181N, E183M, D202N, S236F, S311N, N318I, D346E, Q349K, K355Q, T387S, T393V, D404N, Y422F |
| 352 | Q1L, G4C, T27S, Q28R, E65V, Q69R, A72C, K118Q, D181N, E183M, D202N, D247N, I277V, S311G, T335I, D346E, Q349K, K355Q, T393V, Y422F |
| 353 | Q1L, G4C, Q28R, G30A, E65V, A72C, Y155C, D181N, E183M, D202N, M234T, S311G, D346E, Q349K, T393V, Y422F |
| 354 | Q1L, G4C, Q28R, E65V, Q69R, A72C, K92R, D181N, D202N, D247N, I277V, S311G, N318D, T335I, D346E, Q349K, K355Q, T387S, T393V, Y422F |
| 355 | Q1L, G4C, T27S, Q28R, E65V, Q69R, A72C, D181N, D202N, S236F, I277V, S311G, T335I, D346E, Q349K, K355Q, T387S, T393V, Y422F |
| 356 | Q1L, G4C, N10D, Q28R, E65V, Q69R, A72C, K92R, K118Q, D181N, E183M, D202N, S311G, T335I, D346E, Q349K, T387S, T393V, Y422F |
| 357 | Q1L, G4C, A21T, Q28R, G30A, E65V, A72C, Y155C, D181N, E183M, D202N, M234T, S311G, T335I, D346E, Q349K, T393V, Y422F |
| 358 | Q1L, G4C, Q28R, E65V, A72C, D181N, E183M, P224L, S311G, D320I, D346E, Q349K, T393V, Y422F, T457TAAATT |
| 359 | Q1L, G4C, T26I, Q28R, E65V, A68T, A72C, Y155C, D181N, Q190K, D202N, P224L, M234T, S311G, D320I, D346E, Q349K, D390E, T393V, Y422F |
| 360 | Q1L, G4C, Q28K, E65V, A72C, S86T, E183K, S192L, D202N, D320N, T335I, D346A, Q349R, T393A, Y422F |
| 361 | Q1L, G4C, Q28R, E65V, A72C, D181N, E183M, P224L, S236F, S311G, D320I, D346E, Q349K, T393V, Y422F |
| 362 | Q1L, G4C, T26I, Q28R, E65V, A68T, A72C, Y155C, D181N, D202N, M234T, S311G, T335I, D346E, Q349K, T393V, Y422F |
| 363 | Q1L, G4C, A21T, T26I, Q28R, N29Y, E65V, A72C, Y155C, D181N, E183M, D202N, P224L, M234T, S311G, D320I, T335I, A340S, D346E, Q349K, D390E, T393V, Y422F |
| 364 | Q1L, G4C, Q28R, E65K, A72C, D202I, P224L, S311G, N318Y, D320V, T335I, D346A, Q349R, T392M, T393A |
| 365 | Q1L, G4C, E65M, A72C, S86T, E183V, D202I, P224L, S311G, N318Y, D320V, D346A, Q349K |
| 366 | Q1L, G4C, N10D, Q28R, E65V, A72C, K92R, D181N, E183M, D202N, S311G, D346E, Q349K, T387S, T393V, Y422F |
| 367 | Q2S, G4C, A6L, T7Q, A8S, N10T, Q28K, E65M, A72C, S86T, E183M, D202N, P224L, S311G, D320I, T335I, D346E, Q349K, T393V, Y422F |
| 368 | Q2S, G4C, A6L, T7Q, A8S, N10T, S24T, T26I, Q28R, N29Y, G30A, E65V, A72C, E183M, P224L, S311G, D320I, D346E, Q349K, T393V, Y422F |
| 369 | Q1L, G4C, Q28R, E65V, A72C, K92R, D181N, E183M, P224L, I277V, S311G, D320I, D346E, Q349K, T393V, Y422F |
| 370 | Q2S, G4C, A6L, T7Q, A8S, N10T, Q28R, E65V, A72C, E183M, P224L, S311G, D320I, D346E, Q349K, T393V, Y422F |
| 371 | Q2S, G4C, A6L, T7Q, A8S, N10T, Q28R, E65V, A72C, G151GCGRSG, E183M, P224L, S311G, D320I, D346E, Q349K, T393V, Y422F |
| 372 | Q2S, G4C, A6L, T7Q, A8S, N10T, Q28R, E65V, A72C, K159KCGRNK, E183M, P224L, S311G, D320I, D346E, Q349K, T393V, Y422F |
| 373 | Q2S, G4C, A6L, T7Q, A8S, N10T, Q28K, E65K, A72C, E183M, S311G, N318Y, D320I, T335I, D346E, Q349K, T393V, Y422F |
| 374 | Q2S, G4C, A6L, T7Q, A8S, N10T, Q28K, E65V, A72C, E183M, D202N, P224L, S311G, T335I, D346E, Q349K, T393V, Y422F |

TABLE 3a-continued

| specific mutants with respect to SEQ ID NO: 5: | |
|---|---|
| Mutant Number | Mutants with respect to Seq. ID NO: 5 |
| 375 | Q2S, G4C, A6L, T7Q, A8S, N10T, Q28R, E65M, A72C, S86T, E183M, S311N, N318Y, T335I, D346E, Q349K, T393V, Y422F |
| 376 | Q2S, G4C, A6L, T7Q, A8S, N10T, Q28R, E65M, A72C, E183M, S311G, N318Y, D346E, Q349K, T393V, Y422F |
| 377 | Q2S, G4C, A6L, T7Q, A8S, N10T, Q28R, E65V, A72C, E183M, D202N, P224L, S311G, N318Y, T335I, D346E, Q349K, T393V, Y422F |
| 378 | Q2S, G4C, A6L, T7Q, A8S, N10T, Q28R, E65V, A72C, E183M, P224L, S311G, N318Y, T335I, D346A, Q349K, T393V, Y422F |
| 379 | Q2S, G4C, A6L, T7Q, A8S, N10T, Q28R, E65V, A72C, P224L, S311D, N318Y, D320N, D346A, Q349K, T392M, T393I, Y422F |
| 380 | Q2S, G4C, A6L, T7Q, A8S, N10T, Q28R, E65K, A72C, S311N, N318Y, D346E, Q349K, T393V, Y422F |
| 381 | Q2S, G4C, A6L, T7Q, A8S, N10T, Q28K, N29Y, E65K, A72C, S311G, T335I, D346E, Q349K, T393V, Y422F |
| 382 | Q2S, G4C, A6L, T7Q, A8S, N10T, S24T, T26I, Q28R, N29Y, G30A, E65V, A68T, A72C, E183M, Q190K, P224L, S311G, D320I, D346E, Q349K, T393V, Y422F |
| 383 | Q2S, G4C, A6L, T7Q, A8S, N10T, S24T, T26I, Q28R, N29Y, G30A, Y47F, E65V, A68T, A72C, E183M, Q190K, P224L, T229M, G231D, M234T, S311G, D320I, A340S, D346E, Q349K, D390E, T393V, Y422F |
| 384 | Q1L, G4C, A72C, S86T, D181N, E183K, D202V, P224L, S311G, D320V, D346E, Q349R, T393A, Y422F |
| 385 | Q1L, G4C, Q28R, E65V, A72C, K159CGRNKE183M, P224L, S311G, D320I, D346E, Q349K, T393V, Y422F |
| 386 | Q2S, G4C, A6L, T7Q, A8S, N10T, S24T, Q28R, E65K, A72C, D202N, S311G, T335I, D346E, Q349K, T393I, Y422F |
| 387 | Q2S, G4C, A6L, T7Q, A8S, N10T, Q28R, E65M, A72C, E183K, D202N, P224L, S311G, D320I, D346E, Q349K, T393V, Y422F |
| 388 | Q1L, G4C, Q28K, E65M, A72C, S86T, E183M, D202N, P224L, S311G, D320I, T335I, D346E, Q349K, T393V, Y422F |
| 389 | Q1L, G4C, S24T, T26I, Q28R, N29Y, G30A, E65V, A72C, E183M, P224L, S311G, D320I, D346E, Q349K, T393V, Y422F |
| 390 | Q1L, G4C, Q28R, E65V, A72C, D181N, E183M, P224L, S311G, D320I, D346E, Q349K, T393V, Y422F, Q1L, G4C, Q28R, E65V, A72C, E183M, P224L, S311G, D320I, D346E, Q349K, T393V, Y422F |
| 391 | Q1L, G4C, Q28R, E65V, A72C, G151GCGRSG, E183M, P224L, S311G, D320I, D346E, Q349K, T393V, Y422F |
| 392 | Q1L, G4C, Q28R, E65K, A72C, S311N, N318Y, D346E, Q349K, T393V, Y422F |
| 393 | Q1L, G4C, S24T, T26I, Q28R, N29Y, G30A, E65V, A68T, A72C, E183M, Q190K, P224L, S311G, D320I, D346E, Q349K, T393V, Y422F |
| 394 | Q1L, G4C, S24T, T26I, Q28R, N29Y, G30A, Y47F, E65V, A68T, A72C, E183M, Q190K, P224L, T229M, G231D, M234T, S311G, D320I, A340S, D346E, Q349K, D390E, T393V, Y422F |
| 395 | Q1L, G4C, A21T, T26I, Q28R, N29Y, G30A, E65V, A68T, A72C, D181N, Q190K, D202N, T229M, M234T, S311G, D320I, A340S, D346E, Q349K, D390E, T393V, Y422F |
| 396 | Q1L, G4C, N10D, T27S, Q28R, E65V, A72C, K92R, K118Q, D181N, D202N, S236F, I277V, S311G, D346E, Q349K, K355Q, T387S, T393V, D404N, N417Y, Y422F |
| 397 | Q1L, G4C, A21T, T26I, Q28R, G30A, E65V, A68T, A72C, Y155C, D181N, Q190K, D202N, P224L, T229M, S311N, D320I, D346E, Q349K, T393V, Y422F |
| 398 | Q1L, G4C, N10D, T27S, Q28R, E65V, A72C, K92R, K118Q, D181N, E183M, D202N, D247N, S311G, D320I, T335I, D346E, Q349K, T393V, Y422F |
| 399 | Q1L, G4C, T26I, Q28R, G30A, E65V, A72C, Y155C, D181N, D202N, T229M, G231D, S311G, T335I, D346E, Q349K, T393V, Y422F |
| 400 | Q1L, G4C, S24R, T26I, Q28R, G30A, E65V, A72C, D181N, E183M, D202N, P224L, S311N, T335I, D346E, Q349K, D390E, T393V, Y422F |
| 401 | Q1L, G4C, N10D, T27S, Q28R, E65V, Q69R, A72C, D181N, E183M, D202N, S236F, D247N, I277V, S311N, T335I, D346E, Q349K, T387S, T393V, N417Y, Y422F |
| 402 | Q1L, G4C, A21T, Q28R, E65V, A72C, Y155C, D181N, D202N, P224L, S311G, N318Y, D346E, Q349K, D390E, T393V, Y422F |
| 403 | Q1L, G4C, T26I, Q28R, N29Y, E65V, A68T, A72C, Y155C, D181N, E183M, D202N, P224L, M234T, S311N, N318Y, D346E, Q349K, T393V, Y422F |
| 404 | Q1L, G4C, A21T, T26I, Q28R, N29Y, E65V, A68T, A72C, Y155C, D181N, D202N, P224L, T229M, M234T, S311G, N318Y, D346E, Q349K, T393V, Y422F |
| 405 | Q1L, G4C, N10D, Q28R, E65V, A72C, K92R, K118Q, D181N, E183M, D202N, P224L, S236F, D247N, F306L, S311G, D346E, Q349K, K355Q, T393V, D404N, N417Y, Y422F |

TABLE 3a-continued

| specific mutants with respect to SEQ ID NO: 5: | |
|---|---|
| Mutant Number | Mutants with respect to Seq. ID NO: 5 |
| 406 | Q1L, G4C, N10D, Q28R, E65V, A72C, K92R, K118Q, D181N, E183M, D202N, S236F, D247N, S311G, N318I, T335I, D346E, Q349K, K355Q, T393V, Y422F |
| 407 | G4C, Q28K, E65M, A72C, S86T, G151GCGRSG, E183M, D202N, P224L, S311G, T335I, D346E, Q349K, T393V, Y422F |
| 408 | G4C, Q28K, E65M, A72C, S86T, K159KCGRNK, E183M, D202N, P224L, S311G, T335I, D346E, Q349K, T393V, Y422F |
| 409 | G4C, Q28K, E65M, A72C, S86T, G151GCGRSG, K159KCGRNK, E183M, D202N, P224L, S311G, T335I, D346E, Q349K, T393V, Y422F |
| 410 | Q1L, G4C, Q28K, E65V, A72C, D181N, E183M, D202N, P224L, S311G, T335I, D346E, Q349K, T393V, Y422F |
| 411 | Q1L, G4C, Q28K, E65V, A72C, S86T, D181N, E183K, S192L, D202V, S311G, D320I, D346V, Q349R, T393A, Y422F |
| 412 | Q1L, G4C, Q28R, E65V, A72C, S86T, D181N, D202N, P224L, S311N, N318Y, D320I, D346A, Q349K, T393V, Y422F |
| 413 | Q1L, G4C, A21T, T26I, Q28R, G30A, E65V, A68T, A72C, D181N, E183M, D202N, T229M, S311G, A340S, D346E, Q349K, T393V, Y422F |

Furthermore, the present invention provides a polypeptide having cellobiohydrolase activity comprising an amino acid sequence having at least 85%, preferably at least 95%, more preferably at least 98%, even more preferably at least 99%, and most preferably 100% sequence identity to SEQ ID NO:12 wherein one or more of the following amino acid residues of the sequence defined by SEQ ID NO: 12 are modified by substitution or deletion: Q1. S2. P12. T15. S21. G23. T26. Q28. T29. G30. V32. N37. W40. T48. C50. N54. L60. E65, K69. V84. S90. D114. E119. F120. T121. L122. L123. D132. V133. G142. S148. M149, V155. Y158. N161. T162. K166. G170. Q175. F182. I183. G191. I203. D214. I215. A224, T231. G234. I237. S248. G254. W263. G269. L282. T285. G298. Y303. N307. G308. T310, E317. L318. S322. N324. G340. S341. D345. S357. M360. V363. D369. A372. P382. S388, T389. P390. T399. S400. Q406. N413. F423. P425. I426. G427. T429. P432. G435. N436, P437. G439. N441. R442. T444. T445. T446. T447. R449. P450. A451. T452. T453. S456, S457. P458. G463. P464. S467. H459. C468. G470. G472. S474. P476. V478. C479. S481, G482. T484. V487. L488. N489. Y491. Y492. Q494. C495. L496. Preferably, this polypeptide comprises an amino acid sequence with at least 54%, preferably at least 56%, more preferably at least 58%, particularly preferably at least 60%, such as at least 62%, particularly at least 64%, such as at least 66%, and most preferably preferably at least 68% sequence identity to SEQ ID NO: 5. This polypeptide also preferably lies within the embodiment as defined above, wherein the polypeptide is temperature stable, i.e. has a high IT50 value, such as defined above, for example 62° C. or more, as described above (for more embodiments, see above, in relation to the definition of variants of SEQ ID NO: 5). The skilled person will recognize that SEQ ID NO 12: has about 68% identity with SEQ ID NO: 5. Therefore, a polypeptide derived from the polypeptide defned by SEQ ID NO: 12. which is differs from the polypeptide defined by SEQ ID NO: 12 for example by exchange of one amino acid for another, such as Q1A, for example, is a polypeptide which also has a significant degree of identity with SEQ ID: NO: 5. i.e. at least 66% or more, as defined above. Thus, the skilled person can readily recognize the common inventive concept of this invention, particular when taking into consideration the temperature stability of the polypeptides of this invention.

In a preferred embodiment, the polypeptide having cellobiohydrolase activity comprises an amino acid sequence having at least 85% sequence identity to SEQ ID NO: 12. wherein the polypeptide has the amino acid sequence of SEQ ID NO: 12 wherein one or more of the following amino acid residues are modified by substitution or deletion: Q1. S2. P12. T15. S21, G23. T26. Q28. T29. G30. V32. N37. W40. T48. C50. N54. L60. E65. K69. V84. S90. D114, E119. F120. T121. L122. L123. D132. V133. G142. S148. M149. V155. Y158. N161. T162, K166. G170. Q175. F182. I183. G191. I203. D214. I215. A224. T231. G234. I237. S248, G254. W263. G269. L282. T285. G298. Y303. N307. G308. T310. E317. L318. S322. N324, G340. S341. D345. S357. M360. V363. D369. A372. P382. S388. T389. P390. T399. S400, Q406. N413. F423. P425. T426. G427. T429. P432. G435. N436. P437. G439. N441. R442, T444. T445. T446. T447. R449. P450. A451. T452. T453. S456. S457. P458. G463. P464, S467. H459. C468. G470. G472. S474. P476. V478. C479. S481. G482. T484. V487. L488, N489. Y491. Y492. Q494. C495. L496

| | Exchange with respect to SEQ ID NO: 12 |
|---|---|
| 1 | Q1L |
| 2 | T15S |
| 3 | Q28R |
| 4 | W40R |
| 5 | C72V |
| 6 | V133I |
| 7 | V155A, E |
| 8 | Y158C |
| 9 | T162E |
| 10 | Y247F, H |
| 11 | N307D |
| 12 | G308N |
| 13 | E317V, N |
| 14 | S341M |
| 15 | D345R, K |
| 16 | Y370P, R, H, S, A |
| 17 | T389A |
| 18 | Q406G |
| 19 | N441D |
| 20 | R442S, G |
| 21 | T452A |
| 22 | S456L, P |
| 23 | P458L, del |
| 24 | G459D |

-continued

| | Exchange with respect to SEQ ID NO: 12 |
|---|---|
| 25 | H464L, Q, R |
| 26 | V478A, I |

invention, particular when taking into consideration the temperature stability of the polypeptides of this invention.

In a preferred embodiment, the polypeptide having cellobiohydrolase activity comprises an amino acid sequence having at least 85% sequence identity to SEQ ID NO: 12. wherein the polypeptide has the amino acid sequence of SEQ ID NO: 12 wherein one or more of the following amino acid residues are modified by substitution or deletion: Q1. S2. P12. T15. S21, G23. T26. Q28. T29. G30. V32. N37. W40. T48. C50. N54. L60. E65. K69. V84. S90. D114, E119. F120. T121. L122. L123. D132. V133. G142. S148. M149. V155. Y158. N161. T162, K166. G170. Q175. F182. I183. G191. I203. D214. I215. A224. T231. G234. I237. S248, G254. W263. G269. L282. T285. G298. Y303. N307. G308. T310. E317. L318. S322. N324, G340. S341. D345. S357. M360. V363. D369. A372. P382. S388. T389. P390. T399. S400, Q406. N413. F423. P425. I426. G427. T429. P432. G435. N436. P437. G439. N441. R442, T444. T445. T446. T447. R449. P450. A451. T452. T453. S456, 5457. P458. G463. P464, S467. H459. C468. G470. G472. S474. P476. V478. C479, 5481. G482. T484. V487. L488, N489. Y491. Y492. Q494. C495. L496

Another aspect of the invention relates to the application of the isolated polypeptides and variants thereof of the present invention for the complete or partial hydrolysis of cellulosic material. The cellulosic material can be of natural, processed or artificial nature. “Cellulosic material” herein shall be defined as all sorts of pure, non-pure, mixed, blended or otherwise composed material containing at least a fraction of β-1-4-linked D-glucosyl polymers of at least 7 consecutive subunits. Prominent examples of cellulosic materials are all sort of cellulose containing plant materials like wood (soft and hard), straw, grains, elephant grass, hey, leaves, cotton and materials processed there from or waste streams derived from such processes. Cellulosic material used in an enzymatic reaction is herein also referred to as cellulosic substrate.

The hydrolysis of the cellulose material can be a sequential process following cellobiohydrolase production or contemporary to the production in the yeast cell (consolidated bioprocess). The expression of cellulolytic enzymes in yeast is of special interest due to the ability of many yeasts to ferment the released sugars (C6 or C5) to ethanol or other metabolites of interest.

A further embodiment of the invention thus relates to the application of whole cells expressing the polypeptide or variant thereof according to the present invention for the processing of cellulosic materials.

In a particular embodiment, the present invention discloses the use of a polypeptide and variants thereof or the composition of the present invention for the enzymatic degradation of cellulosic material, preferably lignocellulosic biomass, and/or for textiles processing and/or as ingredient in detergents and/or as ingredient in food or feed compositions.

EXAMPLES

Example 1

Preparation of *Pichia pastoris* Expression Plasmid

Figure 1:
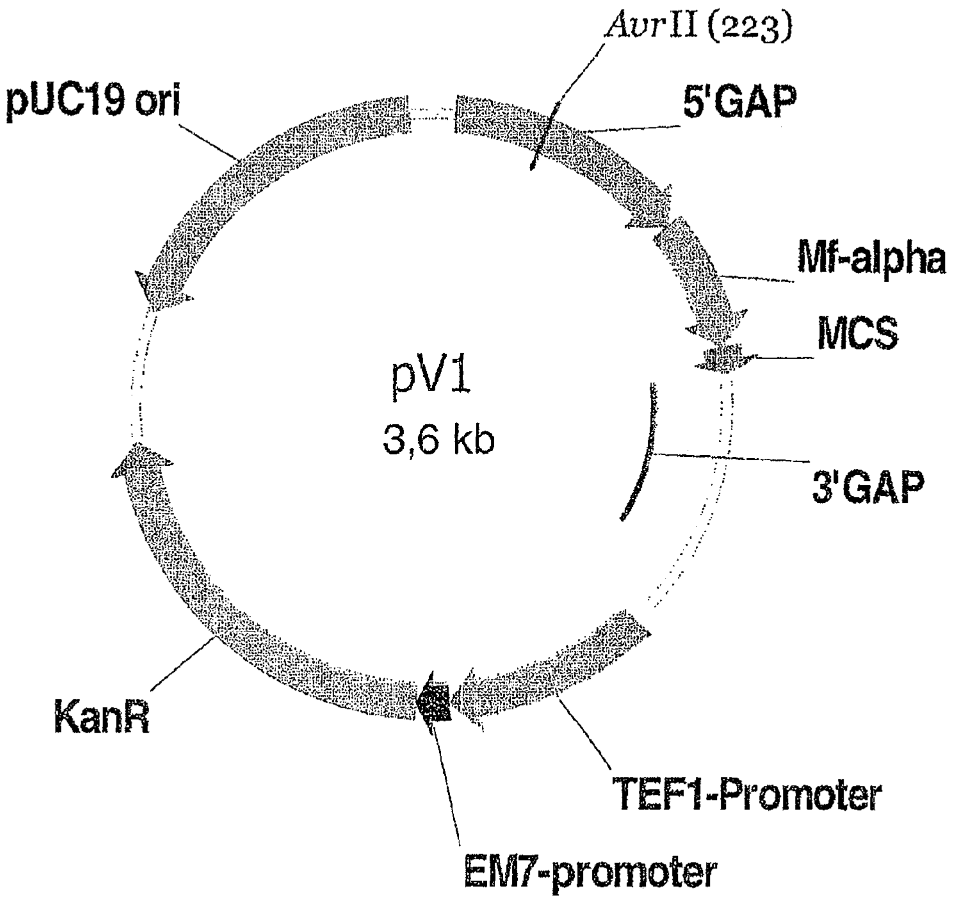
FIG. 1: Restriction Maps of pV1 for constitutive expression of Proteins in *Pichia pastoris:* pUC19—ori: Origin of replication in *E. coli;* KanR: Kanamycine/G418 Resistance with TEF1 and EMZ Promoter sequences for selection in *Pichia pastoris* and *E. coli.* respectively; 5'GAP: glyceraldehyde-3-phosphate dehydrogenase Promoter region; 3'-GAP: terminator region; SP MFalpha: *Saccharomyces cerevisiae* mating factor alpha signal sequence; MCS: multiple cloning site.
Figure 2:
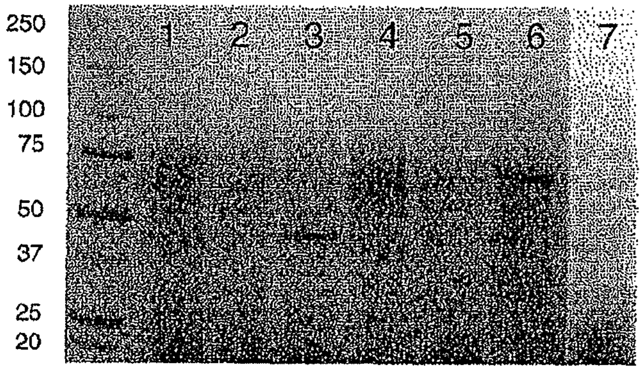
FIG. 2: Commassie stained SDS-PAGE of 10-fold concentrated supernatants of shake-flask cultures of *Pichia pastoris* CBS 7435 containing expression plasmids with coding sequences for the mature CBHI proteins of *Trichoderma viride* (CBH-f; lane 1), *Humicola grisea* (CBH-d; lane 2), *Talaromyces emersonii* (CBH-b; lane 3), *Thermoascus aurantiacus* (CBH-e; lane 4), as well as the *Talaromyces emersonii* CBHI-CBD fusion (CBH-a; lane 6) and the *Humicola grisea*-CBD fusion (CBH-g; lane 7) in N-terminal fusion to the signal peptide of the *Saccharomyces cerevisiae* mating factor alpha under control of the *Pichia pastoris* glyceraldehyde-3-phosphate dehydrogenase promoter
Figure 3:
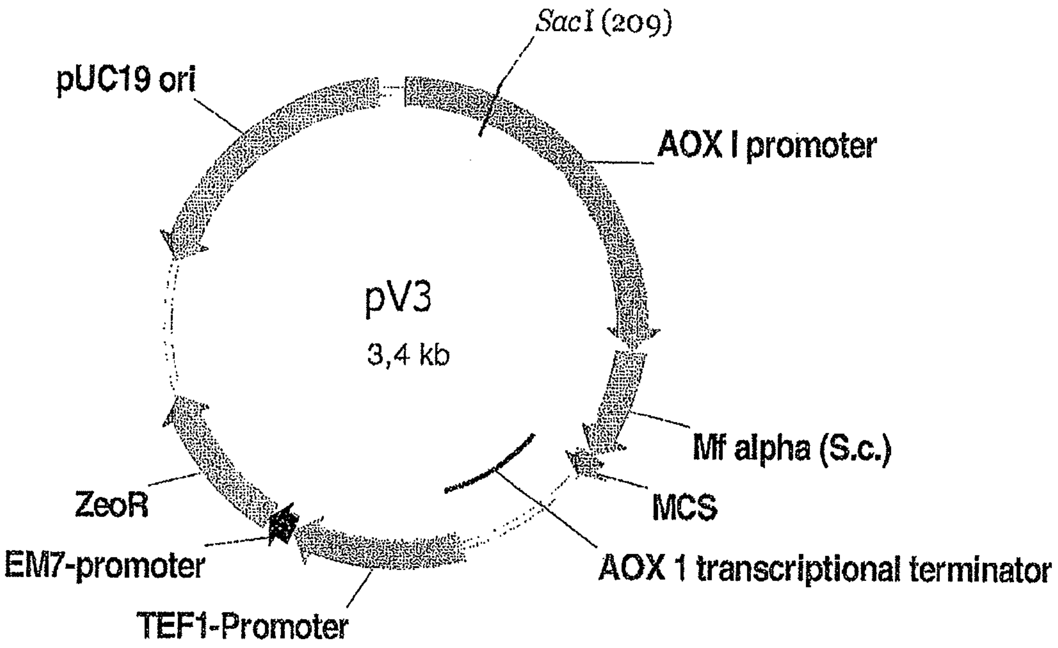
FIG. 3: Map of the pV3 expression plasmid for protein expression in *Pichia pastoris.* Replicons: pUC19—ori: Origin of replication in *E. coli;* ZeoR: Zeocine resistance gene with TEF1 and EM7 Promoter promoter sequences for expression in *Pichia pastoris* and *E. coli,* respectively; AOX I promoter: Promoter region of the *Pichia pastoris* alcohol oxidase I gene; AOX 1 transcriptional terminator: terminator region; SP MFalpha: *Saccharomyces cerevisiae* mating factor alpha signal sequence; MCS: multiple cloning site.
Figure 4:
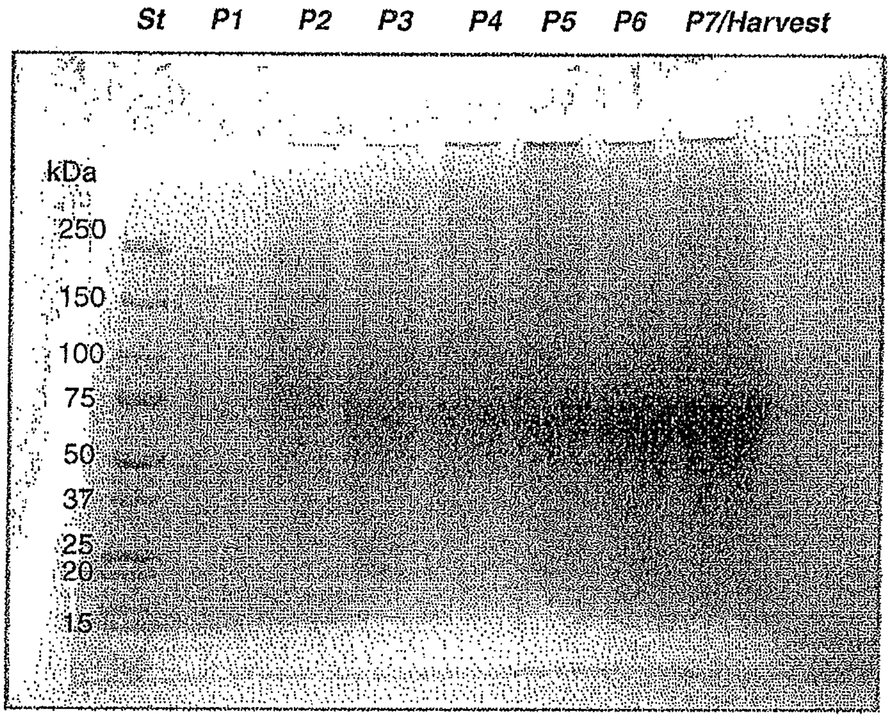
FIG. 4: SDS-PAGE analysis of culture supernatant samples taken from the fermentation of a *Pichia pastoris* strain with a genomic integration of an AOXI-expression cassette, expressing the *Talaromyces emersonii* CBHI/*Trichoderma reesei*-CBD fusion peptide (CBH-a) in a 7I bioreactor during methanol induction. Samples P1-P7 were are taken at the beginning of the methanol induction and after 20, 45, 119.5, 142.5, 145.5 and 167 hours, respectively.
Figure 5:
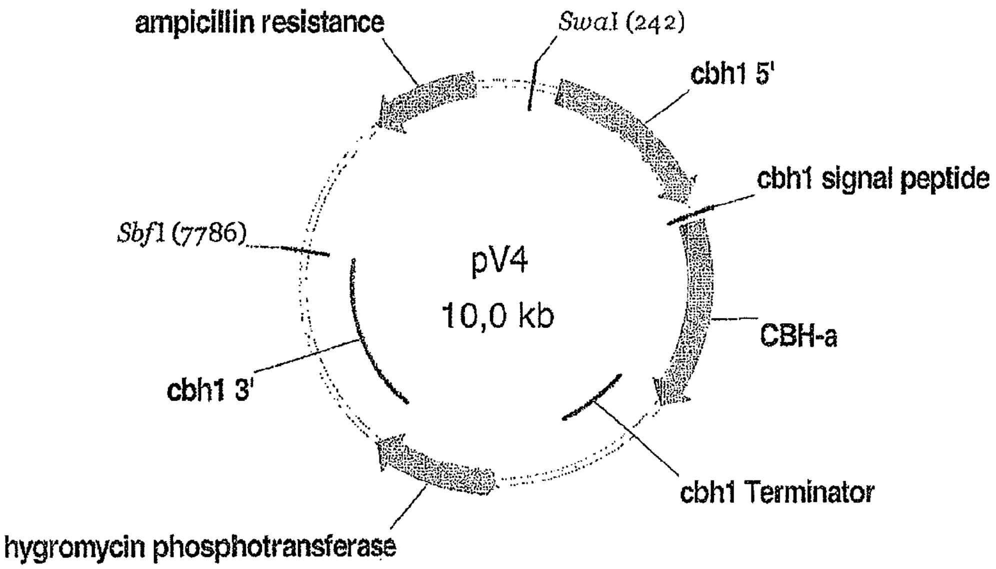
FIG. 5: Map of pV4 expression plasmid for the expression of the *Talaromyces emersonii* CBHI/*Trichoderma reesei*-CBD fusion peptide (CBH-ah) in *Trichoderma reesei.* Replicon: pUC19 for replication in *E. coli.* cbh1 5': 5' promoter region of the *Trichoderma* CBHI gene; cbh1 signal peptide: Coding sequence for the *Trichoderma reesei* CBHI leader peptide; CBH-a: *Talaromyces emersonii* CBHI/*Trichoderma reesei*-CBD fusion peptide: coding region for SeqID NO. 18; cbh1 Terminator: 3' termination region of the *Trichoderma reesei* CBHI locus; hygromycine resistance: coding region of the hygromycine phosphotransferase under control of a *Trichoderma reesei* phosphoglycerate kinase promoter; cbh1 3': homology sequence to the termination region of the *Trichoderma reesei* CBHI locus for double crossover events.
Figure 6:
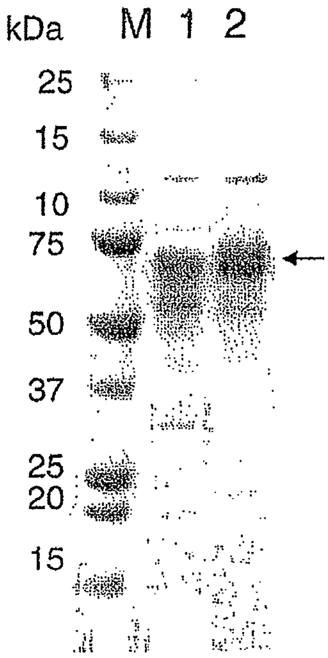
FIG. 6: SDS-Page of *Trichoderma reesei* culture supernatants. Lane 1 shows the expression pattern of a replacement strain carrying a *Talaromyces emersonii* CBHI/*Trichoderma reesei*-CBD fusion (CBH-ah) in place of the native CBHI gene. In comparison lane 2 shows the pattern for the unmodified strain under same conditions. M: molecular size marker

Expression plasmids for the constitutive expression of protein from transformed *Pichia pastoris* hosts are prepared by assembly of an expression cassette consisting of a *Pichia pastoris* gyceraldehyde phosphate dehydrogenase (GAP) promoter, a *Saccharomyces cerevisiae* SPα (mating factor alpha signal peptide), a multiple cloning site (MCS) and the 3'-GAP-terminator sequence. For selection purposes a kanamycine resistance gene is used under control of the EM7 or TEF promoter for bacterial or yeast selection purposes, respectively. The resulting plasmid vectors are designated as pV1 (FIG. 1) and pV2 (alternative MCS) Transformation and expression cultivation are done essentially as described by Waterham, H. R., Digan, M. E., Koutz, P. J., Lair, S. V., Cregg, J. M. (1997). Isolation of the *Pichia pastoris* glyceraldehyde-3-phosphate dehydrogenase gene and regulation and use of its promoter. *Gene,* 186, 37-44 and Cregg, J. M.: *Pichia* Protocols in Methods in Molecular Biology, Second Edition, Humana Press, Totowa N.J. 2007.

Example 2

Construction of *Pichia pastoris* Expression Constructs for CBHI Sequences

CBHI genes of *Trichoderma viride* (CBH-f), *Humicola grisea* (CBH-d), *Thermoascus aurantiacus* (CBH-e), *Talaromyces emersonii* (CBH-b), and fusions of the cellulose binding domain of *Trichoderma reesei* CBHI with the *Talaromyces emersonii* CBHI (CBH-a) or the *Humicola grisea* CBHI (CBH-g) are amplified using the oligo nucleotide pairs and templates (obtained by gene synthesis) as given in the Table 4. The fusion gene encoding Seq ID. NO. 2 is generated by overlap extension PCR using the PCR-Fragments generated from SeqID NO. 5 and 11. Phusion DNA polymerase (Finnzymes) is used for the amplification PCR.

TABLE 4

Primers and templates for the amplification of CBH-a, CBH-b, CBH-d, CBH-e, CBH-f and CBH-g

| Fragment | Primer forward | Primer reverse | Templete |
|---|---|---|---|
| CBH-f *Trichoderma viride* CBHI | GAGGCGGAAGCACCC TCTcaatctgcttgcaccttgca gtc (SEQ ID NO: 20) | GGAGACGCAGAGCC Cttattacaggcactgcgagt agt (SEQ ID NO: 21) | SEQ ID NO. 13 |
| CBH-d *Humicola grisea* GBHI | GAGGCGGAAGCACCC TCTcagcaggctggtactatta ctgc (SEQ ID NO: 22) | GGAGACGCAGAGCC Cttacacgttcacggtagaac cgattgggc (SEQ ID NO: 23) | SEQ ID NO. 7 |
| CBH-e *Thermoascus aurantiacus* CBHI | GAGGCGGAAGCACCC TCTcacgaggccggtaccgta accgc (SEQ ID NO: 24) | GGAGACGCAGAGCC CTTAttagttggcggtgaag gtcgagt (SEQ ID NO: 25) | SEQ ID NO. 9 |

TABLE 4-continued

Primers and templates for the amplification of CBH-a, CBH-b, CBH-d, CBH-e, CBH-f and CBH-g

| Fragment | Primer forward | Primer reverse | Templete |
|---|---|---|---|
| CBH-b*Talaromyces emersonii* CBHI | GAGGCGGAAGCACCC TCTcagcaggccggcacggc gacggc (SEQ ID NO: 26) | GGAGACGCAGAGCC CTTAtcacgaagcggtgaa ggtcgagt (SEQ ID NO: 27) | SEQ ID NO. 5 |
| CBH-a*Talaromyces* part1*emersonii* CBH fusion fragment part 1 | GAGGCGGAAGCACCC TCTcagcaggccggcacggc gacggc (SEQ ID NO: 28) | ATTACCTGTGCTACC gatcggaccaaacttaatgttc g (SEQ ID NO: 29) | SEQ ID NO. 5 |
| CBH-a*Trichoderma* part2*reesei* CBHI binding domain fusion fragment part2 | AAGTTTGGTCCGATCg gtagcacaggtaatccttcagg (SEQ ID NO: 30) | GGAGACGCAGAGCC CTTATTAtagacactgtga gtagtaagggt (SEQ ID NO: 31) | SEQ ID NO. 11 |
| CBH-a*Talaromyces emersonii* CBHI fusion protein | GAGGCGGAAGCACCC TCTcagcaggccggcacggc gacggc (SEQ ID NO: 32) | GGAGACGCAGAGCC CTTAtcattaatggtggtggt gatgatgag (SEQ ID NO: 33) | 5a + 5b SEQ ID NO. 2 |
| CBH-g*Humicola grisea* part1CBHI fusion fragment part1 | aggcggaagcatgctcgcagc aggctggtacaattactgc (SEQ ID NO: 34) | ggattacctgttaagcttccaat tggtccgaatctgatgtt (SEQ ID NO: 35) | SEQ ID NO. 19 |
| CBH-g*Trichoderma* part2*reesei* CBHI binding domain fusion fragment part2 | accaattggaagcttaacaggta atccttcaggtggtaatcc (SEQ ID NO: 36) | atcttgcaggtcgacttatcatt aatgatgatgatgatggtgtgc a (SEQ ID NO: 37) | SEQ ID NO. 11 |
| CBH-g*Humicula grisea* fusion protein | aggcggaagcatgctcgcagc aggctggtacaattactgc (SEQ ID NO: 38) | atcttgcaggtcgacttatcatt aatgatgatgatgatggtgtgc a (SEQ ID NO: 39) | 6a + 6b SEQ ID NO. 15 |

PCR fragments of expected length are purified from agarose gels after electrophoresis using the Promega® SV PCR and Gel Purification kit. Concentration of DNA fragments are measured on a Spectrophotometer and 0.2 pmol of fragments are treated with 9U of T4-DNA polymerase in the presence of 2.5 mM dATP for 37.5 min at 22.5° C. and treated fragments are annealed with T4-DNA-Polymerase/dTTP treated SmaI-linearized pV1 plasmid DNA and afterwards transformed into chemically competent *Escherichia coli* Top10 cells. Deviant from the described procedure the product generated by the primer pair according to the table lane 11 encoding the *Humicula grisea* fusion protein fragments are cloned via the introduced SphI and SafI site to pV2. Transformants are controlled by sequencing of isolated plasmid DNA.

Example 3

Expression of CBHI Genes in *Pichia pastoris*

Plasmids of Example 2 are transformed to electro-competent *Pichia pastoris* CBS 7435 cells and transformants are used to inoculate cultures in YPD medium containing 200 mg/l, which are incubated for 5 days at 27° C. in a rotary shaker at 250 rpm. Culture supernatants were separated by centrifugation at 5000×g for 30 minutes in a Sorvall Avant centrifuge. Supernatants were concentrated on spin columns with cut-off size of 10 kDa. Protein pattern of such concentrated supernatants were analyzed by SDS-PAGE (Laemmli et al.) and gels were stained with colloidal Commassie blue stain. Enzymatic activity was determined by incubation of the supernatant with 2 mM solutions of p-nitrophenyl-β-D-lactoside or 200 μM solutions of 4-methyl-umbelliferyl-β-D-lactoside in 50 mM sodium acetate buffer (pH 5) for 1 hour. The reaction was stopped my addition of equal volumes of 1 M sodium carbonate solution and determination of released p-nitrophenol or 4-methyl umbelliferone by measurement of the absorbance at 405 nm or the fluorescence at 360 nm/450 nm excitation/emission.

Example 4

Genome Integration and Expression of the *Talaromyces emersonii* CBHI-*T. reesei* CBHII-CBD Fusion Sequence in *Pichia pastoris*

TABLE 5

| Fragment | Primer forward | Primer reverse | Template |
|---|---|---|---|
| *Talaromyces emersonii* CBH fusion fragment part1 | GAGGCGGAAGCACCCTCTc agcaggccggcacggcgacggc (SEQ ID NO: 26) | ATTACCTGTGCTACCg atcggaccaaacttaatgttcg (SEQ ID NO: 29) | SEQ ID NO. 5 |

TABLE 5-continued

| Fragment | Primer forward | Primer reverse | Template |
|---|---|---|---|
| *Trichoderma reesei* CBHI binding domain fusion fragment with 6x His-Tag part2 | AAGTTTGGTCCGATCggtagc acaggtaatccttcagg (SEQ ID NO: 30) | GGAGACGCAGAGCC Cttatcattaatggtggtggtgat gatgag (SEQ ID NO: 33) | SEQ ID NO. 11 |
| *Talaromyces emersonii* CBHI fusion protein with 6x His-Tag part2 | GAGGCGGAAGCACCCTCTc agcaggccggcacggcgacggc (SEQ ID NO: 26) | GGAGACGCAGAGCC Cttatcattaatggtggtggtgat gatgag (SEQ ID NO: 33) | OE 1a + 1b: SEQ ID NO. 17 |

The DNA-fragment of the fusion gene are generated by 2 step overlap extension PCR using the oligo nucleotide pairs and synthetic templates as indicated in the Table 4 (of Example 2). T4-DNA polymerase treated full length fragment was annealed with the linear pV3 vector fragment by slowly reducing the temperature from 75° C. to 4° C. The pV3 plasmid contains a fusion of the mating factor alpha signal peptide to a multiple cloning site, situated downstream the of a *Pichia pastoris* AOXI promoter. Transformation of the annealed solution into chemical competent *E. coli* cells yields transformants, which are selected by their Teocine resistance checked for containing expected construct plasmid by restriction analysis and sequencing. pV3-CBH-a plasmid preparations are linearized with SacI and approximately 1 μg of linear DNA-fragments are transformed to *Pichia pastoris* electrocompetent cells. 94 Transformants from YPD-Zeocin plates are afterwards checked for expression by cultivation in 500 μl 96-deepwell Plate cultures in BMMY-medium containing 1% methanol and 0.5% methanol was fed every 24 h for 5 days (350 rpm/27° C.; humidified orbital shaker with 2.5 cm amplitude. Supernatants are tested for activity on 4-MUL and clones with highest expression levels are selected and again evaluated under same conditions.

For fermentation in an Infors Multifors bioreactor the strain producing the highest enzyme concentration is selected. A YPD-Zeocin (100g/l) pre-culture is chosen for inoculation of Mineral medium consisting of phosphate-buffer, magnesium sulphate and chloride, trace elements/biotin and glycerol, with pH calibration using ammonia and phosphoric acid. After metabolism of the batch glycerol (2%) additional glycerol feed is maintained for 1 day before the feed is changed to methanol to shift to inductive conditions for the AOXI promoter. Under these conditions the fermentation is kept for 5 days. Cells are separated from the fermentation liquid by centrifugation at 5000×g for 30 minutes. Supernatants are analyzed for total Protein using Bradford Reagent and BSA Standards (Biorad). SDS-PAGE/Coomassie Brilliant blue staining is used to analyze the Protein Pattern on the SDS-PAGE.

Example 5

*Trichoderma reesei* Expression Vector Construct

SbfI/SwaI digested pSCMB100 plasmid DNA was transformed into *Trichoderma reesei* SCF41 essentially as described by Penttilä et al 1997. 10 μg of linear DNA was used for the transformation of $10^7$ protoplasts. Selection of transformants was done by growth of the protoplasts on Mandel's Andreotti media plates with overlay agar, containing hygromycine as selective agent (100 mg/l). Transformants were further purified by passage over sporolation media plates and re-selection of spores on hygromycin media. From re-grown mycelia genomic DNA was isolated and the replacement event verified by PCR. Transformants verified in being true replacement strains were further tested for secretion of recombinant protein.

Example 6

Expression of *Talaromyces emersonii* CBHI/*Trichoderma reesei*-CBD Fusion (CBH-ah) Fusion with 6× His-Tag from *Trichoderma reesei*

Expression of recombinant CBHI replacement strains of *Talaromyces emersonii* CBHI/*Trichoderma reesei*-CBD fusion with 6× His-Tag in *Trichoderma reesei* Q6A (ATCC 13631) was done in shakeflask cultures containing 40 ml Mineral medium containing 2% Avicel in 300 ml flasks and cultivation at 30° C/250 rpm for 6 days. Supernatants recovered by centrifugation and further analyzed by SDS-PAGE and Bradford Protein assays.

Example 7

Screening Thermo Stability Variants

Random mutagenesis libraries of the *Talaromyces emersonii* CBHI/*Trichoderma reesei*-CBD fusion (with 6× His-Tag) gene were generated using error prone PCR applying manganese containing bufferers and inbalanced dNTP concentrations in the Taq-DNA polymerase reaction mixture, used for PCR-amplification, essentially as described by Craig and Joyce (R. Craig Cadwell and G. F. Joyce, 1995. Mutagenic PCR, in PCR Primer: a laboratory manual, ed. C. W. Dieffenbach and G. S. Dveksier, Cold Spring Harbor Press, Cold Spring Harbor, Me., 583-589). As template the wild type fusion gene (SeqID. NO. 17) or mutants thereof were chosen. Mutated PCR-Fragments were cloned to the pPKGMe Plasmid using SphI and HindIII endonucleases and T4-DNA-ligase.

Libraries of the *Talaromyces emersonii* CBHI/*Trichoderma reesei*-CBD fusion (with 6× His-Tag) gene variants were distributed in 1536 well plates with well occupation number close to 1. Enzyme was expressed over 7 days in a volume of 4 μl YPG-G418 medium. For evaluation of the properties of the variants 2 μl samples of culture supernatants were transferred to plates containing a suspension of milled straw, acetate buffer and beta-glucosidase. After incubation of the sealed reaction plates for 48 hours at defined temperatures the glucose concentration was determined using Amplex red in the presence of GOX and HRP by analyzing the fluorescence level. Best-performing Hits were re-cultivated and re-evaluated. Plasmids of confirmed CBH-ah variants were recovered (Pierce DNAzol Yeast genomic DNA Kit) and sequenced using oligonucleotides alpha-f (5' TACTATTGCCAGCATTGCTGC-3',SEQ ID NO: 40) and oli740 (5'-TCAGCTATTTCACATA-CAAATCG-3' SEQ ID NO: 41).

Example 8

Determination of Substrate Conversion Capacity at Different Temperatures for Indication of the Thermostability of CBH-ah-Variants Using 4-methylumbellifery-β-D-lactoside (4-MUL)

Figure 7:
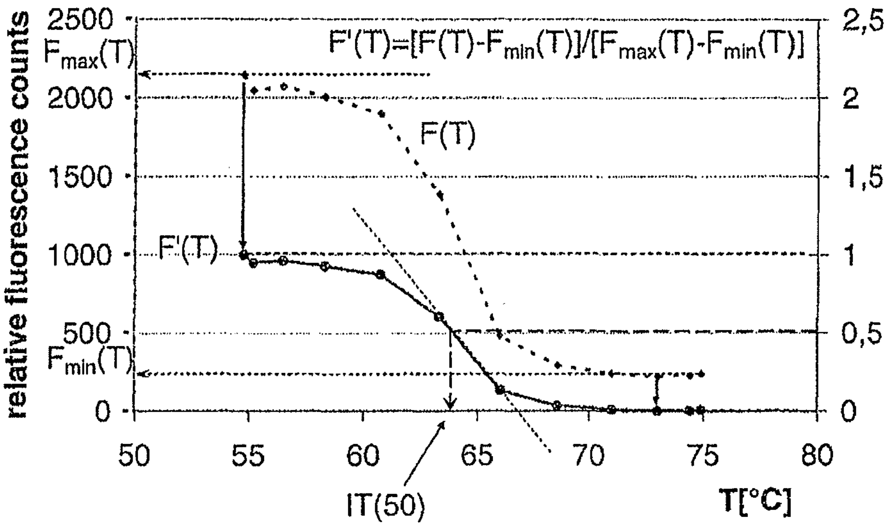
FIG. 7: Determination of IT50 values from Substrate Conversion Capacity vs. temperature graphs after normalization. For the normalization step the maximum and the minimum fluorescence values for the selected temperature are correlated to 1 or 0. respectively. Linear interpolation to F'(T)=0.5 between the nearest two temperature points with normalized values next to 0.5 results in the defined IT50 temperature.
Figure 8:
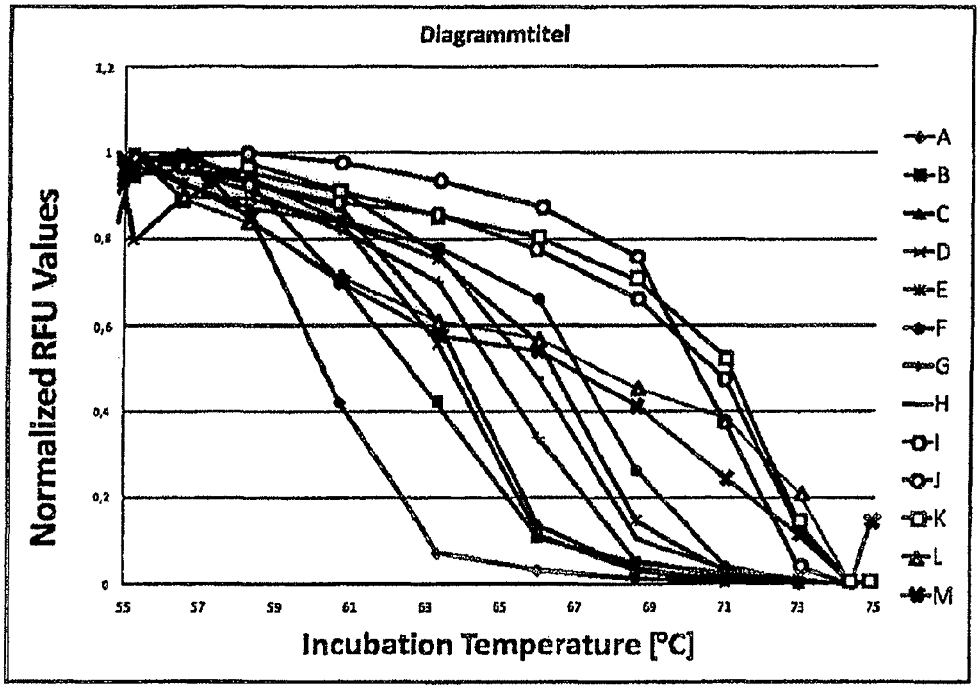
FIG. 8: Normalized Conversion Capacity vs. temperature graphs of "wt" *Talaromyces emersonii* CBHI/*Trichoderma reesei*-CBD fusions (CBH-ah: SeqID NO. 18=SeqID NO. 2+6× His-Tag) and mutants based on 4-Methylumbelliferyl-β-D-lactoside hydrolysis results evaluated at various temperatures. The fluorescence values were normalized according to FIG. 8 over the temperature range from 55° C. to 75° C.

For precise comparison of the thermal stability culture supernatants containing the secreted cellobiohydrolase variants were diluted tenfold in sodium acetate buffer (50 mM, pH 5) and 10 μl samples were incubated with 90 μl of 200 μM 4-MUL (in buffer) in the temperature gradient of an Eppendorff Gradient Thermocycler. A temperature gradient of 20° C. reaching from 55° C. to 75° C. was applied to 12 reaction mixtures for each sample for one hour. The temperature profile could be recorded after addition of 100 μl 1M sodium carbonate solution to each reaction and measurement of the fluorescence intensity at 360 nm/454 nm in a Tecan Infinite M200 plate reader. For comparison of the thermostability the values were normalized between 1 and 0 for the maximum and minimum fluorescence count (FIG. 7).

TABLE 6

Listing of Mutants of SeqID NO. 18 with improved IT50 values.

| | Mutations with respect to Seq. ID NO. 18 | IT50-value (4-MUL) |
|---|---|---|
| 1 | wt | 60.4 +/− 0.6 |
| 2 | R446G | 60.6 |
| 3 | Q1L, G4C, Q28R, A72C, S86T, E183M, D202V, S311N, D320N, T335I, D346E, Q349R, P442S, N445D, R446G, H468Q | 60.7 |
| 4 | D346G, R453G | 60.9 |
| 5 | Y496F | 60.9 |
| 6 | T335I, D346A, T393A, D410G | 61 |
| 7 | T243I, T325A, V482A | 61 |
| 8 | N194R, T243R, Y374D, A375D | 61.1 |
| 9 | Q1L, G4C, Q28R, W40R, E65V, A72C, S86T, E183K, S192I, D202I, H203R, F260C, S311N, D320N, T335I, D346G, Q349K, T392M, P442S, R446G, H468L, V482A | 61.1 |
| 10 | E65K | 61.1 |
| 11 | T48A | 61.2 |
| 12 | G4C, A72C, T344M | 61.2 |
| 13 | T243R, A375D | 61.3 |
| 14 | W40R, K159E, N445D | 61.3 |
| 15 | T344M | 61.3 |
| 16 | W40R, M234K | 61.3 |
| 17 | Q349R, T393A, P436S, N445D | 61.4 |
| 18 | Q349R, A354T, D373E, N445D | 61.4 |
| 19 | G4C, W40R, A72C, T344M | 61.4 |
| 20 | G4C, A72C, N194L, T243Y, Q349R, Y374R, A375L | 61.5 |
| 21 | G4C, D64N, A72C, Q349K | 61.5 |
| 22 | Q349R, N445D | 61.5 +/− 0.1 |
| 23 | W40R, T344M | 61.5 |
| 24 | W40R, D346A, T393A | 61.6 |
| 25 | N158D, G486S, Y495C | 61.6 |
| 26 | D320E | 61.6 |
| 27 | A72V | 61.6 |
| 28 | E183V | 61.6 |
| 29 | W40R, C489R | 61.7 |
| 30 | A72V, T335I, D346A, T393A, N445D | 61.7 |
| 31 | G4C, W40R, A72C, V313I, Q349R | 61.8 |
| 32 | W40R, Q349K | 61.9 |
| 33 | Q1L, G4C, T26N, A72C, D181N, E183K, Q349R | 61.9 |
| 34 | G4C, A72C, Q349K, E65V, Q349R | 61.9 |
| 35 | S311N | 62 |
| 36 | D320V, D346A, Q349R, T393A, N445D | 62.1 |
| 37 | T335I | 62.2 |
| 38 | A72V, D346A | 62.2 |
| 39 | D320V, D346A, T393A, N445D | 62.2 |
| 40 | G4C, A72C, N194S, T243W, Q349R, Y374S, A375G | 62.3 |
| 41 | E65V, Q349R | 62.3 |
| 42 | Q1L, G4C, A72C, F179I, D181N, E183K, L290H, S301C, Q349R, Q361R, D390G, G474S, Q498K | 62.3 |
| 43 | A72V, T335I, D346A, N445D | 62.3 |
| 44 | G4C, A72C, N194L, T243Q, Q349R, Y374P, A375V | 62.3 |
| 45 | Q1L, G4C, G23D, A72C, D111E, I116V, K118A, D181N, E183K, V212L, Q349R, Q362G | 62.3 |
| 46 | G4C, A72C, D346G | 62.3 |
| 47 | W40R, T344M, Q349K | 62.3 |
| 48 | G4C, Y163C | 62.4 |

TABLE 6-continued

Listing of Mutants of SeqID NO. 18 with improved IT50 values.

| | Mutations with respect to Seq. ID NO. 18 | IT50-value (4-MUL) |
|---|---|---|
| 49 | G4C, V32G, N49S, A72C, S193L, Q349R | 62.4 |
| 50 | A72V, Q349R, N445D | 62.4 +/− 0.4 |
| 51 | G4C, A72C, D346G, Q349R | 62.5 +/− 0.1 |
| 52 | Q1L, G4C, A72C, D181N, E183K, I321N, Q349R | 62.6 |
| 53 | W40R, D320V, Q349K, P436S, N445D | 62.7 |
| 54 | G4C, A72C, D181N, Q349R | 62.7 |
| 55 | G4C, A72C, Q349K | 62.7 |
| 56 | G4C, A72C, T344M, Q349K | 62.8 |
| 57 | G4C, A72C, T344M, D346G, Q349R | 62.8 +/− 0.2 |
| 58 | G4C, A72C, D320V, Q349K | 62.8 |
| 59 | G4C, A72C, P224L, F306Y, Q349R | 62.9 |
| 60 | G4C, A72C | 62.9 +/− 0.6 |
| 61 | A72V, D346A, T393A | 63 |
| 62 | G4C, A72C, Q349R, R446S, T456A | 63 |
| 63 | G4C, W40R, A72C, T344M, Q349K | 63 |
| 64 | A72V, D320V, D346A | 63.1 |
| 65 | G4C, A72C, N194Y, T243L, Q349R, Y374S, A375R | 63.1 |
| 66 | G4C, A72C, Q349K, T448A, T449A | 63.2 |
| 67 | G4C, E65V, A72C, Y244H, Q349R | 63.3 |
| 68 | G4C, A72C, D202G, D320N, Q349R, A358E | 63.4 |
| 69 | G4C, A72C, D320V, Q349R | 63.4 |
| 70 | G4C, A72C, Q349K, S86T | 63.4 |
| 71 | A72V, T335I, D346A, T393A, P436S | 63.4 |
| 72 | G4C, A72C, E183V, K304R, Q349K | 63.5 |
| 73 | G4C, A72C, T243G, Q349R, Y374P, A375M | 63.5 |
| 74 | G4C, A72C, Q349R, T465I | 63.6 |
| 75 | G4C, A72C, Q349R | 63.6 +/− 0.5 |
| 76 | G4C, A72C, N194V, T243M, Q349R, Y374A, A375T | 63.6 |
| 77 | G4C, D64N, A72C, Q349R, A358E, P464Q | 63.6 |
| 78 | G4C, A72C, Q349K, Q28R, S193T, Q490L | 63.6 |
| 79 | G4C, A72C, E183K, Q349K | 63.6 |
| 80 | G4C, A72C, S311N, Q349K, A455T | 63.6 |
| 81 | G4C, A72C, N194K, Q349R, Y374P, A375Q | 63.6 |
| 82 | G4C, A72C, D181N, Q349K | 63.6 |
| 83 | W40R, D320V, Q349K, T393A, N445D | 63.7 |
| 84 | W40R, T335I, D346A, T393A | 63.7 |
| 85 | Q1L, G4C, A72C, D181N, E183K, N327Y, Q349R | 63.7 |
| 86 | A72C, L119L, T335I, Q349R, G486D | 63.7 |
| 87 | G4C, A72C, N194K, T243P, Q349R, Y374H, A375E | 63.7 |
| 88 | G4C, A72V, Q349R, P462del | 63.8 |
| 89 | G4C, A72C, S236Y, Q349R | 63.8 |
| 90 | G4C, A72C, S311G, Q349K | 63.8 |
| 91 | A72V, D320V, T335I, D346A, T393A, N445D | 63.8 |
| 92 | G4C, A72C, S86T, M234V, Q349K | 63.8 |
| 93 | Insertion at position K159(CGRNK)undT457(AAATT), Q1L, G4C, Q28R, E65V, A72C, D181N, E183M, P224L, S311G, D320I, D346E, Q349K, T393V, Y422F, P442S, N445D, R446G, H468L, V482I | 63.9 |
| 94 | G4C, A72C, G251R, Q349R | 63.9 |
| 95 | G4C, A72C, Q349K, D320V | 63.9 +/− 0.7 |
| 96 | A72V, T335I, D346A, T393A | 63.9 |
| 97 | G4C, A72C, E183K, Q349R | 63.9 |
| 98 | Q1L, G4C, A72C, H203R, Q349K, P442S | 63.9 |
| 99 | G4C, A72C, Q349K, G434S, G470D | 64 |
| 100 | G4C, W40R, A72C, Q349K | 64 |
| 101 | G4C, A72C, Q349R, V367A | 64 |
| 102 | Q1L, G4C, A6V, C50S, A72C, I180N, D181N, E183K, Q349R, T457P, C472R, C499G | 64 |
| 103 | G4C, A72C, S311G, D320V, Q349K | 64 |
| 104 | W40R, T335I, D346A, T393A, P436S | 64 |
| 105 | Q1L, G4C, A72C, D181N, E183K, T243S, Q349R, P386S | 64.1 |
| 106 | A72V, D346A, T393A, N445D | 64.1 |
| 107 | Q1L, G4C, A72C, K154R, Q349K, T393I | 64.1 |
| 108 | G4C, A72C, N194G, T243F, Q349R, Y374P, A375R | 64.1 |
| 109 | A72V, D320V, D346A, T393A, N445D | 64.1 |
| 110 | A72C, L119L, Q172Q, Q349K, T488I | 64.1 |
| 111 | G4C, A72C, E183V, Q349K | 64.1 |
| 112 | G4C, A72C, E183K, N318Y, Q349K | 64.1 |
| 113 | W40R, A221V, T449A, C483R | 64.1 |
| 114 | G4C, A72C, K92R, Q349K, N493D | 64.1 |
| 115 | M234I, G438del | 64.2 |
| 116 | Q1L, G4C, A72C, S90T, D181N, E183K, Q349R | 64.2 |
| 117 | G4C, A72C, Q349R, G459D | 64.2 |
| 118 | G4C, A72C, Q349R, Y422F | 64.2 |
| 119 | G4C, T48A, A72C, Q349R, P480S | 64.2 |
| 120 | E187K, D320V, P442del | 64.2 |

TABLE 6-continued

| | Listing of Mutants of SeqID NO. 18 with improved IT50 values. | |
|---|---|---|
| | Mutations with respect to Seq. ID NO. 18 | IT50-value (4-MUL) |
| 121 | G4C, S24N, E65K, A72C, Q349R, I430L, G439D | 64.2 |
| 122 | A72V, D320V, T335I, D346A, T393A, P436S | 64.3 |
| 123 | Q1L, G4C, A72C, S193P, Q349K, V482I | 64.3 |
| 124 | G4C, A72C, D320V, Q349K, G443D, L492Q | 64.3 |
| 125 | Q1L, G4C, A72C, DV152-K159, D181N, E183K, Q349R | 64.4 |
| 126 | Q1L, G4C, A72C, Q349K | 64.4 +/− 0.5 |
| 127 | Q1L, G4C, A72C, D181N, E183K, M234L, V313I, Q349R, H468R | 64.4 |
| 128 | Q1L, G4C, A72C, D181N, E183K, I200N, Q349R | 64.4 |
| 129 | G4C, A72C, N194K, T243Y, Q349R, A375N | 64.4 |
| 130 | Q1L, G4C, Q28R, A72C, Q349K, H468L | 64.5 |
| 131 | G4C, E65V, A72C, Q349R | 64.5 |
| 132 | D320V, Q349K | 64.5 |
| 133 | Q1L, G4C, A72C, S311G, Q349K, H468R | 64.5 |
| 134 | G4C, A72C, T243Q, Q349R, Y374P, A375M | 64.5 |
| 135 | Q1L, G4C, A72C, D320V, Q349R | 64.5 |
| 136 | Q1L, G4C, T15S, A72C, Y244F, Q349K | 64.5 |
| 137 | G4C, A72C, E183K, D346E, Q349R | 64.6 |
| 138 | T243C, A375C | 64.6 |
| 139 | Q1L, G4C, A72C, Q349K, T392M | 64.6 |
| 140 | G4C, A72C, D202N, S311N, Q349R, N493D | 64.6 |
| 141 | G4C, A72C, N194D, T243A, Q349R, Y374P, A375Y | 64.6 |
| 142 | G4C, A72C, N194Y, T243V, Q349R, Y374P | 64.7 |
| 143 | Q1L, G4C, A72C, Q349R | 64.7 |
| 144 | G4C, Q28R, E65K, A72C, S86T, D202N, H203R, S311N, D320I, A340G, D346A, Q349K, T393A, Y422F, P442S, R446S, H468L, V482A | 64.7 |
| 145 | G4C, A72C, D202N, Q349R | 64.7 |
| 146 | G4C, A72C, P224L, Q349R | 64.7 |
| 147 | N194C, Y374C | 64.7 |
| 148 | Q1L, G4C, A72C, D181N, E183K, T229M, A340T, Q349R, V491I | 64.7 |
| 149 | Q1L, G4C, A72C, D181N, Q349R | 64.8 |
| 150 | G4C, A72C, D320V, D346V, Q349K | 64.8 |
| 151 | Q1L, G4C, A72C, V152A, Q349K | 64.8 |
| 152 | Q1L, G4C, Q28R, A72C, Q349K | 64.8 |
| 153 | Q1L, G4C, A72C, Q349K, Y422F | 64.8 |
| 154 | G4C, A72C, D202V, D320V, Q349K | 64.8 |
| 155 | Q1L, G4C, A72C, Y155S, D181N, E183K, Q349R | 64.8 |
| 156 | Q1L, G4C, A72C, D181N, D247N, Q349K | 64.8 |
| 157 | Q1L, G4C, A68T, A72C, Q349K, G439D, R453S | 64.9 |
| 158 | Q1L, G4C, A72C, Q349K, H468R | 64.9 |
| 159 | Q1L, G4C, D64N, A72C, Q349K | 64.9 |
| 160 | G4C, A72C, E183K, Q349R, P464L | 64.9 |
| 161 | G4C, A72C, D181N, P224L, Q349K | 65 +/− 0.6 |
| 162 | G4C, A72C, N194I, T243Y, Q349R, Y374P, A375R | 65 |
| 163 | Q1L, G4C, A72C, Q349K, P462L | 65 |
| 164 | Q1L, G4C, A72C, E183K, Q349R | 65 |
| 165 | G4C, A72C, S311G, Q349R | 65 |
| 166 | Q1L, G4C, A72C, S311N, Q349K, G463D | 65.1 |
| 167 | Q1L, G4C, A72C, S86T, Q349R | 65.1 |
| 168 | Q1L, G4C, A72C, D181N, E183K, G231D, Q349R | 65.1 |
| 169 | Q1L, G4C, A72C, S89N, D181N, E183K, Q349R | 65.2 |
| 170 | Q1L, G4C, E65K, A72C, Q349K | 65.2 |
| 171 | Q1L, Q2P, G4C, W40R, E65M, A72C, S86T, S192L, D202N, H203R, S311D, D320I, T335I, D346G, Q349K, T392M, Y422F, R446G | 65.2 |
| 172 | Q1L, G4C, S24T, T26I, Q28R, N29Y, G30A, E65V, A68T, A72C, Y155C, D181N, E183M, Q190K, P224L, S311G, D320I, D346E, Q349K, T393V, Y422F, P442S, N445D, R446G, H468L, V482I | 65.2 |
| 173 | G4C, A72C, E183K, D202Y, N310D, Q349R | 65.3 +/− 0.7 |
| 174 | G4C, A72C, N194I, T243D, Q349R, Y374P, A375Y | 65.3 |
| 175 | Q1L, G4C, A72C, D181N, E183K, Q349R, T456I | 65.3 |
| 176 | G4C, Q28R, A72C, S86T, E183K, P224L, S311N, N318Y, T335I, D346G, Q349R, T393I, P441A, P442S, R446G, H468L, V482I | 65.3 |
| 177 | Q1L, G4C, A72C, D181N, Q349K, T451S | 65.3 +/− 0.1 |
| 178 | Q1L, G4C, A72C, D181N, E183K, T243I, N246D, Q349R, T488I | 65.4 |
| 179 | Q1L, G4C, G23N, A72C, D110G, I116V, L119I, D181N, E183K, D211G, D293R, N310D, Q349R, Q362R, G363P, M364S | 65.4 |
| 180 | G439V, N440E, P441S, P442Q | 65.4 |
| 181 | G431D, S431V, T433E, G434S, N435Q | 65.5 |
| 182 | Q1L, G4C, Q28R, E65V, A68T, A72C, Y155C, D181N, E183M, P224L, S311G, D320I, D346E, Q349K, T393V, Y422F, P442S, N445D, R446G, H468L, V482I | 65.6 |
| 183 | G4C, A72C, N194C, Y374C | 65.6 |
| 184 | Q1L, G4C, A72C, S86T, D181N, E183K, Q349R, T393S | 65.6 |
| 185 | Q1L, G4C, A72C, D181N, E183K, Q349R, S485T | 65.7 |
| 186 | Q1L, G4C, G23N, A72C, V84A, D110G, D111H, I116E, F117Y, K118A, D181N, E183K, D293R, T295S, Q349R, M364L | 65.7 |

TABLE 6-continued

Listing of Mutants of SeqID NO. 18 with improved IT50 values.

| | Mutations with respect to Seq. ID NO. 18 | IT50-value (4-MUL) |
|---|---|---|
| 187 | Q1L, G4C, A72C, D181N, E183K, Q349R, R453K | 65.8 |
| 188 | Q1L, G4C, A72C, A145T, H203R, Q349K, T403K | 65.8 |
| 189 | Q1L, G4C, A72C, D181N, E183K, Q349R, N445S | 65.8 |
| 190 | Q1L, G4C, A72C, D181N, E183K, M234I, Q349R | 65.8 |
| 191 | Q1L, G4C, A72C, D181N, E183K, Q349R, T465S | 65.9 |
| 192 | Q1L, G4C, A72C, D181N, E183K, T297N, Q349R | 66 |
| 193 | Q1L, G4C, A72C, S311G, Q349K | 66 |
| 194 | G4C, Q28R, E65M, A72C, S86T, E183K, S192I, H203R, S311N, D346E, Q349K, T392M, T393A, Y422F, N445D, R446S | 66 |
| 195 | Q1L, G4C, A72C, D202N, Q349K, G486D | 66 |
| 196 | Q1L, G4C, A72C, S99T, D181N, E183K, Q349R, T450I | 66 |
| 197 | Q1L, G4C, A72C, I200F, Q349K, L500I | 66 |
| 198 | Q1L, G4C, A72C, D181N, E183K, Q349R, G434S | 66 |
| 199 | Q1L, G4C, A31S, A72C, D181N, E183K, Q349R | 66 |
| 200 | Q1L, G4C, Q28L, A72C, D181N, E183K, Q349R | 66 |
| 201 | Q1L, G4C, A72C, D181N, E183K, Q349R, P436S | 66.1 |
| 202 | Q1L, G4C, A72C, D181N, E183K, T233S, Q349R | 66.1 |
| 203 | Q1L, G4C, A72C, D202N, Q349K | 66.1 +/− 0.1 |
| 204 | Q1L, G4C, A68T, A72C, Q349K | 66.1 |
| 205 | Q1L, G4C, A21T, A72C, D181N, E183K, Q349R, P454S | 66.1 +/− 0.1 |
| 206 | Q1L, G4C, A72C, D346V, Q349K | 66.2 |
| 207 | Q1L, G4C, Y47F, A72C, D181N, E183K, Q349R, P436S, S461R | 66.2 |
| 208 | Q1L, G4C, A72C, D181N, E183K, M234T, Q349R | 66.3 |
| 209 | Q1L, G4C, A72C, N157S, D181N, E183K, Q349R | 66.3 |
| 210 | Q1L, G4C, A72C, D181N, E183K, Q349R | 66.3 +/− 0.4 |
| 211 | As1-72ausT. reesei, D181N, P224L, S311D, N318Y, D320N, D346A, Q349K, T392M, T393I, Y422F, N445D, R446G, H468Q, V482I | 66.3 |
| 212 | G4C, A72C, N194Q, T243V, Q349R, Y374P, A375Y | 66.3 |
| 213 | Q1L, G4C, A72C, D181N, E183K, I314F, Q349R, N445D | 66.3 |
| 214 | Q1L, G4C, A72C, Q349K, T392K | 66.3 |
| 215 | Q1L, G4C, A72C, D181N, E183K, Q349R, T451A | 66.4 |
| 216 | Q1L, G4C, A72C, D181N, E183K, M234V, Q349R | 66.4 |
| 217 | Q1L, G4C, A21S, A72C, D181N, E183K, Q349R | 66.5 |
| 218 | A21C, P429C | 66.5 +/− 0.4 |
| 219 | Q1L, G4C, A72C, D181N, E183K, Q349R, N493D | 66.5 |
| 220 | Q1L, G4C, A72C, S311N, Q349K | 66.5 |
| 221 | Q1L, G4C, Q28R, E65V, A72C, D181N, E183V, D228N, S311N, N318Y, D346E, Q349R, Y422F, P442S, N445D, R446G, H468L, V482T | 66.5 |
| 222 | G4C, A72C, N194C, Q349R, Y374C | 66.5 |
| 223 | Q1L, G4C, A72C, D181N, E183K, Q349R, A455V | 66.5 +/− 0.3 |
| 224 | Q1L, G4C, A72C, D181N, E183K, Q349R, T400S | 66.6 |
| 225 | Q1L, G4C, T26I, A72C, D181N, E183K, Q349R | 66.6 +/− 0 |
| 226 | Q1L, G4C, A72C, D181N, E183K, N310D, Q349R, T392S, G463D | 66.7 |
| 227 | Q1L, G4C, A72C, D129N, D181N, E183K, Q190L, G266S, I276V, Q349R, P386L, F427Y | 66.7 +/− 0.2 |
| 228 | Q1L, G4C, A72C, D181N, E183K, D202N, Q349R | 66.7 |
| 229 | Q1L, G4C, A72C, Y155C, D181N, E183K, Q349R | 66.8 |
| 230 | Insertion at position P454(ATAAA), Q1L, G4C, Q28R, E65V, A72C, D181N, E183M, P224L, S311G, D320I, D346E, Q349K, T393V, Y422F, P442S, N445D, R446G, H468L, V482I | 66.8 |
| 231 | Insertion at position K159(CGRNK), Q1L, G4C, Q28R, E65V, A72C, D181N, E183M, P224L, S311G, D320I, D346E, Q349K, T393V, Y422F, P442S, N445D, R446G, H468L, V482I | 66.8 |
| 232 | Q1L, G4C, A72C, D181N, E183K, N246K, Q349R | 67 +/− 0.6 |
| 233 | G4C, W40R, E65V, A72C, S86T, D181N, E183K, D202I, H203R, S311D, D320N, D346V, Q349R, T392M, T393A, Y422F, P442S, H468Q, V482A | 67 +/− 0.5 |
| 234 | Q1L, G4C, A72C, Y155C, Q349K | 67 +/− 0.4 |
| 235 | Q1L, G4C, A68T, A72C, D181N, E183K, Q349R | 67 +/− 0.3 |
| 236 | Q1L, G4C, S24T, T26I, Q28R, N29Y, G30A, Y47F, E65V, A68T, A72C, Y155C, D181N, E183M, Q190K, P224L, T229M, G231D, M234T, S311G, D320I, A340S, D346E, Q349K, D390E, T393V, Y422F, P442S, N445D, R446G, T448A, R453G, H468L, P480S, V482I | 67.3 |
| 237 | Q1L, G4C, W40R, E65M, A72C, S86T, S192L, D202N, H203R, S311D, D320I, T335I, D346G, Q349K, T392M, Y422F, R446G | 67.3 |
| 238 | Q1L, G4C, A72C, S86T, D181N, E183K, D320V, Q349R | 67.3 +/− 0.4 |
| 239 | G4C, Q28K, A72C, S86T, E183M, D202N, P224L, S311G, N318Y, D320N, D346A, Q349R, T392M, T393I, P442S, H468L, V482I | 67.4 |
| 240 | Q1L, Q2P, G4C, Q28R, W40R, E65K, A72C, D181N, S192L, D202I, H203R, P224L, S311G, D320I, D343A, D346A, Q349K, P442S, N445D, R446G, V482A | 67.4 |
| 241 | Q1L, G4C, Q28R, E65K, A72C, E183M, D202I, P224L, D320N, D346V, Q349K, T392M, T393V, Y422F, N445D, R446G, H468L, V482T | 67.4 |

TABLE 6-continued

Listing of Mutants of SeqID NO. 18 with improved IT50 values.

| | Mutations with respect to Seq. ID NO. 18 | IT50-value (4-MUL) |
|---|---|---|
| 242 | Q1L, G4C, Q28R, E65V, A72C, S86T, E183K, D202V, S311G, N318Y, D320I, D346G, Q349K, T393V, Y422F, N445D, R446S, H468Q, V482T | 67.4 |
| 243 | Q1L, G4C, W40R, E65M, A72C, D181N, E183K, S192P, D202N, P224L, S311D, N318Y, D320V, D346G, Q349K, T392M, N445D, R446G, H468L, V482T | 67.4 |
| 244 | Q1L, G4C, E65V, A72C, D181N, E183K, P224L, S311G, D320N, D346G, Q349R, T392M, T393I, R446G, H468L, V482I | 67.6 |
| 245 | Insertion at position G151(CGRSG), Q1L, G4C, Q28R, E65V, A72C, D181N, E183M, P224L, S311G, D320I, D346E, Q349K, T393V, Y422F, P442S, N445D, R446G, H468L, V482I | 67.6 |
| 246 | Q1L, G4C, E65M, A72C, D181N, E183M, D202Y, P224L, S311D, N318Y, D320I, T335I, D346A, Q349K, T392M, T393I, N445D, R446G, T448A, H468Q, V482A | 67.6 |
| 247 | Q1L, G4C, G23A, A72C, D110S, D111H, I116V, F117Y, K118A, L120M, D181N, E183K, D293H, G294A, N310E, Q349R, Q362G, M364S | 67.6 |
| 248 | Q1L, G4C, A72C, D181N, E183K, Q349R, T421I, G439D | 67.7 |
| 249 | G4C, Q28K, E65M, A72C, S86T, V152A, D181N, E183V, S192L, D202N, S311N, D320N, D346E, Q349R, T387A, T392M, T393I, Y422F, P442S, R446S, H468L, G476D, V482I | 67.7 +/− 0.3 |
| 250 | Q1L, G4C, W40R, E65V, A72C, S86T, E183V, G188C, S192T, D202Y, H203R, P224L, S311N, D320V, D346E, Q349K, T393V, Y422F, N445D, R446G, H468Q, V482I | 67.7 |
| 251 | Q1L, G4C, E65M, A72C, S86T, E183M, D202N, P224L, T335I, D346G, Q349K, T392M, T393A, P442S, N445D, R446G, H468Q, V482A | 67.7 |
| 252 | Q1L, G4C, Q28R, E65V, A72C, D181N, E183M, P224L, S311G, D320I, A340S, D346E, Q349K, D390E, T393V, Y422F, P442S, N445D, R446G, H468L, P480S, V482I | 67.8 |
| 253 | Q1L, G4C, W40R, E65K, A72C, S86T, E183K, S192L, D202Y, P224L, D320I, D346E, Q349R, P442S, R446G, H468R, V482T | 67.9 +/− 0.4 |
| 254 | Q1L, G4C, A21T, T26I, Q28R, E65V, A68T, A72C, Y155C, D181N, E183M, Q190K, D202N, P224L, S311G, N318Y, D320I, D346E, Q349K, T393V, Y422F, N445D, R446G, R453G, H468Q, P480S, V482I | 67.9 |
| 255 | Q1L, G4C, Q28R, E65V, A72C, S86T, D181N, D202N, P224L, S311G, N318Y, D320I, T335I, D346E, Q349K, T393V, Y422F, N445D, R446G, H468Q, V482I | 68 |
| 256 | Insertion at position P464(THAAA), Q1L, G4C, Q28R, E65V, A72C, D181N, E183M, P224L, S311G, D320I, D346E, Q349K, T393V, Y422F, P442S, N445D, R446G, H468L, V482I | 68 |
| 257 | Q1L, G4C, Q28R, E65V, A72C, E183M, S311G, D346E, Q349K, T393V, Y422F, P442S, N445D, R446G, H468L, V482I | 68 |
| 258 | Q1L, G4C, T7Q, A8S, N10T, S24T, T27Q, Q28R, N29T, V41T, G46S, Y47S, T52D, D57S, D64N, E65V, Q69K, A72C, D181N, P224L, S311D, N318Y, D320N, D346A, Q349K, T392M, T393I, Y422F, N445D, R446G, H468Q, V482I | 68 |
| 259 | Insertion at position K159(CGRNK)undT457(AAATT), Q1L, G4C, Q28R, E65V, A72C, E183M, P224L, S311G, D320I, D346E, Q349K, T393V, Y422F, P442S, N445D, R446G, H468L, V482I | 68.1 +/− 1.9 |
| 260 | Q1L, G4C, Q28K, W40R, E65V, A72C, D181N, E183V, S192P, D202V, H203R, S311G, D320N, D346E, Q349K, T392M, T393A, Y422F, V482I | 68.1 |
| 261 | Q1L, G4C, Q28R, E65V, A72C, G139S, D181N, E183M, P224L, S311G, D320I, D346E, Q349K, T393V, Y422F, P442S, N445D, R446G, H468L, V482I | 68.1 |
| 262 | Q1L, G4C, Q28R, E65V, A72C, S86T, D181N, E183M, D202N, P224L, S311G, N318Y, T335I, D346E, Q349K, T393V, Y422F, N445D, R446G, H468L, V482I | 68.2 |
| 263 | Q1L, G4C, Q28R, E65K, A72C, D181N, S311N, N318Y, D346E, Q349K, T393V, Y422F, N445D, R446G, H468Q, V482I | 68.2 +/− 0.7 |
| 264 | Q1L, G4C, W40R, A72C, S192L, D202N, H203R, P224L, S311N, D320I, T335I, D346V, Q349R, T393I, N445D, R446G, H468Q, V482T | 68.2 +/− 0 |
| 265 | Q1L, G4C, Q28K, E65K, A72C, E183M, D202N, P224L, T229S, S311G, D320I, T335I, D346V, Q349R, T393V, H468Q, V482A | 68.2 |
| 266 | Q1L, G4C, Q28R, G30A, E65M, A72C, D181N, D202N, P224L, S311D, N318Y, D346E, Q349K, T392M, T393V, Y422F, P442S, N445D, R446S | 68.2 |
| 267 | Q1L, G4C, Q28R, E65V, A72C, S68T, E183M, S311N, T335I, D346E, Q349K, T393V, Y422F, N445D, R446G, H468L, V482T | 68.2 |
| 268 | Q1L, G4C, Q28K, E65K, A72C, D181N, D202N, S311N, N318Y, T335I, D346E, Q349K, T393V, Y422F, P442S, N445D, R446G, H468L, V482I | 68.3 |
| 269 | T243C, A375C, N194C, Y374C | 68.3 |
| 270 | Q1L, G4C, Q28K, E65K, A72C, S86T, E183M, S311G, D346V, Q349R, T392M, T393V, Y422F, P442S, N445D, R446G, H468L, S478Y, V482I | 68.3 |
| 271 | Q1L, G4C, Q28R, E65V, A72C, D181N, E183M, S311G, D346E, Q349K, T393V, Y422F, P442S, N445D, R446G, H468L, V482I | 68.3 |

TABLE 6-continued

Listing of Mutants of SeqID NO. 18 with improved IT50 values.

| | Mutations with respect to Seq. ID NO. 18 | IT50-value (4-MUL) |
|---|---|---|
| 272 | Q1L, G4C, Q28R, E65V, A72C, S86T, D181N, D202N, S311N, N318Y, D320I, T335I, D346E, Q349K, T393I, Y422F, N445D, R446G, H468Q, V482I | 68.4 |
| 273 | Q1L, G4C, Q28R, E65K, A72C, S86T, E183K, D202N, P224L, S311G, T335I, D346A, Q349K, T393V, Y422F, N445D, R446G, H468L, V482T | 68.4 |
| 274 | Q1L, G4C, Q28R, E65V, A72C, L120P, D181N, E183M, P224L, S311G, D320I, D346E, Q349K, T393V, Y422F, P442S, N445D, R446G, H468L, V482I | 68.4 |
| 275 | Q1L, G4C, Q28K, E65V, A72C, S86T, E183M, S311N, N318H, D320V, D346V, Q349K, T392M, T393A, R446S, H468L, V482I | 68.4 |
| 276 | Q1L, G4C, Q28K, E65V, A72C, D202N, H203R, S311G, T335I, D346V, Q349K, T393A, P442S, R446G, H468L, V482I | 68.4 |
| 277 | M146C, G167C | 68.5 |
| 278 | Q1L, G4C, Q28R, E65V, A72C, E183M, S311G, D320I, D346E, Q349K, T393V, Y422F, P442S, N445D, R446G, H468L, V482I | 68.5 |
| 279 | Q1L, G4C, Q28R, E65K, A72C, D181N, D202N, H203R, P224L, S311D, D346G, Q349K, P442S, R446S, H468Q, V482T | 68.5 |
| 280 | Q1L, G4C, Q28R, E65M, A72C, D181N, E183M, S311G, N318Y, D320I, T335I, D346E, Q349K, D390E, T393V, Y422F, P442S, N445D, R446G, H468Q, V482T | 68.5 |
| 281 | Q1L, G4C, T27S, Q28R, E65V, Q69R, A72C, L120P, D181N, E183M, D202N, D247N, S311G, D346E, Q349K, K355Q, T387S, T393V, Y422F, N445D, R446G, T451S, G463V, H468Q, V482T, S485T | 68.5 |
| 282 | Q1L, G4C, Q28R, E65K, A72C, E183V, S192T, D202N, S311G D320V, D346A, Q349K, P442S, N445D, R446G, H468R, V482A | 68.6 +/− 0.6 |
| 283 | Q1L, G4C, W40R, E65V, A72C, S86T, E183M, D202N, P224L, S311G, D320V, D346E, Q349R, T393I, P442S, R446G, H468R, V482I | 68.6 |
| 284 | Q1L, G4C, Q28N, E65K, A72C, D181N, E183M, D202N, H203R, S311G, N318Y, D320N, Q349R, T393V, Y422F, P442S, N445D, R446G, H468L, V482I | 68.6 |
| 285 | Q1L, G4C, Q28R, V41T, G46S, Y47S, T52D, E65V, A72C, D181N, P224L, S311D, N318Y, D320N, D346A, Q349K, T392M, T393I, Y422F, N445D, R446G, H468Q, V482I | 68.6 |
| 286 | Q1L, G4C, Q28R, E65K, A72C, D181N, E183M, P224L, S311G, D320I, D346E, Q349K, T393V, Y422F, P442S, N445D, R446G, H468L, V482I | 68.6 |
| 287 | Q1L, G4C, Q28R, W40R, A72C, S86T, D181N, S192T, D202N, P224L, S311G, N318Y, D320V, D346E, Q349K, T392M, T393I, P442S, N445D, R446G, H468Q, V482I | 68.6 +/− 1 |
| 288 | Q1L, G4C, A21T, T26I, Q28R, G30A, E65V, A68T, A72C, Y155C, D181N, Q190K, D202N, P224L, T229M, S311G, N318Y, D320I, T335I, D346E, Q349K, T393V, Y422F, N445D, R446G, R453G, H468Q, V482I | 68.6 |
| 289 | Q1L, G4C, Q28K, W40R, A72C, S86T, D181N, E183M, S192I, D202Y, T299S, S311N, N318Y, D320I, D346V, Q349R, T393I, P442S, H468L | 68.6 +/− 0.4 |
| 290 | Q1L, G4C, Q28R, E65V, A72C, D181N, E183M, P224L, T229M, G231D, M234T, S311G, D320I, D346E, Q349K, T393V, Y422F, P442S, N445D, R446G, H468L, V482I | 68.6 |
| 291 | Q1L, G4C, S24T, T26I, Q28R, N29Y, G30A, E65V, A68T, A72C, Y155C, D181N, E183M, Q190K, P224L, T229M, G231D, M234T, S311G, D320I, A340S, D346E, Q349K, D390E, T393V, Y422F, P442S, N445D, R446G, T448A, R453G, H468L, P480S, V482I | 68.7 |
| 292 | Q1L, G4C, Q28R, E65V, A72C, D181N, E183M, P224L, S311G, D320I, D346E, Q349K, T393V, Y422F, P442S, N445D, R446G, G463V, H468L, V482I | 68.7 |
| 293 | Q1L, G4C, Q28R, E65K, A72C, E183M, P224L, S311G, D346E, Q349K, T393V, Y422F, P442S, N445D, R446G, H468L, V482I | 68.7 |
| 294 | Q1L, G4C, Q28R, E65V, A72C, S86T, D181N, E183M, D202N, P224L, S311G, N318Y, D346E, Q349K, T393V, Y422F, P442S, N445D, R446G, H468L, V482T | 68.7 |
| 295 | Q1L, G4C, Q28R, W40R, E65V, A72C, S86T, S192T, D202V, H203R, S311N, N318Y, D346A, Q349K, T392M, T393A, Y422F, P442S, N445D, V482A | 68.7 |
| 296 | Insertion at position K159(CGRNK), G434(AAATG)undT457(AAATT), Q1L, G4C, Q28R, E65V, A72C, E183M, P224L, S311G, D320I, D346E, Q349K, T393V, Y422F, P442S, N445D, R446G, H468L, V482I | 68.7 +/− 1.1 |
| 297 | Q1L, G4C, Q28K, E65K, A72C, D181N, H203R, P224L, S311G, D320V, D346G, Q349K, T392M, T393I, P442S, N445D, R446G, H468L, V482A | 68.7 +/− 0 |
| 298 | Q1L, G4C, Q28R, E65K, A72C, E183M, S311G, D346E, Q349K, T393V, Y422F, P442S, N445D, R446G, H468L, V482I | 68.8 |
| 299 | Q1L, G4C, Q28R, E65K, A72C, E183M, S311G, D346E, Q349K, T393V, Y422F, P442S, N445D, R446G, H468L, V482I | 68.8 +/− 0.2 |
| 300 | Q1L, G4C, Q28R, E65V, A72C, E183K, D202I, P224L, S311G, D320I, Q349K, T393V, P442S, N445D, R446S, H468L, V482I | 68.8 |

TABLE 6-continued

Listing of Mutants of SeqID NO. 18 with improved IT50 values.

| | Mutations with respect to Seq. ID NO. 18 | IT50-value (4-MUL) |
|---|---|---|
| 301 | Q1L, G4C, Q28K, A72C, S86T, D181N, E183V, S192T, D202N, P224L, S311G, N318Y, D320V, D346G, Q349R, T392M, Y422F, P442S, N445D, R446S, H468L, V482A | 68.8 |
| 302 | G4C, Q28R, E65K, A72C, S86T, D181N, E183M, S192L, D202N, H203R, P224L, S311D, D346E, Q349R, T392M, T393A, Y422F, P442S, N445D, R446G, P462L, H468L, V482T | 68.8 |
| 303 | Q1L, G4C, W40R, E65K, A72C, Q109R, D181N, E183M, S192I, D202I, H203R, S245T, D346A, Q349R, T393A, Y422F, P442S, N445D, R446G, H468R, V482A | 68.8 +/− 0.2 |
| 304 | Q1L, G4C, Q28K, E65M, A72C, D181N, D202N, S311N, T335I, D346E, Q349K, T393I, Y422F, P442S, N445D, R446G, H468Q, V482I | 68.9 |
| 305 | Q1L, G4C, N10D, Q28R, E65V, Q69R, A72C, D181N, E183M, P224L, S311G, D320I, D346E, Q349R, T393V, N417Y, Y422F, P442S, N445D, R446G, H468L, V482I | 68.9 |
| 306 | Q1L, G4C, Q28R, W40R, E65V, A72C, D202Y, H203R, P224L, T299I, N318Y, D320V, D346A, Q349K, T392M, T393A, P442S, N445D, R446G, H468R, V482T | 68.9 |
| 307 | G4C, Q28R, E65V, A72C, E183M, D202N, P224L, S311G, N318Y, D320V, D346G, Q349K, T392M, Y422F, R446G, H468Q | 68.9 |
| 308 | Q1L, G4C, Q28K, A72C, S86T, E183K, S311G, D320V, D346A, Q349R, T392M, T393I, Y422F, P442S, R446S, H468Q | 68.9 |
| 309 | Q1L, G4C, Q28R, E65M, A72C, D181N, P224L, S311N, D320N, T335I, D346E, Q349K, T392M, Y422F, N445D, R446S, H468L, V482T | 68.9 |
| 310 | Q1L, G4C, Q28K, E65V, A72C, D181N, D202N, S311G, T335I, D346E, Q349K, T393V, Y422F, N445D, R446G, H468Q, V482I | 68.9 |
| 311 | Q1L, G4C, Q28R, E65K, A72C, D181N, E183M, S311N, N318Y, T335I, D346E, Q349K, T393V, Y422F, N445D, R446G, H468L, V482I | 68.9 |
| 312 | Q1L, G4C, Q28R, E65K, A72C, E183M, S311G, D320I, D346E, Q349K, T393V, Y422F, P442S, N445D, R446G, H468L, V482I | 68.9 |
| 313 | Q1L, G4C, Q28R, E65V, A72C, D181N, E183M, S311G, D320I, D346E, Q349K, T393V, Y422F, P442S, N445D, R446G, H468L, V482I | 69 |
| 314 | Q1L, G4C, W40R, E65V, A72C, S86T, D181N, S192T, D202N, H203R, P224L, S311G, N318Y, T335I, D346G, Q349K, T392M, T393V, Y422F, N445D, R446G, H468Q | 69 +/− 0.3 |
| 315 | Q1L, G4C, Q28R, E65K, A72C, E183M, S311N, D320I, D346E, Q349K, T393I, Y422F, P442S, N445D, R446G, H468Q, V482T | 69 |
| 316 | Q1L, G4C, T7Q, A8S, N10T, Q28R, D57S, D64N, E65V, Q69K, A72C, D181N, P224L, S311D, N318Y, D320N, D346A, Q349K, T392M, T393I, Y422F, N445D, R446G, H468Q, V482I | 69 |
| 317 | Q1L, G4C, Q28R, E65M, A72C, S86T, D181N, E183M, D202N, P224L, S311G, D346A, Q349K, T393I, Y422F, P442S, N445D, R446G, H468Q, V482T | 69 +/− 0.9 |
| 318 | Q1L, G4C, N10D, Q28R, E65V, Q69R, A72C, K92R, K118Q, D181N, E183M, D202N, T280A, S311G, T335I, D346E, Q349K, K355Q, T387S, T393V, D404N, Y422F, N445D, R446G, P462L, G463V, H468Q, V482I, S485T | 69 |
| 319 | Q1L, G4C, Q28R, E65M, A72C, E183M, D202N, S311G, D320I, T335I, D346E, Q349K, T393I, Y422F, N445D, R446G, H468Q, V482I | 69 |
| 320 | Q1L, G4C, Q28K, E65K, A72C, D181N, E183M, D202N, S311D, D320V, T335I, D346G, Q349K, T393I, Y422F, P442S, N445D, H468L, V482I | 69 |
| 321 | Q1L, G4C, Q28K, E65K, A72C, S86T, P224L, S311N, D320I, T335I, D346E, Q349K, T393V, Y422F, N445D, R446G, H468Q, V482T | 69 |
| 322 | Q1L, G4C, Q28R, E65V, A72C, S86T, D181N, E183M, D202N, P224L, S311N, D320I, D346E, Q349K, T393V, Y422F, P442S, N445D, R446G, H468Q, V482T | 69 |
| 323 | G4C, E65K, A72C, S86T, E183M, D202I, P224L, S311N, N318Y, D320N, T335I, D346V, Q349R, T393V, Y422F, P442S, R446S, H468L | 69 |
| 324 | Q1L, G4C, Q28R, E65K, A72C, D202N, S311N, T335I, D346E, Q349K, T393I, Y422F, P442S, N445D, R446G, H468L, V482T | 69 |
| 325 | Q1L, G4C, E65V, A72C, D181N, E183K, D202G, Q349R | 69 +/− 1.2 |
| 326 | Q1L, G4C, Q28R, E65K, A72C, E183M, P224L, S311G, D320I, D346E, Q349K, T393V, Y422F, P442S, N445D, R446G, H468L, V482I | 69 |
| 327 | Q1L, G4C, Q28R, E65V, A72C, D181N, E183M, P224L, F306L, S311G, D320I, D346E, Q349K, T393V, Y422F, P442S, N445D, R446G, H468L, V482I | 69 |
| 328 | Q1L, G4C, Q28R, E65V, A72C, S86T, D202N, P224L, S311G, N318Y, D320I, D346A, Q349K, T393I, Y422F, N445D, R446G, H468Q, V482T | 69 |
| 329 | Q1L, G4C, Q28K, E65K, A72C, D181N, E183K, S192P, P224L, S311G, N318Y, D320V, D346E, Q349R, T392M, T393I, Y422F, P442S, H468Q | 69 +/− 0.1 |
| 330 | Q1L, G4C, Q28K, E65M, A72C, S86T, E183M, H203R, S311D, D320V, T335I, D346E, Q349R, T393A, N445D, R446G, H468Q, V482A | 69 |
| 331 | Q1L, G4C, Q28R, A72C, D181N, E183V, D202I, H203R, P224L, S311D, D320V, D346V, Q349R, T392M, T393I, N445D, H468L | 69 |

TABLE 6-continued

Listing of Mutants of SeqID NO. 18 with improved IT50 values.

| | Mutations with respect to Seq. ID NO. 18 | IT50-value (4-MUL) |
|---|---|---|
| 332 | Q1L, G4C, Q28K, W40R, E65K, A72C, S86T, D181N, E183K, S192L, D202I, H203R, S311N, D320N, D346V, Q349K, T392M, T393A, Y422F, N445D, R446S | 69 |
| 333 | G4C, E65V, A72C, S86T, Y155H, D181N, E183V, Q190K, P224L, S311N, D320V, D346V, Q349K, T392M, T393V, Y422F, P442S, N445D, R446G, H468L, V482A | 69.1 |
| 334 | Q1L, G4C, Q28R, E65M, A72C, S86T, E183M, D202N, S311D, N318Y, D320N, T335I, D346A, Q349R, T392M, T393I, Y422F, P442S, N445D, R446G, H468L, V482A | 69.1 |
| 335 | Q1L, G4C, Q28R, E65V, A72C, D181N, E183M, S311N, N318Y, D320I, T335I, D346E, Q349K, T393V, Y422F, N445D, R446G, H468L, V482T | 69.1 |
| 336 | Q1L, G4C, Q28R, E65K, A72C, S86T, D181N, D202N, S311G, D346E, Q349K, T393I, Y422F, N445D, R446G, H468L, V482I | 69.1 |
| 337 | Q1L, G4C, Q28R, E65K, A72C, D181N, D202N, S311N, N318Y, D320I, D346E, Q349K, T393I, Y422F, N445D, R446G, H468L, V482T | 69.1 +/− 0.6 |
| 338 | Q1L, G4C, T7Q, A8S, N10T, S24T, T27Q, Q28R, N29T, D57S, D64N, E65V, Q69K, A72C, D181N, P224L, S311D, N318Y, D320N, D346A, Q349K, T392M, T393I, Y422F, N445D, R446G, H468Q, V482I | 69.1 |
| 339 | Q1L, G4C, Q28R, E65K, A72C, S86T, D202N, S311G, N318Y, D320I, D346A, Q349K, T393I, Y422F, N445D, R446G, H468L, V482I | 69.1 |
| 340 | Q1L, G4C, Q28R, A72C, D181N, S311G, N318Y, D320V, D346E, Q349K, T393I, Y422F, P442S, N445D, R446G, H468Q | 69.1 |
| 341 | Q1L, G4C, Q28R, E65K, A72C, D181N, E183M, S311G, D320I, D346E, Q349K, T393V, Y422F, P442S, N445D, R446G, H468L, V482I | 69.1 |
| 342 | Q1L, G4C, Q28R, E65K, A72C, D181N, E183M, S311G, D346E, Q349K, T393V, Y422F, P442S, N445D, R446G, H468L, V482I | 69.1 |
| 343 | Q1L, G4C, Q28R, E65V, A72C, E183M, D202N, S311N, D320I, D346E, Q349K, T393V, Y422F, N445D, R446G, H468Q, V482T | 69.1 |
| 344 | Q1L, G4C, Q28R, E65K, A72C, E183M, S311G, T335I, D346E, Q349K, T393V, Y422F, N445D, R446G, H468Q, V482I | 69.2 |
| 345 | Q1L, G4C, Q28R, E65V, A72C, S86T, D181N, D202N, S311N, N318Y, T335I, D346E, Q349K, T393V, Y422F, N445D, R446G, H468Q, V482I | 69.2 |
| 346 | Q1L, G4C, E65M, A72C, S86T, E183K, D202Y, S311G, D320N, T335I, D346A, Q349K, T393V, Y422F, R446G, H468Q, V482T | 69.2 |
| 347 | Q1L, G4C, Q28R, E65V, A72C, S86T, E183M, D202N, P224L, S331N, D320I, T335I, A340S, D346A, Q349K, T393V, Y422F, N445D, R446G, H468Q, V482T | 69.2 |
| 348 | Q1L, G4C, Q28K, E65K, A72C, S86T, D181N, E183M, H203R, P224L, S311D, D320I, D346E, Q349R, T392M, Y422F, R446G, H468L | 69.2 |
| 349 | Q1L, G4C, Q28K, E65V, A72C, S86T, D181N, E183M, P224L, S311G, D320I, D346E, Q349K, T393V, Y422F, P442S, N445D, R446G, H468Q, V482I | 69.2 +/− 0.5 |
| 350 | Q1L, G4C, Q28K, N29Y, E65K, A72C, D181N, S311G, T335I, D346E, Q349K, T393V, Y422F, N445D, R446G, H468Q, V482T | 69.2 +/− 0.1 |
| 351 | Q1L, G4C, Q28K, E65M, A72C, E183M, S311G, D346E, Q349K, T393V, Y422F, P442S, N445D, R446G, H468L, V482T | 69.3 |
| 352 | Q1L, G4C, Q28K, E65V, A72C, S86T, D181N, E183K, D202N, S311N, N318Y, D320N, T335I, D346A, Q349K, T392M, T393V, P442S, N445D, R446G, H468Q | 69.3 |
| 353 | Q1L, G4C, Q28K, E65K, A72C, S86T, D181N, E183M, D202N, S311G, N318Y, T335I, D346E, Q349K, T393I, Y422F, N445D, R446G, H468Q, V482I, | 69.3 |
| 354 | Q1L, G4C, Q28R, E65K, A72C, E183V, S192T, D202N, S311G, D320V, D346A, Q349K, T393V, P442S, N445D, H468L, V482A | 69.3 +/− 0.3 |
| 355 | Q1L, G4C, Q28R, E65V, A72C, E183M, D202N, S311N, N318Y, D320I, T335I, D346E, Q349K, T393V, Y422F, N445D, R446G, H468L, V482T | 69.3 |
| 356 | Q1L, G4C, S24T, Q28R, E65K, A72C, D202N, S311G, T335I, D346E, Q349K, T393I, Y422F, N445D, R446G, H468Q, V482T | 69.3 +/− 0.1 |
| 357 | Q1L, G4C, A72C, S86T, D181N, S192L, D202N, P224L, S311G, N318Y, D320V, T335I, D346E, Q349K, T393I, R446G, H468Q | 69.3 |
| 358 | Q1L, G4C, Q28R, E65V, A72C, D181N, P224L, S311D, N318Y, D320N, D346A, Q349K, T392M, T393I, Y422F, N445D, R446G, H468Q, V482I | 69.4 +/− 0.5 |
| 359 | Q1L, G4C, Q28R, E65M, A72C, D181N, E183M, D202N, P224L, S311G, D346A, Q349K, T393I, Y422F, P442S, N445D, R446G, H468L, V482T | 69.4 |
| 360 | Q1L, G4C, Q28K, E65V, A72C, S86T, E183V, S192I, D202V, D320I, T335I, D346V, Q349K, T392M, T393I, Y422F, P442S, N445D, R446G, H468R, V482A | 69.4 +/− 0.1 |
| 361 | Q1L, G4C, Q28K, E65M, A72C, S86T, D181N, E183M, D202N, P224L, S311G, D320I, T335I, D346E, Q349K, T393V, Y422F, N445D, R446G, H468Q, V482T | 69.4 +/− 0.2 |

TABLE 6-continued

Listing of Mutants of SeqID NO. 18 with improved IT50 values.

| | Mutations with respect to Seq. ID NO. 18 | IT50-value (4-MUL) |
|---|---|---|
| 362 | Q1L, G4C, Q28K, A72C, D181N, D202I, S311D, N318Y, T335I, D346E, Q349K, T392M, Y422F, R446G, H468L | 69.4 |
| 363 | Q1L, G4C, Q28R, E65V, A72C, D181N, E183M, P224L, S311G, D320N, D346E, Q349K, T393V, Y422F, T433S, P442S, N445D, R446G, H468L, V482I | 69.4 |
| 364 | Q1L, G4C, Q28K, E65V, A72C, D181N, E183M, D202N, S311G, N318Y, D346E, Q349K, T393I, Y422F, N445D, R446G, H468Q, V482I | 69.4 +/− 0.2 |
| 365 | Q1L, G4C, Q28K, E65K, A72C, D181N, D202N, S311G, N318Y, D346A, Q349K, T393I, Y422F, N445D, R446G, H468Q, V482T | 69.4 +/− 0.5 |
| 366 | Q1L, G4C, Q28R, E65K, A72C, S86T, E183M, D202N, D320I, T335I, D346A, Q349K, T392M, Y422F, N445D, R446G, H468L, V482T | 69.4 |
| 367 | Q1L, G4C, Q28K, E65M, A72C, S86T, E183M, S311N, N318Y, D320I, T335I, D346E, Q349K, T393I, Y422F, P442S, H468Q, V482I | 69.4 |
| 368 | Q1L, G4C, E65M, A72C, S86T, E183V, S192L, D202I, H203R, P224L, S311G, N318Y, D320V, D346A, Q349K, P442S, N445D, R446G, H468R, V482A | 69.4 +/− 0.1 |
| 369 | Q1L, G4C, T7Q, A8S, N10T, Q28R, E65V, A72C, D181N, P224L, S311D, N318Y, D320N, D346A, Q349K, T392M, T393I, Y422F, N445D, R446G, H468Q, V482I | 69.4 |
| 370 | Q1L, G4C, E66K, A72C, S86T, D202V, S311N, D320V, T335I, D346V, Q349R, T392M, Y422F, N445D, R446G, H468L | 69.4 |
| 371 | Q1L, G4C, Q28R, E65K, A72C, D181N, E183M, P224L, S311G, D346E, Q349K, T393V, Y422F, P442S, N445D, R446G, H468L, V482I | 69.4 |
| 372 | Q1L, G4C, Q28R, D57S, D64N, E65V, Q69K, A72C, D181N, P224L, S311D, N318Y, D320N, D346A, Q349K, T392M, T393I, Y422F, N445D, R446G, H468Q, V482I | 69.4 |
| 373 | Q1L, G4C, Q28R, A72C, S86T, E183M, S192T, D202N, H203R, P224L, S311N, T335I, D346V, Q349R, T392M, T393V, P442S, N445D, R446G, H468Q, V482A | 69.4 |
| 374 | Q1L, G4C, Q28K, E65V, A72C, D181N, D202N, S311N, D346A, Q349K, T393I, Y422F, N445D, R446G, H468Q, V482I | 69.4 +/− 0.8 |
| 375 | Q1L, G4C, Q28R, E65V, A72C, D181N, E183M, P224L, S311G, D320I, D346E, Q349K, T393V, Y422F, P442S, N445D, R446G, H468L, V482I, S485T | 69.5 |
| 376 | G4C, Q28K, E65M, A72C, S86T, E183M, D202N, P224L, S311G, T335I, D346E, Q349K, T393V, Y422F, P442S, N445D, R446G, H468L, V482I | 69.5 |
| 377 | Q1L, G4C, Q28R, E65V, A72C, E183M, P224L, S311G, D320I, D346E, Q349K, T393V, Y422F, G434(AAATG) P442S, N445D, R446G, T457(AAATT), H468L, V482I | 69.5 +/− 0.4 |
| 378 | G4C, Q28R, E65M, A72C, S86T, D181N, E183M, D202Y, P224L, S311N, D346A, Q349K, T393I, Y422F, N445D, R446S, H468Q, V482A | 69.5 |
| 379 | Q1L, G4C, Q28K, E65V, A72C, S86T, D181N, E183K, D202N, P224L, S311G, D320I, D346E, Q349K, T393I, Y422F, P442S, N445D, R446G, H468Q, V482T | 69.5 +/− 1.8 |
| 380 | Q1L, G4C, T27S, Q28R, E65V, A72C, D181N, E183M, P224L, S311G, D320I, D346E, Q349K, T393V, Y422F, P442S, N445D, R446G, H468L, V482I | 69.5 |
| 381 | Q1L, G4C, Q28R, E65M, A72C, S86T, D181N, E183M, P224L, S311G, T335I, D346A, Q349K, T393V, Y422F, P442S, N445D, R446G, H468Q, V482T | 69.5 |
| 382 | As1-10ausT.reesei, Q28R, E65V, A72C, D181N, P224L, S311D, N318Y, D320N, D346A, Q349K, T392M, T393I, Y422F, N445D, R446G, H468Q, V482I | 69.5 |
| 383 | Q1L, G4C, Q28R, E65V, A72C, S86T, D202N, P224L, S311G, D320I, D346E, Q349K, T393V, Y422F, N445D, R446G, H468Q, V482I | 69.5 |
| 384 | Q1L, G4C, Q28K, E65V, A72C, E183M, D202N, S311G, G320I, D346E, Q349K, T393V, Y422F, P442S, N445D, R446G, H468L, V482I | 69.6 +/− 0.1 |
| 385 | Q1L, G4C, Q28R, E65K, A72C, D181N, P224L, S311N, N318Y, D320I, D346E, Q349K, T393V, Y422F, N445D, R446G, H468L, V482I | 69.6 |
| 386 | Q1L, G4C, Q28R, E65M, A72C, S90F, D181N, P224L, S311G, N318Y, D346E, Q349K, T393I, Y422F, P442S, N445D, R446G, H468Q, V482I | 69.6 |
| 387 | G4C, Q28R, A72C, S86T, D181N, E183V, S192L, D202V, N246S, S311D, N318Y, D320V, D346A, Q349K, T393V, P442S, N445D, H468L, V482A | 69.6 |
| 388 | Q1L, G4C, Q28K, E65V, A72C, D181N, E183M, D202N, P224L, S311N, N318Y, G320I, T335I, D346A, Q349K, T393I, Y422F, N445D, R446G, H468Q, V482T | 69.6 |
| 389 | Q1L, G4C, Q28R, A72C, S86T, E183M, S192L, H203R, S311D, D320V, T335I, D346V, Q349K, N445D, H468Q, V482A | 69.6 |
| 390 | Q1L, G4C, Q28R, T59M, E65K, A68T, A72C, S86T, D181N, S192L, D202N, H203R, S311D, D320V, T335I, Q349R, T393A, P442S, N445D, R446G, H468L, V482A | 69.6 |

TABLE 6-continued

Listing of Mutants of SeqID NO. 18 with improved IT50 values.

| | Mutations with respect to Seq. ID NO. 18 | IT50-value (4-MUL) |
|---|---|---|
| 391 | Q1L, G4C, Q28R, E65V, A72C, D181N, E183M, D202N, P224L, S311G, N318Y, T335I, D346E, Q349K, T393V, Y422F, P442S, N445D, R446G, H468Q, V482I | 69.6 |
| 392 | Q1L, G4C, Q28R, E65V, A72C, D181N, E183M, P224L, S311G, D320I, D346E, Q349K, K355Q, T393V, Y422F, P442S, N445D, R446G, H468L, V482I | 69.6 |
| 393 | Q1L, G4C, Q28R, E65V, A72C, D181N, E183M, P224L, S311G, N318Y, T335I, D346A, Q349K, T393V, Y422F, P442S, N445D, R446G, H468L, V482T | 69.6 |
| 394 | Q1L, G4C, Q28R, E65V, A72C, D181N, E183M, P224L, S311G, D320I, D346E, Q349K, T393V, Y422F, P442S, N445D, R446G, T448A, R453G, H468L, V482I | 69.6 |
| 395 | Q1L, G4C, Q28R, E65M, A72C, S86T, D181N, E183M, S311N, N318Y, T335I, D346E, Q349K, T393V, Y422F, N445D, R446G, H468Q, V482I | 69.6 +/− 0.5 |
| 396 | Q1L, G4C, E65M, A72C, E183M, D202I, P224L, S311D, N318Y, D320V, T335I, D346A, Q349K, T393A, Y422F, P442S, N445D, R446G, R453G, H468Q, V482I | 69.6 |
| 397 | Q1L, G4C, Q28R, E65V, A72C, E183M, P224L, S311G, D346E, Q349K, T393V, Y422F, P442S, N445D, R446G, H468L, V482I | 69.7 |
| 398 | Q1L, G4C, Q28R, E65V, A72C, S86T, D181N, E183M, S311G, N318Y, D346A, Q349K, T393V, Y422F, N445D, R446G, H468L, V482T | 69.7 +/− 1 |
| 399 | Q1L, G4C, S24T, T27Q, Q28R, N29T, E65V, A72C, D181N, P224L, S311D, N318Y, D320N, D346A, Q349K, T392M, T393I, Y422F, N445D, R446G, H468Q, V482I | 69.7 |
| 400 | Q1L, G4C, E65V, A72C, D181N, E183M, S192I, P224L, S311G, D320V, T335I, D346G, Q349K, T393A, Y422F, P442S, N445D, R446G, H468L, V482T | 69.7 |
| 401 | Q1L, G4C, Q28R, E65V, A72C, D181N, E183M, P224L, S311G, D320I, D346E, Q349K, T393V, Y422F, P442S, N445D, R446G, H468L, V482I | 69.8 +/− 0.8 |
| 402 | Q1L, G4C, Q28R, E65V, A72C, D181N, E183M, D202F, S311G, N318Y, T335I, Q349K, T393V, Y422F, P442S, N445D, R446G, H468Q | 69.8 |
| 403 | Q1L, G4C, Q28K, E65K, A72C, S86T, D181N, D202N, P224L, S311D, N318Y, D320N, D346A, Q349R, T392M, T393I, Y422F, N445D, R446G, H468R | 69.8 |
| 404 | Q1L, G4C, Q28R, E65V, A72C, D181N, D202N, S311N, D320I, T335I, D346E, Q349K, T393V, Y422F, N445D, R446G, H468Q, V482T | 69.8 +/− 0 |
| 405 | Q1L, G4C, Q28K, E65K, A72C, D181N, D202N, P224L, S311G, N318Y, T335I, D346E, Q349K, T393V, Y422F, N445D, R446G, H468Q, V482I | 69.8 |
| 406 | Q1L, G4C, Q28R, E65V, A72C, D181N, E183M, D202N, P224L, S311G, D320I, D346E, Q349K, T393V, Y422F, P442S, N445D, R446G, H468L, V482I | 69.8 |
| 407 | Q1L, G4C, Q28R, E65V, A72C, D181N, E183M, D202N, S311N, T335I, D346A, Q349K, T393V, Y422F, P442S, N445D, R446G, H468L, V482T | 69.8 |
| 408 | Q1L, G4C, Q28K, E65K, A72C, S86T, E183M, P224L, S311G, N318Y, D320I, T335I, D346E, Q349K, T393V, Y422F, P442S, N445D, R446G, H468Q, V482T | 69.8 |
| 409 | Q1L, G4C, A21T, T26I, Q28R, G30A, E65V, A68T, A72C, Y155C, D181N, Q190K, D202N, T229M, S311G, D320I, T335I, D346E, Q349K, T393V, Y422F, N445D, R446G, H468Q, P480S, V482I | 69.9 |
| 410 | Q1L, G4C, Q28K, E65M, A72C, D181N, E183M, S311G, T335I, D346E, G349K, T393V, Y422F, N445D, R446G, H468L, V482T | 69.9 |
| 411 | Q1L, G4C, Q28R, E65V, A72C, D181N, E183M, P224L, S311G, D320I, D346E, Q349K, T393V, D404N, Y422F, P442S, N445D, R446G, T451S, H468L, V482I | 69.9 |
| 412 | Q1L, G4C, Q28R, E65V, A72C, D181N, E183M, P224L, S311G, D320I, D346E, Q349K, T393V, Y422F, P442S, N445D, R446G, P462L, H468L, V482I | 69.9 |
| 413 | Q1L, G4C, Q28R, E65V, A72C, E183M, D202N, P224L, S311G, N318Y, T335I, D346E, Q349K, T393V, Y422F, N445D, R446G, H468L, V482I | 69.9 |
| 414 | Q1L, G4C, Q28R, E65V, A72C, D181N, E183M, P224L, T280A, S311G, D320I, D346E, Q349K, T393V, Y422F, P442S, N445D, R446G, H468L, V482I | 69.9 |
| 415 | Q1L, G4C, Q28R, E65V, Q69R, A72C, D181N, E183M, P224L, S311G, D320I, D346E, Q349K, T393V, Y422F, P442S, N445D, R446G, H468L, V482I | 69.9 |
| 416 | Q1L, G4C, Q28R, E65V, A72C, D181N, E183M, P224L, K275E, S311G, D320I, D346E, Q349K, T393V, Y422F, P442S, N445D, R446G, H468L, V482I | 69.9 |
| 417 | Q1L, G4C, Q28K, E65V, A72C, E183K, D202N, P224L, S311N, D320I, D346E, Q349K, T393V, Y422F, P442S, N445D, R446G, H468L, V482T | 69.9 |
| 418 | Q1L, G4C, Q28K, E65V, A72C, D181N, E183M, S311G, N318Y, D320I, D346A, Q349K, T393I, Y422F, N445D, R446G, H468Q, V482T | 69.9 +/− 0.2 |

TABLE 6-continued

Listing of Mutants of SeqID NO. 18 with improved IT50 values.

| | Mutations with respect to Seq. ID NO. 18 | IT50-value (4-MUL) |
|---|---|---|
| 419 | Insertion at position A455(AAAPA), Q1L, G4C, Q28R, E65V, A72C, D181N, E183M, P224L, S311G, D320I, D346E, Q349K, T393V, Y422F, P442S, N445D, R446G, H468L, V482I | 70 |
| 420 | Q1L, G4C, S24T, T26I, Q28R, N29Y, G30A, E65V, A72C, D181N, E183M, P224L, S311G, D320I, D346E, Q349K, T393V, Y422F, P442S, N445D, R446G, H468L, V482I | 70 |
| 422 | Q1L, G4C, Q28R, E65M, A72C, E183M, S311G, D320I, D346A, Q349K, T393V, Y422F, N445D, R446G, H468Q, V482I | 70 |
| 423 | Q1L, G4C, Q28R, E65V, A72C, D181N, E183M, D202N, S311G, D346E, Q349K, T393I, Y422F, N445D, R446G, H468Q, V482I | 70.1 |
| 424 | Q1L, G4C, Q28R, E65V, A72C, E183M, P224L, S311G, D320I, D346E, Q349K, T393V, Y422F, P442S, N445D, R446G, H468L, V482I | 70.1 |
| 425 | Q1L, G4C, Q28K, E65K, A72C, D181N, E183M, S311G, N318Y, D320I, T335I, D346E, Q349K, T393V, Y422F, N445D, R446G, H468Q V482T | 70.1 +/− 0.2 |
| 426 | Q1L, G4C, Q28R, E65V, A72C, S311G, N318Y, D320I, T335I, D346E, Q349K, T393V, Y422F, N445D, R446G, H468L, V482T | 70.1 |
| 427 | Q1L, G4C, S24C, Q28R, G30A, E65V, A72C, Y155C, D181N, Q190K, D202N, P224L, S311G, T335I, D346E, Q349K, D390E, T393V, Y422F, N445D, R446G, R453G, H468Q, P480S, V482I | 70.1 |
| 428 | Q1L, G4C, Q28R, E65V, A72C, D181N, E183M, P224L, S311G, D320I, D346E, Q349K, T393V, P402S, Y422F, P442S, N445D, R446G, H468L, V482I | 70.1 |
| 429 | Q1L, G4C, Q28R, E65K, A72C, E183M, D202N, P224L, S311N, N318Y, T335I, D346E, Q349K, T393V, Y422F, P442S, N445D, R446G, H468Q, V482I | 70.1 |
| 430 | Q1L, G4C, A21T, T26I, Q28R, N29Y, E65V, A72C, Y155C, D181N, D202N, P224L, M234T, S311G, D320I, D346E, Q349K, D390E, T393V, Y422F, N445D, R446G, R453G, H468Q, V482I | 70.1 |
| 431 | Q1L, G4C, Q28R, E65K, A72C, S86T, D202N, P224L, S311D, D320N, T335I, D346V, Q349K, T392M, T393V, Y422F, P442S, R446S, H468L | 70.2 |
| 432 | Q1L, G4C, Q28R, E65V, A72C, S86T, E183K, D202N, S311G, N318Y, D320I, D346A, Q349K, T393V, Y422F, P442S, N445D, R446G, H468Q, V482I | 70.2 |
| 433 | Q1L, G4C, W40R, E65M, A72C, S86T, E183V, S192L, D202I, H203R, P224L, S311G, N318Y, D320V, D346A, Q349K, P442S, N445D, R446G, H468R, V482A | 70.2 +/− 0.3 |
| 434 | Q1L, G4C, Q28R, E65V, A72C, D181N, E183M, P224L, S311G, D346E, Q349K, T393V, Y422F, P442S, N445D, R446G, H468L, V482I | 70.2 |
| 435 | Insertion at position G434(AAATG) and T457(AAATT), Q1L, G4C, Q28R, E65V, A72C, D181N, E183M, P224L, S311G, D320I, D346E, Q349K, T393V, Y422F, P442S, N445D, R446G, H468L, V482I | 70.2 +/− 0.2 |
| 436 | Q1L, G4C, Q28R, E65V, A72C, K118Q, D181N, E183M, P224L, D247N, S311G, D320I, D346E, Q349K, T393V, Y422F, P442S, N445D, R446G, H468L, V482I | 70.3 |
| 437 | Q1L, G4C, Q28R, E65V, A72C, D181N, E183M, D202N, P224L, S311N, D320I, D346E, Q349K, T393V, Y422F, N445D, R446G, H468Q, V482I | 70.4 +/− 0 |
| 438 | Q1L, G4C, Q28R, E65V, A72C, S86T, D202N, P224L, S311G, N318Y, T335I, D346E, Q349K, T393V, Y422F, N445D, R446G, H468L, V482T | 70.4 +/− 0.9 |
| 439 | Q1L, G4C, Q28K, E65M, A72C, D181N, E183M, D202N, S311G, N318Y, D346A, Q349K, T393V, Y422F, P442S, N445D, R446G, H468L, V482T | 70.4 +/− 0.5 |
| 440 | Insertion at position P454(VRPQP), Q1L, G4C, Q28R, E65V, A72C, D181N, E183M, P224L, S311G, D320I, D346E, Q349K, T393V, Y422F, P442S, N445D, R446G, H468L, V482I | 70.5 |
| 441 | Q1L, G4C, Q28R, A72C, D181N, E183V, S192M, D202N, P224L, S311D, N318Y, D320N, D346E, Q349R, T393V, Y422F, P442S, R446G, H468L, P480S | 70.5 |
| 442 | Q1L, G4C, Q28R, A72C, S86T, D181N, S192L, D202N, P224L, S311G, N318Y, D320V, T335I, D345E, D346A, Q349K, Y422F, P442S, N445D, R446G, H468Q, H505Q | 70.5 |
| 443 | Q1L, G4C, Q28R, E65V, A72C, S86T, D181N, E183K, P224L, S311G, N318Y, D320I, D346A, Q349K, T393V, Y422F, P442S, N445D, R446G, H468L, V482I | 70.6 +/− 0 |
| 444 | Q1L, G4C, Q28R, E65M, A72C, D181N, E183K, D202N, P224L, S311G, D320I, D346E, Q349K, T393V, Y422F, P442S, N445D, R446G, H468Q, V482I | 70.6 +/− 0.6 |
| 445 | Q1L, G4C, Q28R, E65V, A72C, D181N, D202N, S311G, T335I, D346A, Q349K, T393I, Y422F, P442S, N445D, R446G, H468L, V482I | 70.7 +/− 0.5 |
| 446 | Q1L, G4C, Q28R, E65V, A72C, D181N, E183M, P224L, D247N, S311G, D320I, D346E, Q349K, T387S, T393V, Y422F, P442S, N445D, R446G, H468L, V482I | 70.7 |
| 447 | Q1L, G4C, Q28R, E65V, A72C, D181N, D202N, P224L, S311G, D346A, Q349K, T393V, Y422F, N445D, R446G, H468L, V482I | 70.8 +/− 0.4 |

TABLE 6-continued

| Listing of Mutants of SeqID NO. 18 with improved IT50 values. | | |
|---|---|---|
| | Mutations with respect to Seq. ID NO. 18 | IT50-value (4-MUL) |
| 448 | insertion at G434(AAATG), Q1L, G4C, Q28R, E65V, A72C, D181N, E183M, P224L, S311G, D320I, D346E, Q349K, T393V, Y422F, P442S, N445D, R446G, H468L, V482I | 70.9 |
| 449 | insertion at T457(AAATT), Q1L, G4C, Q28R, E65V, A72C, D181N, E183M, P224L, S311G, D320I, D346E, Q349K, T393V, Y422F, P442S, N445D, R446G, H468L, V482I | 70.9 |
| 450 | Q1L, G4C, Q28K, E65V, A72C, S86T, E183K, S192L, D202N, D320N, T335I, D346A, Q349R, T393A, Y422F, P442S, R446G, H468R, V482A | 71 |
| 451 | Q1L, G4C, Q28R, E65V, A72C, D181N, E183M, P224L, S236F, S311G, G320I, D346E, Q349K, T393V, Y422F, P442S, N445D, R446G, H468L, V482I | 71 |
| 452 | Q1L, G4C, Q28R, E65K, A72C, D202I, P224L, S311G, N318Y, D320V, T335I, D346A, Q349R, T392M, T393A, N445D, R446G, H468L | 71.1 |
| 453 | Q1L, G4C, E65M, A72C, S86T, E183V, D202I, P224L, S311G, N318Y, D320V, D346A, Q349K, P442S, N445D, R446G, H468L, V482A | 71.1 |
| 454 | Q1L, G4C, Q28R, E65V, A72C, K92R, D181N, E183M, P224L, I277V, S311G, D320I, D346E, Q349K, T393V, Y422F, P442S, N445D, R446G, H468L, V482I | 71.1 |
| 455 | Q1L, G4C, A72C, S86T, D181N, E183K, D202V, P224L, S311G, D320V, D346E, Q349R, T393A, Y422F, P442S, N445D, R446G, H468L | 71.1 |
| 456 | Q1L, G4C, Q28K, E65V, A72C, D181N, E183M, D202N, P224L, S311G, T335I, D346E, Q349K, T393V, Y422F, P442S, N445D, R446G, H468Q, V482I | 71.1 +/- 0 |
| 457 | Q1L, G4C, Q28K, E65V, A72C, S86T, D181N, E183K, S192L, D202V, S311G, D320I, D346V, Q349R, T393A, Y422F, P442S, N445D, R446G, H468Q, V482I | 71.1 |
| 458 | Q1L, G4C, Q28R, E65V, A72C, S86T, D181N, D202N, P224L, S311N, N318Y, D320I, D346A, Q349K, T393V, Y422F, N445D, R446G, H468L, V482T | 71.2 +/- 0 |
| 459 | Q1L, G4C, A21T, T26I, Q28R, G30A, E65V, A68T, A72C, D181N, E183M, D202N, T229M, S311G, A340S, D346E, Q349K, T393V, Y422F, N445D, R446G, H468Q, V482T | 71.3 |

Example 9

Characterization of Variants of the *Talaromyces emersonii* CBHI/*Trichoderma reesei*-CBD Fusion (with 6× His-Tag)

80 mL. of fermentation broth were concentrated to a final volume of approx. 1 mL. After determination of protein concentration (Bradford reagent, Biorad, Germany, Standard is BSA form Sigma-Aldrich, Germany) 1.2 mg of protein were purified with the Ni-NTA Spin kit (Qiagen, Germany). The purified CBH1 fraction was subsequently assayed by performing a hydrolysis reaction on pretreated (acid pretreatment) wheat straw. 12.5 mg (dry mass) of pre-treated wheat straw is mixed with 0.0125 mg of purified CBHI and 40CBU Novo188 (Novozymes, Denmark) per mg of CBH1. 50 mM sodium acetate (Sigma-Aldrich, Germany) is added up to 500 µL. The assay is kept at temperatures ranging from 50° C. to 65° C. for 48 hours and analysed by HPLC to determine the temperature dependent glucose content.

Example 10

Hydrolysis of Straw with Seq. ID NO:2 Variant Proteins Expressed from *Trichoderma reesei*

Selected cellobiohydrolase sequences (Table 7) are expressed from *Trichoderma reesei* as described in Example 5 by replacement of the native CBHI reading frame with the corresponding sequence fusions to the CBHI signal peptide. Samples of the mutant proteins are isolated from the culture supernatant and purified by Ni-NTA affinity chromatography. The characterization of the proteins is done by incubation of the proteins (E) with acid-pretreated straw substrate (S) (2.5% dry matter content and E/S=0.1% w/w in the reaction) at temperatures between 50° C. and 75° C. for 48 hours in the presence of a non-limiting amount of beta-glucosidase followed by determination of the released glucose concentration by HPLC. The results are shown in the Table 7. As indication for the performance the glucose release after 48 hours at 60° C. was taken and found significantly increased in comparison to the wild type protein. In the Table 7 the Temperatures where still 50% of the maximum glucose yield is reached are given.

TABLE 7

| Performance of Trichoderma expressed Cellobiohydrolases on straw | | |
|---|---|---|
| | Mutation with respect to Seq. ID NO: 2 | Temperature [° C.] of halve optimum sugar release from acid pretreated straw (48 h 0.1% Enzyme to Substrate ratio (40 CBU/mg Cellulase BGL added) |
| 1 | | 59.3 ± 0.4 |
| 2 | , Q1L, G4C, A72C, D181N, E183K, Q349R | 61.3 |

TABLE 7-continued

| Performance of Trichoderma expressed Cellobiohydrolases on straw | | |
|---|---|---|
| | Mutation with respect to Seq. ID NO: 2 | Temperature [° C.] of halve optimum sugar release from acid pretreated straw (48 h 0.1% Enzyme to Substrate ratio (40 CBU/mg Cellulase BGL added) |
| 3 | , Q1L, G4C, A72C, Y155C, Q349K | 64.3 |
| 4 | , G4C, Q28K, E65M, A72C, S86T, E183M, D202N, P224L, S311G, T335I, D346E, Q349K, T393V, Y422F, P442S, N445D, R446G, H468L, V482I | 73.0 |
| 5 | , Q1L, G4C, Q28R, E65V, A72C, D181N, P224L, S311D, N318Y, D320N, D346A, Q349K, T392M, T393I, Y422F, N445D, R446G, H468Q, V482I | 68.7 |
| 6 | , Q1L, G4C, Q28R, E65V, A72C, D181N, E183M, P224L, S311G, D320I, D346E, Q349K, T393V, Y422F, P442S, N445D, R446G, H468L, V482I | 69.3 |
| 7 | , Q1L, G4C, Q28R, E65V, A72C, E183M, D202N, P224L, S311G, N318Y, T335I, D346E, Q349K, T393V, Y422F, N445D, R446G, H468L, V482I | 69.5 |
| 8 | , Q1L, G4C, Q28R, E65V, A72C, S86T, E183K, D202N, S311G, N318Y, D320I, D346A, Q349K, T393V, Y422F, P442S, N445D, R446G, H468Q, V482I | 67.5 |
| 9 | , Q1L, G4C, Q28R, E65V, A72C, E183M, P224L, S311G, D320I, D346E, Q349K, T393V, Y422F, P442S, N445D, R446G, H468L, V482I | 68.2 |
| 10 | , Q1L, G4C, Q28R, E65V, A72C, P224L, S311G, D320I, D346E, Q349K, T393V, Y422F, P442S, N445D, R446G, H468L, V482I | 68.4 |
| 11 | , Q1L, G4C, Q28R, E65V, A72C, D202N, S311N, D320I, T335I, D346E, Q349K, T393V, Y422F, N445D, R446G, H468Q, V482T | 67.8 |
| 12 | , Q1L, G4C, Q28K, E65V, A72C, E183M, D202N, S311G, N318Y, D346E, Q349K, T393I, Y422F, N445D, R446G, H468Q, V482I | 68.0 |
| 13 | , Q2S, G4C, A6L, T7Q, A8S, N10T, Q28K, E65K, A72C, E183M, S311G, N318Y, D320I, T335I, D346E, Q349K, T393V, Y422F, N445D, R446G, H468Q, V482T | 72.0 |
| 14 | , Q2S, G4C, A6L, T7Q, A8S, N10T, Q28K, E65V, A72C, E183M, D202N, P224L, S311G, T335I, D346E, Q349K, T393V, Y422F, P442S, N445D, R446G, H468Q, V482I | 73.8 |
| 15 | , Q2S, G4C, A6L, T7Q, A8S, N10T, Q28R, E65V, A72C, P224L, S311D, N318Y, D320N, D346A, Q349K, T392M, T393I, Y422F, N445D, R446G, H468Q, V482I | 73.6 |
| 16 | , Q2S, G4C, A6L, T7Q, A8S, N10T, Q28K, N29Y, E65K, A72C, S311G, T335I, D346E, Q349K, T393V, Y422F, N445D, R446G, H468Q, V482T | 71.9 |
| 17 | , Q1L, G4C, Q28R, E65V, A72C, K159KCGRNK, E183M, P224L, S311G, D320I, D346E, Q349K, T393V, Y422F, T433TGAAAT, P442S, N445D, R446G, H468L, V482I | 70.5 |
| 18 | , Q2S, G4C, A6L, T7Q, A8S, N10T, S24T, Q28R, E65K, A72C, D202N, S311G, T335I, D346E, Q349K, T393I, Y422F, N445D, R446G, H468Q, V482T | 72.2 |
| 19 | , Q1L, G4C, Q28R, E65V, A72C, E183M, P224L, S311G, D320I, D346E, Q349K, T393V, Y422F, P442S, N445D, R446G, P454PVRPQP, H468L, V482I | 69.1 |

TABLE 7-continued

| Performance of Trichoderma expressed Cellobiohydrolases on straw | | |
|---|---|---|
| | Mutation with respect to Seq. ID NO: 2 | Temperature [° C.] of halve optimum sugar release from acid pretreated straw (48 h 0.1% Enzyme to Substrate ratio (40 CBU/mg Cellulase BGL added) |
| 20 | , Q1L, G4C, Q28R, E65V, A72C, K159KCGRNK, E183M, P224L, S311G, D320I, D346E, Q349K, T393V, Y422F, P442S, N445D, R446G, H468L, V482I | 68.2 |
| 21 | , Q1L, G4C, S24T, T26I, Q28R, N29Y, G30A, E65V, A68T, A72C, E183M, Q190K, P224L, S311G, D320I, D346E, Q349K, T393V, Y422F, P442S, N445D, R446G, H468L, V482I | 70.2 |
| 22 | Seq ID No. 12 | 58.6 ± 0.4 |

Example 11

Performance of Seq. ID NO: 5 Variants with Improved Thermostability

PCR-Techniques were user for the transfer of selected mutations into the Seq. ID NO:5 backbone, as deduced from screened Seq. ID NO: 2 Mutants with superior performance. Protein expressed from *Pichia pastoris* was taken from the culture supernatant and tested for their Substrate Conversion Capacity by the procedure given in example 8. In the table the calculated IT50 values for the 4-MUL Substrate are given. Slightly higher stability of Proteins without CBD compared to the fusion proteins are found under these conditions. Results are shown in Table 8.

TABLE 8

| Comparison of IT50 Values of SEQ. ID NO: 5 and SEQ. ID NO 2 Mutants | | | |
|---|---|---|---|
| | Mutation Pattern with respect to Seq. ID NO: 5 | IT50 of the original Seq. ID NO: 5 mutant | IT50 of the original Seq. ID NO: 2 mutant |
| 1 | wt | 61.3 | 60.4 +/− 0.5 |
| 2 | , G4C, Q28K, E65M, A72C, S86T, E183M, D202N, P224L, S311G, T335I, D346E, Q349K, T393V, Y422F | 70.0 | 69.5 |
| 3 | , Q1L, G4C, Q28R, E65V, A72C, D181N, E183M, P224L, S311G, D320I, D346E, Q349K, T393V, Y422F | 72.0 | 69.8 +/− 0.8 |
| 4 | , Q1L, G4C, Q28K, E65K, A72C, D181N, E183M, S311G, N318Y, D320I, T335I, D346E, Q349K, T393V, Y422F | 70.3 | 70.1 +/− 0.2 |
| 5 | , Q1L, G4C, Q28K, E65V, A72C, D181N, E183M, D202N, P224L, S311G, T335I, D346E, Q349K, T393V, Y422F | 71.9 | 71.1 +/− 0 |
| 6 | Q1L, G4C, Q28R, E65V, A72C, G151GCGRSG, D181N, E183M, P224L, S311G, D320I, D346E, Q349K, T393V, Y422F | 72.7 | 68.2 |

Example 12

Influence of Different Cellulose Binding Domains on IT 50 Values

To evaluate the interchangeability of the CBDs a stabilized Seq.ID NO: 5 mutant (Q1L, G4C, Q28R, E65V, A72C, D181N, E183M, P224L, S311G, D320I, D346E, Q349K, T393V, Y422F) is connected with a series of cellulose binding domains and linker regions from cellobiohydrolases from different sources by OE-PCR. The resulting coding sequences (SEQ. IDs NO: 21, 23, 25, 27 and 29) are cloned to a *Pichia pastoris* expression vector for the expression of the corresponding fusion proteins according to SEQ. IDs NO: 20, 22, 24, 26 and 28). IT50 values for the variants are evaluated as described before and are listed in the Table 9. Only small influences of different CBD modules on the stability are observed.

TABLE 9

Performance of different fusions of CBD with their linkers to stabilized and non-stabilized Seq. ID. NO: 5 variants in comparison

| | DNA Sequence Listing | Protein Sequence Listing | Origin of linker and CBD | IT50 [° C.] (4-MUL Test) | Temperature [° C.] of halve optimum sugar release from cellulose (48 h 0.1% Enzyme to Substrate ratio (40 CBU/ mg Cellulase BGL added) | Comment |
|---|---|---|---|---|---|---|
| 1 | 1 | 2 | *T. reesei* | 60.4 +/− 0.5 | 57.4 +/− 0.5 | non stabilized core (wild type) |
| 2 | 21 | 20 | *C. thermophilum* | 69.5 +/− 0.5 | 65.6 | |
| 3 | 23 | 22 | *P. chrysosporium* | 69.3 +/− 0.2 | 65.6 | |
| 4 | 25 | 24 | *P. janthinellum* | 68.4 +/− 1.2 | 65.0 | |
| 5 | 27 | 26 | *I. lacteus* | 68.8 +/− 0.1 | 65.2 | |
| 6 | 29 | 28 | *T. reesei* | 69.8 +/− 0.8 | 65.0 +/− 0.7 | stabilized core and CBD-linker region |

TABLE 10

Sequence Listings (Overview)

| SEQID | Nucleic acid [N]/ Protein [P] | Description | ID |
|---|---|---|---|
| SEQID NO 01 | [N] | Coding Sequence for *Talaromyces emersonii* CBHI/ *Trichoderma reesei* -CBD fusion including the alpha factor signal peptide. | |
| SEQID NO 02 | [P] | Mature Sequence of *Talaromyces emersonii* CBHI/ *Trichoderma reesei* -CBD | CBH-a |
| SEQID NO 03 | [N] | Coding sequence of the fusion of CBH-a with *Trichoderma reesei* CBHI Signal peptide | |
| SEQID NO 04 | [P] | *Trichoderma reesei* CBHI cellulose binding domain and linker sequence | |
| SEQID NO 05 | [P] | *Talaromyces emersonii* CBHI | CBH-b |
| SEQID NO 06 | [N] | *Talaromyces emersonii* CBHI | |
| SEQID NO 07 | [N] | *Humicola grisea* CBHI | |
| SEQID NO 08 | [P] | *Humicola grisea* CBHI | CBH-d |
| SEQID NO 09 | [N] | *Thermoascus aurantiacus* CBHI | |
| SEQID NO 10 | [P] | *Thermoascus aurantiacus* CBHI | CBH-e |
| SEQID NO 11 | [N] | *Trichoderma reesei* CBHI | |
| SEQID NO 12 | [P] | *Trichoderma reesei* CBHI | CBH-c |
| SEQID NO 13 | [N] | *Trichoderma viridae* CBHI | |
| SEQID NO 14 | [P] | *Trichoderma viridae* CBHI | CBH-f |
| SEQID NO 15 | [N] | fusion *Humicola grisea* CBHI/*Trichoderma reesei* -CBD | |
| SEQID NO 16 | [P] | fusion *Humicola grisea* CBHI/*Trichoderma reesei* -CBD | CBH-g |
| SEQID NO 17 | [N] | Coding Sequence for. *Talaromyces emersonii* CBHI/ *Trichoderma reesei* -CBD including the alpha factor signal peptide and a 6x His Tag. | |
| SEQID NO 18 | [P] | Mature Sequence of *Talaromyces emersonii* CBHI/ *Trichoderma reesei* -CBD fusion peptide with 6x His Tag | CBH-ah |

TABLE 10-continued

| Sequence Listings (Overview) | | | |
|---|---|---|---|
| SEQID | Nucleic acid [N]/ Protein [P] | Description | ID |
| SEQID NO 19 | [N] | *Humicola grisea* CBHI, alternative coding sequence | |
| SEQID NO: 20 to 41 | [N] | Oligonucleotide primers used with this invention | |
| SEQID NO 42 | [P] | *Talaromyces emersonii* CBHI Mutant with Chaetmium thermophilum cellobiohydrolase I CBD with 6x His-TAG | |
| SEQID NO 43 | [N] | Coding Sequence for *Talaromyces emersonii* CBHI with 6x His-TAG Mutant with Chaetmium thermophilum cellobiohydrolase I CBD | |
| SEQID NO 44 | [P] | *Talaromyces emersonii* CBHI Mutant with *Phanerochaete chrysosporium* cellobiohydrolase CBD with 6x His-TAG | |
| SEQID NO 45 | [N] | Coding Sequence for *Talaromyces emersonii* CBHI Mutant with *Phanerochaete chrysosporium* cellobiohydrolase CBD with 6x His-TAG | |
| SEQID NO 46 | [P] | Talaromyces emersonii CBHI Mutant with *Penicillium jantinellum* cellobiohydrolase CBD with 6x His-TAG | |
| SEQID NO 47 | [N] | Coding Sequence for *Talaromyces emersonii* CBHI Mutant with *Penicillium jantinellum* cellobiohydrolase CBD with 6x His-TAG | |
| SEQID NO 48 | [P] | *Talaromyces emersonii* CBHI Mutant with *Irpex lacteus* cellobiohydrolase CBD with 6x His-TAG | |
| SEQID NO 49 | [N] | Coding Sequence for *Talaromyces emersonii* CBHI Mutant with *Irpex lacteus* cellobiohydrolase CBD with 6x His-TAG | |
| SEQID NO 50 | [P] | *Talaromyces emersonii* CBHI Mutant with mutated *Trichoderma reesei* CBD with 6x His-TAG | |
| SEQID NO 51 | [N] | Coding Sequence for *Talaromyces emersonii* CBHI Mutant with mutated *Trichoderma reesei* CBD with 6x His-TAG | |

SEQID.NO. 01 cagcaggccggcacggcgacggcagagaaccacccgcccctgacatggcaggaatgcaccgcccctgggagctgc
accacccagaacggggcggtcgttcttgatgcgaactggcgttgggtgcacgatgtgaacggatacaccaactgc
tacacgggcaatacctgggaccccacgtactgccctgacgacgaaacctgcgcccagaactgtgcgctggacggc
gcggattacgagggcacctacggcgtgacttcgtcgggcagctccttgaaactcaatttcgtcaccgggtcgaac
gtcggatcccgtctctacctgctgcaggacgactcgacctatcagatcttcaagctcctgaaccgcgagttcagc
tttgacgtcgatgtctccaatcttccgtgcggattgaacggcgctctgtactttgtcgccatggacgccgacggc
ggcgtgtccaagtacccgaacaacaaggctggtgccaagtacggaaccgggtattgcgactcccaatgcccacgg
gacctcaagttcatcgacggcgaggccaacgtcgagggctggcagccgtcttcgaacaacgccaacaccggaatt
ggcgaccacggctcctgctgtgcggagatggatgtctgggaagcaaacagcatctccaatgcggtcactccgcac
ccgtgcgacacgccaggccagacgatgtgctctggagatgactgcggtggcacatactctaacgatcgctacgcg
ggaacctgcgatcctgacggctgtgacttcaacccttaccgcatgggcaacacttctttctacgggcctggcaag
atcatcgataccaccaagcccttcactgtcgtgacgcagttcctcactgatgatggtacggatactggaactctc
agcgagatcaagcgcttctacatccagaacagcaacgtcattccgcagcccaactcggacatcagtggcgtgacc
ggcaactcgatcacgacggagttctgcactgctcagaagcaggcctttggcgacacggacgacttctctcagcac
ggtggcctggccaagatgggagcggccatgcagcagggtatggtcctggtgatgagtttgtgggacgactacgcc
gcgcagatgctgtggttggattccgactacccgacggatgcggaccccacgacccctggtattgcccgtggaacg
tgtccgacggactcgggcgtcccatcggatgtcgagtcgcagagccccaactcctacgtgacctactcgaacatt
aagtttggtccgatcggtagcacaggtaatccttcaggtggtaatcctccaggtggaaacagaggaacaacgaca
actagaagaccagctactacaactggttcaagtccaggtccaactcaatcacactacggtcaatgtggtggtata
ggttactctggtcccaccgtttgtgcttctggtactacttgccaagttctgaacccttactactcacagtgtcta
taatgataa
Coding Sequence for CBH-a (mature)

SEQID.NO. 02

QQAGTATAENHPPLTWQECTAPGSCTTQNGAVVLDANWRWVHDVNGYTNCYTGNTWDPTYCPDDETCAQNCALDG
ADYEGTYGVTSSGSSLKLNFVTGSNVGSRLYLLQDDSTYQIFKLLNREFSFDVDVSNLPCGLNGALYFVAMDADG
GVSKYPNNKAGAKYGTGYCDSQCPRDLKFIDGEANVEGWQPSSNNANTGIGDHGSCCAEMDVWEANSISNAVTPH
PCDTPGQTMCSGDDCGGTYSNDRYAGTCDPDGCDFNPYRMGNTSFYGPGKIIDTTKPFTVVTQFLTDDGTDTGTL

TABLE 10-continued

| Sequence Listings (Overview) | | | |
|---|---|---|---|
| SEQID | Nucleic acid [N]/ Protein [P] | Description | ID |

SEIKRFYIQNSNVIPQPNSDISGVTGNSITTEFCTAQKQAFGDTDDFSQHGGLAKMGAAMQQGMVLVMSLWDDYA
AQMLWLDSDYPTDADPTTPGIARGTCPTDSGVPSDVESQSPNSYVTYSNIKFGPIGSTGNPSGGNPPGGNRGTTT
TRRPATTTGSSPGPTQSHYGQCGGIGYSGPTVCASGTTCQVLNPYYSQCL
Mature Sequence of CBH-a

SEQID.NO. 03 atgtatcggaagttggccgtcatctcggccttcttggccacagctcgtgctcagcaggccggcacggcgacggca
gagaaccacccgcccctgacatggcaggaatgcaccgcccctgggagctgcaccacccagaacggggcggtcgtt
cttgatgcgaactggcgttgggtgcacgatgtgaacggatacaccaactgctacacgggcaatacctgggacccc
acgtactgccctgacgacgaaacctgcgcccagaactgtgcgctggacggcgcggattacgagggcacctacggc
gtgacttcgtcgggcagctccttgaaactcaatttcgtcaccgggtcgaacgtcggatcccgtctctacctgctg
caggacgactcgacctatcagatcttcaagctcctgaaccgcgagttcagctttgacgtcgatgtctccaatctt
ccgtgcggattgaacggcgctctgtactttgtcgccatggacgccgacggcggcgtgtccaagtacccgaacaac
aaggctggtgccaagcacggaaccgggtattgcgactcccaatgcccacgggacctcaagttcatcgacggcgag
gccaacgtcgagggctggcagccgtcttcgaacaacgccaacaccggaattggcgaccacggctcctgccgtgcg
gagatggatgtctgggaagcaaacagcatctccaatgcggtcactccgcacccgtgcgacacgccaggccagacg
atgtgctctggagatgactgcggtggcacatactctaacgatcgctacgcgggaacctgcgatcctgacggctgt
gacttcaacccttaccgcatgggcaacacttctttctacgggcctggcaagatcatcgataccaccaagcccttc
actgtcgtgacgcagttcctcactgatgatggtacggatactggaactctcagcgagatcaagcgcttctacatc
cagaacagcaacgtcattccgcagcccaactcggacatcagtggcgtgaccggcaactcgatcacgacggagttc
tgcactgctcagaagcaggcctttggcgacacggacgacttctctcagcacggtggcctggccaagatgggagcg
gccatgcagcagggtatggtcctggtgatgagtttgtgggacgactacgccgcgcagatgctgtggttggattcc
gactacccgacggatgcggaccccacgacccctggtattgcccgtggaacgtgtccgacggacccgggcgtccca
tcggatgtcgagtcgcagagccccaactcctacgtgacctactcgaacattaagtttggtccgatcggtagcaca
ggtaatccttcaggtggtaatcctccaggtggaaacagaggaacaacgacaactagaagaccagctactacaact
ggttcaagtccaggtccaactcaatcacactacggtcaatgtggtggtataggttactctggtcccactgtctgt
gcttctggtactacttgccaagttctgaacccttactactcacagtgtctagcttctgcacatcatcaccaccac
cattaa
Coding sequence of the fusion of CBH-a with *Trichoderma reesei* CBHI Signal peptide

SEQID.NO. 04

GSTGNPSGGNPPGGNRGTTTTRRPATTTGSSPGPTQSHYGQCGGIGYSGPTVCASGTTCQVLNPYYSQCL
*Trichoderma reesei* CBHI cellulose binding domain and linker sequence

SEQID.NO. 05

QQAGTATAENHPPLTWQECTAPGSCTTQNGAVVLDANWRWVHDVNGYTNCYTGNTWDPTYCPDDETCAQNCALDG
ADYEGTYGVTSSGSSLKLNFVTGSNVGSRLYLLQDDSTYQIFKLLNREFSFDVDVSNLPCGLKGALYFVAMDADG
GVSKYPNNKAGAKYGTGYCDSQCPRDLKFIDGEANVEGWQPSSNNANTGIGDHGSCCAEMDVWEANSISNAVTPH
PCDTPGQTMCSGDDCGGTYSNDRYAGTCDPDGCDFNPYRMGNTSFYGPGKIIDTTKPFTVVTQFLTDDGTDTGTL
SEIKRFYIQNSNVIPQPNSDISGVTGNSITTEFCTAQKQAFGDTDDFSQHGGLAKMGAAMQQGMVLVMSLWDDYA
AQMLWLDSDYPTDADPTTPGIARGTCPTDSGVPSDVESQSPNSYVTYSNIKFGPINSTFTAS
*Talaromyces emersonii* CBHI sequence (CBH-b)

SEQID.NO. 06 atgagatttccttcaatttttactgcagttttattcgcagcatcctccgcattagctgctccagtcaacactaca
acagaagatgaaacggcacaaattccggctgaagctgtcatcggttacttagatttagaaggggatttcgatgtt
gctgttttgccattttccaacagcacaaataacgggttattgtttataaatactactattgccagcattgctgct
aaagaagaaggggtatctttggataaacgtgaggcggaagcaccctctcagcaggccggcacggcgacggcagag
aaccacccgcccctgacatggcaggaatgcaccgcccctgggagctgcaccacccagaacggggcggtcgttctt
gatgcgaactggcgttgggtgcacgatgtgaacggatacaccaactgctacacgggcaatacctgggaccccacg
tactgccctgacgacgaaacctgcgcccagaactgtgcgctggacggcgcggattacgagggcacctacggcgtg
acttcgtcgggcagctccttgaaactcaatttcgtcaccgggtcgaacgtcggatcccgtctctacctgctgcag
gacgactcgacctatcagatcttcaagcttctgaaccgcgagttcagctttgacgtcgatgtctccaatcttccg
tgcggattgaacggcgctctgtactttgtcgccatggacgccgacggcggcgtgtccaagtacccgaacaacaag
gctggtgccaagtacggaaccgggtattgcgactcccaatgcccacgggacctcaagttcatcgacggcgaggcc
aacgtcgagggctggcagccgtcttcgaacaacgccaacaccggaattggcgaccacggctcctgctgtgcggag
atggatgtctgggaagcaaacagcatctccaatgcggtcactccgcacccgtgcgacacgccaggccagacgatg
tgctctggagatgactgcggtggcacatactctaacgatcgctacgcgggaacctgcgatcctgacggctgtgac
ttcaacccttaccgcatgggcaacacttctttctacgggcctggcaagatcatcgataccaccaagcccttcact
gtcgtgacgcagttcctcactgatgatggtacggatactggaactctcagcgagatcaagcgcttctacatccag
aacagcaacgtcattccgcagcccaactcggacatcagtggcgtgaccggcaactcgatcacgacggagttctgc
actgctcagaagcaggcctttggcgacacggacgacttctctcagcacggtggcctggccaagatgggagcggcc
atgcagcagggtatggtcctggtgatgagtttgtgggacgactacgccgcgcagatgctgtggttggattccgac
tacccgacggatgcggaccccacgacccctggtattgcccgtggaacgtgtccgacggactcgggcgtcccatcg TABLE 10-continued

| Sequence Listings (Overview) | | | |
|---|---|---|---|
| SEQID | Nucleic acid [N]/ Protein [P] | Description | ID |

gatgtcgagtcgcagagccccaactcctacgtgacctactcgaacattaagtttggtccgatcaactcgaccttc
accgcttcgtgataa
Coding sequence of *Talaromyces emersonii* CBHI fused to the alpha factor signal peptide SEQID.NO. 07
QQAGTITAENHPRMTWKRCSGPGNCQTVQGEVVIDANWRWLHNNGQNCYEGNKWTSQCSSATDCAQRCALDGANY
QSTYGASTSGDSLTLKFVTKHEYGTNIGSRFYLMANQNKYQMFTLMNNEFAFDVDLSKVECGINSALYFVAMEED
GGMASYPSNRAGAKYGTGYCDAQCARDLKFIGGKANIEGWRPSTNDPNAGVGPMGACCAEIDVWESNAYAYAFTP
HACGSKNRYHICETNNCGGTYSDDRFAGYCDANGCDYNPYRMGNKDFYGKGKTVDTNRKFTVVSRFERNRLSQFF
VQDGRKIEVPPPTWPGLPNSADITPELCDAQFRVFDDRNRFAETGGFDALNEALTIPMVLVMSIWDDHHSNMLWL
DSSYPPEKAGLPGGDRGPCPTTSGVPAEVEAQYPDAQVVWSNIRFGPIGSTVNV
*Humicola grisea* CBHI (CBH-d)

SEQID.NO. 08
atgagatttccttcaatttttactgcagttttattcgcagcatcctccgcattagctgctccagtcaacactaca
acagaagatgaaacggcacaaattccggctgaagctgtcatcggttacttagatttagaaggggatttcgatgtt
gctgttttgccattttccaacagcacaaataacgggttattgtttataaatactactattgccagcattgctgct
aaagaagaaggggtatctttggataaacgtgaggcggaagcaccctctcagcaggctggtactattactgctgag
aaccacccaagaatgacctggaagagatgctctggtccaggaaactgtcagactgttcagggcgaggttgtgatt
gacgctaattggagatggttgcacaacaacggccagaactgttacgagggtaacaagtggacctctcagtgttct
tctgctaccgactgtgctcagagatgtgctttggacggtgccaactaccagtctacctacggtgcttctacctct
ggtgactctctgaccctgaagttcgttaccaagcacgagtacggaaccaacatcggctctagattctacctgatg
gccaaccagaacaagtaccagatgttcaccctgatgaacaacgagttcgcctttgacgttgacctgtctaaggtg
gagtgcggtatcaactctgccctgtacttcgttgctatggaagaggacggtggaatggcttcttacccatctaac
agagccggtgctaagtacggtactggttactgtgacgcccagtgtgctagagacctgaagttcatcggtggaaag
gccaacattgagggttggagaccatctaccaacgacccaaacgctggtgttggtccaatgggagcttgttgtgcc
gagattgatgtgtgggagtctaacgcttacgcctacgcttttaccccacacgcttgcggttctaagaacagatac
cacatctgcgagaccaacaactgtggtggaacctactctgacgacagattcgctggatactgcgacgctaacggt
tgtgactacaacccatacagaatgggcaacaaggacttctacggcaagggaaagaccgttgacaccaacagaaag
ttcaccgtggtgtcgagattcgagagaaacagactgtcgcagttctttgtgcaggacggcagaaagattgaggtc
ccaccaccaacttggccaggattgccaaactctgccgacattaccccagagttgtgtgacgctcagttcagagtg
ttcgacgacagaaacagatttgctgagaccggtggttttgacgctttgaacgaggctctgaccattccaatggtg
ctggtgatgtctatttgggacgaccaccactctaacatgttgtggctggactcttcttacccaccagagaaggct
ggattgccaggtggtgacagaggaccatgtccaactacttcgggtgttccagctgaggttgaggctcagtaccca
gacgctcaggttgtgtggtcgaacatcagattcggcccaatcggttctaccgtgaacgtgtaa
Coding sequence of *Humicola grisea* CBHI fused to the alpha factor signal peptide SEQID.NO. 09
heagtvtaenhpsltwqqcssggscttqngkvvidanwrwvhttsgytncytgntwdtsicpddvtcaqncaldg
adysgtygvttsgnalrlnfvtqssgknigsrlyllqddttyqifkllgqeftfdvdvsnlpcglngalyfvamd
adgnlskypgnkagakygtgycdsqcprdlkfingqnnvegwqpsandpnagvgnhgsscaemdvweansistav
tphpcdtpgqtmcqgddcggtyssträyagtcdtdgcdfnpyqpgnhsfygpgkivdtsskftvvtqfitddgtpe
gtlteikrfyvqngkvipqsestisgvtgnsitteyctaqkaafdntgffthgglqkisqalaqgmvlvmslwdd
haanmlwldstyptdadpdtpgvargtcpttsgvpadvesqnpnsyviysnikvgpinstftan
*Thermoascus auratiacus* CBHZ (CBH-e)

SEQID.NO. 10
atgagatttccttcaatttttactgcagttttattcgcagcatcctccgcattagctgctccagtcaacactaca
acagaagatgaaacggcacaaattccggctgaagctgtcaccggttacttagatttagaaggggatttcgatgtt
gctgttttgccattttccaacagcacaaataacgggttattgtttataaatactactattgccagcattgctgct
aaagaagaaggggtatctttggataaacgtgaggcggaagcaccctctcacgaggccggtaccgtaaccgcagag
aatcacccttccctgacctggcagcaatgctccagcggcggtagttgtaccacgcagaatggaaaagtcgttatc
gatgcgaactggcgttgggtccataccacctctggatacaccaactgctacacgggcaatacgtgggacaccagt
atctgtcccgacgacgtgacctgcgctcagaattgtgccttggatggagcggattacagtggcacctatggtgtt
acgaccagtggcaacgccctgagactgaactttgtcacccaaagctcagggaagaacattggctcgcgcctgtac
ctgctgcaggacgacaccacttatcagatcttcaagctgctgggtcaggagtttaccttcgatgtcgacgtctcc
aatctcccttgcgggctgaacggcgccctctactttgtggccatggacgccgacggcaatttgtccaaatacccct
ggcaacaaggcaggcgctaagtatggcactggttactgcgactctcagtgccctcgggatctcaagttcatcaac
ggtcaggccaacgttgaaggctggcagccgtctgccaacgacccaaatgccggcgttggtaaccacggttcctcg
tgcgctgagatggatgtctgggaagccaacagcatctctactgcggtgacgcctcacccatgcgacaccccggc
cagaccatgtgccagggagacgactgtggtggaacctactcctccactcgatatgctggtacctgcgacactgat
ggctgcgacttcaatccttaccagccaggcaaccactcgttctacggccccgggaagatcgtcgacactagctcc
aaattcaccgtcgtcacccagttcatcaccgacgagggacaccctccggcaccctgacggagatcaaacgcttc
tacgtccagaacggcaaggtgatcccccagtcggagtcgacgatcagcggcgtcaccggcaactcaatcaccacc
gagtattgcacggcccagaaggcagccttcgacaacaccggcttcttcacgcacggcgggctccagaagatcagt
caggctctggctcagggcatggtcctcgtcatgagcctgtgggacgatcacgccgccaacatgctctggctggac
agcacctacccgactgatgcggacccggacacccctggcgtcgcgcgcggcacctgccccacgacctccggcgtc TABLE 10-continued Sequence Listings (Overview)

| SEQID | Nucleic acid [N]/ Protein [P] | Description | ID |
|---|---|---|---|

ccggccgacgtggagccgcagaaccccaattcatatgttatctactccaacatcaaggtcggacccatcaactcg
accttcaccgccaactaa
Coding sequence of *Thermoascus auratiacus* CBHI fused to the alpha factor signal peptide

SEQID.NO. 11 atgagatttccttcaatttttactgcagttttattcgcagcatcctccgcattagctgctccagtcaacactaca
acagaagatgaaacggcacaaattccggctgaagctgtcatcggttacttagatttagaaggggatttcgatgtt
gctgttttgccattttccaacagcacaaataacgggttattgtttataaatactactattgccagcattgctgcc
aaagaagaaggggtatctttggataaacgtgaggcggaagcaccctcttcagcttgtacactgcaatccgagact
catccacctttaacgtggcaaaagtgtagttctggcggaacttgtactcaacagactggtagtgtcgtgatagat
gctaactggagatggacacatgcaacgaactcctcaactaactgctacgatggtaacacctggtcttctacattg
tgtcctgacaacgaaacctgcgctaagaactgttgtcttgatggagcagcttacgcaagtacatatggtgtgact
acctctggtaacagcctttccattggttttgtaacccagtcggctcagaagaatgttggtgctagattgtacctg
atggcttcagacaccacataccaggagtttaccttgttgggaaacgagttctctttcgacgtagatgtgtctcag
ctaccatgtggattgaatggagccttgtactttgtctcaatggatgcagacggaggtgtttcaaagtaccctact
aacacagctggtgctaagtatggaactgg&tactgcgattctcaatgcccaagagacctgaagttcatcaacgga
caagctaacgttgaaggttgggaaccttctagcaacaacgcaaacactggaattggtggtcatggttcttgctgt
tcagagatggacatttgggaagccaactccatcagtgaagctttgactccacatccatgcacaactgtcgggcaa
gaaatttgcgaaggtgatggttgtggtggcacttactctgataacagatacggcggaacatgtgatccagatgga
tgtgattggaacccatacagactgggtaacacttcgttttacggaccaggttcttccttcactctagacactacg
aagaagttgactgtggtcacccaatttgagacttctggtgccattaaccgatactacgtgcagaacggagttact
ttccaacagccaaacgctgaattgggtagttactcaggcaacgagcttaacgatgactactgcactgctgaagaa
gcagaatttggtggatcttcctttcggataagggtggattgacgcagttcaagaaagctacctctggtggaatg
gttctagtcatgagtctgtgggacgatcactacgctaacatgctttggctggactctacttaccctacaaacgag
acatcttctactcctggtgctgtaagaggtagctgttctacatcttctggagttccagcccaagttgagagtcaa
agtccaaatgccaaggtcaccttctccaacatcaagttcggaccaattggtagcacaggtaatccttcaggtggt
aatcctccaggtggaaacagaggaacaacgacaactagaagaccagctactacaactggttcaagtccaggtcca
actcaatcacactacggtcaatgcggtggtataggttactctggtcccactgtttgtgcttctggtactacttgc
caagttctgaacccttactactcacagtgtctagcttctgcacaccatcatcatcatcattaatgataa
Coding sequence for *Trichoderma reesei* CBHI (CBH-c), including the alpha factor signal peptide and a 6x His Tag.

SEQID.NO. 12

QSACTLCSETHPPLTWQKCSSGGTCTQQTGSVVIDANWRWTHATNSSTNCYDGNTWSSTLCPDNETCAKNCCLDG
AAYASTYGVTTSGNSLSIGFVTQSAQKNVGARLYLMASDTTYQEFTLLGNEFSFDVDVSQLPCGLNGALYFVSMD
ADGGVSKYPTNTAGAKYGTGYCDSQCPRDLKFINGQANVEGWEPSSNNANTGIGGHGSCCSEMDIWEANSISEAL
TPHPCTTVGQEICEGDGCGGTYSDNRYGGTCDPDGCDWNPYRLGNTSFYGPGSSFTLDTTKKLTVVTQFETSGAI
NRYYVQNGVTFQQPNAELGSYSGNELNDDYCTAEEAEFGGSSFSDKGGLTQFKKATSGGMVLVMSLWDDYYANML
WLDSTYPTNETSSTPGAVRGSCSTSSGVPAQVESQSPNAKVTFSNIKFGPIGSTGNPSGGNPPGGNRGTTTTRRP
ATTTGSSPGPTQSHYGQCGGIGYSGPTVCASGTTCQVLNPYYSQCL
*Trichoderma reesei* CBHI (CBH-c)

SEQID.NO. 13 atgagatttccttcaatttttactgcagttttattcgcagcatcctccgcattagctgctccagtcaacactaca
acagaagatgaaacggcacaaattccggctgaagctgtcatcggttacttagatttagaaggggatttcgatgtt
gctgttttgccattttccaacagcacaaataacgggttattgtttataaatactactattgccagcattgctgct
aaagaagaaggggtatctttggataaacgtgaggcggaagcaccctctcaatctgcttgcaccttgcagtctgaa
actcacccaccattgacctggcagaagtgttcttctggcggtacttgtactcagcagaccggttctgttgttatc
gacgccaactggagatggactcacgctaccaactcttctaccaactgctacgacggtaacacttggtcgtctacc
ttgtgtccagacaacgagacctgtgccaagaactgttgtttggacggtgctgcttacgcttctacctacggtgtt
accacctctggtaactcgctgtctatcggtttcgttacccagtctgcccagaaaaatgttggtgccagactgtac
ttgatggcttctgacaccacctaccaagagtttaccctgctgggtaacgagttctctttcgacgtggacgtttct
caactgccatgtggactgaacggtgccctgtacttcgtttctatggacgctgacggtggtgtttctaagtaccca
accaacaccgctggtgctaaatacggaaccggttactgcgattctcagtgcccaagagacctgaagttcatcaac
ggacaggctaacgttgaaggatgggagccatcttctaacaacgccaacaccggtattggtggtcacggttcttgc
tgttctgagatggacatctgggaggccaactctatttctgaggctttgaccccacacccatgtactactgtgggt
caagagatctgtgagggtgatggttgtggtggtacttactcggacaacagatacggtggtacttgtgacccagac
ggttgtgattgggacccatacagactgggtaacacctctttctacggtccaggatcttcttttaccctggacacc
accaagaagttgaccgttgttacccagtttgagacctctggtgccatcaacagatactacgtgcagaacggtgtt
actttccagcagccaaacgctgaactgggatcttactctggtaacggactgaacgacgactactgtactgctgag
gaagctgagttcggtggttcttctttctctgacaagggtggactgacccagtttaagaaggctacctctggcgga
atggtgctggttatgtctttgtgggacgactactacgctaacatgctgtggcttgactctacctacccaactaac
gagacctcttctaccccaggtgctgttagaggatcttgctctacctcttctggtgttccagctcaggttgagtct
cagtctccaaacgccaaggtgaccttctctaacatcaagttcggtccaatcggttctactggtgacccatctggt
ggtaacccaccaggtggaaacccacctggtactaccactaccagaagaccagctaccaccactggttcttctcca TABLE 10-continued Sequence Listings (Overview)

| SEQID | Nucleic acid [N]/ Protein [P] | Description | ID |
|---|---|---|---|

ggtccaacccaatctcactacggtcagtgtggtggtattggttactctggtccaaccgtttgtgcttctggaacc
acctgtcaggttctgaacccatactactcgcagtgcctgtaa
Coding sequence for *Trichoderma viride* CBHI, including the alpha factor signal peptide.

SEQID.NO. 14
QSACTLQSETHPPLTWQKCSSGGTCTQQTGSVVIDANWRWTHATNSSTNCYDGNTWSSTLCPDNETCAKNCCLDG
AAYASTYGVTTSGNSLSIGFVTQSAQKNVGARLYLMASDTTYQEFTLLGNEFSFDVDVSQLPCGLNGALYFVSMD
ADGGVSKYPTNTAGAKYGTGYCDSQCPRDLKFINGQANVEGWEPSSNNANTGIGGHGSCCSEMDIWEANSISEAL
TPHPCTTVGQEICEGDGCGGTYSDNRYGGTCDPDGCDWDPYRLGNTSFYGPGSSFTLDTTKKLTVVTQFETSGAI
NRYYVQNGVTFQQPNAELGSYSGNGLNDDYCTAEEAEFGGSSFSDKGGLTQFKKATSGGMVLVMSLWDDYYANML
WLDSTYPTNETSSTPGAVRGSCSTSSGVPAQVESQSPNAKVTFSNIKFGPIGSTGDPSGGNPPGGNPPGTTTTRR
PATTTGSSPGPTQSHYGQCGGIGYSGPTVCASGTTCQVLNPYYSQCL
*Trichoderma viride* CBHI (CBH-f)

SEQID.NO. 15
atgagatttccttcaatttttactgcagttttattcgcagcatcctccgcattagctgctccagtcaacactaca
acagaagatgaaacggcacaaattccggctgaagctgtcatcggttacttagatttagaaggggatttcgatgtt
gctgttttgccattttccaacagcacaaataacgggttattgtttataaatactactattgccagcattgctgct
aaagaagaaggggtatctttggataaacgtgaggcggaagcatgctcgcagcaggctggtacaattactgctgag
aaccatccaagaatgacgtggaagagatgtagtggtccaggaaactgtcagactgttcagggtgaggtcgtgata
gatgctaactggagatggttgcataacaacggccagaactgctacgagggtaacaagtggacctctcagtgttct
tctgctaccgactgcgctcagagatgtgctcttgatggagcaaactaccagagtacatatggtgcttctacctct
ggtgacagccttaccctgaagtttgtaaccaagcacgagtacggaaccaatatcggttctagattctacctgatg
gctaaccagaacaagtaccagatgtttaccttgatgaacaacgagttcgccttcgacgtagatctgtctaaggtg
gagtgtggaatcaattctgccttgtactttgtcgctatggaagaggacggaggtatggcttcttacccttctaac
agagctggtgctaagtatggaactggatactgcgatgcccaatgcgctagagacctgaagttcatcggtggaaag
gctaacattgaaggttggagaccttctaccaacgacccaaacgctggagttggtccaatgggtgcttgctgtgcc
gagattgacgtgtgggaatctaacgcttacgcctacgcttttactccacatgcttgcggttctaagaacagatac
cacatttgcgaaaccaacaactgaggtggcacttactctgatgacagattcgctggatactgtgatgctaacgga
tgtgattacaacccatacagaatgggtaacaaggacttttacggaaagggtaagactgttgacactaacagaaag
ttcactgtggtctcgagatttgagagaaacagactgtcgcagttctttgtgcaggacggaagaaagattgaggtc
ccaccaccaacttggccaggattgccaaactctgccgacattaccccagagttgtgcgacgctcagttcagagtg
tttgacgacagaaacagatttgctgagaccggtggatttgacgctttgaacgaggctctgaccattccaatggtt
ctagtcatgagtatttgggacgatcaccactctaacatgctttggctggactcttcttaccctccagagaaggct
ggattgcctggtggtgacagaggtccatgtccaacaacttctggagttccagccgaggttgaggctcaatacca
gacgcccaggtcgtgtggtccaacatcagattcggaccaattggaagcttaacaggtaatccttcaggtggtaat
cctccaggtggaaacagaggaacaacgacaactagaagaccagctactacaactggttcaagtccaggtccaact
caatcacactacggtcaatgtggtggtataggttactctggtcccactgtttgtgcttctggtactacttgccaa
gttctgaacccttactactcacagtgtctagcttctgcacaccatcatcatcatcattaa
Coding Sequence for *Humicola grisea* CBHI- *Trichoderma reesei* CBHI cellulose binding domain fusion protein including the alpha factor signal peptide and a 6x His Tag.

SEQID.NO. 16
qqagtitaenhprmtwkrcsgpgncqtvggevvidanwrwlhnngqncyegnkwtsqcssatdcaqrcaldgany
gstygastsgdsltlkfvtkheygtnigsrfylmanqnkyqmftlmnnefafdvdlskvecginsalyfvameed
ggmasypsnragakygtgycdaqcardlkfiggkaniegwrpstndpnagvgpmgaccaeidvwesnayayaftp
hacgsknryhicetnncggtysddrfagycdangcdynpyrmgnkdfygkgktvdtnrkftvvsrfernrlsqff
vqdgrkievppptwpglpnsaditpelcdaqfrvfddrnrfaetggfdalnealtipmvlvmsiwddhhsnmlwl
dssyppekaglpggdrgpcpttsgvpaeveaqypdaqvvwsnirfgpigsltgnpsggnppggnrgttttrrpat
ttgsspgptqshygqcggigysgptvcasgttcqvlnpyysqclasahhhhhh
*Humicola grisea* CBHI- *Trichoderma reesei* CBHI cellulose binding domain fusion protein including a 6x His Tag (CBH-g)

SEQID.NO. 17
atgagatttccttcaatttttactgcagttttatccgcagcatcctccgcattagctgctccagtcaacactaca
acagaagatgaaacggcacaaattccggctgaagctgtcatcggttacttagatttagaaggggatttcgatgtt
gctgttttgccattttccaacagcacaaataacgggttattgtttataaatactactattgccagcattgctgct
aaagaagaaggggtatctttggataaacgtgaggcggaagcatgctcgcagcaggccggcacggcgacggcagag
aaccacccgcccctgacatggcaggaatgcaccgcccctgggagctgcaccacccagaacggggcggtcgttctt
gatgcgaactggcgttgggtgcacgatgtgaacggatacaccaactgctacacgggcaatacctgggaccccacg
tactgccctgacgacgaaacctgcgcccagaactgtgcgctggacggcgcggattacgagggcacctacggcgtg
acttcgtcgggcagctcctcgaaactcaatttcgtcaccgggtcgaacgtcggatcccgtctctacctgctgcag
gacgactcgacctatcagatcttcaagctcctgaaccgcgagttcagctctgacgtcgatgtccccaatcttccg
tgcggattgaacggcgctctgtactttgtcgccatggacgccgacggcggcgtgtccaagtacccgaacaacaag
gctggtgccaagtacggaaccgggtattgcgactcccaatgcccacgggacctcaagttcatcgacggcgaggcc
aacgtcgagggctggcagccgtcttcgaacaacgccaacaccggaattggcgaccacggctcctgctgtgcggag
atggatgtctgggaagcaaacagcatctccaatgcggtcactccgcacccgtgcgacacgccaggccagacgatg
tgctctggagatgactgcggtggcacatactctaacgatcgctacgcgggaacctgcgatcctgacggctgtgac
ttcaacccttaccgcatgggcaacacttctttctacgggcctggcaagatcatcgataccaccaagcccttcact
gtcgtgacgcagttcctcactgatgatggtacggatactggaactctcagcgagatcaagcgcttctacatccag TABLE 10-continued Sequence Listings (Overview)

| SEQID | Nucleic acid [N]/ Protein [P] | Description | ID |
|---|---|---|---|

aacagcaacgtcattccgcagcccaactcggacatcagtggcgtgaccggcaactcgatcacgacggagttctgc
actgctcagaagcaggcctttggcgacacggacgacttctctcagcacggtggcctggccaagatgggagcggcc
atgcagcagggtatggtcctggtgatgagtttgtgggacgactacgccgcgcagatgctgtggttggattccgac
tacccgacggatgcggaccccacgacccctggtattgcccgtggaacgtgtccgacggactcgggcgtcccatcg
gatgtcgagtcgcagagccccaactcctacgtgacctactcgaacattaagtttggtccgatcggtagcacaggt
aatccttcaggtggtaatcctccaggtggaaacagaggaacaacgacaactagaagaccagctactacaactggt
tcaagtccaggtccaactcaatcacactacggtcaatgtggtggtataggttactctggtcccactgtttgtgct
tctggtactacttgccaagttctgaacccttactactcacagtgtctagcctctgcacatcatcaccaccaccac
taatgataa Coding sequence for *Talaromyces emersonii* CBHI/*Trichoderma reesei* -CBD fusion including the alpha factor signal peptide and a 6x His Tag.

SEQID.NO. 18

QQAGTATAENHPPLTWQECTAPGSCTTQNGAVVLDANWRWVHDVNGYTNCYTGNTWDPTYCPDDETCAQNCALDG
ADYEGTYGVTSSGSSLKLNFVTGSNVGSRLYLLQDDSTYQIFKLLNREFSFDVDVSNLPCGLNGALYFVAMDADG
GVSKYPNNKAGAKYGTGYCDSQCPRDLKFIDGEANVEGWQPSSNNANTGIGDHGSCCAEMDVWEANSISNAVTPH
PCDTPGQTMCSGDDCGGTYSNDRYAGTCDPDGCDFNPYRMGNTSFYGPGKIIDTTKPFTVVTQFLTDDGTDTGTL
SEIKRFYIQNSNVIPQPNSDISGVTGNSITTEFCTAQKQAFGDTDDFSQHGGLAKMGAAMQQGMVLVMSLWDDYA
AQMLWLDSDYPTDADPTTPGIARGTCPTDSGVPSDVESQSPNSYVTYSNIKFGPIGSTGNPSGGNPPGGNRGTTT
TRRPATTTGSSPGPTQSHYGQGGGIGYSGPTVCASGTTCQVLNPYYSQCLASAHHHHHH

Mature Sequence of *Talaromyces emersonii* CBHI/*Trichoderma reesei* -CBD fusion with 6x-His tag (CBH-ah)

SEQID.NO 19 atggccagcgatctggcacagcaggctggtacaattactgctgagaaccatccaagaatgacgtggaagagatgt
agtggtccaggaaactgtcagactgttcagggtgaggtcgtgatagatgctaactggagatggttgcataacaac
ggccagaactgctacgagggtaacaagtggacctctcagtgttcttctgctaccgactgcgctcagagatgtgct
cttgatggagcaaactaccagagtacatatggtgcttctacctctggtgacagccttaccctgaagtttgtaacc
aagcacgagtacggaaccaatatcggttctagattctacctgatggctaaccagaacaagtaccagatgtttacc
ttgatgaacaacgagttcgccttcgacgtagatctgtctaaggtggagtgtggaatcaattctgccctgtacttt
gtcgctatggaagaggacggaggtatggcttcttacccttctaacagagctggtgctaagtatggaactggatac
tgcgatgcccaatgcgctagagacctgaagttcatcggtggaaaggctaacattgaaggttggagaccttctacc
aacgacccaaacgctggagttggtccaatgggtgcttgctgtgccgagattgacgtgtgggaatctaacgcttac
gcctacgcttttactccacatgcttgcggttctaagaacagataccacacttgcgaaaccaacaactgtggtggc
acttactctgatgacagattcgctggatactgtgatgctaacggatgtgattacaacccacacagaatgggtaac
aaggacttttacggaaagggtaagactgttgacactaacagaaagttcactgtggtctcgagatttgagagaaac
agaccgtcgcagttctttgtgcaggacggaagaaagattgaggtcccaccaccaacctggccaggattgccaaac
tctgccgacattaccccagagttgtgcgacgctcagttcagagtgttcgacgacagaaacagatttgctgagacc
ggtggatttgacgctttgaacgaggctctgaccattccaatggttctagtcatgagtatttgggacgatcaccac
tctaacatgctttggctggactcttcttaccctccagagaaggctggattgcctggtggtgacagaggtccatgt
ccaacaacttctggagttccagccgaggttgaggctcaatacccagacgcccaggtcgtgtggtccaacatcaga
ttcggaccaattggtagcacagtgaatgtggcttctgcacaccatcatcatcatcattga Alternative coding sequence of *Humicola grisea* CBHI with signal sequence

SEQID NO 42 [P]

LQACTATAENHPPLTWQECTAPGSCTTRNGAVVIMANWRWVHDVNGYTNCYTGNTWDPTYCPDDVTCAQNCCLDG
ADYEGTYGVTSSGSSLKLNFVTGSNVGSRLYLLQDDSTYQIFKLLNREFSFDVDVSNLPCGLNGALYFVAMDADG
GVSKYPNNKAGAKYGTGYCDSQCPRDLKFINGMANVEGWQPSSNNANTGIGDHGSCCAEMDVWEANSISNAVTLH
PCDTPGQTMCSGDDCGGTYSNDRYAGTCDPDGCDFNPYRMGNTSFYGPGKIIDTTKPFTVVTQFLTDDGTDTGTL
SEIKRFYIQNGNVIPQPNSIISGVTGNSITTEFCTAQKQAFGDTDEFSKHGGLAKMGAAMQQGMVLVMSLIDDYA
AQMLWLDSDYPTDADPTVPGIARGTCPTDSGVPSDVESQSPNSYVTFSNIKFGPINSTVPGLDGSTPSNPTATVA
PPTSTTTSVRSSTTQISTPTSQPGGCTTQKWGQCGGIGYTGCTNCVAGTTCTELNPWYSQCLASAHHHHHH

*Talaromyces emersonii* CBHI Mutant with *Chaetomium thermophilum* cellobiohydrolase I CBD with 6x His-TAG

SEQID NO 43 [N]

ctgcaggcctgcacggcgacggcagagaaccacccgcccctgacatggcaggaatgcaccgcccctgggagctgc
accaccaggaacggggcggtcgttgttgatgcgaactggcgttgggtgcacgatgtgaacggatacaccaactgc
tacacgggcaatacctgggaccccacgtactgccctgacgacgtaacctgcgcccagaactgttgcctggacggc
gcggattacgagggcacctacggcgtgacttcgtcgggcagctccttgaaactcaatttcgtcaccgggtcgaac
gtcggatcccgtctctacctgctgcaggacgactcgacctatcagatcttcaagctcctgaaccgcgagttcagc
tttgacgtcgatgtctccaatcttccgtgcggattgaacggcgctctgtactttgtcgccatggacgccgacggc
ggcgtgtccaagtacccgaacaacaaggctggtgccaagtacggaaccgggtattgcgactcccaatgcccacgg
gacctcaagttcatcaacggcatggccaacgtcgagggctggcagccgtcatcgaacaacgccaacaccggaatt
ggcgaccacggctcctgctgtgcggagatggatgtctgggaagcaaacagcatctccaatgcggtcactctgcac
ccgtgcgacacgccaggccagacgatgtgctctggagatgactgcggtggcacatactctaacgatcgctacgcg
ggaacctgcgatcctgacggctgtgacttcaacccttaccgcatgggcaacacttctttctacgggcctggcaag
atcatcgataccaccaagcccttcactgtcgtgacgcagttcctcactgatgatggtacggatactggaactctc
agcgagatcaagcgcttctacatccagaacggcaacgtcattccgcagcccaactcgatcatcagtggcgtgacc
ggcaactcgatcacgacggagttctgcactgctcagaagcaggcctttggcgacacggacgaattctctaagcac
ggtggcctggccaagatgggagcggccatgcagcagggtatggtcctggtgatgagtttgtgggacgactacgcc
gcgcagatgctgtggttggattccgactacccgacggatgcggaccccacggtccctggtattgcccgtggaacg TABLE 10-continued Sequence Listings (Overview)

| SEQID | Nucleic acid [N]/ Protein [P] | Description | ID |
|---|---|---|---|

tgtccgacggactcgggcgtcccatcggatgtcgagtcgcagagccccaactcctacgtgaccttctcgaacatt
aagtttggtccgatcaactcgaccgtccctggcctcgacggcagcacccccagcaacccgaccgccaccgttgct
cctcccacttctaccaccaccagcgtgagaagcagcactactcagatttccaccccgactagccagcccggcggc
tgcaccacccagaagtggggccagtgcggtggtatcggctacaccggctgcactaactgcgttgctggcactacc
tgcactgagctcaacccctggtacagccagtgcctggcttctgctcatcatcaccatcaccac
Coding Sequence for *Talaromyces emersonii* CBHI Mutant with *Chaetmium thermophilum* cellobiohydrolase I CBD with 6x His-TAG

SEQID NO 44 [P]

LQACTATAENHPPLTWQECTAPGSCTTRNGAVVLDANWRWVHDVNGYTNCYTGNTWDPTYCPDDVTCAQNCCLDG
ADYEGTYGVTSSGSSLKLNFVTGSNVGSRLYLLQDDSTYQIFKLLNREFSFDVDVSNLPCGLNGALYFVAMDADG
GVSKYPNNKAGAKYGTGYCDSQCPRDLKFINGMANVEGWQPSSNNANTGIGDHGSCCAEMDVWEANSISNAVTLH
PCDTPGQTMCSGDDCGGTYSNDRYAGTCDPDGCDFNPYRMGNTSFYGPGKIIDTTKPFTVVTQFLTDDGTDTGTL
SEIKRFYIQNGNVIPQPNSIISGVTGNSITTEFCTAQKQAFGDTDEFSKHGGLAKMGAAMQQGMVLVMSLWDDYA
AQMLWLDSDYPTDADPTVPGIARGTCPTDSGVPSDVESQSPNSYVTFSNIKFGPINSTYTGTVSSSSVSSSHSST
STSSSHSSSSTPPTQPTGVTVPQWGQCGGIGYTGSTTCASPYTCHVLNPYYSQCYASAHHHHHH
*Talaromyces emersonii* CBHI Mutant with *Phanerochaete chrysosporium* cellobiohydrolase CBD with 6x His-TAG

SEQID NO 45 [N]

ctgcaggcctgcacggcgacggcagagaaccacccgcccctgacatggcaggaatgcaccgcccctgggagctgc
accaccaggaacggggcggtcgttcttgatgcgaactggcgttgggtgcacgatgtgaacggatacaccaactgc
tacacgggcaatacctgggaccccacgtactgccctgacgacgtaacctgcgcccagaactgttgcctggacggc
gcggattacgagggcacctacggcgtgacttcgtcgggcagctccttgaaactcaatttcgtcaccgggtcgaac
gtcggatcccgtctctacctgctgcaggacgactcgacctatcagatcttcaagctcctgaaccgcgagttcagc
tttgacgtcgatgtctccaatcttccgtgcggattgaacggcgctctgcactttgtcgccatggacgccgacggc
ggcgtgtccaagtacccgaacaacaaggctggtgccaagtacggaaccgggtattgcgactcccaatgcccacgg
gacctcaagttcatcaacggcatggccaacgtcgagggctggcagccgccatcgaacaacgccaacaccggaatt
ggcgaccacggctcctgctgtgcggagatggatgtctgggaagcaaacagcatctccaatgcggtcactctgcac
ccgtgcgacacgccaggccagacgatgtgctctggagatgactgcggtggcacatactctaacgatcgctacgcg
ggaacctgcgatcctgacggctgtgacttcaacccttaccgcatgggcaacacttctttctacgggcctggcaag
atcatcgataccaccaagcccttcactgtcgtgacgcagttcctcactgatgatggtacggatactggaactctc
agcgagatcaagcgcttctacatccagaacggcaacgtcattccgcagcccaactcgatcatcagtggcgtgacc
ggcaactcgatcacgacggagttctgcactgctcagaagcaggcctttggcgacacggacgaattctctaagcac
ggtggcctggccaagatgggagcggccatgcagcagggtatggtcctggtgatgagtttgtgggacgactacgcc
gcgcagatgctgtggttggattccgactacccgacggatgcggaccccacggtccctggtatcgcccgtggaacg
tgtccgacggactcgggcgtcccatcggatgtcgagtcgcagagccccaactcctacgtgaccttctcgaacatt
aagtttggtccgatcaactcgacctacactggaactgtttcttcatcctccgtttcatcttctcactcctccact
tctacttcatcttcccattcctcatcttccactccaccaactcaaccaactggtgttactgttccacaatgggga
caatgtggtggtattggttacactggttccactacttgtgcttccccatactcttgtcacgttttgaacccatac
tactcccaatgttacgcttctgctcatcatcaccatcaccactaa
Coding Sequence for *Talaromyces emersonii* CBHI Mutant with *Phanerochaete chrysosporium* cellobiohydrolase CBD with 6x His-TAG

SEQID NO 46 [P]

lqactataenhppltwqectapgscttrngavvldanwrwvhdvngytcnytgntwdptycpddvtcaqnccldg
adyegtygvtssgeslklnfvtgsnvgsrlyllqddstyqifkllnrefsfdvdvsnlpcglngalyfvamdadg
gvskypnnkagakygtgycdsgcprdlkfingmanvegwqpssnnantgigdhgsccaemdvweanaisnavtlh
pcdtpgqtmcsgddcggtysndryagtcdpdgcdfnpyrmgntsfygpgkiidttkpftvvtqfltddgtdtgtl
seikrfyiqngnvipqpnsiisgvtgnsittefctaqkqafgdtdefskhgglakmgaamqqgmvlvmslwddya
aqmlwldsdyptdadptvpgiargtcptdsgvpsdvesqspnsyvtfsnikfgpinstftggttsssstttttsk
ststssssktttttsvtttttssgssgtgaahwaqcggngwtgpttcvspytctkqndwysqclasahhhhhh
*Talaromyces emersonii* CBHI Mutant with *Penicillium janthinellum* cellobiohydrolase CBD with 6x His-TAG

SEQID NO 47 [N]

ctgcaggcctgcacggcgacggcagagaaccacccgcccctgacatggcaggaatgcaccgcccctgggagctgc
accaccaggaacggggcggtcgttcttgatgcgaactggcgttgggtgcacgatgtgaacggatacaccaactgc
tacacgggcaatacctgggaccccacgtactgccctgacgacgtaacctgcgcccagaactgttgcctggacggc
gcggattacgagggcacctacggcgtgacttcgtcgggcagctccttgaaactcaatttcgtcaccgggtcgaac
gtcggatcccgtctctacctgctgcaggacgactcgacctatcagatcttcaagctcctgaaccgcgagttcagc
tttgacgtcgatgtctccaatcttccgtgcggattgaacggcgctctgtactttgtcgccatggacgccgacggc
ggcgtgtccaagtacccgaacaacaaggctggtgccaagtacggaaccgggtattgcgactcccaatgcccacgg
gacctcaagttcatcaacggcatggccaacgtcgagggctggcagccgtcatcgaacaacgccaacaccggaatt
ggcgaccacggctcctgctgtgcggagatggatgtctgggaagcaaacagcatctccaatgcggtcactctgcac
ccgtgcgacacgccaggccagacgatgtgctctggagatgactgcggtggcacatactctaacgatcgctacgcg
ggaacctgcgatcctgacggctgtgacttcaacccttaccgcatgggcaacacttctttctacgggcctggcaag
atcatcgataccaccaagcccttcactgtcgtgacgcagttcctcactgatgatggtacggatactggaactctc
agcgagatcaagcgcttctacatccagaacggcaacgtcattccgcagcccaactcgatcatcagtggcgtgacc
ggcaactcgatcacgacggagttctgcactgctcagaagcaggcctctggcgacacggacgaattctctaagcac
ggtggcctggccaagatgggagcggccatgcagcagggtatggtcctggtgatgagtttgtgggacgactacgcc
gcgcagatgctgtggttggattccgactacccgacggatgcggaccccacggtccctggtattgcccgtggaacg TABLE 10-continued Sequence Listings (Overview)

| SEQID | Nucleic acid [N]/ Protein [P] | Description | ID |
|---|---|---|---|

tgtccgacggactcgggcgtcccatcggatgtcgagtcgcagagccccaactcctacgtgaccttctcgaacatt
aagtttggtccgatcaactcgaccttcactggtggtactacttcatcctcctccactaccactacaacttccaag
tccacttccacttcatcttcatccaagactacaactacttccgttacaactactactacttcctctggttcttct
ggtactggtgctgctcattgggctcaatgtggtggtaatggatggactggtccaactacttgtgtttccccatac
acttgtactaagcagaacgactggtactctcaatgtttggcttctgctcatcatcaccatcaccac
Coding Sequence for *Talaromyces emersonii* CBHI Mutant with *Penicillium janthinellum* cellobiohydrolase CBD with 6x His-TAG

SEQID NO 48 [P]

lqactataenhppltwqectapgscttrngavvldanwrwvhdvngytncytgntwdptycpddvtcaqnccldg
adyegtygvtssgsslklnfvtgsnvgsrlyllqddstyqifkllnrefsfdvdvsnlpcglngalyfvamdadg
gvskypnnkagakygtgycdsqcprdlkfingmanvegwqpssnnantgigdhgsccaemdvweansisnavtlh
pcdtpgqtmcsgddcggtysndryagtcdpdgcdfnpyrmgntsfygpgkiidttkpftvvtqfltddgtdtgtl
seikrfyiqngnvipqpnsiisgvtgnsittefctaqkqafgdtdefskhgglakmgaamqqgmvlvmslwddya
aqmlwldsdyptdadptvpgiargtcptdsgvpsdvesqspnsyvtfsnikfgpinstftgtgstspsspagpvs
satsvasqptqpaqgtvaqwgqcggtgftgptvcaspftchvvnpyysqcyasahhhhhh
*Talaromyces emersonii* CBHI Mutant with *Irpex lacteus* cellobiohydrolase CBD with 6x His-TAG

SEQID NO 49 [N]

ctgcaggcctgcacggcgacggcagagaaccacccgcccctgacatggcaggaatgcaccgcccctgggagctgc
accaccaggaacggggcggtcgttcttgatgcgaactggcgttgggcgcacgatgtgaacggatacaccaactgc
tacacgggcaatacctggg&ccccacgtactgccctgacgacgtaacctgcgcccagaactgttgcctggacggc
gcggattacgagggcacctacggcgtgacttcgtcgggcagccccttgaaactcaatttcgtcaccgggtcgaac
gtcggatcccgtctctacctgctgcaggacgactcgacctatcagatcttcaagctcccgaaccgcgagttcagc
tttgacgtcgatgtctccaatcttccgtgcggattgaacggcgctctgtactttgtcgccatggacgccgacggc
ggcgtgtccaagtacccgaacaacaaggctggtgccaagtacggaaccgggtattgcgacccccaatgcccacgg
gacctcaagttcatcaacggcatggccaacgtcgagggctggcagccgtcatcgaacaacgccaacaccggaatt
ggcgaccacggctcccgctgtgcggagatggatgtctgggaagcaaacagcatctccaatgcggtcactctgcac
ccgtgcgacacgccaggccagacgatgtgctctggagatgactgcggtggcacatactctaacgatcgctacgcg
ggaacctgcgatcctgacggctgtgacttcaacccttaccgc&tgggcaacacttctttctacgggcctggcaag
atcatcgataccaccaagcccttcactgtcgtgacgcagttcctcactgatgatggtacggatactggaactctc
agcgagatcaagcgcttctacatccagaacggcaacgtcattccgcagcccaactcgatcatcagtggcgtgacc
ggcaactcgatcacgacggagttctgcactgctcagaagcaggcctttggcgacacggacgaattctctaagcac
ggtggcctggccaagatgggagcggccatgcagcagggtatggtcctggtgatgagtttgtgggacgactacgcc
gcgcagatgctgtggttggattccgactacccgacggatgcggacccccacggtccctggtattgcccgtggaacg
tgtccgacggactcgggcgtcccatcggatgtcgagtcgcagagccccaactcctacgtgaccttctcgaacatt
aagtttggtccgatcaactcgaccttcactggtactggttctacttctccatcttctccagctggtccagtttct
tcttccacttccgttgcttcccaaccaactcaaccagctcaaggtactgttgctcaatggggacaatgtggtggt
actggtttcactggtccaactgtttgtgcttccccattcacttgtcacgttgttaacccatactacccccagtgt
tacgcttctgctcatcatcatcaccatcac
Coding Sequence for *Talaromyces emersonii* CBHI Mucant with *Irpex lacteus* cellobiohydrolase CBD witb 6x His-TAG

SEQID NO 50 [P]

lgactataenhppltwqectapgscttrngavvldanwrwvhdvngytncytgntwdptycpddvtcaqnccldg
adyegtygvtssgsslklnfvtgsnvgsrlyllqddstyqifkllnrefsfdvdvsnlpcglngalyfvamdadg
gvskypnnkagakygcgycdsqcprdlkfingmanvegwqpssnnantgigdhgsccaemdvweansisnavtlh
pcdtpgqtmcsgddcggtysndryagtcdpdgcdfnpyrmgntsfygpgkiidttkpftvvtqfltddgtdtgtl
seikrfyiqngnvipqpnsiisgvtgnsittefctaqkqafgdtdetskhgglakmgaamqqgmvlvmslwddya
aqmlwldsdyptdadptvpgiargtcptdsgvpsdvesqspnsyvtfsnikfgpigstgnpsggnpsggdggttt
trrpatttgsspgptqslygqcggigysgpticasgttcqvlnpyysqclasahhhhhh
*Talaromyces emersonii* CBHI Mutant with mutated *Trichoderma reesei* CBD with 6x His-TAG

SEQID NO 51 [N]

ctgcaggcctgcacggcgacggcagagaaccacccgcccctgacatggcaggaatgcaccgcccctgggagctgc
accaccaggaacggggcggtcgttcttgatgcgaactggcgttgggtgcacgatgtgaacggatacaccaactgc
tacacgggcaatacctgggaccccacgtactgccctgacgacgtaacctgcgcccagaactgttgcctggacggc
gcggattacgagggcacctacggcgtgacttcgtcgggcagctccttgaaactcaatttcgtcaccgggtcgaac
gtcggatcccgtatctacctgctgcaggacgactcgacctatcagatcttcaagctcctgaaccgcgagttcagc
tttgacgtcgatgtctccaatcttccgtgcggattgaacggcgctctgtactttgtcgccatggacgccgacggc
ggcgtgtccaagtacccgaacaacaaggctggtgccaagtacggaaccgggtattgcgactcccaatgcccacgg
gacctcaagttcatcaacggcatggccaacgtcgagggctggcagccgtcatcgaacaacgccaacaccggaatt
ggcgaccacggctcctgctgtgcggagatggatgtctgggaagcaaacagcatctccaatgcggtcactctgcac
ccgtgcgacacgccaggccagacgatgtgctctggagatgactgcggtggcacatactctaacgatcgctacgcg
ggaacctgcgatcctgacggctgtgacttcaacccttaccgcatgggcaacacttctttctacgggcctggcaag
atcatcgataccaccaagcccttcactgtcgtgacgcagttcctcactgatgatggtacggatactggaactctc
agcgagatcaagcgcttctacatccagaacggcaacgtcattccgcagcccaactcgatcatcagtggcgtgacc
ggcaactcgatcacgacggagttctgcactgctcagaagcaggcctttggcgacacggacgaattctctaagcac
ggtggcctggccaagatgggagcggccatgcagcagggtatggtcctggtgatgagtttgtgggacgactacgcc
gcgcagatgctgtggttggattccgactacccgacggatgcggaccccacggtccctggtattgcccgtggaacg TABLE 10-continued

| Sequence Listings (Overview) | | | |
|---|---|---|---|
| SEQID | Nucleic acid [N]/ Protein [P] | Description | ID |
| tgtccgacggactcgggcgtcccatcggatgtcgagtcgcagagccccaactcctacgtgaccttctcgaacatt aagtttggtccgatcggtagcacaggtaatccttcaggtggtaatccttcaggtggagacggcggaacaacgaca actagaagaccagctactacaactggttcaagtccaggtccaactcaatcactatacggtcaatgtggtggtata ggttactctggtcccactatttgtgcttctggtactacttgccaagttctgaacccttactactcacagtgtcta gcttctgcacatcatcaccaccaccat Coding Sequence for *Talaromyces emersonii* CBHI Mutant with mutated *Trichoderma reesei* CBD with 6x His-TAG | | | |

What is claimed:

1. A recombinant polypeptide having cellobiohydrolase activity, wherein the recombinant polypeptide comprises at least 90% sequence identity to SEQ ID NO: 5, wherein the recombinant polypeptide is modified at one or more positions selected from the group consisting of Q1, Q2, T7, A8, N10, Q28, E65, S86, D181, E183, D202, P224, S311, N318, T335, D346, Q349, T392, T393, and Y422, and wherein the polypeptide maintains an IT50 for 60 minutes at a temperature of 62° C. or higher.

2. The recombinant polypeptide according to claim 1, comprising additional substitution(s) deletion(s) or insertion(s) while maintaining at least 90% sequence identity to SEQ ID NO: 5.

3. The recombinant polypeptide according to claim 1, comprising additional modification at one or more of the following amino acid residues by substitution or deletion at positions G4, P12, T15, A21, G23, S24, T26, T27, N29, G30, A31, V32, N37, W40, V41, G46, Y47, T48, N49, C50, T52, N54, D57, T59, Y60, D64, A68, Q69, A72, V84, S89, S90, K92, S99, Q109, D110, D111, I116, F117, K118, L119, L120, D120, V130, G139, A145, M146, V152, K154, Y155, N157, N158, K159, K163, G167, Q172, F179, I180, E187, G188, Q190, S192, S193, N194, I200, H203, D211, V212, A221, D228, T229, G231, T233, M234, S236, T243, Y244, S245, N246, D247, G251, F260, G266, K275, I276, I277, T280, L290, D293, G294, T295, T297, T299, S301, K304, F306, N310, V313, I314, D320, I321, T325, N327, A340, F341, D343, T344, D345, H350, A354, K355, A358, Q361, Q362, G363, M364, V367, D373, Y374, A375, A376, P386, T387, D390, T392, P394, T400, P402, T403, D404, D410, N417, S418, T421, F427, P429, I430, G431, T433, G434, N435, P436, S437; or additional one or more insertion group(s) after positions G151, or K159, each said insertion group(s) comprising five amino acids, while maintaining at least 90% sequence identity to SEQ ID NO: 5.

4. The recombinant polypeptide according to claim 1, comprising additional modification at one or more amino acid residues as follows:

| Position | Modified to: |
|---|---|
| G4 | C |
| A6 | G, L, or V |
| P12 | Q |

-continued

| Position | Modified to: |
|---|---|
| T15 | S |
| A21 | S, T, or C |
| G23 | A, D, or N |
| S24 | T, C, or N |
| T26 | I, or N |
| T27 | S, or Q |
| N29 | T, or Y |
| G30 | A |
| A31 | S |
| V32 | G |
| N37 | S |
| W40 | R |
| V41 | T |
| G46 | S |
| Y47 | S, or F |
| T48 | A |
| N49 | S |
| C50 | S |
| T52 | D |
| N54 | S |
| D57 | S |
| T59 | M |
| Y60 | H |
| D64 | N |
| A68 | T |
| Q69 | K, or R |
| A72 | V, or C |
| V84 | A |
| S89 | N |
| S90 | T, or F |
| K92 | R |
| S99 | T |
| Q109 | R |
| D110 | G, S, or N |
| D111 | H, or E |
| I116 | V, K, or E |
| F117 | Y |
| K118 | A, T, or Q |
| L119 | L, or I |
| L120 | P, or M |
| D129 | N |
| V130 | I |
| G139 | S |
| A145 | T |
| M146 | C |
| G151 | GCGRSG |
| V152 | A, or E |
| K154 | R |
| Y155 | S, C, H |
| N157 | S |
| N158 | D |
| K159 | E, KCGRNK |
| K163 | C |
| G167 | C |
| Q172 | Q |
| F179 | I |
| I180 | N |
| E187 | K |
| G188 | C |
| Q190 | L, or K |
| S192 | L, I, P, T, or M |
| S193 | L, P, or T |
| N194 | G, L, I, V, S, C, K, R, D, Q, or Y |
| I200 | N or F |
| H203 | R |
| D211 | G |
| V212 | L |
| A221 | V |
| D228 | N |
| T229 | A, S, or M |
| G231 | D |
| T233 | S |
| M234 | L, I, V, T, or K |
| S236 | F, or Y |
| T243 | G, A, L, I, V, P, S, C, M, R, D, Q, F, Y, or W |

-continued

| Position | Modified to: |
|---|---|
| Y244 | H, F |
| S245 | T |
| N246 | S, K, or D |
| D247 | N |
| G251 | R |
| F260 | C |
| G266 | S |
| K275 | E |
| I276 | V |
| I277 | V |
| T280 | A |
| L290 | H |
| D293 | R, or H |
| G294 | A |
| T295 | S |
| T297 | N |
| T299 | I, or S |
| S301 | C |
| K304 | R |
| F306 | L, Y |
| N310 | D, E |
| V313 | I |
| I314 | F |
| D320 | I, V, E, N |
| I321 | N |
| T325 | A, or I |
| N327 | Y |
| A340 | G, S, or T |
| F341 | C |
| D343 | A |
| T344 | M |
| D345 | E |
| H350 | Y |
| A354 | T |
| K355 | Q |
| A358 | E |
| Q361 | R |
| Q362 | G, R, or H |
| G363 | P |
| M364 | L, or S |
| V367 | A |
| D373 | E |
| Y374 | A, P, S, C, R, H, D |
| A375 | G, L, V, T, C, M, R, D, E, N, Q, or Y |
| A376 | T |
| P386 | L, S |
| T387 | A, S |
| D390 | G, E |
| P394 | C |
| T400 | S |
| P402 | S |
| T403 | K |
| D404 | N |
| D410 | G |
| N417 | Y |
| S418 | P |
| T421 | I |
| F427 | Y |
| P429 | C |
| I430 | L |
| G431 | D |
| T433 | S, or E |
| G434 | S, or GAAATG |
| N435 | Q |
| P436 | S |
| S437 | P |

while maintaining at least 90% sequence identity to SEQ ID NO: 5.

5. The recombinant polypeptide according to claim 1, which is expressed and secreted at a level of more than 100 mg/1 into a supernatant of a yeast culture medium after introduction of a nucleic acid encoding the recombinant polypeptide according to claim 1 into the yeast.

6. The recombinant polypeptide according to claim 1, wherein the one or more modifications are indicated in the following table:

| Position | Modified to: |
|---|---|
| Q1 | L |
| Q2 | P, or S |
| T7 | Q |
| A8 | S |
| N10 | T, or D |
| Q28 | L, K , R, or N |
| E65 | V, M, or K |
| S86 | T |
| D181 | N |
| E183 | V, M, or K |
| D202 | G, I, V, N, F, or Y |
| P224 | L |
| S311 | G, D, or N |
| N318 | I, H, D, or Y |
| T335 | I |
| D346 | G, A, V, or E |
| Q349 | K, or R |
| T392 | S, M, or K |
| T393 | A, I, V, or S |
| Y422 | F. |

7. A method of producing a recombinant polypeptide, comprising the steps:

a. obtaining a host cell:

b. cultivating the host cell under conditions which the recombinant polypeptide according to claim 1 is expressed; and c. recovering the recombinant polypeptide according to claim 1.

8. A process of enzymatically degrading lignocellulosic biomass comprising, degrading lignocellulosic biomass by the recombinant polypeptide according to claim 1, or processing textiles by the recombinant polypeptide according to claim 1 or adding the recombinant polypeptide according to claim 1 as ingredient in detergents or adding the recombinant polypeptide according to claim 1 as ingredient in food or feed compositions.

* * * * *

SEQUENCE LISTING

<160> NUMBER OF SEQ ID NOS: 51

<210> SEQ ID NO 1
<211> LENGTH: 1509
<212> TYPE: DNA
<213> ORGANISM: Artificial
<220> FEATURE:
<223> OTHER INFORMATION: Coding Sequence for Talaromyces emersonii
      CBHI / Trichoderma reesei -CBD fusion (mature CBH-a)

<400> SEQUENCE: 1

```
cagcaggccg gcacggcgac ggcagagaac cacccgcccc tgacatggca ggaatgcacc     60

gcccctggga gctgcaccac ccagaacggg gcggtcgttc ttgatgcgaa ctggcgttgg    120

gtgcacgatg tgaacggata caccaactgc tacacgggca atacctggga ccccacgtac    180

tgccctgacg acgaaacctg cgcccagaac tgtgcgctgg acggcgcgga ttacgagggc    240

acctacggcg tgacttcgtc gggcagctcc ttgaaactca atttcgtcac cgggtcgaac    300

gtcggatccc gtctctacct gctgcaggac gactcgacct atcagatctt caagctcctg    360

aaccgcgagt tcagctttga cgtcgatgtc tccaatcttc cgtgcggatt gaacggcgct    420

ctgtactttg tcgccatgga cgccgacggc ggcgtgtcca agtacccgaa caacaaggct    480

ggtgccaagt acggaaccgg gtattgcgac tcccaatgcc cacgggacct caagttcatc    540

gacggcgagg ccaacgtcga gggctggcag ccgtcttcga acaacgccaa caccggaatt    600

ggcgaccacg gctcctgctg tgcggagatg gatgtctggg aagcaaacag catctccaat    660

gcggtcactc cgcacccgtg cgacacgcca ggccagacga tgtgctctgg agatgactgc    720

ggtggcacat actctaacga tcgctacgcg ggaacctgcg atcctgacgg ctgtgacttc    780

aacccttacc gcatgggcaa cacttctttc tacgggcctg gcaagatcat cgataccacc    840

aagcccttca ctgtcgtgac gcagttcctc actgatgatg gtacggatac tggaactctc    900

agcgagatca agcgcttcta catccagaac agcaacgtca ttccgcagcc caactcggac    960

atcagtggcg tgaccggcaa ctcgatcacg acggagttct gcactgctca gaagcaggcc   1020

tttggcgaca cggacgactt ctctcagcac ggtggcctgg ccaagatggg agcggccatg   1080

cagcagggta tggtcctggt gatgagtttg tgggacgact acgccgcgca gatgctgtgg   1140

ttggattccg actacccgac ggatgcggac cccacgaccc ctggtattgc ccgtggaacg   1200

tgtccgacgg actcgggcgt cccatcggat gtcgagtcgc agagccccaa ctcctacgtg   1260

acctactcga acattaagtt tggtccgatc ggtagcacag gtaatccttc aggtggtaat   1320

cctccaggtg gaaacagagg aacaacgaca actagaagac cagctactac aactggttca   1380
```

```
agtccaggtc caactcaatc acactacggt caatgtggtg gtataggtta ctctggtccc   1440

actgtttgtg cttctggtac tacttgccaa gttctgaacc cttactactc acagtgtcta   1500

taatgataa                                                           1509


<210> SEQ ID NO 2
<211> LENGTH: 500
<212> TYPE: PRT
<213> ORGANISM: Artificial
<220> FEATURE:
<223> OTHER INFORMATION: Mature Sequence of Talaromyces emersonii
      CBHI / Trichoderma reesei -CBD (mature CBH-a)

<400> SEQUENCE: 2

Gln Gln Ala Gly Thr Ala Thr Ala Glu Asn His Pro Pro Leu Thr Trp
1               5                   10                  15

Gln Glu Cys Thr Ala Pro Gly Ser Cys Thr Thr Gln Asn Gly Ala Val
            20                  25                  30

Val Leu Asp Ala Asn Trp Arg Trp Val His Asp Val Asn Gly Tyr Thr
        35                  40                  45

Asn Cys Tyr Thr Gly Asn Thr Trp Asp Pro Thr Tyr Cys Pro Asp Asp
    50                  55                  60

Glu Thr Cys Ala Gln Asn Cys Ala Leu Asp Gly Ala Asp Tyr Glu Gly
65                  70                  75                  80

Thr Tyr Gly Val Thr Ser Ser Gly Ser Ser Leu Lys Leu Asn Phe Val
                85                  90                  95

Thr Gly Ser Asn Val Gly Ser Arg Leu Tyr Leu Leu Gln Asp Asp Ser
            100                 105                 110

Thr Tyr Gln Ile Phe Lys Leu Leu Asn Arg Glu Phe Ser Phe Asp Val
        115                 120                 125

Asp Val Ser Asn Leu Pro Cys Gly Leu Asn Gly Ala Leu Tyr Phe Val
    130                 135                 140

Ala Met Asp Ala Asp Gly Gly Val Ser Lys Tyr Pro Asn Asn Lys Ala
145                 150                 155                 160

Gly Ala Lys Tyr Gly Thr Gly Tyr Cys Asp Ser Gln Cys Pro Arg Asp
                165                 170                 175

Leu Lys Phe Ile Asp Gly Glu Ala Asn Val Glu Gly Trp Gln Pro Ser
            180                 185                 190

Ser Asn Asn Ala Asn Thr Gly Ile Gly Asp His Gly Ser Cys Cys Ala
        195                 200                 205

Glu Met Asp Val Trp Glu Ala Asn Ser Ile Ser Asn Ala Val Thr Pro
    210                 215                 220

His Pro Cys Asp Thr Pro Gly Gln Thr Met Cys Ser Gly Asp Asp Cys
225                 230                 235                 240

Gly Gly Thr Tyr Ser Asn Asp Arg Tyr Ala Gly Thr Cys Asp Pro Asp
                245                 250                 255

Gly Cys Asp Phe Asn Pro Tyr Arg Met Gly Asn Thr Ser Phe Tyr Gly
            260                 265                 270

Pro Gly Lys Ile Ile Asp Thr Thr Lys Pro Phe Thr Val Val Thr Gln
        275                 280                 285

Phe Leu Thr Asp Asp Gly Thr Asp Thr Gly Thr Leu Ser Glu Ile Lys
    290                 295                 300

Arg Phe Tyr Ile Gln Asn Ser Asn Val Ile Pro Gln Pro Asn Ser Asp
305                 310                 315                 320

Ile Ser Gly Val Thr Gly Asn Ser Ile Thr Thr Glu Phe Cys Thr Ala
```

```
                325                 330                 335

Gln Lys Gln Ala Phe Gly Asp Thr Asp Asp Phe Ser Gln His Gly Gly
            340                 345                 350

Leu Ala Lys Met Gly Ala Ala Met Gln Gln Gly Met Val Leu Val Met
        355                 360                 365

Ser Leu Trp Asp Asp Tyr Ala Ala Gln Met Leu Trp Leu Asp Ser Asp
    370                 375                 380

Tyr Pro Thr Asp Ala Asp Pro Thr Thr Pro Gly Ile Ala Arg Gly Thr
385                 390                 395                 400

Cys Pro Thr Asp Ser Gly Val Pro Ser Asp Val Glu Ser Gln Ser Pro
                405                 410                 415

Asn Ser Tyr Val Thr Tyr Ser Asn Ile Lys Phe Gly Pro Ile Gly Ser
            420                 425                 430

Thr Gly Asn Pro Ser Gly Gly Asn Pro Pro Gly Gly Asn Arg Gly Thr
        435                 440                 445

Thr Thr Thr Arg Arg Pro Ala Thr Thr Thr Gly Ser Ser Pro Gly Pro
    450                 455                 460

Thr Gln Ser His Tyr Gly Gln Cys Gly Gly Ile Gly Tyr Ser Gly Pro
465                 470                 475                 480

Thr Val Cys Ala Ser Gly Thr Thr Cys Gln Val Leu Asn Pro Tyr Tyr
                485                 490                 495

Ser Gln Cys Leu
            500


<210> SEQ ID NO 3
<211> LENGTH: 1581
<212> TYPE: DNA
<213> ORGANISM: Artificial
<220> FEATURE:
<223> OTHER INFORMATION: Coding sequence of the fusion
      of CBH-a with Trichoderma reesei CBHI Signal peptide

<400> SEQUENCE: 3

atgtatcgga agttggccgt catctcggcc ttcttggcca cagctcgtgc tcagcaggcc     60

ggcacggcga cggcagagaa ccacccgccc ctgacatggc aggaatgcac cgcccctggg    120

agctgcacca cccagaacgg ggcggtcgtt cttgatgcga actggcgttg ggtgcacgat    180

gtgaacggat acaccaactg ctacacgggc aatacctggg accccacgta ctgccctgac    240

gacgaaacct gcgcccagaa ctgtgcgctg gacggcgcgg attacgaggg cacctacggc    300

gtgacttcgt cgggcagctc cttgaaactc aatttcgtca ccgggtcgaa cgtcggatcc    360

cgtctctacc tgctgcagga cgactcgacc tatcagatct tcaagctcct gaaccgcgag    420

ttcagctttg acgtcgatgt ctccaatctt ccgtgcggat tgaacggcgc tctgtacttt    480

gtcgccatgg acgccgacgg cggcgtgtcc aagtacccga acaacaaggc tggtgccaag    540

tacggaaccg ggtattgcga ctcccaatgc ccacgggacc tcaagttcat cgacggcgag    600

gccaacgtcg agggctggca gccgtcttcg aacaacgcca acaccggaat tggcgaccac    660

ggctcctgct gtgcggagat ggatgtctgg gaagcaaaca gcatctccaa tgcggtcact    720

ccgcacccgt gcgacacgcc aggccagacg atgtgctctg gagatgactg cggtggcaca    780

tactctaacg atcgctacgc gggaacctgc gatcctgacg gctgtgactt caacccttac    840

cgcatgggca acacttcttt ctacgggcct ggcaagatca tcgataccac caagcccttc    900

actgtcgtga cgcagttcct cactgatgat ggtacggata ctggaactct cagcgagatc    960

aagcgcttct acatccagaa cagcaacgtc attccgcagc ccaactcgga catcagtggc   1020
```

```
gtgaccggca actcgatcac gacggagttc tgcactgctc agaagcaggc ctttggcgac   1080

acggacgact tctctcagca cggtggcctg gccaagatgg gagcggccat gcagcagggt   1140

atggtcctgg tgatgagttt gtgggacgac tacgccgcgc agatgctgtg gttggattcc   1200

gactacccga cggatgcgga ccccacgacc cctggtattg cccgtggaac gtgtccgacg   1260

gactcgggcg tcccatcgga tgtcgagtcg cagagcccca actcctacgt gacctactcg   1320

aacattaagt ttggtccgat cggtagcaca ggtaatcctt caggtggtaa tcctccaggt   1380

ggaaacagag gaacaacgac aactagaaga ccagctacta caactggttc aagtccaggt   1440

ccaactcaat cacactacgg tcaatgtggt ggtataggtt actctggtcc cactgtttgt   1500

gcttctggta ctacttgcca agttctgaac ccttactact cacagtgtct agcttctgca   1560

catcatcacc accaccatta a                                             1581
```

```
<210> SEQ ID NO 4
<211> LENGTH: 70
<212> TYPE: PRT
<213> ORGANISM: Artificial
<220> FEATURE:
<223> OTHER INFORMATION: Trichoderma reesei CBHI cellulose binding
      domain and linker sequence

<400> SEQUENCE: 4

Gly Ser Thr Gly Asn Pro Ser Gly Gly Asn Pro Pro Gly Gly Asn Arg
1               5                   10                  15

Gly Thr Thr Thr Thr Arg Arg Pro Ala Thr Thr Thr Gly Ser Ser Pro
            20                  25                  30

Gly Pro Thr Gln Ser His Tyr Gly Gln Cys Gly Gly Ile Gly Tyr Ser
        35                  40                  45

Gly Pro Thr Val Cys Ala Ser Gly Thr Thr Cys Gln Val Leu Asn Pro
    50                  55                  60

Tyr Tyr Ser Gln Cys Leu
65                  70


<210> SEQ ID NO 5
<211> LENGTH: 437
<212> TYPE: PRT
<213> ORGANISM: Artificial
<220> FEATURE:
<223> OTHER INFORMATION: Talaromyces emersonii CBHI sequence (CBH-b)

<400> SEQUENCE: 5

Gln Gln Ala Gly Thr Ala Thr Ala Glu Asn His Pro Pro Leu Thr Trp
1               5                   10                  15

Gln Glu Cys Thr Ala Pro Gly Ser Cys Thr Thr Gln Asn Gly Ala Val
            20                  25                  30

Val Leu Asp Ala Asn Trp Arg Trp Val His Asp Val Asn Gly Tyr Thr
        35                  40                  45

Asn Cys Tyr Thr Gly Asn Thr Trp Asp Pro Thr Tyr Cys Pro Asp Asp
    50                  55                  60

Glu Thr Cys Ala Gln Asn Cys Ala Leu Asp Gly Ala Asp Tyr Glu Gly
65                  70                  75                  80

Thr Tyr Gly Val Thr Ser Ser Gly Ser Ser Leu Lys Leu Asn Phe Val
                85                  90                  95

Thr Gly Ser Asn Val Gly Ser Arg Leu Tyr Leu Leu Gln Asp Asp Ser
            100                 105                 110

Thr Tyr Gln Ile Phe Lys Leu Leu Asn Arg Glu Phe Ser Phe Asp Val
```

```
        115                 120                 125

Asp Val Ser Asn Leu Pro Cys Gly Leu Asn Gly Ala Leu Tyr Phe Val
    130                 135                 140

Ala Met Asp Ala Asp Gly Gly Val Ser Lys Tyr Pro Asn Asn Lys Ala
145                 150                 155                 160

Gly Ala Lys Tyr Gly Thr Gly Tyr Cys Asp Ser Gln Cys Pro Arg Asp
                165                 170                 175

Leu Lys Phe Ile Asp Gly Glu Ala Asn Val Glu Gly Trp Gln Pro Ser
            180                 185                 190

Ser Asn Asn Ala Asn Thr Gly Ile Gly Asp His Gly Ser Cys Cys Ala
        195                 200                 205

Glu Met Asp Val Trp Glu Ala Asn Ser Ile Ser Asn Ala Val Thr Pro
    210                 215                 220

His Pro Cys Asp Thr Pro Gly Gln Thr Met Cys Ser Gly Asp Asp Cys
225                 230                 235                 240

Gly Gly Thr Tyr Ser Asn Asp Arg Tyr Ala Gly Thr Cys Asp Pro Asp
                245                 250                 255

Gly Cys Asp Phe Asn Pro Tyr Arg Met Gly Asn Thr Ser Phe Tyr Gly
            260                 265                 270

Pro Gly Lys Ile Ile Asp Thr Thr Lys Pro Phe Thr Val Val Thr Gln
        275                 280                 285

Phe Leu Thr Asp Asp Gly Thr Asp Thr Gly Thr Leu Ser Glu Ile Lys
    290                 295                 300

Arg Phe Tyr Ile Gln Asn Ser Asn Val Ile Pro Gln Pro Asn Ser Asp
305                 310                 315                 320

Ile Ser Gly Val Thr Gly Asn Ser Ile Thr Thr Glu Phe Cys Thr Ala
                325                 330                 335

Gln Lys Gln Ala Phe Gly Asp Thr Asp Asp Phe Ser Gln His Gly Gly
            340                 345                 350

Leu Ala Lys Met Gly Ala Ala Met Gln Gln Gly Met Val Leu Val Met
        355                 360                 365

Ser Leu Trp Asp Asp Tyr Ala Ala Gln Met Leu Trp Leu Asp Ser Asp
    370                 375                 380

Tyr Pro Thr Asp Ala Asp Pro Thr Thr Pro Gly Ile Ala Arg Gly Thr
385                 390                 395                 400

Cys Pro Thr Asp Ser Gly Val Pro Ser Asp Val Glu Ser Gln Ser Pro
                405                 410                 415

Asn Ser Tyr Val Thr Tyr Ser Asn Ile Lys Phe Gly Pro Ile Asn Ser
            420                 425                 430

Thr Phe Thr Ala Ser
        435
```

<210> SEQ ID NO 6
<211> LENGTH: 1590
<212> TYPE: DNA
<213> ORGANISM: Artificial
<220> FEATURE:
<223> OTHER INFORMATION: Coding sequence of Talaromyces emersonii
      CBHI fused to the alpha factor signal peptide

<400> SEQUENCE: 6

```
atgagatttc cttcaatttt tactgcagtt ttattcgcag catcctccgc attagctgct     60

ccagtcaaca ctacaacaga agatgaaacg gcacaaattc cggctgaagc tgtcatcggt    120

tacttagatt tagaagggga tttcgatgtt gctgttttgc cattttccaa cagcacaaat    180
```

-continued

```
aacgggttat tgtttataaa tactactatt gccagcattg ctgctaaaga agaaggggta    240

tctttggata aacgtgaggc ggaagcaccc tctcagcagg ccggcacggc gacggcagag    300

aaccacccgc ccctgacatg gcaggaatgc accgcccctg ggagctgcac cacccagaac    360

ggggcggtcg ttcttgatgc gaactggcgt tgggtgcacg atgtgaacgg atacaccaac    420

tgctacacgg gcaatacctg ggaccccacg tactgccctg acgacgaaac ctgcgcccag    480

aactgtgcgc tggacggcgc ggattacgag ggcacctacg gcgtgacttc gtcgggcagc    540

tccttgaaac tcaatttcgt caccgggtcg aacgtcggat cccgtctcta cctgctgcag    600

gacgactcga cctatcagat cttcaagctt ctgaaccgcg agttcagctt tgacgtcgat    660

gtctccaatc ttccgtgcgg attgaacggc gctctgtact ttgtcgccat ggacgccgac    720

ggcggcgtgt ccaagtaccc gaacaacaag gctggtgcca agtacggaac cgggtattgc    780

gactcccaat gcccacggga cctcaagttc atcgacggcg aggccaacgt cgagggctgg    840

cagccgtctt cgaacaacgc caacaccgga attggcgacc acggctcctg ctgtgcggag    900

atggatgtct gggaagcaaa cagcatctcc aatgcggtca ctccgcaccc gtgcgacacg    960

ccaggccaga cgatgtgctc tggagatgac tgcggtggca catactctaa cgatcgctac   1020

gcgggaacct gcgatcctga cggctgtgac ttcaaccctt accgcatggg caacacttct   1080

ttctacgggc ctggcaagat catcgatacc accaagccct tcactgtcgt gacgcagttc   1140

ctcactgatg atggtacgga tactggaact ctcagcgaga tcaagcgctt ctacatccag   1200

aacagcaacg tcattccgca gcccaactcg gacatcagtg gcgtgaccgg caactcgatc   1260

acgacggagt tctgcactgc tcagaagcag gcctttggcg acacggacga cttctctcag   1320

cacggtggcc tggccaagat gggagcggcc atgcagcagg gtatggtcct ggtgatgagt   1380

ttgtgggacg actacgccgc gcagatgctg tggttggatt ccgactaccc gacggatgcg   1440

gaccccacga cccctggtat tgcccgtgga acgtgtccga cggactcggg cgtcccatcg   1500

gatgtcgagt cgcagagccc caactcctac gtgacctact cgaacattaa gtttggtccg   1560

atcaactcga ccttcaccgc ttcgtgataa                                    1590
```

```
<210> SEQ ID NO 7
<211> LENGTH: 429
<212> TYPE: PRT
<213> ORGANISM: Artificial
<220> FEATURE:
<223> OTHER INFORMATION: Humicola grisea CBHI (CBH-d)

<400> SEQUENCE: 7

Gln Gln Ala Gly Thr Ile Thr Ala Glu Asn His Pro Arg Met Thr Trp
1               5                   10                  15

Lys Arg Cys Ser Gly Pro Gly Asn Cys Gln Thr Val Gln Gly Glu Val
            20                  25                  30

Val Ile Asp Ala Asn Trp Arg Trp Leu His Asn Asn Gly Gln Asn Cys
        35                  40                  45

Tyr Glu Gly Asn Lys Trp Thr Ser Gln Cys Ser Ser Ala Thr Asp Cys
    50                  55                  60

Ala Gln Arg Cys Ala Leu Asp Gly Ala Asn Tyr Gln Ser Thr Tyr Gly
65                  70                  75                  80

Ala Ser Thr Ser Gly Asp Ser Leu Thr Leu Lys Phe Val Thr Lys His
                85                  90                  95

Glu Tyr Gly Thr Asn Ile Gly Ser Arg Phe Tyr Leu Met Ala Asn Gln
            100                 105                 110
```

-continued

```
Asn Lys Tyr Gln Met Phe Thr Leu Met Asn Asn Glu Phe Ala Phe Asp
        115                 120                 125

Val Asp Leu Ser Lys Val Glu Cys Gly Ile Asn Ser Ala Leu Tyr Phe
    130                 135                 140

Val Ala Met Glu Glu Asp Gly Gly Met Ala Ser Tyr Pro Ser Asn Arg
145                 150                 155                 160

Ala Gly Ala Lys Tyr Gly Thr Gly Tyr Cys Asp Ala Gln Cys Ala Arg
                165                 170                 175

Asp Leu Lys Phe Ile Gly Gly Lys Ala Asn Ile Glu Gly Trp Arg Pro
            180                 185                 190

Ser Thr Asn Asp Pro Asn Ala Gly Val Gly Pro Met Gly Ala Cys Cys
        195                 200                 205

Ala Glu Ile Asp Val Trp Glu Ser Asn Ala Tyr Ala Tyr Ala Phe Thr
    210                 215                 220

Pro His Ala Cys Gly Ser Lys Asn Arg Tyr His Ile Cys Glu Thr Asn
225                 230                 235                 240

Asn Cys Gly Gly Thr Tyr Ser Asp Asp Arg Phe Ala Gly Tyr Cys Asp
                245                 250                 255

Ala Asn Gly Cys Asp Tyr Asn Pro Tyr Arg Met Gly Asn Lys Asp Phe
            260                 265                 270

Tyr Gly Lys Gly Lys Thr Val Asp Thr Asn Arg Lys Phe Thr Val Val
        275                 280                 285

Ser Arg Phe Glu Arg Asn Arg Leu Ser Gln Phe Phe Val Gln Asp Gly
    290                 295                 300

Arg Lys Ile Glu Val Pro Pro Pro Thr Trp Pro Gly Leu Pro Asn Ser
305                 310                 315                 320

Ala Asp Ile Thr Pro Glu Leu Cys Asp Ala Gln Phe Arg Val Phe Asp
                325                 330                 335

Asp Arg Asn Arg Phe Ala Glu Thr Gly Gly Phe Asp Ala Leu Asn Glu
            340                 345                 350

Ala Leu Thr Ile Pro Met Val Leu Val Met Ser Ile Trp Asp Asp His
        355                 360                 365

His Ser Asn Met Leu Trp Leu Asp Ser Ser Tyr Pro Pro Glu Lys Ala
    370                 375                 380

Gly Leu Pro Gly Gly Asp Arg Gly Pro Cys Pro Thr Thr Ser Gly Val
385                 390                 395                 400

Pro Ala Glu Val Glu Ala Gln Tyr Pro Asp Ala Gln Val Val Trp Ser
                405                 410                 415

Asn Ile Arg Phe Gly Pro Ile Gly Ser Thr Val Asn Val
            420                 425
```

<210> SEQ ID NO 8
<211> LENGTH: 1563
<212> TYPE: DNA
<213> ORGANISM: Artificial
<220> FEATURE:
<223> OTHER INFORMATION: Coding sequence of Humicola grisea CBHI fused to the alpha factor signal peptide

<400> SEQUENCE: 8

```
atgagatttc cttcaatttt tactgcagtt ttattcgcag catcctccgc attagctgct     60

ccagtcaaca ctacaacaga agatgaaacg gcacaaattc cggctgaagc tgtcatcggt    120

tacttagatt tagaagggga tttcgatgtt gctgttttgc cattttccaa cagcacaaat    180

aacgggttat tgtttataaa tactactatt gccagcattg ctgctaaaga agaaggggta    240
```

```
tctttggata aacgtgaggc ggaagcaccc tctcagcagg ctggtactat tactgctgag    300

aaccacccaa gaatgacctg gaagagatgc tctggtccag gaaactgtca gactgttcag    360

ggcgaggttg tgattgacgc taattggaga tggttgcaca acaacggcca gaactgttac    420

gagggtaaca agtggacctc tcagtgttct tctgctaccg actgtgctca gagatgtgct    480

ttggacggtg ccaactacca gtctacctac ggtgcttcta cctctggtga ctctctgacc    540

ctgaagttcg ttaccaagca cgagtacgga accaacatcg gctctagatt ctacctgatg    600

gccaaccaga acaagtacca gatgttcacc ctgatgaaca acgagttcgc ctttgacgtt    660

gacctgtcta aggtggagtg cggtatcaac tctgccctgt acttcgttgc tatggaagag    720

gacggtggaa tggcttctta cccatctaac agagccggtg ctaagtacgg tactggttac    780

tgtgacgccc agtgtgctag agacctgaag ttcatcggtg gaaaggccaa cattgagggt    840

tggagaccat ctaccaacga cccaaacgct ggtgttggtc caatgggagc ttgttgtgcc    900

gagattgatg tgtgggagtc taacgcttac gcctacgctt ttaccccaca cgcttgcggt    960

tctaagaaca gataccacat ctgcgagacc aacaactgtg gtggaaccta ctctgacgac   1020

agattcgctg gatactgcga cgctaacggt tgtgactaca acccatacag aatgggcaac   1080

aaggacttct acggcaaggg aaagaccgtt gacaccaaca gaaagttcac cgtggtgtcg   1140

agattcgaga gaaacagact gtcgcagttc tttgtgcagg acggcagaaa gattgaggtc   1200

ccaccaccaa cttggccagg attgccaaac tctgccgaca ttaccccaga gttgtgtgac   1260

gctcagttca gagtgttcga cgacagaaac agatttgctg agaccggtgg ttttgacgct   1320

ttgaacgagg ctctgaccat tccaatggtg ctggtgatgt ctatttggga cgaccaccac   1380

tctaacatgt tgtggctgga ctcttcttac ccaccagaga aggctggatt gccaggtggt   1440

gacagaggac catgtccaac tacttcgggt gttccagctg aggttgaggc tcagtaccca   1500

gacgctcagg ttgtgtggtc gaacatcaga ttcggcccaa tcggttctac cgtgaacgtg   1560

taa                                                                 1563
```

<210> SEQ ID NO 9
<211> LENGTH: 439
<212> TYPE: PRT
<213> ORGANISM: Artificial
<220> FEATURE:
<223> OTHER INFORMATION: Thermoascus auratiacus CBHI (CBH-e)

<400> SEQUENCE: 9

```
His Glu Ala Gly Thr Val Thr Ala Glu Asn His Pro Ser Leu Thr Trp
1               5                   10                  15

Gln Gln Cys Ser Ser Gly Gly Ser Cys Thr Thr Gln Asn Gly Lys Val
            20                  25                  30

Val Ile Asp Ala Asn Trp Arg Trp Val His Thr Thr Ser Gly Tyr Thr
        35                  40                  45

Asn Cys Tyr Thr Gly Asn Thr Trp Asp Thr Ser Ile Cys Pro Asp Asp
    50                  55                  60

Val Thr Cys Ala Gln Asn Cys Ala Leu Asp Gly Ala Asp Tyr Ser Gly
65                  70                  75                  80

Thr Tyr Gly Val Thr Thr Ser Gly Asn Ala Leu Arg Leu Asn Phe Val
                85                  90                  95

Thr Gln Ser Ser Gly Lys Asn Ile Gly Ser Arg Leu Tyr Leu Leu Gln
            100                 105                 110

Asp Asp Thr Thr Tyr Gln Ile Phe Lys Leu Leu Gly Gln Glu Phe Thr
        115                 120                 125
```

```
Phe Asp Val Asp Val Ser Asn Leu Pro Cys Gly Leu Asn Gly Ala Leu
    130                 135                 140

Tyr Phe Val Ala Met Asp Ala Asp Gly Asn Leu Ser Lys Tyr Pro Gly
145                 150                 155                 160

Asn Lys Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Gln Pro Ser Ala Asn Asp Pro Asn Ala Gly Val Gly Asn His Gly Ser
        195                 200                 205

Ser Cys Ala Glu Met Asp Val Trp Glu Ala Asn Ser Ile Ser Thr Ala
    210                 215                 220

Val Thr Pro His Pro Cys Asp Thr Pro Gly Gln Thr Met Cys Gln Gly
225                 230                 235                 240

Asp Asp Cys Gly Gly Thr Tyr Ser Ser Thr Arg Tyr Ala Gly Thr Cys
                245                 250                 255

Asp Thr Asp Gly Cys Asp Phe Asn Pro Tyr Gln Pro Gly Asn His Ser
            260                 265                 270

Phe Tyr Gly Pro Gly Lys Ile Val Asp Thr Ser Ser Lys Phe Thr Val
        275                 280                 285

Val Thr Gln Phe Ile Thr Asp Asp Gly Thr Pro Ser Gly Thr Leu Thr
    290                 295                 300

Glu Ile Lys Arg Phe Tyr Val Gln Asn Gly Lys Val Ile Pro Gln Ser
305                 310                 315                 320

Glu Ser Thr Ile Ser Gly Val Thr Gly Asn Ser Ile Thr Thr Glu Tyr
                325                 330                 335

Cys Thr Ala Gln Lys Ala Ala Phe Asp Asn Thr Gly Phe Phe Thr His
            340                 345                 350

Gly Gly Leu Gln Lys Ile Ser Gln Ala Leu Ala Gln Gly Met Val Leu
        355                 360                 365

Val Met Ser Leu Trp Asp Asp His Ala Ala Asn Met Leu Trp Leu Asp
    370                 375                 380

Ser Thr Tyr Pro Thr Asp Ala Asp Pro Asp Thr Pro Gly Val Ala Arg
385                 390                 395                 400

Gly Thr Cys Pro Thr Thr Ser Gly Val Pro Ala Asp Val Glu Ser Gln
                405                 410                 415

Asn Pro Asn Ser Tyr Val Ile Tyr Ser Asn Ile Lys Val Gly Pro Ile
            420                 425                 430

Asn Ser Thr Phe Thr Ala Asn
        435
```

<210> SEQ ID NO 10
<211> LENGTH: 1593
<212> TYPE: DNA
<213> ORGANISM: Artificial
<220> FEATURE:
<223> OTHER INFORMATION: Coding sequence of Thermoascus auratiacus CBHI fused to the alpha factor signal peptide

<400> SEQUENCE: 10

```
atgagatttc cttcaatttt tactgcagtt ttattcgcag catcctccgc attagctgct      60

ccagtcaaca ctacaacaga agatgaaacg gcacaaattc cggctgaagc tgtcatcggt     120

tacttagatt tagaagggga tttcgatgtt gctgttttgc cattttccaa cagcacaaat     180

aacgggttat tgtttataaa tactactatt gccagcattg ctgctaaaga agaaggggta     240
```

```
tctttggata aacgtgaggc ggaagcaccc tctcacgagg ccggtaccgt aaccgcagag    300

aatcaccctt ccctgacctg gcagcaatgc tccagcggcg gtagttgtac cacgcagaat    360

ggaaaagtcg ttatcgatgc gaactggcgt tgggtccata ccacctctgg atacaccaac    420

tgctacacgg gcaatacgtg ggacaccagt atctgtcccg acgacgtgac ctgcgctcag    480

aattgtgcct tggatggagc ggattacagt ggcacctatg gtgttacgac cagtggcaac    540

gccctgagac tgaactttgt cacccaaagc tcagggaaga acattggctc gcgcctgtac    600

ctgctgcagg acgacaccac ttatcagatc ttcaagctgc tgggtcagga gtttaccttc    660

gatgtcgacg tctccaatct cccttgcggg ctgaacggcg ccctctactt tgtggccatg    720

gacgccgacg gcaatttgtc caaataccct ggcaacaagg caggcgctaa gtatggcact    780

ggttactgcg actctcagtg ccctcgggat ctcaagttca tcaacggtca ggccaacgtt    840

gaaggctggc agccgtctgc caacgaccca aatgccggcg ttggtaacca cggttcctcg    900

tgcgctgaga tggatgtctg ggaagccaac agcatctcta ctgcggtgac gcctcaccca    960

tgcgacaccc ccggccagac catgtgccag ggagacgact gtggtggaac ctactcctcc   1020

actcgatatg ctggtacctg cgacactgat ggctgcgact tcaatcctta ccagccaggc   1080

aaccactcgt tctacggccc cgggaagatc gtcgacacta gctccaaatt caccgtcgtc   1140

acccagttca tcaccgacga cgggacaccc tccggcaccc tgacggagat caaacgcttc   1200

tacgtccaga acggcaaggt gatcccccag tcggagtcga cgatcagcgg cgtcaccggc   1260

aactcaatca ccaccgagta ttgcacggcc cagaaggcag ccttcgacaa caccggcttc   1320

ttcacgcacg gcgggcttca gaagatcagt caggctctgg ctcagggcat ggtcctcgtc   1380

atgagcctgt gggacgatca cgccgccaac atgctctggc tggacagcac ctacccgact   1440

gatgcggacc cggacacccc tggcgtcgcg cgcggtacct gccccacgac ctccggcgtc   1500

ccggccgacg tggagtcgca gaaccccaat tcatatgtta tctactccaa catcaaggtc   1560

ggacccatca actcgacctt caccgccaac taa                                1593
```

<210> SEQ ID NO 11
<211> LENGTH: 1794
<212> TYPE: DNA
<213> ORGANISM: Artificial
<220> FEATURE:
<223> OTHER INFORMATION: Coding sequence for Trichoderma reesei CBHI (CBH-c), including the alpha factor signal peptide and a 6x His Tag

<400> SEQUENCE: 11

```
atgagatttc cttcaatttt tactgcagtt ttattcgcag catcctccgc attagctgct     60

ccagtcaaca ctacaacaga agatgaaacg gcacaaattc cggctgaagc tgtcatcggt    120

tacttagatt tagaagggga tttcgatgtt gctgttttgc cattttccaa cagcacaaat    180

aacgggttat tgtttataaa tactactatt gccagcattg ctgctaaaga agaaggggta    240

tctttggata aacgtgaggc ggaagcaccc tcttcagctt gtacactgca atccgagact    300

catccacctt taacgtggca aaagtgtagt tctggcggaa cttgtactca acagactggt    360

agtgtcgtga tagatgctaa ctggagatgg acacatgcaa cgaactcctc aactaactgc    420

tacgatggta acacctggtc ttctacattg tgtcctgaca acgaaacctg cgctaagaac    480

tgttgtcttg atggagcagc ttacgcaagt acatatggtg tgactacctc tggtaacagc    540

ctttccattg gttttgtaac ccagtcggct cagaagaatg ttggtgctag attgtacctg    600
```

-continued

```
atggcttcag acaccacata ccaggagttt accttgttgg gaaacgagtt ctctttcgac    660

gtagatgtgt ctcagctacc atgtggattg aatggagcct tgtactttgt ctcaatggat    720

gcagacggag gtgtttcaaa gtaccctact aacacagctg gtgctaagta tggaactgga    780

tactgcgatt ctcaatgccc aagagacctg aagttcatca acggacaagc taacgttgaa    840

ggttgggaac cttctagcaa caacgcaaac actggaattg gtggtcatgg ttcttgctgt    900

tcagagatgg acatttggga agccaactcc atcagtgaag ctttgactcc acatccatgc    960

acaactgttg ggcaagaaat ttgcgaaggt gatggttgtg gtggcactta ctctgataac   1020

agatacggcg gaacatgtga tccagatgga tgtgattgga acccatacag actgggtaac   1080

acttcgtttt acggaccagg ttcttccttc actctagaca ctacgaagaa gttgactgtg   1140

gtcacccaat ttgagacttc tggtgccatt aaccgatact acgtgcagaa cggagttact   1200

ttccaacagc caaacgctga attgggtagt tactcaggca acgagcttaa cgatgactac   1260

tgcactgctg aagaagcaga atttggtgga tcttcctttt cggataaggg tggattgacg   1320

cagttcaaga aagctacctc tggtggaatg gttctagtca tgagtctgtg ggacgattac   1380

tacgctaaca tgctttggct ggactctact taccctacaa acgagacatc ttctactcct   1440

ggtgctgtaa gaggtagctg ttctacatct tctggagttc cagcccaagt tgagagtcaa   1500

agtccaaatg ccaaggtcac cttctccaac atcaagttcg gaccaattgg tagcacaggt   1560

aatccttcag gtggtaatcc tccaggtgga aacagaggaa caacgacaac tagaagacca   1620

gctactacaa ctggttcaag tccaggtcca actcaatcac actacggtca atgtggtggt   1680

ataggttact ctggtcccac tgtttgtgct tctggtacta cttgccaagt tctgaaccct   1740

tactactcac agtgtctagc ttctgcacac catcatcatc atcattaatg ataa         1794
```

<210> SEQ ID NO 12
<211> LENGTH: 496
<212> TYPE: PRT
<213> ORGANISM: Artificial
<220> FEATURE:
<223> OTHER INFORMATION: Trichoderma reesei CBHI (CBH-c)

<400> SEQUENCE: 12

```
Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160
```

-continued

```
Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
    370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
            420                 425                 430

Ser Gly Gly Asn Pro Pro Gly Gly Asn Arg Gly Thr Thr Thr Thr Arg
        435                 440                 445

Arg Pro Ala Thr Thr Thr Gly Ser Ser Pro Gly Pro Thr Gln Ser His
    450                 455                 460

Tyr Gly Gln Cys Gly Gly Ile Gly Tyr Ser Gly Pro Thr Val Cys Ala
465                 470                 475                 480

Ser Gly Thr Thr Cys Gln Val Leu Asn Pro Tyr Tyr Ser Gln Cys Leu
                485                 490                 495
```

<210> SEQ ID NO 13
<211> LENGTH: 1767
<212> TYPE: DNA
<213> ORGANISM: Artificial
<220> FEATURE:
<223> OTHER INFORMATION: Coding sequence for Trichoderma viride CBHI, including the alpha factor signal peptide

<400> SEQUENCE: 13

```
atgagatttc cttcaatttt tactgcagtt ttattcgcag catcctccgc attagctgct      60

ccagtcaaca ctacaacaga agatgaaacg gcacaaattc cggctgaagc tgtcatcggt     120
```

-continued

```
tacttagatt tagaagggga tttcgatgtt gctgttttgc cattttccaa cagcacaaat    180

aacgggttat tgtttataaa tactactatt gccagcattg ctgctaaaga agaaggggta    240

tctttggata aacgtgaggc ggaagcaccc tctcaatctg cttgcacctt gcagtctgaa    300

actcacccac cattgacctg gcagaagtgt tcttctggcg gtacttgtac tcagcagacc    360

ggttctgttg ttatcgacgc caactggaga tggactcacg ctaccaactc ttctaccaac    420

tgctacgacg gtaacacttg gtcgtctacc ttgtgtccag acaacgagac ctgtgccaag    480

aactgttgtt tggacggtgc tgcttacgct tctacctacg gtgttaccac ctctggtaac    540

tcgctgtcta tcggtttcgt tacccagtct gcccagaaaa atgttggtgc cagactgtac    600

ttgatggctt ctgacaccac ctaccaagag tttaccctgc tgggtaacga gttctctttc    660

gacgtggacg tttctcaact gccatgtgga ctgaacggtg ccctgtactt cgtttctatg    720

gacgctgacg gtggtgtttc taagtaccca accaacaccg ctggtgctaa atacggaacc    780

ggttactgcg attctcagtg cccaagagac ctgaagttca tcaacggaca ggctaacgtt    840

gaaggatggg agccatcttc taacaacgcc aacaccggta ttggtggtca cggttcttgc    900

tgttctgaga tggacatctg ggaggccaac tctatttctg aggctttgac ccccacaccca    960

tgtactactg tgggtcaaga gatctgtgag ggtgatggtt gtggtggtac ttactcggac   1020

aacagatacg gtggtacttg tgacccagac ggttgtgatt gggacccata cagactgggt   1080

aacacctctt tctacggtcc aggatcttct tttaccctgg acaccaccaa gaagttgacc   1140

gttgttaccc agtttgagac ctctggtgcc atcaacagat actacgtgca gaacggtgtt   1200

actttccagc agccaaacgc tgaactggga tcttactctg gtaacggact gaacgacgac   1260

tactgtactg ctgaggaagc tgagttcggt ggttcttctt tctctgacaa gggtggactg   1320

acccagttta agaaggctac ctctggcgga atggtgctgg ttatgtcttt gtgggacgac   1380

tactacgcta acatgctgtg gcttgactct acctacccaa ctaacgagac ctcttctacc   1440

ccaggtgctg ttagaggatc ttgctctacc tcttctggtg ttccagctca ggttgagtct   1500

cagtctccaa acgccaaggt gaccttctct aacatcaagt tcggtccaat cggttctact   1560

ggtgacccat ctggtggtaa cccaccaggt ggaaacccac ctggtactac cactaccaga   1620

agaccagcta ccaccactgg ttcttctcca ggtccaaccc aatctcacta cggtcagtgt   1680

ggtggtattg gttactctgg tccaaccgtt tgtgcttctg gaaccacctg tcaggttctg   1740

aacccatact actcgcagtg cctgtaa                                       1767
```

```
<210> SEQ ID NO 14
<211> LENGTH: 497
<212> TYPE: PRT
<213> ORGANISM: Artificial
<220> FEATURE:
<223> OTHER INFORMATION: Trichoderma viride CBHI (CBH-f)

<400> SEQUENCE: 14

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
```

-continued

```
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asp Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Gly Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
    370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asp Pro
            420                 425                 430

Ser Gly Gly Asn Pro Pro Gly Gly Asn Pro Pro Gly Thr Thr Thr Thr
        435                 440                 445

Arg Arg Pro Ala Thr Thr Thr Gly Ser Ser Pro Gly Pro Thr Gln Ser
    450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495
```

Leu

<210> SEQ ID NO 15
<211> LENGTH: 1785
<212> TYPE: DNA
<213> ORGANISM: Artificial
<220> FEATURE:
<223> OTHER INFORMATION: Coding Sequence for Humicola grisea CBHI-
Trichoderma reesei CBHI cellulose binding domain fusion protein
including the alpha factor signal peptide and a 6x His Tag

<400> SEQUENCE: 15
atgagatttc cttcaatttt tactgcagtt ttattcgcag catcctccgc attagctgct 60
ccagtcaaca ctacaacaga agatgaaacg gcacaaattc cggctgaagc tgtcatcggt 120
tacttagatt tagaagggga tttcgatgtt gctgttttgc cattttccaa cagcacaaat 180
aacgggttat tgtttataaa tactactatt gccagcattg ctgctaaaga agaaggggta 240
tctttggata aacgtgaggc ggaagcatgc tcgcagcagg ctggtacaat tactgctgag 300
aaccatccaa gaatgacgtg gaagagatgt agtggtccag gaaactgtca gactgttcag 360
ggtgaggtcg tgatagatgc taactggaga tggttgcata acaacggcca gaactgctac 420
gagggtaaca agtggacctc tcagtgttct tctgctaccg actgcgctca gagatgtgct 480
cttgatggag caaactacca gagtacatat ggtgcttcta cctctggtga cagccttacc 540
ctgaagtttg taaccaagca cgagtacgga accaatatcg gttctagatt ctacctgatg 600
gctaaccaga acaagtacca gatgtttacc ttgatgaaca acgagttcgc cttcgacgta 660
gatctgtcta aggtggagtg tggaatcaat tctgccttgt actttgtcgc tatggaagag 720
gacggaggta tggcttctta cccttctaac agagctggtg ctaagtatgg aactggatac 780
tgcgatgccc aatgcgctag agacctgaag ttcatcggtg gaaaggctaa cattgaaggt 840
tggagacctt ctaccaacga cccaaacgct ggagttggtc caatgggtgc ttgctgtgcc 900
gagattgacg tgtgggaatc taacgcttac gcctacgctt ttactccaca tgcttgcggt 960
tctaagaaca gataccacat ttgcgaaacc aacaactgtg gtggcactta ctctgatgac 1020
agattcgctg gatactgtga tgctaacgga tgtgattaca acccatacag aatgggtaac 1080
aaggactttt acggaaaggg taagactgtt gacactaaca gaaagttcac tgtggtctcg 1140
agatttgaga gaaacagact gtcgcagttc tttgtgcagg acggaagaaa gattgaggtc 1200
ccaccaccaa cttggccagg attgccaaac tctgccgaca ttaccccaga gttgtgcgac 1260
gctcagttca gagtgtttga cgacagaaac agatttgctg agaccggtgg atttgacgct 1320
ttgaacgagg ctctgaccat tccaatggtt ctagtcatga gtatttggga cgatcaccac 1380
tctaacatgc tttggctgga ctcttcttac cctccagaga aggctggatt gcctggtggt 1440
gacagaggtc catgtccaac aacttctgga gttccagccg aggttgaggc tcaataccca 1500
gacgcccagg tcgtgtggtc caacatcaga ttcggaccaa ttggaagctt aacaggtaat 1560
ccttcaggtg gtaatcctcc aggtggaaac agaggaacaa cgacaactag aagaccagct 1620
actacaactg gttcaagtcc aggtccaact caatcacact acggtcaatg tggtggtata 1680
ggttactctg gtcccactgt ttgtgcttct ggtactactt gccaagttct gaacccttac 1740
tactcacagt gtctagcttc tgcacaccat catcatcatc attaa 1785

<210> SEQ ID NO 16
<211> LENGTH: 503
<212> TYPE: PRT

<213> ORGANISM: Artificial
<220> FEATURE:
<223> OTHER INFORMATION: Humicola grisea CBHI- Trichoderma reesei CBHI cellulose binding domain fusion protein including a 6x His Tag (CBH-g)

<400> SEQUENCE: 16

```
Gln Gln Ala Gly Thr Ile Thr Ala Glu Asn His Pro Arg Met Thr Trp
1               5                   10                  15

Lys Arg Cys Ser Gly Pro Gly Asn Cys Gln Thr Val Gln Gly Glu Val
            20                  25                  30

Val Ile Asp Ala Asn Trp Arg Trp Leu His Asn Asn Gly Gln Asn Cys
        35                  40                  45

Tyr Glu Gly Asn Lys Trp Thr Ser Gln Cys Ser Ser Ala Thr Asp Cys
    50                  55                  60

Ala Gln Arg Cys Ala Leu Asp Gly Ala Asn Tyr Gln Ser Thr Tyr Gly
65                  70                  75                  80

Ala Ser Thr Ser Gly Asp Ser Leu Thr Leu Lys Phe Val Thr Lys His
                85                  90                  95

Glu Tyr Gly Thr Asn Ile Gly Ser Arg Phe Tyr Leu Met Ala Asn Gln
            100                 105                 110

Asn Lys Tyr Gln Met Phe Thr Leu Met Asn Asn Glu Phe Ala Phe Asp
        115                 120                 125

Val Asp Leu Ser Lys Val Glu Cys Gly Ile Asn Ser Ala Leu Tyr Phe
    130                 135                 140

Val Ala Met Glu Glu Asp Gly Gly Met Ala Ser Tyr Pro Ser Asn Arg
145                 150                 155                 160

Ala Gly Ala Lys Tyr Gly Thr Gly Tyr Cys Asp Ala Gln Cys Ala Arg
                165                 170                 175

Asp Leu Lys Phe Ile Gly Gly Lys Ala Asn Ile Glu Gly Trp Arg Pro
            180                 185                 190

Ser Thr Asn Asp Pro Asn Ala Gly Val Gly Pro Met Gly Ala Cys Cys
        195                 200                 205

Ala Glu Ile Asp Val Trp Glu Ser Asn Ala Tyr Ala Tyr Ala Phe Thr
    210                 215                 220

Pro His Ala Cys Gly Ser Lys Asn Arg Tyr His Ile Cys Glu Thr Asn
225                 230                 235                 240

Asn Cys Gly Gly Thr Tyr Ser Asp Asp Arg Phe Ala Gly Tyr Cys Asp
                245                 250                 255

Ala Asn Gly Cys Asp Tyr Asn Pro Tyr Arg Met Gly Asn Lys Asp Phe
            260                 265                 270

Tyr Gly Lys Gly Lys Thr Val Asp Thr Asn Arg Lys Phe Thr Val Val
        275                 280                 285

Ser Arg Phe Glu Arg Asn Arg Leu Ser Gln Phe Phe Val Gln Asp Gly
    290                 295                 300

Arg Lys Ile Glu Val Pro Pro Pro Thr Trp Pro Gly Leu Pro Asn Ser
305                 310                 315                 320

Ala Asp Ile Thr Pro Glu Leu Cys Asp Ala Gln Phe Arg Val Phe Asp
                325                 330                 335

Asp Arg Asn Arg Phe Ala Glu Thr Gly Gly Phe Asp Ala Leu Asn Glu
            340                 345                 350

Ala Leu Thr Ile Pro Met Val Leu Val Met Ser Ile Trp Asp Asp His
        355                 360                 365

His Ser Asn Met Leu Trp Leu Asp Ser Ser Tyr Pro Pro Glu Lys Ala
    370                 375                 380
```

```
Gly Leu Pro Gly Gly Asp Arg Gly Pro Cys Pro Thr Thr Ser Gly Val
385                 390                 395                 400

Pro Ala Glu Val Glu Ala Gln Tyr Pro Asp Ala Gln Val Val Trp Ser
                405                 410                 415

Asn Ile Arg Phe Gly Pro Ile Gly Ser Leu Thr Gly Asn Pro Ser Gly
            420                 425                 430

Gly Asn Pro Pro Gly Gly Asn Arg Gly Thr Thr Thr Thr Arg Arg Pro
        435                 440                 445

Ala Thr Thr Thr Gly Ser Ser Pro Gly Pro Thr Gln Ser His Tyr Gly
    450                 455                 460

Gln Cys Gly Gly Ile Gly Tyr Ser Gly Pro Thr Val Cys Ala Ser Gly
465                 470                 475                 480

Thr Thr Cys Gln Val Leu Asn Pro Tyr Tyr Ser Gln Cys Leu Ala Ser
                485                 490                 495

Ala His His His His His His
            500


<210> SEQ ID NO 17
<211> LENGTH: 1809
<212> TYPE: DNA
<213> ORGANISM: Artificial
<220> FEATURE:
<223> OTHER INFORMATION: Coding sequence for Talaromyces emersonii
      CBHI / Trichoderma reesei -CBD fusion including the alpha factor
      signal peptide and a 6x His Tag

<400> SEQUENCE: 17

atgagatttc cttcaatttt tactgcagtt ttattcgcag catcctccgc attagctgct     60

ccagtcaaca ctacaacaga agatgaaacg gcacaaattc cggctgaagc tgtcatcggt    120

tacttagatt tagaagggga tttcgatgtt gctgttttgc cattttccaa cagcacaaat    180

aacgggttat tgtttataaa tactactatt gccagcattg ctgctaaaga agaaggggta    240

tctttggata aacgtgaggc ggaagcatgc tcgcagcagg ccggcacggc gacggcagag    300

aaccacccgc ccctgacatg gcaggaatgc accgcccctg ggagctgcac cacccagaac    360

ggggcggtcg ttcttgatgc gaactggcgt tgggtgcacg atgtgaacgg atacaccaac    420

tgctacacgg gcaatacctg ggaccccacg tactgccctg acgacgaaac ctgcgcccag    480

aactgtgcgc tggacggcgc ggattacgag ggcacctacg gcgtgacttc gtcgggcagc    540

tccttgaaac tcaatttcgt caccgggtcg aacgtcggat cccgtctcta cctgctgcag    600

gacgactcga cctatcagat cttcaagctc ctgaaccgcg agttcagctt tgacgtcgat    660

gtctccaatc ttccgtgcgg attgaacggc gctctgtact ttgtcgccat ggacgccgac    720

ggcggcgtgt ccaagtaccc gaacaacaag gctggtgcca agtacggaac cgggtattgc    780

gactcccaat gcccacggga cctcaagttc atcgacggcg aggccaacgt cgagggctgg    840

cagccgtctt cgaacaacgc caacaccgga attggcgacc acggctcctg ctgtgcggag    900

atggatgtct gggaagcaaa cagcatctcc aatgcggtca ctccgcaccc gtgcgacacg    960

ccaggccaga cgatgtgctc tggagatgac tgcggtggca catactctaa cgatcgctac   1020

gcgggaacct gcgatcctga cggctgtgac ttcaaccctt accgcatggg caacacttct   1080

ttctacgggc ctggcaagat catcgatacc accaagccct tcactgtcgt gacgcagttc   1140

ctcactgatg atggtacgga tactggaact ctcagcgaga tcaagcgctt ctacatccag   1200

aacagcaacg tcattccgca gcccaactcg gacatcagtg gcgtgaccgg caactcgatc   1260
```

```
acgacggagt tctgcactgc tcagaagcag gcctttggcg acacggacga cttctctcag   1320

cacggtggcc tggccaagat gggagcggcc atgcagcagg gtatggtcct ggtgatgagt   1380

ttgtgggacg actacgccgc gcagatgctg tggttggatt ccgactaccc gacggatgcg   1440

gaccccacga cccctggtat tgcccgtgga acgtgtccga cggactcggg cgtcccatcg   1500

gatgtcgagt cgcagagccc caactcctac gtgacctact cgaacattaa gtttggtccg   1560

atcggtagca caggtaatcc ttcaggtggt aatcctccag gtggaaacag aggaacaacg   1620

acaactagaa gaccagctac tacaactggt tcaagtccag gtccaactca atcacactac   1680

ggtcaatgtg gtggtatagg ttactctggt cccactgttt gtgcttctgg tactacttgc   1740

caagttctga acccttacta ctcacagtgt ctagcttctg cacatcatca ccaccaccat   1800

taatgataa                                                           1809
```

```
<210> SEQ ID NO 18
<211> LENGTH: 509
<212> TYPE: PRT
<213> ORGANISM: Artificial
<220> FEATURE:
<223> OTHER INFORMATION: Mature Sequence of Talaromyces emersonii
      CBHI / Trichoderma reesei -CBD fusion with 6x-His tag (CBH-ah)

<400> SEQUENCE: 18

Gln Gln Ala Gly Thr Ala Thr Ala Glu Asn His Pro Pro Leu Thr Trp
1               5                   10                  15

Gln Glu Cys Thr Ala Pro Gly Ser Cys Thr Thr Gln Asn Gly Ala Val
            20                  25                  30

Val Leu Asp Ala Asn Trp Arg Trp Val His Asp Val Asn Gly Tyr Thr
        35                  40                  45

Asn Cys Tyr Thr Gly Asn Thr Trp Asp Pro Thr Tyr Cys Pro Asp Asp
    50                  55                  60

Glu Thr Cys Ala Gln Asn Cys Ala Leu Asp Gly Ala Asp Tyr Glu Gly
65                  70                  75                  80

Thr Tyr Gly Val Thr Ser Ser Gly Ser Ser Leu Lys Leu Asn Phe Val
                85                  90                  95

Thr Gly Ser Asn Val Gly Ser Arg Leu Tyr Leu Leu Gln Asp Asp Ser
            100                 105                 110

Thr Tyr Gln Ile Phe Lys Leu Leu Asn Arg Glu Phe Ser Phe Asp Val
        115                 120                 125

Asp Val Ser Asn Leu Pro Cys Gly Leu Asn Gly Ala Leu Tyr Phe Val
    130                 135                 140

Ala Met Asp Ala Asp Gly Gly Val Ser Lys Tyr Pro Asn Asn Lys Ala
145                 150                 155                 160

Gly Ala Lys Tyr Gly Thr Gly Tyr Cys Asp Ser Gln Cys Pro Arg Asp
                165                 170                 175

Leu Lys Phe Ile Asp Gly Glu Ala Asn Val Glu Gly Trp Gln Pro Ser
            180                 185                 190

Ser Asn Asn Ala Asn Thr Gly Ile Gly Asp His Gly Ser Cys Cys Ala
        195                 200                 205

Glu Met Asp Val Trp Glu Ala Asn Ser Ile Ser Asn Ala Val Thr Pro
    210                 215                 220

His Pro Cys Asp Thr Pro Gly Gln Thr Met Cys Ser Gly Asp Asp Cys
225                 230                 235                 240

Gly Gly Thr Tyr Ser Asn Asp Arg Tyr Ala Gly Thr Cys Asp Pro Asp
                245                 250                 255
```

```
Gly Cys Asp Phe Asn Pro Tyr Arg Met Gly Asn Thr Ser Phe Tyr Gly
            260                 265                 270

Pro Gly Lys Ile Ile Asp Thr Thr Lys Pro Phe Thr Val Val Thr Gln
        275                 280                 285

Phe Leu Thr Asp Asp Gly Thr Asp Thr Gly Thr Leu Ser Glu Ile Lys
    290                 295                 300

Arg Phe Tyr Ile Gln Asn Ser Asn Val Ile Pro Gln Pro Asn Ser Asp
305                 310                 315                 320

Ile Ser Gly Val Thr Gly Asn Ser Ile Thr Thr Glu Phe Cys Thr Ala
                325                 330                 335

Gln Lys Gln Ala Phe Gly Asp Thr Asp Asp Phe Ser Gln His Gly Gly
            340                 345                 350

Leu Ala Lys Met Gly Ala Ala Met Gln Gln Gly Met Val Leu Val Met
        355                 360                 365

Ser Leu Trp Asp Asp Tyr Ala Ala Gln Met Leu Trp Leu Asp Ser Asp
    370                 375                 380

Tyr Pro Thr Asp Ala Asp Pro Thr Thr Pro Gly Ile Ala Arg Gly Thr
385                 390                 395                 400

Cys Pro Thr Asp Ser Gly Val Pro Ser Asp Val Glu Ser Gln Ser Pro
                405                 410                 415

Asn Ser Tyr Val Thr Tyr Ser Asn Ile Lys Phe Gly Pro Ile Gly Ser
            420                 425                 430

Thr Gly Asn Pro Ser Gly Gly Asn Pro Pro Gly Gly Asn Arg Gly Thr
        435                 440                 445

Thr Thr Thr Arg Arg Pro Ala Thr Thr Thr Gly Ser Ser Pro Gly Pro
    450                 455                 460

Thr Gln Ser His Tyr Gly Gln Cys Gly Gly Ile Gly Tyr Ser Gly Pro
465                 470                 475                 480

Thr Val Cys Ala Ser Gly Thr Thr Cys Gln Val Leu Asn Pro Tyr Tyr
                485                 490                 495

Ser Gln Cys Leu Ala Ser Ala His His His His His His
            500                 505
```

<210> SEQ ID NO 19
<211> LENGTH: 1335
<212> TYPE: DNA
<213> ORGANISM: Artificial
<220> FEATURE:
<223> OTHER INFORMATION: Alternative coding sequence of Humicola grisea CBHI with signal sequence

<400> SEQUENCE: 19

```
atggccagcg atctggcaca gcaggctggt acaattactg ctgagaacca tccaagaatg      60

acgtggaaga gatgtagtgg tccaggaaac tgtcagactg ttcagggtga ggtcgtgata     120

gatgctaact ggagatggtt gcataacaac ggccagaact gctacgaggg taacaagtgg     180

acctctcagt gttcttctgc taccgactgc gctcagagat gtgctcttga tggagcaaac     240

taccagagta catatggtgc ttctacctct ggtgacagcc ttaccctgaa gtttgtaacc     300

aagcacgagt acggaaccaa tatcggttct agattctacc tgatggctaa ccagaacaag     360

taccagatgt ttaccttgat gaacaacgag ttcgccttcg acgtagatct gtctaaggtg     420

gagtgtggaa tcaattctgc cttgtacttt gtcgctatgg aagaggacgg aggtatggct     480

tcttaccctt ctaacagagc tggtgctaag tatggaactg gatactgcga tgcccaatgc     540

gctagagacc tgaagttcat cggtggaaag gctaacattg aaggttggag accttctacc     600
```

-continued

```
aacgacccaa acgctggagt tggtccaatg ggtgcttgct gtgccgagat tgacgtgtgg    660

gaatctaacg cttacgccta cgcttttact ccacatgctt gcggttctaa gaacagatac    720

cacatttgcg aaaccaacaa ctgtggtggc acttactctg atgacagatt cgctggatac    780

tgtgatgcta acggatgtga ttacaaccca tacagaatgg gtaacaagga cttttacgga    840

aagggtaaga ctgttgacac taacagaaag ttcactgtgg tctcgagatt tgagagaaac    900

agactgtcgc agttctttgt gcaggacgga agaaagattg aggtcccacc accaacttgg    960

ccaggattgc caaactctgc cgacattacc ccagagttgt gcgacgctca gttcagagtg   1020

tttgacgaca gaaacagatt tgctgagacc ggtggatttg acgctttgaa cgaggctctg   1080

accattccaa tggttctagt catgagtatt tgggacgatc accactctaa catgctttgg   1140

ctggactctt cttaccctcc agagaaggct ggattgcctg gtggtgacag aggtccatgt   1200

ccaacaactt ctggagttcc agccgaggtt gaggctcaat acccagacgc ccaggtcgtg   1260

tggtccaaca tcagattcgg accaattggt agcacagtga atgtggcttc tgcacaccat   1320

catcatcatc attga                                                    1335


<210> SEQ ID NO 20
<211> LENGTH: 41
<212> TYPE: DNA
<213> ORGANISM: Artificial
<220> FEATURE:
<223> OTHER INFORMATION: Primer forward

<400> SEQUENCE: 20

gaggcggaag caccctctca atctgcttgc accttgcagt c                          41


<210> SEQ ID NO 21
<211> LENGTH: 38
<212> TYPE: DNA
<213> ORGANISM: Artificial
<220> FEATURE:
<223> OTHER INFORMATION: Primer reverse

<400> SEQUENCE: 21

ggagacgcag agcccttatt acaggcactg cgagtagt                              38


<210> SEQ ID NO 22
<211> LENGTH: 41
<212> TYPE: DNA
<213> ORGANISM: Artificial
<220> FEATURE:
<223> OTHER INFORMATION: Primer forward

<400> SEQUENCE: 22

gaggcggaag caccctctca gcaggctggt actattactg c                          41


<210> SEQ ID NO 23
<211> LENGTH: 44
<212> TYPE: DNA
<213> ORGANISM: Artificial
<220> FEATURE:
<223> OTHER INFORMATION: Primer reverse

<400> SEQUENCE: 23

ggagacgcag agcccttaca cgttcacggt agaaccgatt gggc                       44


<210> SEQ ID NO 24
<211> LENGTH: 41
<212> TYPE: DNA
<213> ORGANISM: Artificial
```

<220> FEATURE:
<223> OTHER INFORMATION: Primer forward

<400> SEQUENCE: 24
gaggcggaag caccctctca cgaggccggt accgtaaccg c 41

<210> SEQ ID NO 25
<211> LENGTH: 41
<212> TYPE: DNA
<213> ORGANISM: Artificial
<220> FEATURE:
<223> OTHER INFORMATION: Primer reverse

<400> SEQUENCE: 25
ggagacgcag agcccttatt agttggcggt gaaggtcgag t 41

<210> SEQ ID NO 26
<211> LENGTH: 41
<212> TYPE: DNA
<213> ORGANISM: Artificial
<220> FEATURE:
<223> OTHER INFORMATION: Primer forward

<400> SEQUENCE: 26
gaggcggaag caccctctca gcaggccggc acggcgacgg c 41

<210> SEQ ID NO 27
<211> LENGTH: 41
<212> TYPE: DNA
<213> ORGANISM: Artificial
<220> FEATURE:
<223> OTHER INFORMATION: Primer reverse

<400> SEQUENCE: 27
ggagacgcag agcccttatc acgaagcggt gaaggtcgag t 41

<210> SEQ ID NO 28
<211> LENGTH: 41
<212> TYPE: DNA
<213> ORGANISM: Artificial
<220> FEATURE:
<223> OTHER INFORMATION: Primer forward

<400> SEQUENCE: 28
gaggcggaag caccctctca gcaggccggc acggcgacgg c 41

<210> SEQ ID NO 29
<211> LENGTH: 38
<212> TYPE: DNA
<213> ORGANISM: Artificial
<220> FEATURE:
<223> OTHER INFORMATION: Primer reverse

<400> SEQUENCE: 29
attacctgtg ctaccgatcg gaccaaactt aatgttcg 38

<210> SEQ ID NO 30
<211> LENGTH: 38
<212> TYPE: DNA
<213> ORGANISM: Artificial
<220> FEATURE:
<223> OTHER INFORMATION: Primer forward

<400> SEQUENCE: 30
aagtttggtc cgatcggtag cacaggtaat ccttcagg 38

<210> SEQ ID NO 31
<211> LENGTH: 44
<212> TYPE: DNA
<213> ORGANISM: Artificial
<220> FEATURE:
<223> OTHER INFORMATION: Primer reverse

<400> SEQUENCE: 31
ggagacgcag agcccttatt atagacactg tgagtagtaa gggt 44

<210> SEQ ID NO 32
<211> LENGTH: 41
<212> TYPE: DNA
<213> ORGANISM: Artificial
<220> FEATURE:
<223> OTHER INFORMATION: Primer forward

<400> SEQUENCE: 32
gaggcggaag caccctctca gcaggccggc acggcgacgg c 41

<210> SEQ ID NO 33
<211> LENGTH: 44
<212> TYPE: DNA
<213> ORGANISM: Artificial
<220> FEATURE:
<223> OTHER INFORMATION: Primer reverse

<400> SEQUENCE: 33
ggagacgcag agcccttatc attaatggtg gtggtgatga tgag 44

<210> SEQ ID NO 34
<211> LENGTH: 40
<212> TYPE: DNA
<213> ORGANISM: Artificial
<220> FEATURE:
<223> OTHER INFORMATION: Primer forward

<400> SEQUENCE: 34
aggcggaagc atgctcgcag caggctggta caattactgc 40

<210> SEQ ID NO 35
<211> LENGTH: 41
<212> TYPE: DNA
<213> ORGANISM: Artificial
<220> FEATURE:
<223> OTHER INFORMATION: Primer reverse

<400> SEQUENCE: 35
ggattacctg ttaagcttcc aattggtccg aatctgatgt t 41

<210> SEQ ID NO 36
<211> LENGTH: 42
<212> TYPE: DNA
<213> ORGANISM: Artificial
<220> FEATURE:
<223> OTHER INFORMATION: Primer forward

<400> SEQUENCE: 36
accaattgga agcttaacag gtaatccttc aggtggtaat cc 42

<210> SEQ ID NO 37
<211> LENGTH: 46
<212> TYPE: DNA
<213> ORGANISM: Artificial
<220> FEATURE:
<223> OTHER INFORMATION: Primer reverse

<400> SEQUENCE: 37
atcttgcagg tcgacttatc attaatgatg atgatgatgg tgtgca 46

<210> SEQ ID NO 38
<211> LENGTH: 40
<212> TYPE: DNA
<213> ORGANISM: Artificial
<220> FEATURE:
<223> OTHER INFORMATION: Primer forward

<400> SEQUENCE: 38
aggcggaagc atgctcgcag caggctggta caattactgc 40

<210> SEQ ID NO 39
<211> LENGTH: 46
<212> TYPE: DNA
<213> ORGANISM: Artificial
<220> FEATURE:
<223> OTHER INFORMATION: Primer reverse

<400> SEQUENCE: 39
atcttgcagg tcgacttatc attaatgatg atgatgatgg tgtgca 46

<210> SEQ ID NO 40
<211> LENGTH: 21
<212> TYPE: DNA
<213> ORGANISM: Artificial
<220> FEATURE:
<223> OTHER INFORMATION: Oligonucleotide alpha-f

<400> SEQUENCE: 40
tactattgcc agcattgctg c 21

<210> SEQ ID NO 41
<211> LENGTH: 23
<212> TYPE: DNA
<213> ORGANISM: Artificial
<220> FEATURE:
<223> OTHER INFORMATION: Oligonucleotide oli740

<400> SEQUENCE: 41
tcagctattt cacatacaaa tcg 23

<210> SEQ ID NO 42
<211> LENGTH: 521
<212> TYPE: PRT
<213> ORGANISM: artificial
<220> FEATURE:
<223> OTHER INFORMATION: Talaromyces emersonii CBHI Mutant with
Chaetomium thermophilum cellobiohydrolase I CBD with 6x His-TAG

<400> SEQUENCE: 42

```
Leu Gln Ala Cys Thr Ala Thr Ala Glu Asn His Pro Pro Leu Thr Trp
1               5                   10                  15

Gln Glu Cys Thr Ala Pro Gly Ser Cys Thr Thr Arg Asn Gly Ala Val
            20                  25                  30

Val Leu Asp Ala Asn Trp Arg Trp Val His Asp Val Asn Gly Tyr Thr
        35                  40                  45

Asn Cys Tyr Thr Gly Asn Thr Trp Asp Pro Thr Tyr Cys Pro Asp Asp
    50                  55                  60

Val Thr Cys Ala Gln Asn Cys Cys Leu Asp Gly Ala Asp Tyr Glu Gly
65                  70                  75                  80
```

-continued

```
Thr Tyr Gly Val Thr Ser Ser Gly Ser Ser Leu Lys Leu Asn Phe Val
                85                  90                  95

Thr Gly Ser Asn Val Gly Ser Arg Leu Tyr Leu Leu Gln Asp Asp Ser
            100                 105                 110

Thr Tyr Gln Ile Phe Lys Leu Leu Asn Arg Glu Phe Ser Phe Asp Val
        115                 120                 125

Asp Val Ser Asn Leu Pro Cys Gly Leu Asn Gly Ala Leu Tyr Phe Val
    130                 135                 140

Ala Met Asp Ala Asp Gly Gly Val Ser Lys Tyr Pro Asn Asn Lys Ala
145                 150                 155                 160

Gly Ala Lys Tyr Gly Thr Gly Tyr Cys Asp Ser Gln Cys Pro Arg Asp
                165                 170                 175

Leu Lys Phe Ile Asn Gly Met Ala Asn Val Glu Gly Trp Gln Pro Ser
            180                 185                 190

Ser Asn Asn Ala Asn Thr Gly Ile Gly Asp His Gly Ser Cys Cys Ala
        195                 200                 205

Glu Met Asp Val Trp Glu Ala Asn Ser Ile Ser Asn Ala Val Thr Leu
    210                 215                 220

His Pro Cys Asp Thr Pro Gly Gln Thr Met Cys Ser Gly Asp Asp Cys
225                 230                 235                 240

Gly Gly Thr Tyr Ser Asn Asp Arg Tyr Ala Gly Thr Cys Asp Pro Asp
                245                 250                 255

Gly Cys Asp Phe Asn Pro Tyr Arg Met Gly Asn Thr Ser Phe Tyr Gly
            260                 265                 270

Pro Gly Lys Ile Ile Asp Thr Thr Lys Pro Phe Thr Val Val Thr Gln
        275                 280                 285

Phe Leu Thr Asp Asp Gly Thr Asp Thr Gly Thr Leu Ser Glu Ile Lys
    290                 295                 300

Arg Phe Tyr Ile Gln Asn Gly Asn Val Ile Pro Gln Pro Asn Ser Ile
305                 310                 315                 320

Ile Ser Gly Val Thr Gly Asn Ser Ile Thr Thr Glu Phe Cys Thr Ala
                325                 330                 335

Gln Lys Gln Ala Phe Gly Asp Thr Asp Glu Phe Ser Lys His Gly Gly
            340                 345                 350

Leu Ala Lys Met Gly Ala Ala Met Gln Gln Gly Met Val Leu Val Met
        355                 360                 365

Ser Leu Trp Asp Asp Tyr Ala Ala Gln Met Leu Trp Leu Asp Ser Asp
    370                 375                 380

Tyr Pro Thr Asp Ala Asp Pro Thr Val Pro Gly Ile Ala Arg Gly Thr
385                 390                 395                 400

Cys Pro Thr Asp Ser Gly Val Pro Ser Asp Val Glu Ser Gln Ser Pro
                405                 410                 415

Asn Ser Tyr Val Thr Phe Ser Asn Ile Lys Phe Gly Pro Ile Asn Ser
            420                 425                 430

Thr Val Pro Gly Leu Asp Gly Ser Thr Pro Ser Asn Pro Thr Ala Thr
        435                 440                 445

Val Ala Pro Pro Thr Ser Thr Thr Thr Ser Val Arg Ser Ser Thr Thr
    450                 455                 460

Gln Ile Ser Thr Pro Thr Ser Gln Pro Gly Gly Cys Thr Thr Gln Lys
465                 470                 475                 480

Trp Gly Gln Cys Gly Gly Ile Gly Tyr Thr Gly Cys Thr Asn Cys Val
                485                 490                 495

Ala Gly Thr Thr Cys Thr Glu Leu Asn Pro Trp Tyr Ser Gln Cys Leu
```

```
            500                 505                 510

Ala Ser Ala His His His His His His
        515                 520


<210> SEQ ID NO 43
<211> LENGTH: 1563
<212> TYPE: DNA
<213> ORGANISM: artificial
<220> FEATURE:
<223> OTHER INFORMATION: Coding Sequence for Talaromyces emersonii
      CBHI Mutant with Chaetmium thermophilum cellobiohydrolase I CBD
      with 6x His-TAG

<400> SEQUENCE: 43

ctgcaggcct gcacggcgac ggcagagaac cacccgcccc tgacatggca ggaatgcacc     60

gcccctggga gctgcaccac caggaacggg gcggtcgttc ttgatgcgaa ctggcgttgg    120

gtgcacgatg tgaacggata caccaactgc tacacgggca atacctggga ccccacgtac    180

tgccctgacg acgtaacctg cgcccagaac tgttgcctgg acggcgcgga ttacgagggc    240

acctacggcg tgacttcgtc gggcagctcc ttgaaactca atttcgtcac cgggtcgaac    300

gtcggatccc gtctctacct gctgcaggac gactcgacct atcagatctt caagctcctg    360

aaccgcgagt tcagctttga cgtcgatgtc tccaatcttc cgtgcggatt gaacggcgct    420

ctgtactttg tcgccatgga cgccgacggc ggcgtgtcca agtacccgaa caacaaggct    480

ggtgccaagt acggaaccgg gtattgcgac tcccaatgcc cacgggacct caagttcatc    540

aacggcatgg ccaacgtcga gggctggcag ccgtcatcga acaacgccaa caccggaatt    600

ggcgaccacg gctcctgctg tgcggagatg gatgtctggg aagcaaacag catctccaat    660

gcggtcactc tgcacccgtg cgacacgcca ggccagacga tgtgctctgg agatgactgc    720

ggtggcacat actctaacga tcgctacgcg ggaacctgcg atcctgacgg ctgtgacttc    780

aacccttacc gcatgggcaa cacttctttc tacgggcctg gcaagatcat cgataccacc    840

aagcccttca ctgtcgtgac gcagttcctc actgatgatg gtacggatac tggaactctc    900

agcgagatca agcgcttcta catccagaac ggcaacgtca ttccgcagcc caactcgatc    960

atcagtggcg tgaccggcaa ctcgatcacg acggagttct gcactgctca gaagcaggcc   1020

tttggcgaca cggacgaatt ctctaagcac ggtggcctgg ccaagatggg agcggccatg   1080

cagcagggta tggtcctggt gatgagtttg tgggacgact acgccgcgca gatgctgtgg   1140

ttggattccg actacccgac ggatgcggac cccacggtcc ctggtattgc ccgtggaacg   1200

tgtccgacgg actcgggcgt cccatcggat gtcgagtcgc agagccccaa ctcctacgtg   1260

accttctcga acattaagtt tggtccgatc aactcgaccg tccctggcct cgacggcagc   1320

acccccagca acccgaccgc caccgttgct cctcccactt ctaccaccac cagcgtgaga   1380

agcagcacta ctcagatttc caccccgact agccagcccg gcggctgcac cacccagaag   1440

tggggccagt gcggtggtat cggctacacc ggctgcacta actgcgttgc tggcactacc   1500

tgcactgagc tcaacccctg gtacagccag tgcctggctt ctgctcatca tcaccatcac   1560

cac                                                                 1563


<210> SEQ ID NO 44
<211> LENGTH: 514
<212> TYPE: PRT
<213> ORGANISM: artificial
<220> FEATURE:
<223> OTHER INFORMATION: Talaromyces emersonii CBHI Mutant with
      Phanerochaete chrysosporium cellobiohydrolase CBD with 6x His-TAG
```

<400> SEQUENCE: 44

Leu Gln Ala Cys Thr Ala Thr Ala Glu Asn His Pro Pro Leu Thr Trp
1 5 10 15

Gln Glu Cys Thr Ala Pro Gly Ser Cys Thr Thr Arg Asn Gly Ala Val
20 25 30

Val Leu Asp Ala Asn Trp Arg Trp Val His Asp Val Asn Gly Tyr Thr
35 40 45

Asn Cys Tyr Thr Gly Asn Thr Trp Asp Pro Thr Tyr Cys Pro Asp Asp
50 55 60

Val Thr Cys Ala Gln Asn Cys Cys Leu Asp Gly Ala Asp Tyr Glu Gly
65 70 75 80

Thr Tyr Gly Val Thr Ser Ser Gly Ser Ser Leu Lys Leu Asn Phe Val
85 90 95

Thr Gly Ser Asn Val Gly Ser Arg Leu Tyr Leu Leu Gln Asp Asp Ser
100 105 110

Thr Tyr Gln Ile Phe Lys Leu Leu Asn Arg Glu Phe Ser Phe Asp Val
115 120 125

Asp Val Ser Asn Leu Pro Cys Gly Leu Asn Gly Ala Leu Tyr Phe Val
130 135 140

Ala Met Asp Ala Asp Gly Gly Val Ser Lys Tyr Pro Asn Asn Lys Ala
145 150 155 160

Gly Ala Lys Tyr Gly Thr Gly Tyr Cys Asp Ser Gln Cys Pro Arg Asp
165 170 175

Leu Lys Phe Ile Asn Gly Met Ala Asn Val Glu Gly Trp Gln Pro Ser
180 185 190

Ser Asn Asn Ala Asn Thr Gly Ile Gly Asp His Gly Ser Cys Cys Ala
195 200 205

Glu Met Asp Val Trp Glu Ala Asn Ser Ile Ser Asn Ala Val Thr Leu
210 215 220

His Pro Cys Asp Thr Pro Gly Gln Thr Met Cys Ser Gly Asp Asp Cys
225 230 235 240

Gly Gly Thr Tyr Ser Asn Asp Arg Tyr Ala Gly Thr Cys Asp Pro Asp
245 250 255

Gly Cys Asp Phe Asn Pro Tyr Arg Met Gly Asn Thr Ser Phe Tyr Gly
260 265 270

Pro Gly Lys Ile Ile Asp Thr Thr Lys Pro Phe Thr Val Val Thr Gln
275 280 285

Phe Leu Thr Asp Asp Gly Thr Asp Thr Gly Thr Leu Ser Glu Ile Lys
290 295 300

Arg Phe Tyr Ile Gln Asn Gly Asn Val Ile Pro Gln Pro Asn Ser Ile
305 310 315 320

Ile Ser Gly Val Thr Gly Asn Ser Ile Thr Thr Glu Phe Cys Thr Ala
325 330 335

Gln Lys Gln Ala Phe Gly Asp Thr Asp Glu Phe Ser Lys His Gly Gly
340 345 350

Leu Ala Lys Met Gly Ala Ala Met Gln Gln Gly Met Val Leu Val Met
355 360 365

Ser Leu Trp Asp Asp Tyr Ala Ala Gln Met Leu Trp Leu Asp Ser Asp
370 375 380

Tyr Pro Thr Asp Ala Asp Pro Thr Val Pro Gly Ile Ala Arg Gly Thr
385 390 395 400

Cys Pro Thr Asp Ser Gly Val Pro Ser Asp Val Glu Ser Gln Ser Pro

```
                405                 410                 415

Asn Ser Tyr Val Thr Phe Ser Asn Ile Lys Phe Gly Pro Ile Asn Ser
            420                 425                 430

Thr Tyr Thr Gly Thr Val Ser Ser Ser Ser Val Ser Ser Ser His Ser
        435                 440                 445

Ser Thr Ser Thr Ser Ser Ser His Ser Ser Ser Ser Thr Pro Pro Thr
    450                 455                 460

Gln Pro Thr Gly Val Thr Val Pro Gln Trp Gly Gln Cys Gly Gly Ile
465                 470                 475                 480

Gly Tyr Thr Gly Ser Thr Thr Cys Ala Ser Pro Tyr Thr Cys His Val
                485                 490                 495

Leu Asn Pro Tyr Tyr Ser Gln Cys Tyr Ala Ser Ala His His His His
            500                 505                 510

His His


<210> SEQ ID NO 45
<211> LENGTH: 1545
<212> TYPE: DNA
<213> ORGANISM: artificial
<220> FEATURE:
<223> OTHER INFORMATION: Coding Sequence for Talaromyces emersonii
      CBHI Mutant with Phanerochaete chrysosporium cellobiohydrolase
      CBD with 6x His-TAG

<400> SEQUENCE: 45

ctgcaggcct gcacggcgac ggcagagaac cacccgcccc tgacatggca ggaatgcacc      60

gcccctggga gctgcaccac caggaacggg gcggtcgttc ttgatgcgaa ctggcgttgg     120

gtgcacgatg tgaacggata caccaactgc tacacgggca atacctggga ccccacgtac     180

tgccctgacg acgtaacctg cgcccagaac tgttgcctgg acggcgcgga ttacgagggc     240

acctacggcg tgacttcgtc gggcagctcc ttgaaactca atttcgtcac cgggtcgaac     300

gtcggatccc gtctctacct gctgcaggac gactcgacct atcagatctt caagctcctg     360

aaccgcgagt tcagctttga cgtcgatgtc tccaatcttc cgtgcggatt gaacggcgct     420

ctgtactttg tcgccatgga cgccgacggc ggcgtgtcca agtacccgaa caacaaggct     480

ggtgccaagt acggaaccgg gtattgcgac tcccaatgcc cacgggacct caagttcatc     540

aacggcatgg ccaacgtcga gggctggcag ccgtcatcga acaacgccaa caccggaatt     600

ggcgaccacg gctcctgctg tgcggagatg gatgtctggg aagcaaacag catctccaat     660

gcggtcactc tgcacccgtg cgacacgcca ggccagacga tgtgctctgg agatgactgc     720

ggtggcacat actctaacga tcgctacgcg ggaacctgcg atcctgacgg ctgtgacttc     780

aacccttacc gcatgggcaa cacttctttc tacgggcctg gcaagatcat cgataccacc     840

aagcccttca ctgtcgtgac gcagttcctc actgatgatg gtacggatac tggaactctc     900

agcgagatca agcgcttcta catccagaac ggcaacgtca ttccgcagcc caactcgatc     960

atcagtggcg tgaccggcaa ctcgatcacg acggagttct gcactgctca gaagcaggcc    1020

tttggcgaca cggacgaatt ctctaagcac ggtggcctgg ccaagatggg agcggccatg    1080

cagcagggta tggtcctggt gatgagtttg tgggacgact acgccgcgca gatgctgtgg    1140

ttggattccg actacccgac ggatgcggac cccacggtcc ctggtattgc ccgtggaacg    1200

tgtccgacgg actcgggcgt cccatcggat gtcgagtcgc agagccccaa ctcctacgtg    1260

accttctcga acattaagtt tggtccgatc aactcgacct acactggaac tgtttcttca    1320

tcctccgttt catcttctca ctcctccact tctacttcat cttcccattc ctcatcttcc    1380
```

-continued

```
actccaccaa ctcaaccaac tggtgttact gttccacaat ggggacaatg tggtggtatt   1440

ggttacactg gttccactac ttgtgcttcc ccatacactt gtcacgtttt gaacccatac   1500

tactcccaat gttacgcttc tgctcatcat caccatcacc actaa                   1545


<210> SEQ ID NO 46
<211> LENGTH: 522
<212> TYPE: PRT
<213> ORGANISM: artificial
<220> FEATURE:
<223> OTHER INFORMATION: Talaromyces emersonii CBHI Mutant with
      Penicillium janthinellum cellobiohydrolase CBD with 6x His-TAG

<400> SEQUENCE: 46

Leu Gln Ala Cys Thr Ala Thr Ala Glu Asn His Pro Pro Leu Thr Trp
1               5                   10                  15

Gln Glu Cys Thr Ala Pro Gly Ser Cys Thr Thr Arg Asn Gly Ala Val
            20                  25                  30

Val Leu Asp Ala Asn Trp Arg Trp Val His Asp Val Asn Gly Tyr Thr
        35                  40                  45

Asn Cys Tyr Thr Gly Asn Thr Trp Asp Pro Thr Tyr Cys Pro Asp Asp
    50                  55                  60

Val Thr Cys Ala Gln Asn Cys Cys Leu Asp Gly Ala Asp Tyr Glu Gly
65                  70                  75                  80

Thr Tyr Gly Val Thr Ser Ser Gly Ser Ser Leu Lys Leu Asn Phe Val
                85                  90                  95

Thr Gly Ser Asn Val Gly Ser Arg Leu Tyr Leu Leu Gln Asp Asp Ser
            100                 105                 110

Thr Tyr Gln Ile Phe Lys Leu Leu Asn Arg Glu Phe Ser Phe Asp Val
        115                 120                 125

Asp Val Ser Asn Leu Pro Cys Gly Leu Asn Gly Ala Leu Tyr Phe Val
    130                 135                 140

Ala Met Asp Ala Asp Gly Gly Val Ser Lys Tyr Pro Asn Asn Lys Ala
145                 150                 155                 160

Gly Ala Lys Tyr Gly Thr Gly Tyr Cys Asp Ser Gln Cys Pro Arg Asp
                165                 170                 175

Leu Lys Phe Ile Asn Gly Met Ala Asn Val Glu Gly Trp Gln Pro Ser
            180                 185                 190

Ser Asn Asn Ala Asn Thr Gly Ile Gly Asp His Gly Ser Cys Cys Ala
        195                 200                 205

Glu Met Asp Val Trp Glu Ala Asn Ser Ile Ser Asn Ala Val Thr Leu
    210                 215                 220

His Pro Cys Asp Thr Pro Gly Gln Thr Met Cys Ser Gly Asp Asp Cys
225                 230                 235                 240

Gly Gly Thr Tyr Ser Asn Asp Arg Tyr Ala Gly Thr Cys Asp Pro Asp
                245                 250                 255

Gly Cys Asp Phe Asn Pro Tyr Arg Met Gly Asn Thr Ser Phe Tyr Gly
            260                 265                 270

Pro Gly Lys Ile Ile Asp Thr Thr Lys Pro Phe Thr Val Val Thr Gln
        275                 280                 285

Phe Leu Thr Asp Asp Gly Thr Asp Thr Gly Thr Leu Ser Glu Ile Lys
    290                 295                 300

Arg Phe Tyr Ile Gln Asn Gly Asn Val Ile Pro Gln Pro Asn Ser Ile
305                 310                 315                 320

Ile Ser Gly Val Thr Gly Asn Ser Ile Thr Thr Glu Phe Cys Thr Ala
```

-continued

```
                325                 330                 335

Gln Lys Gln Ala Phe Gly Asp Thr Asp Glu Phe Ser Lys His Gly Gly
            340                 345                 350

Leu Ala Lys Met Gly Ala Ala Met Gln Gln Gly Met Val Leu Val Met
        355                 360                 365

Ser Leu Trp Asp Asp Tyr Ala Ala Gln Met Leu Trp Leu Asp Ser Asp
    370                 375                 380

Tyr Pro Thr Asp Ala Asp Pro Thr Val Pro Gly Ile Ala Arg Gly Thr
385                 390                 395                 400

Cys Pro Thr Asp Ser Gly Val Pro Ser Asp Val Glu Ser Gln Ser Pro
                405                 410                 415

Asn Ser Tyr Val Thr Phe Ser Asn Ile Lys Phe Gly Pro Ile Asn Ser
            420                 425                 430

Thr Phe Thr Gly Gly Thr Thr Ser Ser Ser Ser Thr Thr Thr Thr Thr
        435                 440                 445

Ser Lys Ser Thr Ser Thr Ser Ser Ser Ser Lys Thr Thr Thr Thr Ser
    450                 455                 460

Val Thr Thr Thr Thr Thr Ser Ser Gly Ser Ser Gly Thr Gly Ala Ala
465                 470                 475                 480

His Trp Ala Gln Cys Gly Gly Asn Gly Trp Thr Gly Pro Thr Thr Cys
                485                 490                 495

Val Ser Pro Tyr Thr Cys Thr Lys Gln Asn Asp Trp Tyr Ser Gln Cys
            500                 505                 510

Leu Ala Ser Ala His His His His His His
        515                 520


<210> SEQ ID NO 47
<211> LENGTH: 1566
<212> TYPE: DNA
<213> ORGANISM: artificial
<220> FEATURE:
<223> OTHER INFORMATION: Coding Sequence for Talaromyces emersonii
      CBHI Mutant with Penicillium janthinellum cellobiohydrolase
      CBD with 6x His-TAG

<400> SEQUENCE: 47

ctgcaggcct gcacggcgac ggcagagaac cacccgcccc tgacatggca ggaatgcacc      60

gcccctggga gctgcaccac caggaacggg gcggtcgttc ttgatgcgaa ctggcgttgg     120

gtgcacgatg tgaacggata caccaactgc tacacgggca atacctggga ccccacgtac     180

tgccctgacg acgtaacctg cgcccagaac tgttgcctgg acggcgcgga ttacgagggc     240

acctacggcg tgacttcgtc gggcagctcc ttgaaactca atttcgtcac cgggtcgaac     300

gtcggatccc gtctctacct gctgcaggac gactcgacct atcagatctt caagctcctg     360

aaccgcgagt tcagctttga cgtcgatgtc tccaatcttc cgtgcggatt gaacggcgct     420

ctgtactttg tcgccatgga cgccgacggc ggcgtgtcca agtacccgaa caacaaggct     480

ggtgccaagt acggaaccgg gtattgcgac tcccaatgcc cacgggacct caagttcatc     540

aacggcatgg ccaacgtcga gggctggcag ccgtcatcga acaacgccaa caccggaatt     600

ggcgaccacg gctcctgctg tgcggagatg gatgtctggg aagcaaacag catctccaat     660

gcggtcactc tgcacccgtg cgacacgcca ggccagacga tgtgctctgg agatgactgc     720

ggtggcacat actctaacga tcgctacgcg ggaacctgcg atcctgacgg ctgtgacttc     780

aacccttacc gcatgggcaa cacttctttc tacgggcctg gcaagatcat cgataccacc     840

aagcccttca ctgtcgtgac gcagttcctc actgatgatg gtacggatac tggaactctc     900
```

```
agcgagatca agcgcttcta catccagaac ggcaacgtca ttccgcagcc caactcgatc    960

atcagtggcg tgaccggcaa ctcgatcacg acggagttct gcactgctca gaagcaggcc   1020

tttggcgaca cggacgaatt ctctaagcac ggtggcctgg ccaagatggg agcggccatg   1080

cagcagggta tggtcctggt gatgagtttg tgggacgact acgccgcgca gatgctgtgg   1140

ttggattccg actacccgac ggatgcggac cccacggtcc ctggtattgc ccgtggaacg   1200

tgtccgacgg actcgggcgt cccatcggat gtcgagtcgc agagccccaa ctcctacgtg   1260

accttctcga acattaagtt tggtccgatc aactcgacct tcactggtgg tactacttca   1320

tcctcctcca ctactactac aacttccaag tccacttcca cttcatcttc atccaagact   1380

acaactactt ccgttacaac tactactact tcctctggtt cttctggtac tggtgctgct   1440

cattgggctc aatgtggtgg taatggatgg actggtccaa ctacttgtgt ttccccatac   1500

acttgtacta agcagaacga ctggtactct caatgtttgg cttctgctca tcatcaccat   1560

caccac                                                              1566
```

```
<210> SEQ ID NO 48
<211> LENGTH: 510
<212> TYPE: PRT
<213> ORGANISM: artificial
<220> FEATURE:
<223> OTHER INFORMATION: Talaromyces emersonii CBHI Mutant with Irpex
      lacteus cellobiohydrolase CBD with 6x His-TAG

<400> SEQUENCE: 48

Leu Gln Ala Cys Thr Ala Thr Ala Glu Asn His Pro Pro Leu Thr Trp
1               5                   10                  15

Gln Glu Cys Thr Ala Pro Gly Ser Cys Thr Thr Arg Asn Gly Ala Val
            20                  25                  30

Val Leu Asp Ala Asn Trp Arg Trp Val His Asp Val Asn Gly Tyr Thr
        35                  40                  45

Asn Cys Tyr Thr Gly Asn Thr Trp Asp Pro Thr Tyr Cys Pro Asp Asp
    50                  55                  60

Val Thr Cys Ala Gln Asn Cys Cys Leu Asp Gly Ala Asp Tyr Glu Gly
65                  70                  75                  80

Thr Tyr Gly Val Thr Ser Ser Gly Ser Ser Leu Lys Leu Asn Phe Val
                85                  90                  95

Thr Gly Ser Asn Val Gly Ser Arg Leu Tyr Leu Leu Gln Asp Asp Ser
            100                 105                 110

Thr Tyr Gln Ile Phe Lys Leu Leu Asn Arg Glu Phe Ser Phe Asp Val
        115                 120                 125

Asp Val Ser Asn Leu Pro Cys Gly Leu Asn Gly Ala Leu Tyr Phe Val
    130                 135                 140

Ala Met Asp Ala Asp Gly Gly Val Ser Lys Tyr Pro Asn Asn Lys Ala
145                 150                 155                 160

Gly Ala Lys Tyr Gly Thr Gly Tyr Cys Asp Ser Gln Cys Pro Arg Asp
                165                 170                 175

Leu Lys Phe Ile Asn Gly Met Ala Asn Val Glu Gly Trp Gln Pro Ser
            180                 185                 190

Ser Asn Asn Ala Asn Thr Gly Ile Gly Asp His Gly Ser Cys Cys Ala
        195                 200                 205

Glu Met Asp Val Trp Glu Ala Asn Ser Ile Ser Asn Ala Val Thr Leu
    210                 215                 220

His Pro Cys Asp Thr Pro Gly Gln Thr Met Cys Ser Gly Asp Asp Cys
```

```
225                 230                 235                 240

Gly Gly Thr Tyr Ser Asn Asp Arg Tyr Ala Gly Thr Cys Asp Pro Asp
                245                 250                 255

Gly Cys Asp Phe Asn Pro Tyr Arg Met Gly Asn Thr Ser Phe Tyr Gly
            260                 265                 270

Pro Gly Lys Ile Ile Asp Thr Thr Lys Pro Phe Thr Val Val Thr Gln
        275                 280                 285

Phe Leu Thr Asp Asp Gly Thr Asp Thr Gly Thr Leu Ser Glu Ile Lys
    290                 295                 300

Arg Phe Tyr Ile Gln Asn Gly Asn Val Ile Pro Gln Pro Asn Ser Ile
305                 310                 315                 320

Ile Ser Gly Val Thr Gly Asn Ser Ile Thr Thr Glu Phe Cys Thr Ala
                325                 330                 335

Gln Lys Gln Ala Phe Gly Asp Thr Asp Glu Phe Ser Lys His Gly Gly
            340                 345                 350

Leu Ala Lys Met Gly Ala Ala Met Gln Gln Gly Met Val Leu Val Met
        355                 360                 365

Ser Leu Trp Asp Asp Tyr Ala Ala Gln Met Leu Trp Leu Asp Ser Asp
    370                 375                 380

Tyr Pro Thr Asp Ala Asp Pro Thr Val Pro Gly Ile Ala Arg Gly Thr
385                 390                 395                 400

Cys Pro Thr Asp Ser Gly Val Pro Ser Asp Val Glu Ser Gln Ser Pro
                405                 410                 415

Asn Ser Tyr Val Thr Phe Ser Asn Ile Lys Phe Gly Pro Ile Asn Ser
            420                 425                 430

Thr Phe Thr Gly Thr Gly Ser Thr Ser Pro Ser Ser Pro Ala Gly Pro
        435                 440                 445

Val Ser Ser Ser Thr Ser Val Ala Ser Gln Pro Thr Gln Pro Ala Gln
    450                 455                 460

Gly Thr Val Ala Gln Trp Gly Gln Cys Gly Gly Thr Gly Phe Thr Gly
465                 470                 475                 480

Pro Thr Val Cys Ala Ser Pro Phe Thr Cys His Val Val Asn Pro Tyr
                485                 490                 495

Tyr Ser Gln Cys Tyr Ala Ser Ala His His His His His His
            500                 505                 510
```

```
<210> SEQ ID NO 49
<211> LENGTH: 1530
<212> TYPE: DNA
<213> ORGANISM: artificial
<220> FEATURE:
<223> OTHER INFORMATION: Coding Sequence for Talaromyces emersonii
      CBHI Mutant with Irpex lacteus cellobiohydrolase CBD with
      6x His-TAG

<400> SEQUENCE: 49

ctgcaggcct gcacggcgac ggcagagaac cacccgcccc tgacatggca ggaatgcacc      60

gcccctggga gctgcaccac caggaacggg gcggtcgttc ttgatgcgaa ctggcgttgg     120

gtgcacgatg tgaacggata caccaactgc tacacgggca atacctggga ccccacgtac     180

tgccctgacg acgtaacctg cgcccagaac tgttgcctgg acggcgcgga ttacgagggc     240

acctacggcg tgacttcgtc gggcagctcc ttgaaactca atttcgtcac cgggtcgaac     300

gtcggatccc gtctctacct gctgcaggac gactcgacct atcagatctt caagctcctg     360

aaccgcgagt tcagctttga cgtcgatgtc tccaatcttc cgtgcggatt gaacggcgct     420
```

-continued

```
ctgtactttg tcgccatgga cgccgacggc ggcgtgtcca agtacccgaa caacaaggct    480

ggtgccaagt acggaaccgg gtattgcgac tcccaatgcc cacgggacct caagttcatc    540

aacggcatgg ccaacgtcga gggctggcag ccgtcatcga acaacgccaa caccggaatt    600

ggcgaccacg gctcctgctg tgcggagatg gatgtctggg aagcaaacag catctccaat    660

gcggtcactc tgcacccgtg cgacacgcca ggccagacga tgtgctctgg agatgactgc    720

ggtggcacat actctaacga tcgctacgcg ggaacctgcg atcctgacgg ctgtgacttc    780

aacccttacc gcatgggcaa cacttctttc tacgggcctg gcaagatcat cgataccacc    840

aagcccttca ctgtcgtgac gcagttcctc actgatgatg gtacggatac tggaactctc    900

agcgagatca agcgcttcta catccagaac ggcaacgtca ttccgcagcc caactcgatc    960

atcagtggcg tgaccggcaa ctcgatcacg acggagttct gcactgctca gaagcaggcc   1020

tttggcgaca cggacgaatt ctctaagcac ggtggcctgg ccaagatggg agcggccatg   1080

cagcagggta tggtcctggt gatgagtttg tgggacgact acgccgcgca gatgctgtgg   1140

ttggattccg actacccgac ggatgcggac cccacggtcc ctggtattgc ccgtggaacg   1200

tgtccgacgg actcgggcgt cccatcggat gtcgagtcgc agagccccaa ctcctacgtg   1260

accttctcga acattaagtt tggtccgatc aactcgacct tcactggtac tggttctact   1320

tctccatctt ctccagctgg tccagtttct tcttccactt ccgttgcttc ccaaccaact   1380

caaccagctc aaggtactgt tgctcaatgg ggacaatgtg gtggtactgg tttcactggt   1440

ccaactgttt gtgcttcccc attcacttgt cacgttgtta acccatacta ctcccagtgt   1500

tacgcttctg ctcatcatca tcaccatcac                                    1530
```

<210> SEQ ID NO 50
<211> LENGTH: 509
<212> TYPE: PRT
<213> ORGANISM: artificial
<220> FEATURE:
<223> OTHER INFORMATION: Talaromyces emersonii CBHI Mutant with mutated Trichoderma reesei CBD with 6x His-TAG

<400> SEQUENCE: 50

```
Leu Gln Ala Cys Thr Ala Thr Ala Glu Asn His Pro Pro Leu Thr Trp
1               5                   10                  15

Gln Glu Cys Thr Ala Pro Gly Ser Cys Thr Thr Arg Asn Gly Ala Val
            20                  25                  30

Val Leu Asp Ala Asn Trp Arg Trp Val His Asp Val Asn Gly Tyr Thr
        35                  40                  45

Asn Cys Tyr Thr Gly Asn Thr Trp Asp Pro Thr Tyr Cys Pro Asp Asp
    50                  55                  60

Val Thr Cys Ala Gln Asn Cys Cys Leu Asp Gly Ala Asp Tyr Glu Gly
65                  70                  75                  80

Thr Tyr Gly Val Thr Ser Ser Gly Ser Ser Leu Lys Leu Asn Phe Val
                85                  90                  95

Thr Gly Ser Asn Val Gly Ser Arg Leu Tyr Leu Leu Gln Asp Asp Ser
            100                 105                 110

Thr Tyr Gln Ile Phe Lys Leu Leu Asn Arg Glu Phe Ser Phe Asp Val
        115                 120                 125

Asp Val Ser Asn Leu Pro Cys Gly Leu Asn Gly Ala Leu Tyr Phe Val
    130                 135                 140

Ala Met Asp Ala Asp Gly Gly Val Ser Lys Tyr Pro Asn Asn Lys Ala
145                 150                 155                 160
```

-continued

```
Gly Ala Lys Tyr Gly Thr Gly Tyr Cys Asp Ser Gln Cys Pro Arg Asp
                165                 170                 175

Leu Lys Phe Ile Asn Gly Met Ala Asn Val Glu Gly Trp Gln Pro Ser
            180                 185                 190

Ser Asn Asn Ala Asn Thr Gly Ile Gly Asp His Gly Ser Cys Cys Ala
        195                 200                 205

Glu Met Asp Val Trp Glu Ala Asn Ser Ile Ser Asn Ala Val Thr Leu
    210                 215                 220

His Pro Cys Asp Thr Pro Gly Gln Thr Met Cys Ser Gly Asp Asp Cys
225                 230                 235                 240

Gly Gly Thr Tyr Ser Asn Asp Arg Tyr Ala Gly Thr Cys Asp Pro Asp
                245                 250                 255

Gly Cys Asp Phe Asn Pro Tyr Arg Met Gly Asn Thr Ser Phe Tyr Gly
            260                 265                 270

Pro Gly Lys Ile Ile Asp Thr Thr Lys Pro Phe Thr Val Val Thr Gln
        275                 280                 285

Phe Leu Thr Asp Asp Gly Thr Asp Thr Gly Thr Leu Ser Glu Ile Lys
    290                 295                 300

Arg Phe Tyr Ile Gln Asn Gly Asn Val Ile Pro Gln Pro Asn Ser Ile
305                 310                 315                 320

Ile Ser Gly Val Thr Gly Asn Ser Ile Thr Thr Glu Phe Cys Thr Ala
                325                 330                 335

Gln Lys Gln Ala Phe Gly Asp Thr Asp Glu Phe Ser Lys His Gly Gly
            340                 345                 350

Leu Ala Lys Met Gly Ala Ala Met Gln Gln Gly Met Val Leu Val Met
        355                 360                 365

Ser Leu Trp Asp Asp Tyr Ala Ala Gln Met Leu Trp Leu Asp Ser Asp
    370                 375                 380

Tyr Pro Thr Asp Ala Asp Pro Thr Val Pro Gly Ile Ala Arg Gly Thr
385                 390                 395                 400

Cys Pro Thr Asp Ser Gly Val Pro Ser Asp Val Glu Ser Gln Ser Pro
                405                 410                 415

Asn Ser Tyr Val Thr Phe Ser Asn Ile Lys Phe Gly Pro Ile Gly Ser
            420                 425                 430

Thr Gly Asn Pro Ser Gly Gly Asn Pro Ser Gly Gly Asp Gly Gly Thr
        435                 440                 445

Thr Thr Thr Arg Arg Pro Ala Thr Thr Thr Gly Ser Ser Pro Gly Pro
    450                 455                 460

Thr Gln Ser Leu Tyr Gly Gln Cys Gly Gly Ile Gly Tyr Ser Gly Pro
465                 470                 475                 480

Thr Ile Cys Ala Ser Gly Thr Thr Cys Gln Val Leu Asn Pro Tyr Tyr
                485                 490                 495

Ser Gln Cys Leu Ala Ser Ala His His His His His His
            500                 505
```

<210> SEQ ID NO 51
<211> LENGTH: 1527
<212> TYPE: DNA
<213> ORGANISM: artificial
<220> FEATURE:
<223> OTHER INFORMATION: Coding Sequence for Talaromyces emersonii CBHI Mutant with mutated Trichoderma reesei CBD with 6x His-TAG

<400> SEQUENCE: 51

```
ctgcaggcct gcacggcgac ggcagagaac cacccgcccc tgacatggca ggaatgcacc     60
```

-continued

```
gcccctggga gctgcaccac caggaacggg gcggtcgttc ttgatgcgaa ctggcgttgg    120

gtgcacgatg tgaacggata caccaactgc tacacgggca atacctggga ccccacgtac    180

tgccctgacg acgtaacctg cgcccagaac tgttgcctgg acggcgcgga ttacgagggc    240

acctacggcg tgacttcgtc gggcagctcc ttgaaactca atttcgtcac cgggtcgaac    300

gtcggatccc gtctctacct gctgcaggac gactcgacct atcagatctt caagctcctg    360

aaccgcgagt tcagctttga cgtcgatgtc tccaatcttc cgtgcggatt gaacggcgct    420

ctgtactttg tcgccatgga cgccgacggc ggcgtgtcca agtacccgaa caacaaggct    480

ggtgccaagt acggaaccgg gtattgcgac tcccaatgcc cacgggacct caagttcatc    540

aacggcatgg ccaacgtcga gggctggcag ccgtcatcga acaacgccaa caccggaatt    600

ggcgaccacg gctcctgctg tgcggagatg gatgtctggg aagcaaacag catctccaat    660

gcggtcactc tgcacccgtg cgacacgcca ggccagacga tgtgctctgg agatgactgc    720

ggtggcacat actctaacga tcgctacgcg ggaacctgcg atcctgacgg ctgtgacttc    780

aacccttacc gcatgggcaa cacttctttc tacgggcctg gcaagatcat cgataccacc    840

aagcccttca ctgtcgtgac gcagttcctc actgatgatg gtacggatac tggaactctc    900

agcgagatca agcgcttcta catccagaac ggcaacgtca ttccgcagcc caactcgatc    960

atcagtggcg tgaccggcaa ctcgatcacg acggagttct gcactgctca gaagcaggcc   1020

tttggcgaca cggacgaatt ctctaagcac ggtggcctgg ccaagatggg agcggccatg   1080

cagcagggta tggtcctggt gatgagtttg tgggacgact acgccgcgca gatgctgtgg   1140

ttggattccg actacccgac ggatgcggac cccacggtcc ctggtattgc ccgtggaacg   1200

tgtccgacgg actcgggcgt cccatcggat gtcgagtcgc agagccccaa ctcctacgtg   1260

accttctcga acattaagtt tggtccgatc ggtagcacag gtaatccttc aggtggtaat   1320

ccttcaggtg gagacggcgg aacaacgaca actagaagac cagctactac aactggttca   1380

agtccaggtc caactcaatc actatacggt caatgtggtg gtataggtta ctctggtccc   1440

actatttgtg cttctggtac tacttgccaa gttctgaacc cttactactc acagtgtcta   1500

gcttctgcac atcatcacca ccaccat                                        1527
```